(12) United States Patent
Discher et al.

(10) Patent No.: US 10,946,042 B2
(45) Date of Patent: Mar. 16, 2021

(54) COMPOSITIONS AND METHODS FOR SELECTIVE PHAGOCYTOSIS OF HUMAN CANCER CELLS

(71) Applicant: THE TRUSTEES OF THE UNIVERSITY OF PENNSYLVANIA, Philadelphia, PA (US)

(72) Inventors: Dennis E. Discher, Philadelphia, PA (US); Kyle R. Spinler, La Jolla, CA (US); Cory Alvey, Philadelphia, PA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 133 days.

(21) Appl. No.: 15/366,844

(22) Filed: Dec. 1, 2016

(65) Prior Publication Data

US 2017/0151282 A1 Jun. 1, 2017

Related U.S. Application Data

(60) Provisional application No. 62/261,690, filed on Dec. 1, 2015, provisional application No. 62/376,712, filed on Aug. 18, 2016.

(51) Int. Cl.

| | |
|---|---|
| *A61K 35/15* | (2015.01) |
| *C12N 5/0786* | (2010.01) |
| *A61K 35/28* | (2015.01) |
| *A61K 49/00* | (2006.01) |
| *A61K 35/12* | (2015.01) |
| *A61K 47/68* | (2017.01) |

(52) U.S. Cl.
CPC ............ *A61K 35/15* (2013.01); *A61K 35/28* (2013.01); *A61K 47/6851* (2017.08); *A61K 49/0041* (2013.01); *A61K 49/0097* (2013.01); *C12N 5/0645* (2013.01); *A61K 2035/124* (2013.01); *C12N 2510/00* (2013.01)

(58) Field of Classification Search
CPC .. A61K 35/15; A61K 35/28; A61K 2035/124; A61K 2039/505; A61K 2039/5154; A61K 39/3955; C12N 5/0645; C07K 16/28; C07K 16/30; C07K 16/32
See application file for complete search history.

(56) References Cited

U.S. PATENT DOCUMENTS

| | | | |
|---|---|---|---|
| 4,444,887 A | 4/1984 | Hoffmann | |
| 4,716,111 A | 12/1987 | Osband et al. | |
| 2003/0235868 A1* | 12/2003 | Hoogenboom | C07K 16/18 435/7.2 |
| 2007/0113297 A1* | 5/2007 | Yang | A01K 67/0276 800/17 |
| 2012/0282174 A1* | 11/2012 | Weissman | C07K 16/2887 424/1.49 |
| 2014/0068797 A1 | 3/2014 | Doudna et al. | |

FOREIGN PATENT DOCUMENTS

WO 2013063419 A2 5/2013

OTHER PUBLICATIONS

Padlan (Advance Protein Chemistry 49:57-133; 1996).*
Corada et al. (Blood, 2001; 97:1679-84).*
King Saud (Medical Supply Department, Request form, 2014) (Year: 2014).*
Baumann, et al., "Enhancing the Efficacy of Drug-loaded Nanocarriers against Brain Tumors by Targeted Radiation Therapy", Oncotarget 2013; 4: 64-79.
Cai, et al., "Micelles of Different Morphologies—Advantages of Worm-like Filomicelles of PEO-PCL in Paclitaxel Delivery", Pharm. Res. 24, 2099-109 (2007).
Chao, et al., "Calreticulin is the dominant pro-phagocytic signal on multiple human cancers and is counterbalanced by CD47", Sci Transl Med. Dec. 22, 2010; 2(63): 63ra94.
Christian, et al., "Flexible Filaments for in vivo Imaging and Delivery: Persistent Circulation of Filomicelles Opens the Dosage Window for Sustained Tumor Shrinkage", Mol Pharm. 2009 ; 6(5): 1343-1352.
De Almeida, et al., "The role of glucocorticoid in SIRPα and SHP-1 gene expression in AIHA patients.", 2009, Immunopharmacol. Immunotoxicol. 31(4):636-40.
Desnoyers, et al., "Tumor-Specific Activation of an EGFR-Targeting Probody Enhances Therapeutic Index", Science Translational Medicine 5 (207), 207ra144.
Gardai, et al., "Cell-Surface Calreticulin Initiates Clearance of Viable or Apoptotic Cells through trans-Activation of LRP on the Phagocyte", Cell, vol. 123, 321-334, Oct. 21, 2005.
Kaur, et al., "Thrombospondin-1 Signaling through CD47 Inhibits Self-renewal by Regulating c-Myc and Other Stem Cell Transcription Factors", Sci. Rep. 3, 1673; DOI:10.1038/srep01673 (2013).
Kufe, "Mucins in cancer: function, prognosis and therapy", Nat Rev Cancer. Dec. 2009 ; 9(12): 874-885.
Lavin, et al., "Tissue-Resident Macrophage Enhancer Landscapes Are Shaped by the Local Microenvironment", Cell 159, 1312-1326, Dec. 4, 2014.
Nair, et al., "Filomicelles from aromatic diblock copolymers increase paclitaxel-induced tumor cell death and aneuploidy compared with aliphatic copolymers", 2016, Nanomedicine 11(12):1551-1569.
Oldenborg, "Role of CD47 in erythroid cells and in autoimmunity." 2004, Leuk. Lymphoma 45(7):1319-27, 2004, Leuk. Lymphoma 45(7):1319-27.
Pallasch, et al., "Sensitizing Protective Tumor Microenvironments to Antibody-Mediated Therapy", Cell 156, 590-602, Jan. 30, 2014.
Steinert, et al., "Immune Escape and Survival Mechanisms in Circulating Tumor Cells of Colorectal Cancer", Cancer Res; 74(6) Mar. 15, 2014.

(Continued)

*Primary Examiner* — Karen A. Canella
(74) *Attorney, Agent, or Firm* — Saul Ewing Arnstein & Lehr LLP; Kathryn Doyle; Justin Crotty

(57) ABSTRACT

The present invention relates to compositions and methods that provide novel therapies in cancer. The invention includes a phagocytic cell modified with a repressor of signal regulatory protein-alpha (SIRPα) and bound to a targeting antibody to enhance phagocytic activity of the phagocytic cell toward tumor tissue. Methods of enhancing phagocytic activity and treating a tumor are also included.

36 Claims, 88 Drawing Sheets

(56) References Cited

OTHER PUBLICATIONS

Tsai, et al., "Inhibition of "self" engulfment through deactivation of myosin-II at the phagocytic synapse between human cells", The Journal of Cell Biology, vol. 180, No. 5, Mar. 10, 2008 989-1003.
Wang, et al., "Intravenous Delivery of siRNA Targeting CD47 Effectively Inhibits Melanoma Tumor Growth and Lung Metastasis", Molecular Therapy vol. 21 No. 10, 1919-1929 Oct. 2013.
Weiskopf, et al., "Engineered SIRPα variants as immunotherapeutic adjuvants to anti-cancer antibodies", Science. Jul. 5, 2013; 341 (6141): . doi:10.1126/science.1238856.
Willingham, et al., "The CD47-signal regulatory protein alpha (SIRPa) interaction is a therapeutic target for human solid tumors", 2012, PNAS 109(17):6662-6667.

\* cited by examiner

Fig. 7

Human Marrow Donors

| Age | Weight (lbs) | Height (Ft) | Sex | Race | Blood Type | Smoker? |
|---|---|---|---|---|---|---|
| 30 | 166 | 5'5" | | Non Hispanic White | O- | No |
| 31 | 226 | 5'10" | Female | African American | B+ | No |
| 31 | 240 | 6'3" | Male | Irish/Italian | A+ | No |
| 22 | 180 | 5'8" | Male | Hispanic | O+ | No |

| | Total IgG | Adult mouse | | Ab injections | |
|---|---|---|---|---|---|
| | mg/mL | Blood (mL)[1] | mg IgG | | % of IgG |
| C57BL/6[2] | 1.5 | 2.4 | 3.6 | | 17% |
| Humanized NSG[3] | 0.165 | 2.4 | 0.4 | | 154% |
| | mg/mL | Adult Human | | 0.3 mg Rhogam | |
| | | Blood (mL) | mg IgG | | % of IgG |
| Hu Serum | 10 | 5000 | 50000 | | 0.0006% |

Fig. 16

| | Area (μm²) | *In Vitro* | | *In Vivo* | |
|---|---|---|---|---|---|
| | | CD47 (norm) | CD47/μm² | CD47 (norm) | CD47/μm² |
| WT Scr | | 5.00±0.04 | 463 | 5.5±0.2 | 509 |
| CD47 KD⁺ | | 2.12±0.05 | 196 | 4.1±0.1 | 379 |
| CD47 KD⁺⁺ | 382 | 1.26±0.04 | 117 | 2.37±0.07 | 219 |
| GFP⁺, CD47hi | | 6.20±0.02 | 574 | 3.9±0.2 | 361 |
| GFP⁻, CD47hi | | 4.73±0.03 | 438 | 2.7±0.2 | 250 |
| GFP⁻, CD47lo | | 0.41±0.05 | 38 | 0.66±0.03 | 61 |
| hRBC | 141±3.0 | 1.00 | 250 | | |
| | Engstrom 1998 | | Tsai 2008 | | |

Mosaic

E

|  | Total IgG | For 30 g mouse | | Inject 0.6 mg IgG Ab |
|---|---|---|---|---|
|  | mg/mL | Blood (mL)[1] | mg IgG | % of IgG |
| C57BL/6[2] | 1.5 | 2.4 | 3.6 | 17% |
| Humanized NSG[3] | 0.165 | 2.4 | 0.4 | 154% |

|  |  |  |  | 300 ug Rhogam |
|---|---|---|---|---|
|  | mg/mL | L | mg IgG | % of IgG |
| Hu IgG | 10 | 5 | 50000 | 0.0006% |

| | | Area (µm²) | In Vitro | | In Vivo | |
|---|---|---|---|---|---|---|
| | | | CD47 (norm) | CD47/µm² | CD47 (norm) | CD47/µm² |
| | WT Scr | | 5.00±0.04 | 463 | 5.5±0.2 | 509 |
| | CD47 KD⁺ | | 2.12±0.05 | 196 | 4.1±0.1 | 379 |
| | CD47 KD⁺⁺ | 382 | 1.26±0.04 | 117 | 2.37±0.07 | 219 |
| | GFP⁺, CD47hi | | 6.20±0.02 | 574 | 3.9±0.2 | 361 |
| Mosaic | GFP⁻, CD47hi | | 4.73±0.03 | 438 | 2.7±0.2 | 250 |
| | GFP⁻, CD47lo | | 0.41±0.05 | 38 | 0.66±0.03 | 61 |
| | hRBC | 141±3.0 | 1.00 | 250 | | |
| | | Engstrom 1998 | | Tsai 2008 | | |

A

B

C

F

A

| | CV% = A +B /(1+10((log(conc)-log(IC$_{50}$)))) | | | |
|---|---|---|---|---|
| | A | B | IC$_{50}$ | R$^2$ |
| WT (Scr) | 29.03 | 70.15 | 0.014 | 0.9784 |
| CD47 KD$^{++}$ | 24.05 | 75.86 | 0.026 | 0.9693 |

B

| | | Mouse weight (g) | | [Tax] (mg/kg) | |
|---|---|---|---|---|---|
| Injection date | [Taxol](ug/mL) | Scr Ab+TW | KD$^{++}$ Ab+TW | Scr Ab+TW | KD$^{++}$ Ab+TW |
| d0 | 710 | 30.7 | 30.7 | 4.63 | 4.63 |
| d2 | 690 | 30.6 | 31.1 | 4.06 | 3.99 |
| d6 | 730 | 30.3 | 30.5 | 4.82 | 4.79 |
| d9 | 580 | 30.6 | 31.3 | 3.79 | 3.71 |

A

B

COMPOSITIONS AND METHODS FOR SELECTIVE PHAGOCYTOSIS OF HUMAN CANCER CELLS

STATEMENT REGARDING FEDERALLY SPONSORED RESEARCH OR DEVELOPMENT

This invention was made with government support under grant numbers EB007049, HL062352, DK032094, CA016520, DK090969, CA193417, TR000003, and GM084979 awarded by the National Institutes of Health. The government has certain rights in the invention.

BACKGROUND OF THE INVENTION

Macrophages and monocytes engorge and accumulate within solid tissues in various inflammatory diseases, but the relevance of 'engorge and accumulate' to solid tumors has remained unclear as general mechanisms. Tumor associated macrophages (TAMs) are highly motile even within highly collagenous solid tumors, but TAMs seem less phagocytic than macrophages in other tissues and a high density of TAMs correlates with a poor clinical prognosis. 'Patrolling monocytes' in blood can pinch off tumor material within hours of cancer cells lodging in the lung after intravenous injection of tumor cells. However, mechanisms remain unclear as to how bone marrow derived monocytes or macrophages might enter a well-established solid tumor, completely engulf the cancer cells, and most importantly, accumulate in sufficient numbers to shrink a tumor.

How any cell avoids being engulfed by a macrophage could include signaling by the ubiquitous "marker of self" CD47 to the phagocyte receptor SIRPα. SIRPα signaling ultimately inhibits myosin-II, which otherwise makes engulfment highly efficient when not inhibited, but a broader role is likely since SIRPα also contributes to integrin-stimulated cytoskeleton remodeling. CD47 is expressed on all cells and was first identified as overexpressed on solid tumors, with recent evidence for regulatory roles of C-MYC and hypoxia-inducible factor 1. Hypoxia in tumors can also help recruit macrophages. For syngeneic mouse tumors in the first week of engraftment, tumor growth is prevented by knockdown of mouse CD47, which is a process dependent on macrophages but no obvious TAM-activating factors. For mice bearing human tumor xenografts, shrinkage of well-established tumors can be achieved—presumably by mouse TAMs—after systemic injections of high doses of anti-human-CD47 together with Ab's that opsonize tumor cells. However, because CD47 is expressed on all cells, intravenous injection of species-appropriate anti-CD47 antibody causes rapid decreases of blood cells in primates as well as mice. CD47 knockout mice can also exhibit autoimmune responses including auto-antibodies, anemia, and ~60% shorter lifespan. Safety of intravenous anti-CD47 is therefore one critical metric in several ongoing clinical trials. Safety of systemic anti-SIRPα is equally problematic because recent studies show this at least causes SIRPα blockade on splenic macrophages which again leads to rapid clearance of circulating components.

Systemic injections of highly phagocytic, bone marrow derived monocytes/macrophages have proven ineffective in trials against solid tumors. Furthermore, injection of SIRPα-knockdown macrophages has already been reported to promote growth of solid tumors despite the likely presence of tumor-enriched opsonins that activate phagocytosis by TAMs.

Therefore, a great need remains in the art for identifying novel anti-tumor therapies and novel methods for enhancing the activity of phagocytes to specifically target tumor cells. The present invention addresses this need.

SUMMARY OF THE INVENTION

In one aspect the invention comprises a modified macrophage comprising a repressor of signal regulatory protein-alpha (SIRPα), wherein the macrophage is bound to a targeting antibody and possesses phagocytic activity against tumor tissue.

In one embodiment, the repressor of SIRPα comprises at least one selected from the group consisting of anti-SIRPα antibody, SIRPα-shRNA, SIRPα-siRNA, SIRPα antagonist, a CRISPR system targeted to SIRPα, and a combination thereof.

In one embodiment, the targeting antibody is bound to a Fc receptor on the macrophage.

In one embodiment, the targeting antibody is a tumor specific antibody.

In one embodiment, the composition further comprises a pharmaceutically acceptable carrier.

In one embodiment, the composition has a therapeutic effect on tumor tissue.

In another aspect the invention comprises a composition comprising a signal regulatory protein-alpha (SIRPα) repressed bone marrow cell bound to a targeting antibody.

In one embodiment, the targeting antibody is bound to a Fc receptor on the bone marrow cell.

In one embodiment, the composition has a therapeutic effect on tumor tissue.

In one embodiment, the therapeutic effect comprises tumor shrinkage of at least 60% of the tumor.

In one embodiment, the tumor tissue comprises a brain cancer, bladder cancer, breast cancer, cervical cancer, colorectal cancer, liver cancer, kidney cancer, lymphoma, leukemia, lung cancer, melanoma, metastatic melanoma, mesothelioma, neuroblastoma, ovarian cancer, prostate cancer, gastric cancer, pancreatic cancer, renal cancer, skin cancer, thymoma, sarcoma, non-Hodgkin's lymphoma, Hodgkin's lymphoma, uterine cancer, and the like.

In another aspect the invention comprises a method of enhancing phagocytic activity of a phagocytic cell toward tumor tissue in a mammal, the method comprising administering to the mammal an effective amount of a composition comprising a signal regulatory protein-alpha (SIRPα) repressed phagocytic cell bound to a targeting antibody, wherein the effective amount of the composition enhances phagocytic activity and has a therapeutic effect in the mammal.

In one embodiment, the phagocytic cell is selected from the group consisting of a macrophage and a monocyte.

In one embodiment, the phagocytic cell is a bone marrow cell.

In one embodiment, the bone marrow cell differentiates into a mature macrophage.

In one embodiment, the therapeutic effect comprises tumor tissue shrinkage of at least 60% of the tumor tissue.

In one embodiment, the phagocytic cell is modified by at least one selected from the group consisting of anti-SIRPα antibody, SIRPα-shRNA, SIRPα-siRNA, SIRPα antagonist, a CRISPR system targeted to SIRPα, and a combination thereof.

In one embodiment, the phagocytic cell is bound to the targeting antibody through a Fc receptor on the phagocytic cell.

In one embodiment, wherein the targeting antibody is a tumor specific antibody.

In one embodiment, the phagocytic cell is administered intravenously to the mammal.

In one embodiment, the mammal is a human.

In another aspect the invention comprises a method of treating a tumor in a mammal, the method comprising administering to the mammal an effective amount of a composition comprising a signal regulatory protein-alpha (SIRPα) repressed phagocytic cell bound to a targeting antibody, wherein the effective amount of the composition has a therapeutic effect in the mammal, thereby treating the tumor tissue.

In one embodiment, the phagocytic cell is selected from the group consisting of a macrophage and a monocyte.

In one embodiment, the phagocytic cell is a bone marrow cell.

In one embodiment, the bone marrow cell differentiates into a mature macrophage.

In one embodiment, the therapeutic effect comprises tumor tissue shrinkage of at least 60% of the tumor tissue.

In one embodiment, the phagocytic cell is modified by at least one selected from the group consisting of anti-SIRPα antibody, SIRPα-shRNA, SIRPα-siRNA, SIRPα antagonist, a CRISPR system targeted to SIRPα, and a combination thereof.

In one embodiment, the phagocytic cell is bound to the targeting antibody through a Fc receptor on the phagocytic cell.

In one embodiment, the targeting antibody is a tumor specific antibody.

In one embodiment, the phagocytic cell is administered intravenously to the mammal.

In one embodiment, the mammal is a human.

In another aspect the invention comprises a method of modifying a phagocytic activity to target a specific tissue in a mammal, the method comprising contacting a phagocytic cell with a repressor of signal regulatory protein-alpha (SIRPα) and a targeting antibody, wherein the phagocytic cell has enhanced phagocytic activity and a therapeutic effect on the tissue in the mammal.

In one embodiment, the phagocytic cell is selected from the group consisting of a macrophage and a monocyte.

In one embodiment, the phagocytic cell is a bone marrow cell.

In one embodiment, the bone marrow cell differentiates into a mature macrophage.

In one embodiment, the targeting antibody is a tumor specific antibody.

In one embodiment, the phagocytic cell has a stronger phagocytic activity than the native phagocytic cell of the mammal.

In another aspect the invention comprises a composition comprising a repressor of CD47-signal regulatory protein-alpha (CD47-SIRPα) interaction and an opsonin, wherein the composition has a therapeutic effect on a tumor tissue.

In another aspect the invention comprises a composition comprising a signal regulatory protein-alpha (SIRPα) repressed bone marrow cell and an opsonin, wherein the composition has a therapeutic effect on a tumor tissue.

In another aspect the invention comprises a method of modulating phagocytic activity to target a specific tissue in a mammal, the method comprising administering to the mammal an effective amount of a composition comprising a repressor of CD47-signal regulatory protein-alpha (CD47-SIRPα) interaction and an opsonin, wherein the effective amount of the composition modulates phagocytic activity and has a therapeutic effect on the tissue in the mammal.

In another aspect the invention comprises a method of modulating phagocytic activity to target a specific tissue in a mammal, the method comprising administering to the mammal an effective amount of a composition comprising a signal regulatory protein-alpha (SIRPα) repressed bone marrow cell and an opsonin, wherein the effective amount of the composition modulates phagocytic activity and has a therapeutic effect on the tissue in the mammal.

In another aspect the invention comprises a method of treating a tumor in a mammal, the method comprising administering to the mammal an effective amount of a composition comprising a repressor of CD47-signal regulatory protein-alpha (CD47-SIRPα) interaction and opsonin, thereby treating the tumor tissue.

In another aspect the invention comprises a method of treating a tumor in a mammal, the method comprising administering to the mammal an effective amount of a composition comprising a signal regulatory protein-alpha (SIRPα) repressed bone marrow cell and opsonin, thereby treating the tumor tissue.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1A is a schematic of NSG bone marrow harvest, labeling, and transfusion. Bone marrow cells taken from the femur and tibia were labeled with CFDA, their SIRPα receptor blocked with anti-mSIRPα, Fc receptor loaded with a targeting antibody then tail-vein injected into tumor-bearing NSG mice. In some experiments, instead of pre-loading Fc receptor, targeting Ab was systemically injected. Recipient mice were given an Ab boost on day 3 and subsequently sacrificed ~3 hours later. Bone marrow, peripheral blood, spleen, liver and tumor tissue were harvested after and analyzed for macrophage eating by flow cytometry. FIG. 1B shows the percentage of tissue isolated macrophages that have tdTomato protein from A549 tumor cells. A'PB Pre-immune n=2, donor+anti-hum n=6, APB anti-hum n=8, recipient no antibody n=2, and recipient+anti-hum n=10 (mean±SEM). FIG. 1B, inset, shows representative flow plots of macrophages that are tdTomato positive comparing APB MΦ eating to recipient MΦ eating. FIG. 1C illustrates measuring A'PB MΦ eating of tumor cells by determining the number of A'PB MΦ that are tdTomato positive and comparing it to recipient macrophages. A'PB MΦ n=8 and recipient no antibody n=4 (mean±SEM). FIG. 1D shows phagocytosis of CD47 KD++ tumor cells with donor cells and recipient TAMs n=6 mean±SEM; * significant between donor and recipient (P<0.05). FIG. 1E shows quantification of tdTomato intensity in CD11b$^+$ F4/80$^+$ macrophages normalized to A549 tumor cells. Ratios not significant from 100% indicating ~1 tumor cell/macrophage (CD47 KD$^{++}$ or WT/shCtl APB: n=8; WT tumors TAMs: n=6). Value shown is mean±STD. Quantification of Hoechst intensity in CD11b+F4/80+ macrophage normalized to Hoechst intensity of tdTomato A549 tumor cells. Sample size for all conditions n=4. Value shown is mean±STD. FIG. 1E, inset, shows a representative histogram of tdTomato intensity distribution from tdTomato positive macrophages (top graph-left peak) and tdTomato A549 tumor cells (top graph-right peak). The lower histogram shows that tdTomato positive macrophages (right peak) have a higher Hoechst signal than tdTomato negative macrophages (left peak). FIG. 1F is a 3D reconstruction of a confocal image of a phagocytic macrophage pulled directly from the tumor. Inside the macrophage is a completely engulfing tdTomato A549 tumor cell with two additional A549 cells outside the macrophage ready to be eaten. FIG. 1G shows donor and recipient CD11b+F4/80+ macrophages found in various tissues. Measured are the macrophages found per 100k cells screened using flow cytometry. Sample size for each condition n=2, n=4, n=4, n=4, n=4, n=4, n=2, and n=10 respectively. Marrow, spleen, and liver sample sizes: donor+anti-hum n=1, APB MO high n=3, recipient no antibody n=3, and recipient+antibody n=1. All other conditions were not measured. Values displayed are mean±SEM. FIG. 1G, inset, is a plot of percent tdTomato positive macrophages from FIGS. 1B-1D vs. number of macrophages per 100k showing a strong linear correlation ($R^2$=0.88).

FIG. 2A is a schematic of the 3D-motility assay used to assess macrophage eating and migration from primary NSG mouse marrow, lung, and tdTomato A549 subcutaneous tumors. Bone marrow from donor-1 was harvested, engineered (SIRPA blocked and FCY receptor primed with anti-hum), and injected into NSG mice with 8 wk old subcutaneous tdTomato A549 tumors on both flanks. Three days after injection a boost of anti-hum was given and 3 hrs later tumors were isolated and plated on tops of 3 um and 5 um transwells at 300k cells per well and allowed to migrate for 24 hrs. In some conditions marrow from a second donor was spiked with the disaggregated tumor. The transwells were scrapped, stained and analyzed by flow cytometry. FIG. 2B illustrates 3D migration of donor marrow, lung, and tumor macrophages as a function of macrophage phagocytic activity of tdTomato A549 cells on 3 um and 5 um pores. All conditions have n=3, but TAMs which have n=7 and donor 1 tumor A'PB n=4 (mean±SEM). The FIG. 2B inset table illustrates macrophage eating of tdTomato A549 cells on the bottom of 3 um and 5 um transwells along with migration of tdTomato A549 tumor cells. Only one condition shows eating on bottom (most phagocytic with largest pores). All conditions have same (n) as main plot, but tdTomato A549 has n=7. FIG. 2C shows transwells with different pore sizes have different numbers of pores (3 um=$2\times10^6$, Sum=$0.4\times10^6$, etc.), which must be accounted for in the total pore area in order to calculate cell flux (#/area). Thus the flux of cells through Sum pores should be smaller by $(5/3)\hat{}(0.4\times10^6/2\times10^6)=0.56$-fold, but the Sum transwell instead allows 3-fold more of each macrophage phenotype through because the Sum constriction is far less severe than the 3 um. The plotted flux of macrophages is therefore 5.4-fold higher for this larger pore, whereas the much larger 8 um pore does not greatly increase this flux, so that 3 um pores are by far the most restrictive.

FIG. 3A shows an in vivo growth curve of subcutaneous tdTomato A549 tumors. Tumor growth was measured by projected tumor area. Tumors were approximately 70 mm$^2$ in size at the start of treatment. Male mice were treated with 10 million NSG mouse donor marrow cells that were SIRPA blocked and FCY receptor pre-loaded with targeting Ab or pre-immune antibody ex-vivo then tail vein injected back into mice. Donor injection was given on day 0 with no systemic antibody treatment. On treatment day 3, biweekly systemic injection of antibody. Male mice were divided into the following treatment groups: untreated n=6, pre-immune n=2, anti-MUC1 n=3, Cetuximab n=3, and anti-hum n=6 (this is a representative sample as we have treated 16 additional tumors with A'PB macrophages) mean±SEM. FIG. 3B shows an in vivo growth curve of subcutaneous WT tdTomato A549 tumors. Tumor growth was measured by projected tumor area. Tumors were approximately 70 mm$^2$ in size at the start of treatment. Treatment day 0-10 mice were injected with 10 million marrow donor cells with biweekly anti-hum injection. On day 10, a mixture of male and female mice received a second treatment donor cells, but with SIRPA block. Treatment groups were untreated n=2, donor+pre-immune n=4, and donor+anti-hum n=4 (mean±SEM). FIG. 3C, left panel, shows treatment of mosaic tumors with a ratio of 2 WT:1 CD47 tumor cell with 600 μg anti-human twice a week. Dashed lines are corresponding linear fits with $R^2$>0.97. Dashed line is fit of average of final three points each of which are insignificant from day 15. (*$P<0.05$, compared to previous data point, within a treatment arm. (GFP WT/shCtl, KD$^{++}$, and Mosaic-antibody: n=2 mice, 4 tumors; CD47 KD$^+$: n=2 mice, 4 tumors; Mosaic+antibody: n=4 mice, 8 tumors. mean±SEM). FIG. 3C, right panel, shows the ratio of GFP$^-$:GFP$^+$ as determined by flow cytometry following removal of tumors from sacrificed mice. (Xenograft d0: n=9, 3 independent experiments done in triplicate; Untreated: n=4 tumors; Ab Treated: n=8 tumors. mean±SEM). Xenograft d0 was measured using cells reserved during xenotransplantation and subsequently measured by flow cytometry. FIG. 3D shows an in vivo growth curve of CD47 KD$^+$"deep knockdown" measured by cross-section tumor area. Treatment started when tumors reached 70 mm$^2$ in size. Male mice were split into four groups: untreated n=2 tumors, pre-immune n=2, ant-hum F(ab')2 n=2, and anti-hum n=2 mean±SEM. FIG. 3D, inset, is a bar graph of anti-hum and anti-hum F(ab'2) A549 binding Kd. Using a variety of concentrations and flow cytometry to analyze antibody binding, the Kd of anti-hum (n=3) and anti-hum F(ab')2 (n=3) was determined to be the same. Secondary antibody only was used as a control Kd. FIG. 3E—left panel shows an in vivo growth curve of CD47 KD$^+$"deep knockdown" during 2 periods of no treatment. (WT/shCtl: n=4 mice, 8 tumors; CD47 KD$^+$: n=6 mice, 12 tumors. mean±SEM). Slope of linear fit=1.02 mm$^2$/day corresponding to tumor growth rate ($R^2$=0.99). FIG. 3E, inset, shows representative fluorescent overlays of untreated (left) and Ab treated (right) mice at the end of the treatment period. FIG. 3E—right panel shows tumor response to 200 and 600 μg anti-human/mouse followed by removal of antibody and subsequent re-administration. (WT/shCtl antibody, CD47 KD$^+$–antibody: n=2 mice, 4 tumors; CD47 KD$^+$+antibody: n=4 mice, 8 tumors. mean±SEM). FIG. 3F shows in vivo measured growth of subcutaneous tdTomato A549 tumors in male mice. Correlation of measuring tumors using calipers (cross sectional area) or by tdTomato intensity over a 30 day period. Male n=4 mean±SEM in X and Y.

Phenotype difference of phagocytic and non-phagocytic cells was attributed to SIRPA expression. FIG. 4A shows tdTomato A549 depletion from tumors as a function of cumulative phagocytosis by macrophages after two treatments of donor cells. Recipient no antibody n=2 and donor+ anti-hum, APB MO, and A'PB MO n=4 (mean±SEM in X and Y). FIG. 4A, inset, shows representative flow cytometry plots of tdTomato A549 abundance in untreated tumors (left plot) and treated tumor (right plot). FIG. 4B shows correlating tumor shrinkage measured by cross-sectional tumor area to cumulative phagocytosis in donor and recipient macrophages. Every condition has an n=4, except for untreated tumors which has n=2. Shown is mean±SEM, in X and Y. FIG. 4C is an illustration comparing macrophages that have been found to be non-phagocytic in this study to macrophages that were found to be phagocytic. FIG. 4D shows Euclidian clustering analysis of RNA sequencing data generated from extracting RNA from macrophage from different tissues and further separating tumor macrophage by whether they were tdTomato positive or negative. Macrophages were isolated from 4 different NSG mice and each sample had >8M reads. FIG. 4E shows quantification of RNA expression of Sirpa and Cd47 taken from RNA data generated in FIG. 4B. Quantification was done by taking mRNA expression of Sirpa (which was the sum of 2 variants) and Cd47 (1 variant) and normalizing to the number of total mouse reads in each macrophage sample. Samples taken from the tumor have n=2, whereas spleen and marrow have n=1 and n=3 respectively. FIG. 4F shows quantification of Sirpa and Cd47 protein expression in macrophages pulled from 2 mice to verify mRNA expression. Displayed are representative histograms of fluorescent intensities from proteins expressed in macrophages isolated from the tumor, marrow, and spleen. FIG. 4G shows Sirpa: Cd47 ratios also increases in macrophages with increasing microenvironment stiffness. FIG. 4H shows an in vitro experiment using PMA differentiating THP-1s on different matrix stiffness, (soft-marrow and stiff-tumor). After 7 days of culturing, THP-1 were fixed and stained for LAMIN-B, and SIRPA. Fluorescent intensity for each protein was normalized to the soft condition. LAMIN-B remained unchanged while SIRPA significantly increased P<0.05. For all conditions n=3 and displayed is mean±SEM.

FIG. 5A is a normalized in vivo growth curve of tdTomato A549 subcutaneous and intraperitoneal tumors. Growth of tumors was monitored by tdTomato fluorescent intensity. Tumors grew at a similar rate for 30 days then were treated with NSG A'PB MO. All tumors shrank comparably until days 9-13 when shrinkage plateaus. Mean±SEM, n=3 for all conditions, but untreated IP and sub n=6. FIG. 5A, inset, shows fluorescent images of tdTomato signal from IP tumors comparing tumor intensities of treatment day 0 to day 13. FIG. 5B shows on Day 13, all tumors were removed and analyzed by flow cytometry. TdTomato A549 cells remaining in the tumors were identified by forward scatter (size) and tdTomato intensity with CD11b+ F4/80+ cells being gated out. Tumors treated with A'PB MO all showed decreased A549 populations in proportion to measured florescent intensity. FIG. 5C is an in vivo growth curve of tdTomato A549 tumor measured by cross sectional tumor area. Tumors grew for 70 days to approximately 70 mm$^2$ before starting treatment. Male and female mice were split into 3 treatment groups on treatment day 0: APB macrophage n=8, APB macrophage treatment with pre-immune n=4, and untreated n=8; mean±SEM. Mice were given biweekly antibody treatment and donor marrow on day 0, 14, and 35. Mice in pre-immune treatment group were switched to full treatment group on day 14 due to tumor burden. Approximately 10 million donor marrow cells were injected per mouse. FIG. 5C, inset, shows tumor imaging on treatment day 28 after two full donor marrow treatment cycles. Red regions are tdTomato signal acquired from tumors. Left two mice were treated with APB macrophage and right two mice were untreated. Treatment of tdTomato A549 subcutaneous that grew for 60 days with engineered human marrow. FIG. 5D is an in vivo growth curve measure by tdTomato intensity of 16 mice each with two tumors (one on each flank). Mice treated with human marrow+anti-hum all shrank, but SIRPA blocking further increased rate of shrinkage. Mice that received human marrow SIRPA block+ nonspecific antibody all continued to grow similar to untreated. Human+anti-hum n=2, hAPB n=4, hA'PB n=4, human+pre-immune n=2, APB+pre-immune n=2, and untreated n=2 (mean±SEM). FIG. 5D, inset, shows representative tdTomato images of treated and untreated mice on day 52 of treatment. Mice are arranged by treatment effectiveness with hA'PB>hAPB>hdonor>ctrl. FIG. 5E shows blood profiles of all 16 mice before and after treatment. Gray area shows the pretreatment and untreated variance in blood profiles (normal range). All treated mice remain in the normal during the 60 days of multiple engineered human donor treatment.

FIG. 7 is a table showing donor macrophage mRNA contains an abundance of human RNA and expresses high levels of RNA encoding for matrix proteins. RNA isolated from FIG. 4B was realigned to human sequences. top row: comparison of the total number of reads from each sample between mouse and human alignments; MO markers: protein markers used to identify macrophages have low human alignment and high mouse alignment; epithelial makers: only macrophages in the tumor have high mRNA reads for human E-cadherin and keratin with donor MO having the highest; matrix to nucleus pathway: donor MO have a significant amount of mRNA that aligns to mouse matrix mRNA compared to non-tumor macrophages and even TAMs.

FIG. 8 is a table showing profiles of human marrow donors. Human marrow used was isolated from 4 different donors with very different profiles to ensure that donor to donor variations have no effect on treatment outcome.

FIGS. 9A-9B show binding curves for anti-hum against hRBC, A549, EC4s, and IPS-MSC of different passage number. Each point is n=3, with 10,000 cells for each (n). FIG. 9C shows flow cytometry of 67 nM Ab binding to MEG-01 cells. Fitting parameters indicate that when B is similar for mRBC and hRBC K for mRBC>>hRBC indicating weak affinity to mRBC. Mixing human and mouse RBCs did not affect binding to either species. Model: Y=A+B*X/(K+X); hRBC: A=80, B=35524, K=26.5 nM, R2=0.97; mRBC: A=80, B=14210, K=323427 nM, R2=0.22; MEG-01: A=80, B=262480, K=97 nM, $R^2$=0.99. FIG. 9D shows verification of anti-hum binding to A549 cells by immunofluorescence and Western blot. Immunofluorescence confirms anti-human antibody binding to A549 in vitro compared to secondary antibody only control (scale bar=10 μm). Images have been adjusted to allow visualization of cells in control image. Bar graph below the images reflects true fluorescence of each unaltered image. The blot shows three main bands with several lower intensity bands which anti-hum binds to. Shown are possible surface proteins identified by mass spectrometry that correspond to the molecular weight from the 3 most intense bands. FIG. 9E illustrates affinity of anti-SIRPα for NSG macrophages. Data was fit using saturation a binding model (All cells: $R^2$=0.73, Kd=50 ng; Viable cells: $R^2$=0.78, Kd=72 ng). In vitro phagocytosis assay using phorbol myristate acetate (PMA) treated human monocytes (THP-1) cell line and a human lung carcinoma cell line (A549, WT and CD47 KD). FIGS. 9F-9G show binding of systemically injected anti-humMUC1 and Cetuximab antibody (IV.) into NSG mice bearing 8 week old tdTomato A549 tumors. Antibody was allowed to circulate for 3 hrs. The mouse was then sacrificed, tumors were isolated, disaggregated, and split in two. One sample was stained for targeting antibody and the other was directly incubated with anti-MUC1 or Cetuximab (ex vivo) to ensure specific binding and to test non-specific binding. After direct incubation, samples were then stained for targeting antibodies. FIG. 9H shows normalized NSG TAM binding data from subcutaneous and intraperitoneal tdTomato A549 tumors of anti-MUC1 and Cetuximab. 10 ug of each antibody was systemically injected and 3 hrs. later the mouse was sacrificed, tumor tissue stained, and analyzed by flow cytometry.

FIG. 10A is a schematic of the method used to analyze disaggregated tumor tissue. Following dissociation and antibody staining, samples were analyzed using flow cytometry. FIG. 10B is a series of flow cytometry dot plots showing the gating strategy used to identify and analyze macrophage eating and abundance in tissues. FIG. 10C shows quantification of phagocytic cells from donor bone marrow and recipient tumor and spleen in CD47 $KD^{++}$ xenografts. Donor $CFDA^+$ and recipient $CFDA^+$ counts are relative to total $CD11b^+$ cells (left y-axis) while recipient $CFDA^+$ counts are relative to only $CFDA+CD11b^+$ cells (right y-axis) (n=2 tumors, 1 spleen, mean±SEM). Three days after injection of APB engineered NSG mouse marrow, subcutaneous WT A549 tumor were harvest and analyzed by flow cytometry for neutrophils. The lower bar graph of FIG. 10C shows the abundance of neutrophils in the tumor per 100k cells screened. Despite the moderate level of neutrophil eating (30%), the small number of neutrophils in the tumor make them an ineffective anti-tumor effector cell type. Recipient has the opposite problem, high number of neutrophils in the tumor, but they are non-phagocytic. FIG. 10D shows the immune cell makeup of engineered NSG mouse marrow cells before injections into tumor bearing mice. Together macrophages, monocytes, and neutrophils consist of 65% of the marrow injected (n=2 for all conditions mean±SEM). FIG. 10E shows representative histograms of flow data from CFDA stained and SIRPA blocked engineered NSG mouse marrow cells. FIG. 10F is an in vivo growth curve of subcutaneous WT tdTomato A549 tumors. Tumor growth was measured by tdTomato intensity. Tumors were approximately 70 $mm^2$ in size at the start of treatment. Male mice were treated with 10 million NSG mouse donor marrow cells that were SIRPA blocked and FCY receptor pre-loaded with anti-hum or pre-immune antibody ex-vivo then tail vein injected back into mice. Donor injection was giving on day 0 with no systemic antibody treatment. On treatment day 3, biweekly systemic injection of antibody. Male mice were divided into the following treatment groups: untreated n=6, pre-immune n=2, and anti-hum n=6 (this is a representative sample as we have treated 16 additional tumors with A'PB macrophages) mean±SEM. FIG. 10G is an in vivo growth curve of subcutaneous WT tdTomato A549 tumors. Tumor growth was measured by tdTomato intensity. Tumors were approximately 70 $mm^2$ in size at the start of treatment. Treatment day 0-10 mice were injected with 10 million marrow donor cells with biweekly anti-hum injection. On day 10, a mixture of male and female mice received a second treatment of donor cells, but with SIRPA blocked. Treated groups were untreated n=2, donor+pre-immune n=4, and donor+anti-hum n=4 (mean±SEM). FIG. 10H shows fluorescent imaging of tdTomato CD47 knockdown A549 compared to tdTomato WT. FIG. 10I shows CD47 $KD^+$ cells further sorted to generate CD47 $KD^{++}$, an ultra-deep knockdown. Xenotransplants in NSG mouse flanks showed a slight growth advantage for CD47 $KD^{++}$ (linear fit slope=1.56 $mm^2$/day, $R^2$=0.99) compared to tumors comprised of WT GFP Scr (same as WT/shCtl) either in part or in whole (linear fit slope=1.02 $mm^2$/day, $R^2$=0.98). (WT GFP Scr: n=2 mice, 4 tumors; CD47 $KD^{++}$: n=2 mice, 4 tumors; Mosaic: n=6 mice, 12 tumors. mean±SEM). FIG. 10I, inset, shows flow cytometry of cells used in xenotransplants.

FIG. 11A shows Ab binding of various tissue types by anti-human for CD47 $KD^+$ study. Value represents the fraction of a given tissue type that is $Ab^+$ per tissue. (n>10 tumors/spleens per group. mean±SEM). FIG. 11B shows Ab binding of various tissue types by anti-human for the Mosaic Tumor study. Value represents the fraction of a given tissue type that is $Ab^+$ per tissue. (n>4 tumors, n>2 spleens per group, mean±SEM). FIG. 11C shows representative flow cytometry scatter plots of $CD11b^+$ F4/80hi populations depicting Ab binding (x-axis) and phagocytosis (y-axis, $tdTomato^+$) for untreated (left) and Ab treated (right) tumor samples. FIG. 11D shows normalized SIRPA block between injections day 0 and day 3 when tumors are isolated. Approximately 53% of SIRPA blocking remained on macrophages on day 3 (n=2, mean±SEM). FIG. 11E, left panel, shows breakdown of mature macrophage populations as the % of total mature macrophages either $tdTomato^+$ (left) or $tdTomato^-$ (right) for CD47 $KD^+$ study animals (n>5 tumors/spleens per group, mean±SEM). FIG. 11E, right panel shows breakdown of macrophage populations as the % of total mature macrophages either $tdTomato^+$ (left) or $tdTomato^-$ (right) for Mosaic Tumor study animals (n>4 tumors/spleens per group, mean±SEM). FIG. 11F shows efficiency of CFDA labeling of $CD11b^+$ cells from donor marrow and day 3 biodistribution in CD47 $KD^{++}$ tumor or WT tumor recipient (CD47 $KD^{++}$ or WT Scr+anti-SIRPα: n=2 tumors, 1 spleen, blood, marrow, mean±SEM; WT Scr: n=6 tumors, 3 spleens, blood, marrow, mean±SEM; *P<0.005). FIG. 11G shows quantification of F4/80hi (mature) and F4/80lc (immature) macrophages from donor bone marrow and recipient tumor and spleen (CD47 $KD^{++}$ or WT Scr+anti-SIRPα: n=2 tumors, 1 spleen, mean±SEM; WT Scr: n=6 tumors, 3 spleens, mean±SEM; * significant between donor and recipient, # significant from WT Scr-anti-SIRPα, $ significant from CD47 $KD^{++}$, P<0.05).

FIG. 13A shows data mining published macrophage mRNA sequences for Lamin-A and Lamin-B shows that Lamin-A:Lamin-B ratios increase in macrophages with increasing stiffness of resident tissue and flows a linear trend on a log-log scale ($R2=0.95$). Lamin-A:Lamin-B RNA sequence data from macrophages data from FIG. 4B shows the same trend as published data. FIG. 13B shows an in vitro experiment using PMA differentiating THP-1s on different matrix stiffness, (soft-marrow and stiff-tumor). After 7 days of culturing, THP-1 were fixed and stained for LAMIN¬A, LAMIN-B, and SIRPA. Fluorescent intensity for each protein was normalized to the soft condition. LAMIN-B remained unchanged, but LAMIN-A and SIRPA significantly increased $P<0.05$. For all conditions n=3 and displayed is mean±SEM. FIG. 13C shows THP-1 phagocytosis of WT and CD47 KD A549 measured by counting the number tdTomato A549 cells per THP-1 and normalizing to control (cells only) under different eating condition. For all condition n>3 mean±SEM. FIG. 13D shows THP-1 phagocytosis of A549 measured by counting the number A549 cells per THP-1 and normalizing to control (cells only) under different eating condition: cells only, anti-hSIRPA, anti-hum, anti-hSIRPA+anti-hum, or anti-hCD47+anti-hum with n=4, 5, 4, 4, and 5 respectively showing mean±SEM. FIG. 13D, inset, is an image of a positive eating event with CD11b stain in green showing THP-1 and tdTomato fluorescence indicating A549 cancer cell. FIG. 13E shows quantification of internalized tdTomato fluorescent intensity of THP-1s and normalizing to tdTomato intensity from uneaten A549 cells. Quantification was done from the samples taken from FIG. 1A. (Cells only n=4, anti-hum n=5, anti hSIRPA n=4, anti-hum+anti-hSIRPA n=4, anti-hum+anti-hCD47 n=5; mean±SEM). FIG. 13F shows an in vitro phagocytosis assay using PMA treated THP-is and human red blood cells. KD of SIRPA in THP-is resulted in 2.2 fold increase in eating of anti-hum opsonized RBCs over WT THP-1s, n=2 mean±SEM.

FIG. 14A shows weight throughout the duration of the study (including pre-treatment, treatment, and post-treatment). Weight is normalized to weight at date of xenograft implantation. Mice used in Mosaic Study. (WT GFP/shCtl: n=2 mice; CD47 KD$^{++}$: n=2 mice; Mosaic: n=2 mice; Mosaic+Ab: n=4 mice). GFP WT/shCtl, Mosaic, Mosaic+Ab are grouped together and the green solid line reflects the linear fit. CD47 KD$^{++}$ mice show slightly different weight responses as shown by the black solid line. Addition of antibody shows a slight decrease in hematocrit, but no change in thrombocrit. (n>2 per group. mean±SEM). I.V. injection of anti-hum antibody shows no specific binding to mouse RBC or platelets in vivo. (n>2 per group. mean±SEM). FIG. 14B is an in vivo growth curve of CD47 KD tdTomato A549 tumors. Growth was measured by tdTomato fluorescent intensity. Tumor grew for 8 wks before treatment with human marrow. SIRPA blocking didn't significantly increase anti-tumor effect in CD47 KD tumors (n=2 for all condition). FIG. 14C shows quantification of CD14$^+$ CD33$^+$ CD66b$^-$ human macrophages eating in CD47 KD A549 tumors. Three days after injection tumors were harvested and human macrophages were analyzed by flow cytometry. Macrophages±SIRPA block had the same eating percentage, 95% (n=2). FIG. 14D shows SIRPA blocked human macrophages had on averaged engulfed 3.5 tdTomato A549 tumor cells where donor only was 2.2 (n=2). FIG. 14E shows quantification of the number of human macrophages per 100k cells screened on the flow cytometer (n=2 for all conditions). FIG. 14F shows a calculation of the cumulative phagocytosis index using data from FIG. S7C-E. The human APB MO indexes are comparable to indexes from NSG APB MO from FIGS. 4A and 4B. FIG. 14G is an in vivo growth curve of tdTomato A549 tumors. Growth was measured by cross sectional tumor area. Tumor grew for 8 wks before treatment with NSG marrow plus anti-hum at day 0 then (n=2 for all condition). FIG. 14H shows blood profiles taken from male mice treated with APB macrophages n=2, female mice treated with APB macrophage n=1, and a male mouse treated with A'PB macrophages n=1 (mean±SEM) before and after treatment. Parameters were normalized to day 4 of pre-treated.

FIG. 15 is a table showing relative IgG supplementation. Calculated estimate of the IgG percent in immunocompetent mouse strains. Calculation assumes a 30 g mouse and 0.6 mg Ab injection. % of IgG is calculated as 0.6 mg injected Ab/total mg IgG*100%. This value provides a magnitude of the Ab dosage for comparison with what is present in immuncompetent animals. Also as a comparison, a typical 300 µg dose of Rhogam represents 0.0006% of total human IgG.

FIG. 16 is a table showing CD47 cell surface density. In vitro (cells used for xenotransplant) and in vivo (cells recovered from excised tumors) CD47 surface density determined by flow cytometry and immunofluorescence. A549 cell area was determined by measuring area of well spread cells imaged by immunofluorescence. This value was multiplied by two assuming negligible height for well spread cells. We acknowledge that this method underestimates cell area and calculated values for CD47/µ2 are thus likely overestimates. CD47 intensity was determined by flow cytometry mean fluorescence intensity and normalized to human red blood cells. Arrows indicate IgG treatment responsive cells. We previously reported a CD47 surface density value for hRBCs. Multiplying this value by the normalized CD47 intensity and scaling by the ratio of A549 area to hRBC area previously reported, results in the values presented in the table.

FIG. 17A: In vivo growth curve of CD47 KD+"deep knockdown" during 2 periods of no treatment. (WT Scr: n=4 mice, 8 tumors (WT=wildtype); CD47 KD+ (KD=knockdown): n=6 mice, 12 tumors. mean±SEM). The slope of linear fit=1.02 mm$^2$/day corresponds to tumor growth rate (R2=0.99). FIG. 17A, inset image: Representative fluorescent overlays of untreated (left panel) and antibody (Ab) treated (right panel) mice at the end of the treatment period. FIG. 17B: Tumor response to 200 and 600 g anti-hRBC/mouse followed by removal of antibody and subsequent readministration. (WT Scr antibody, CD47 KD+–antibody: n=2 mice, 4 tumors; CD47 KD++antibody: n=4 mice, 8 tumors. mean±SEM). FIG. 17C: Immunofluorescence confirms anti-hRBC antibody binding (left) to A549 in vitro compared to secondary antibody only control (right) (scale bar=10 m). Images have been adjusted to allow visualization of cells in control image. Bar graph below the images reflects true fluorescence of each unaltered image.

FIG. 17D: CD47 KD+ cells were further sorted to generate CD47 KD++, an ultra-deep knockdown. Xenotransplants in NSG mouse flanks show a slight growth advantage for CD47 KD++(linear fit slope=1.56 mm$^2$/day, R2=0.99) compared to tumors comprised of WT GFP Scr either in part or in whole (linear fit slope=1.02 mm$^2$/day, R2=0.98). (WT GFP Scr: n=2 mice, 4 tumors; CD47 KD++: n=2 mice, 4 tumors; Mosaic: n=6 mice, 12 tumors. mean±SEM). FIG. 17D, inset graph: Flow cytometry of cells used in xenotransplants. (gray=isotype; black=CD47 KD++; green dashed outline=WT GFP Scr; green fill=Mosaic) FIG. 17E: Treatment of tumors shown in FIG. 17A with 600 g anti-hRBC/mouse twice a week. Solid lines are corresponding linear fits with R2>0.97. Dashed line is fit of average of final three points each of which are insignificant from day 15. (*P<0.05, compared to previous data point, within a treatment arm. (WT GFP Scr, KD++, and Mosaic –antibody: n=2 mice, 4 tumors; CD47 KD+: n=2 mice, 4 tumors; Mosaic+antibody: n=4 mice, 8 tumors. mean±SEM). FIG. 17F: Ratio of GFP–:GFP+ as determined by flow cytometry following removal of tumors from sacrificed mice. (Xenograft d0: n=9, 3 independent experiments done in triplicate; Untreated: n=4 tumors; Ab Treated: n=8 tumors. mean±SEM). Xenograft d0 was measured using cells reserved during xenotransplantation and subsequently measured by flow cytometry.

FIG. 18A: Treatment with Ab is efficacious only for CD47 knockdown tumors (similar to FIGS. 17A-17F), but paclitaxel loaded polymer worms (TW) shrink tumors regardless of CD47 expression level. Combining Ab, chemotherapy, and CD47 knockdown shows a slight enhancement in tumor responsiveness. Mice were treated 2 times per week (n=2 tumors per treatment arm. mean±SEM). FIG. 18B: Quantification of in vitro cytotoxicity of paclitaxel loaded polymer worms against wild-type (WT) and knockdown (KD) A549 cells. Data fit with the following equation: CV %=A+B/(1+10((log(conc)–log(IC50)))). Fits summarized in FIG. 26A. (n=4 independent experiments, mean±SEM). FIG. 18C: Addition of taxol to the treatment shows a slight decrease in hematocrit and a more significant increase in thrombocrit (n=2 per group. mean±SEM). FIG. 18D: Taxol does not significantly effect opsonization of anucleated peripheral blood cells (n=2 per group. mean±SEM). FIG. 18E: Addition of Taxol to Ab treatment results in a slight reduction in CD11b+ leukocytes (n=2 per group. mean±SEM).

FIG. 19A: Schematic of method used to assess tumor tissue. Tumors are removed and when possible the periphery and core are prepared separately. Following dissociation and antibody incubation, samples are analyzed using flow cytometry. FIG. 19B: Relative CD47 expression (normalized by human RBC, average of at least triplicate) of various tumor types and specific location for CD47 KD+ study. (n=8 tumors per group. mean±SEM). FIG. 19C: Relative CD47 expression, as in B, for specific populations as resolved by WT GFP Scr GFP expression (n=4 per group. mean±SEM). FIG. 19D: Ab binding of various tissue types by anti-hRBC for CD47 KD+ study. Value represents the fraction of a given tissue type that is Ab+ per tissue. (n=10 tumors/spleens per group. mean±SEM). FIG. 19E: Ab binding of various tissue types by anti-hRBC for Mosaic Tumor study. Value represents the fraction of a given tissue type that is Ab+ per tissue. (n=4 tumors, n=2 spleens per group. mean±SEM). FIG. 19F: Quantification of both mature and immature macrophages as represented as the % of total nonhuman cells for the CD47 KD+ and Mosaic Study (left) and Taxol study (right) (*P<0.05).

FIG. 20A: Representative flow cytometry scatter plots of CD11b+F4/80hi populations depicting Ab binding (x-axis) and phagocytosis (y-axis, tdTomato+) for untreated (left) and Ab treated (right) tumor samples. FIG. 20B: Breakdown of mature macrophage populations as the % of total mature macrophages either tdTomato+(left) or tdTomato–(right) for CD47 KD+ study animals (n=5 tumors/spleens per group. mean±SEM). FIG. 20C: Breakdown of mature macrophage populations as the % of total mature macrophages either tdTomato+(left) or tdTomato–(right) for Mosaic Tumor study animals (n=4 tumors/spleens per group. mean±SEM). FIG. 20D: Breakdown of mature macrophage populations as the % of total mature macrophages either tdTomato+(left) or tdTomato–(right) for Taxol study animals (n=4 tumors/spleens per group. mean±SEM).

FIG. 21A: Schematic of NSG bone marrow harvest, labeling, and transfusion. Harvested bone marrow cells from donor femur and tibia were labeled with CFDA, when applicable incubated with anti-mSIRPα, and injected into Ab treated tumor-bearing recipient NSG mouse. Recipient mice were given an Ab booster on day 3 and subsequently sacrificed ~2 hours later. Bone marrow, peripheral blood, spleen, and tumor tissue was harvested after and analyzed for donor cells by flow cytometry. Inset, Quantification of tdTomato intensity in CD11b+F4/80hi macrophages normalized by bare tumor cells. Ratios not significant from 100% indicating ~1 tumor cell/macrophage (CD47 KD++ or WT Scr+anti-SIRPα: n=2; WT Scr: n=6). FIG. 21B: Efficiency of CFDA labeling of CD11b+ cells from donor marrow and day 3 biodistribution in CD47 KD++ tumor or WT CD47 tumor recipient (CD47 KD++ or WT Scr+anti-SIRPα: n=2 tumors, 1 spleen, blood, marrow, mean±SEM; WT Scr: n=6 tumors, 3 spleens, blood, marrow, mean±SEM; *P<0.005). FIG. 21C: Quantification of F4/80hi (mature) and F4/80lo (immature) macrophages from donor bone marrow and recipient tumor and spleen (CD47 KD++ or WT Scr+anti-SIRPα: n=2 tumors, 1 spleen, mean±SEM; WT Scr: n=6 tumors, 3 spleens, mean±SEM; * significant between donor and recipient, # significant from WT Scr–anti-SIRPα, $ significant from CD47 KD++, P<0.05). FIG. 21D: Phagocytosis of WT Scr tdTomato+ or CD47 KD++ tumor cells SIRPα blocking of donor cells (CD47 KD++ or WT Scr+anti-SIRPα: n=2 tumors, 1 spleen, blood, marrow, mean±SEM; WT Scr: n=6 tumors, 3 spleens, blood, marrow, mean±SEM; * significant between donor and recipient, # significant from WT Scr–anti-SIRPα, $ significant from CD47 KD++, P<0.05). FIG. 21E: Cartoon of macrophage influx/efflux into/out of tumor tissue and phagocytosis of tdTomato+ tumor cells.

FIG. 24A: Quantification (left) of immunofluorescence (right) of WT Scr and CD47 KD tdTomato cells (n=40 cells per group. Scale bar=10 µm). FIG. 24B: In vivo growth curves of tdTomato xenografts in NSG flank (n=2 mice, 4 tumors for all tumor types, mean±SEM). FIG. 24C: Treatment of CD47 KD tumors from FIG. 24A with polyclonal anti-human IgG antibody (Treated: n=2 mice, 4 tumors; Untreated: n=3 mice, 6 tumors, *P<0.05 within a cohort compared to the previous day, mean±SEM). FIG. 24D: Western blot of A549 cells for pluripotency markers Oct4 and Sox2.

FIG. 25A: Weight throughout duration of study (including pre-treatment, treatment, and post-treatment). Weight is normalized to weight at date of xenograft implantation. Mice used in Mosaic Study (WT GFP Scr: n=2 mice; CD47 KD++: n=2 mice; Mosaic: n=2 mice; Mosaic+Ab: n=4 mice). WT GFP Scr, Mosaic, Mosaic+Ab are grouped together and the green solid line reflects the linear fit. CD47 KD++ mice show slightly different weight responses as shown by the black solid line. FIG. 25B: Addition of antibody shows a slight decrease in hematocrit, but no change in thrombocrit. (n=2 per group. mean±SEM). FIG. 25C Minimal opsonization of annucleated peripheral blood cells (n=2 per group. mean±SEM).

FIG. 26A: Flow cytometry (gray=isotype control; black=MEG-01) of 67 nM Ab binding to MEG-01 cells. FIG. 26B: Binding curve for Ab to human RBC (hRBC), mouse RBC (mRBC) and MEG-01 (a human megakaryocytic cell line). Fitting parameters indicate that when B is similar for mRBC and hRBC K for mRBC>>hRBC indicating weak affinity to mRBC. Mixing human and mouse RBCs did not affect binding to either species. Model: $Y=A+B*X/(K+X)$; hRBC: $A=80$, $B=35524$, $K=26.5$ nM, $R2=0.97$; mRBC: $A=80$, $B=14210$, $K=323427$ nM, $R2=0.22$; MEG-01: $A=80$, $B=262480$, $K=97$ nM, $R2=0.99$. FIG. 26C: Quantification of CD47 following sorting to establish CD47 KD+. FIG. 26D: Relative average intensity of opsonization by anti-human RBC antibody for various cell types and location (tumor, peripheral blood, and spleen). Intensity normalized to MEG-01 calibration (n>11 per group, mean±SEM). FIG. 26E: Scatter plot of individual CD47 KD+ treated tumors. (n=4 mice, 8 tumors). FIG. 26F: Weight throughout treatment period. Weight is normalized to weight at date of treatment initiation. Mice used in CD47 KD+ study.

FIG. 27A: Fitting parameters from in vitro cytotoxicity assay. FIG. 27B: Summary of taxol doses delivered. FIG. 27C: Monitoring of animal weight during co-therapy does not show any significant weight loss. Weight normalized to weight at initiation of co-therapy. FIG. 27D: Individual tumor response presented in FIG. 19A. FIG. 27E: Relative CD47 expression, normalized by human RBC, for Taxol Study tumors (n=2 per group. mean±SEM). FIG. 27F: Opsonization of various tissue types by Ab for Taxol study. Value represents the fraction of a given tissue type that is opsonized per tissue (n=4 tumors, n=2 spleens per group. mean±SEM).

FIG. 28A: Flow cytometry gating strategy used to analyze mature (CD11b+F4/80hi) and immature (CD11b+F4/80lo) macrophages. FIGS. 28B-28E: Macrophage subpopulation analysis for CD47 KD+ study. FIG. 28B: Percent mature macrophages relative to total mature macrophages in a given tissue/spleen. FIG. 28C: Percent mature macrophages relative to total murine cells in a given tissue/spleen. FIG. 28D: Percent immature macrophages relative to total number of immature macrophages in a given tissue/spleen. FIG. 28E: Percent mature macrophages relative to total murine cells in a given tissue/spleen (n=4 tumors/spleens per group. mean±SEM).

FIG. 29A: Scatter plot of individual tumors presented in FIG. 17B. (WT GFP Scr: n=2 mice, 4 tumors; CD47 KD++: n=2 mice, 4 tumors; Mosaic: n=6 mice, 12 tumors). FIG. 29B: Flow cytometry of cells 1 day after xenograft implantation. CD47 intensity is normalized to human RBC. (n=3 for all groups. mean±SEM). FIG. 29C-29F: Macrophage subpopulation analysis of tumors shown in FIGS. 17C, 17D. FIG. 29C: Percent immature macrophages relative to total murine cells in a given tissue/spleen. FIG. 29D: % immature macrophages relative to total number of immature macrophages in a given tissue/spleen. FIG. 29E: Percent mature macrophages relative to total mature macrophages in a given tissue/spleen. FIG. 29F: Percent mature macrophages relative to total murine cells in a given tissue/spleen (n=4 tumors/spleens per group. mean±SEM).

FIG. 30A: Quantification of phagocytic cells from donor bone marrow and recipient tumor and spleen in CD47 KD++ xenografts. Donor CFDA+ and recipient CFDA− counts are relative to total CD11b+ cells (left y-axis) while recipient CFDA+counts are relative to only CFDA+CD11b+ cells (right y-axis) (n=2 tumors, 1 spleen, mean±SEM). FIGS. 30B-30E: Expanding on the quantification presented in FIG. 22D, phagocytosis of tdTomato+ cells was analyzed with the additional marker Gr-1. The additional marker allowed discernment between FIG. 30B: neutrophils, FIG. 30C: F4/80hi macrophages, FIG. 30D: F4/80lo macrophages, and FIG. 30E: myeloid derived suppressor cells (MΦSC) (n=2 tumors, mean±SEM, *P<0.05). FIG. 30F: Affinity of anti-SIRPα for NSG macrophages. Data fit using saturation a binding model (All cells: R2=0.73, Kd=50 ng; Viable cells: R2=0.78, Kd=72 ng).

FIGS. 31A-31B are graphs showing phagocytosis of lung cancer line, A549, was also enhanced when hSIRPA was blocked. FIG. 31C is a schematic showing a cell therapy approach for A549 solid tumors by blocking SIRPA on donor marrow cells in systemic injections. FIGS. 31D-31E are graphs and images showing large solid tumors shrink upon blocking SIRPA on donor marrow cells when Anti-human Ab is injected, and neither blood parameters nor body weight are significantly affected as tumors shrink.

FIG. 33A shows injection of human donor marrow and antibody does shrink tumors. FIG. 33B shows CD47KD A549 tumors treated with human donor marrow and antibody plus blocking SIRPA shrinks tumors effectively.

DETAILED DESCRIPTION OF THE INVENTION

Definitions

Figure 1A:
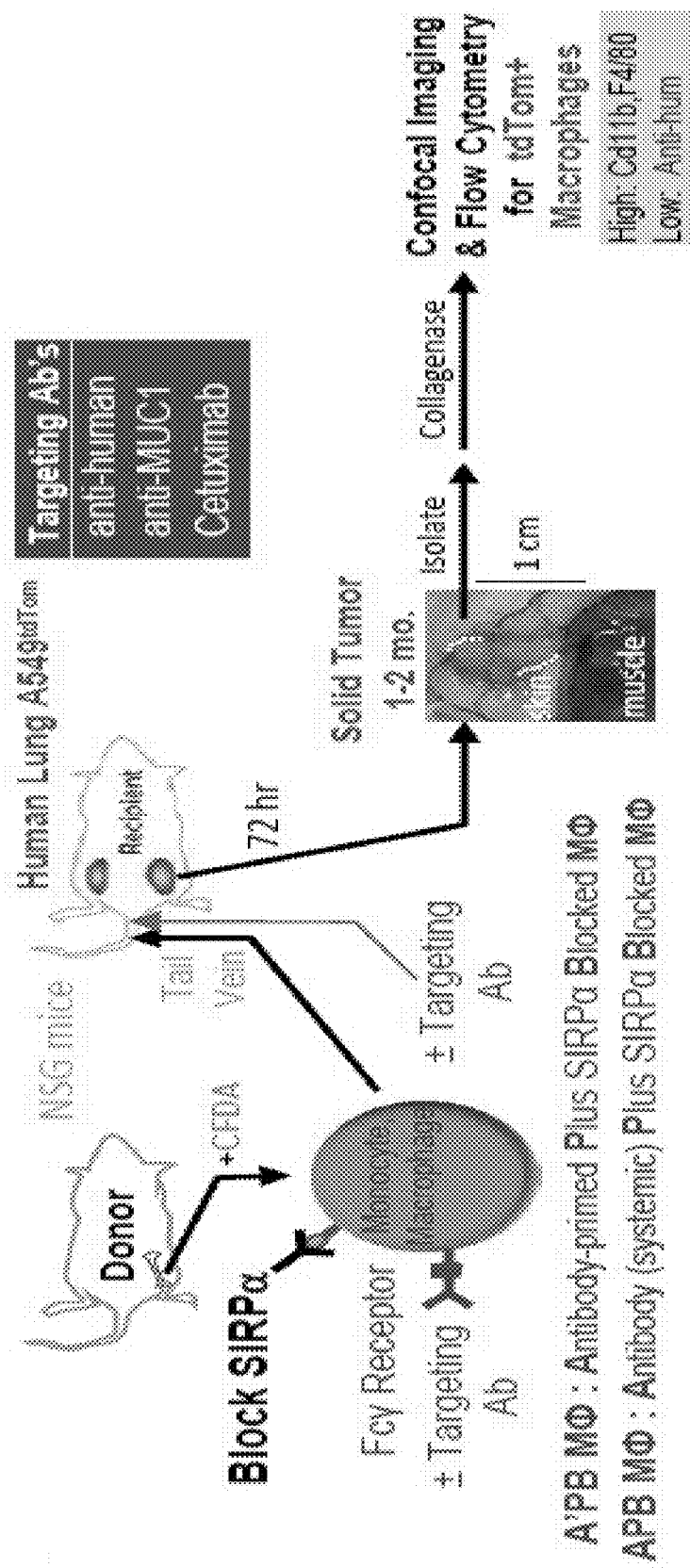
FIGS. 1A-1G are a series of graphs and images showing analysis of in vivo phagocytosis and tumor infiltration by engineered macrophages. Male mice with established tdTomato A549 tumors received NSG donor marrow injections along with systemic antibody injection. Three days later mice were given a boost injection of anti-hum and then 3 hours later mice were sacrificed and tumors were isolated.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section. It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods. Unless otherwise clear from context, all numerical values provided herein are modified by the term about.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies (scFv) and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

As used herein, to "alleviate" a disease, disorder or condition means reducing the severity of one or more symptoms of the disease, disorder or condition.

The terms "binding," "bind," "bound" refer to an interaction between two molecules. The interaction may include a covalent or non-covalent bond. The interaction may also be reversible or irreversible depending on the type of interaction, such as covalent bond formation.

As used herein, the term "C3b" is a fragment of complement protein 3, which when bound to glycoproteins on a cell surface, acts as an opsonin.

As used herein, the term "C4b" is an opsonin molecule formed from cleavage of complement component 4 protein.

The term "cancer" as used herein is defined as disease characterized by the rapid and uncontrolled growth of aberrant cells. Cancer cells can spread locally or through the bloodstream and lymphatic system to other parts of the body.

Examples of various cancers include but are not limited to, brain cancer, bladder cancer, breast cancer, cervical cancer, colorectal cancer, liver cancer, kidney cancer, lymphoma, leukemia, lung cancer, melanoma, metastatic melanoma, mesothelioma, neuroblastoma, ovarian cancer, prostate cancer, gastric cancer, pancreatic cancer, renal cancer, skin cancer, thymoma, sarcoma, non-Hodgkin's lymphoma, Hodgkin's lymphoma, uterine cancer, and the like.

By "CD47 antagonist" or "SIRPa antagonist" is meant a molecule that does not provoke a biological response. The CD47 or SIRPa antagonist can prevent or decrease ligand- or agonist-mediated CD47 and or SIRPa responses. The CD47 or SIRPa antagonist may have affinity for CD47 or SIRPa and bind either receptor where binding disrupts the interaction between CD47 and SIRPa, thereby inhibiting CD47 or SIRPa activation. Other CD47 or SIRPa antagonists may have affinity for CD47 or SIRPa ligands or agonists and compete with CD47 or SIRPa receptors to bind the ligands or agonists, thereby preventing or reducing the ability of a ligand or agonist to bind the receptor. Typically, these CD47 or SIRPa antagonists have a greater affinity or a lower dissociation constant for the CD47 or SIRPa ligands or agonists than the receptor.

The term "CRISPR/CAS," "clustered regularly interspaced short palindromic repeats system," or "CRISPR" refers to DNA loci containing short repetitions of base sequences. Each repetition is followed by short segments of spacer DNA from previous exposures to a virus. Bacteria and archaea have evolved adaptive immune defenses termed CRISPR-CRISPR-associated (Cas) systems that use short RNA to direct degradation of foreign nucleic acids. In bacteria, the CRISPR system provides acquired immunity against invading foreign DNA via RNA-guided DNA cleavage.

In the type II CRISPR/Cas system, short segments of foreign DNA, termed "spacers" are integrated within the CRISPR genomic loci and transcribed and processed into short CRISPR RNA (crRNA). These crRNAs anneal to trans-activating crRNAs (tracrRNAs) and direct sequence-specific cleavage and silencing of pathogenic DNA by Cas proteins. Recent work has shown that target recognition by the Cas9 protein requires a "seed" sequence within the crRNA and a conserved dinucleotide-containing protospacer adjacent motif (PAM) sequence upstream of the crRNA-binding region.

To direct Cas9 to cleave sequences of interest, crRNA-tracrRNA fusion transcripts, hereafter referred to as "guide RNAs" or "gRNAs" may be designed, from human U6 polymerase III promoter. CRISPR/CAS mediated genome editing and regulation, highlighted its transformative potential for basic science, cellular engineering and therapeutics.

The term "CRISPRi" refers to a CRISPR system for sequence specific gene repression or inhibition of gene expression, such as at the transcriptional level.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The terms "effective amount" or "therapeutically effective amount" are used interchangeably herein, and refer to an amount of a compound, formulation, material, or composition, as described herein effective to achieve a particular biological result. Such results may include, but are not limited to, the reduction in tumor size as determined by any means suitable in the art.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

As used herein, the term "fragment," as applied to a nucleic acid, refers to a subsequence of a larger nucleic acid. A "fragment" of a nucleic acid can be at least about 15 nucleotides in length; for example, at least about 50 nucleotides to about 100 nucleotides; at least about 100 to about 500 nucleotides, at least about 500 to about 1000 nucleotides; at least about 1000 nucleotides to about 1500 nucleotides; about 1500 nucleotides to about 2500 nucleotides; or about 2500 nucleotides (and any integer value in between).

As used herein, the term "fragment," as applied to a protein or peptide, refers to a subsequence of a larger protein or peptide. A "fragment" of a protein or peptide can be at least about 20 amino acids in length; for example, at least about 50 amino acids in length; at least about 100 amino acids in length; at least about 200 amino acids in length; at least about 300 amino acids in length; or at least about 400 amino acids in length (and any integer value in between).

As used herein, the terms "gene" and "recombinant gene" refer to nucleic acid molecules comprising an open reading frame encoding a polypeptide. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

The phrases "an immunologically effective amount", "an anti-immune response effective amount," "an immune response-inhibiting effective amount", or "therapeutic amount" refer to the amount of the composition of the present invention to be administered to a subject which amount is determined by a physician, optionally in consultation with a scientist, in consideration of individual differences in age, weight, immune response, type of disease/condition, and the health of the subject (patient) so that the desired result is obtained in the subject.

As used herein, an "instructional material" includes a publication, a recording, a diagram, or any other medium of expression that can be used to communicate the usefulness of the compositions and methods of the invention. The instructional material of the kit of the invention may, for example, be affixed to a container that contains the nucleic acid, peptide, and/or composition of the invention or be shipped together with a container that contains the nucleic acid, peptide, and/or composition. Alternatively, the instructional material may be shipped separately from the container with the intention that the instructional material and the compound be used cooperatively by the recipient.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified. "Purified" can also refer to a molecule separated after a bioconjugation technique from those molecules which were not efficiently conjugated.

By "macrophage" is meant a type of innate immune cell that phagocytose cellular material and act as an antigen presenting cell to other immune cells. Macrophages further stimulate and regulate inflammation by releasing cytokines.

By "monocyte" is meant a precursor to macrophage. Monocytes circulate in the bloodstream and differentiate into macrophages or dendritic cells when they infiltrate tissues.

An "isolated nucleic acid" refers to a nucleic acid segment or fragment that has been separated from sequences that flank it in a naturally occurring state, e.g., a DNA fragment that has been removed from the sequences that are normally adjacent to the fragment, e.g., the sequences adjacent to the fragment in a is genome that it naturally occurs. The term also applies to nucleic acids that have been substantially purified from other components that naturally accompany the nucleic acid, e.g., RNA or DNA or proteins, that naturally accompany it in the cell. The term therefore includes, for example, a recombinant DNA that is incorporated into a vector, into an autonomously replicating plasmid or virus, or into the genomic DNA of a prokaryote or eukaryote, or that exists as a separate molecule (e.g., as a cDNA or a genomic or cDNA fragment produced by PCR or restriction enzyme digestion) independent of other sequences. It also includes a recombinant DNA that is part of a hybrid gene encoding additional polypeptide sequence.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) that "U" replaces "T."

As used herein, an "opsonin" is a molecule that binds to the surface of a particle (e.g. antigen) to enhance the process of phagocytosis. In one aspect, an "opsonizing antibody" refers to an antibody that binds to the surface of a cell, coating the negatively charged molecules on the cell membrane, and enhancing the uptake of the cell by a phagocyte (e.g. macrophage). In another aspect, complement proteins or fragments thereof such as C3b and C4b can bind to cell surfaces and act as opsonins. The term "opsonization" refers to the process in which an opsonin binds to the surface of an antigen so that the antigen will be readily identified and engulfed by phagocytes for destruction.

The term "phagocyte" or "phagocytic cell" is used to refer to an immune cell that is capable of engulfing or ingesting harmful particles, bacteria, infected cells, dead or dying cells, and other cells targeted for phagocytosis. Phagocytic cells include, but are not limited to, macrophages, monocytes, mast cells, neutrophils, and dendritic cells. In one embodiment, the phagocyte is a macrophage or a monocyte. In another embodiment, the phagocyte is a bone marrow cell that differentiates into a mature macrophage.

The terms "phagocytosis" and "phagocytic activity" as used herein refer to the process of engulfing and ingesting particles or cells by an immune cell. The phagocytic cell engulfs or ingests the particle or cell by binding to the particle or cell coated with opsonins.

"Pharmaceutically acceptable" refers to those properties and/or substances that are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

As used herein, the term "pharmaceutical composition" or "pharmaceutically acceptable composition" refers to a mixture of at least one compound or molecule useful within the invention with a pharmaceutically acceptable carrier. The pharmaceutical composition facilitates administration of the compound or molecule to a patient. Multiple techniques of administering a compound or molecule exist in the art including, but not limited to, intravenous, oral, aerosol, parenteral, ophthalmic, pulmonary and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound or molecule useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound or molecule useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences that are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, that there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

A "constitutive" promoter is a nucleotide sequence that, when operably linked with a polynucleotide that encodes or specifies a gene product, causes the gene product to be produced in a cell under most or all physiological conditions of the cell.

An "inducible" promoter is a nucleotide sequence that, when operably linked with a polynucleotide that encodes or specifies a gene product, causes the gene product to be produced in a cell substantially only when an inducer that corresponds to the promoter is present in the cell.

A "tissue-specific" promoter is a nucleotide sequence that, when operably linked with a polynucleotide encodes or specified by a gene, causes the gene product to be produced in a cell substantially only if the cell is a cell of the tissue type corresponding to the promoter.

As used herein, the term "repressor" refers to a molecule or compound which eliminates, decreases, or suppresses the interaction of CD47 with SIRPa. The repressor can prevent or interfere with the interaction between the proteins by inhibiting expression or decreasing expression of one or both proteins, masking or hiding the binding site of one or both proteins, interfering with one or more functions of one or both proteins. Repressors can include, but are not limited to, anti-CD47 antibody, CD47-shRNA, CD47-siRNA, anti-SIRPa antibody, SIRPa-shRNA, SIRPa-siRNA, CD47 antagonists, SIRPa antagonists, anti-CD47-SIRPa antibody, a CRISPR system, and any combination thereof.

As used herein, the term "repressor of SIRPα" refers to a molecule or compound which eliminates, decreases, or suppresses the SIRPα expression, activity, and/or function. The repressor can prevent or interfere with SIRPα by inhibiting expression or decreasing expression of the protein, masking or hiding the binding site on SIRPα, and interfering with one or more functions of SIRPα. Repressors can include, but are not limited to, anti-SIRPα antibody, SIRPα-shRNA, SIRPα-siRNA, SIRPα antagonists, a CRISPR system, and any combination thereof.

As used herein, "sample" or "biological sample" refers to anything, which may contain the cells of interest (e.g., macrophages) for which the screening method or treatment is desired. The sample may be a biological sample, such as a biological fluid or a biological tissue. Such a sample may include diverse cells, proteins, and genetic material. Examples of biological tissues also include organs, tumors, lymph nodes, arteries and individual cell(s). Examples of biological fluids include urine, blood, plasma, serum, saliva, semen, stool, sputum, cerebral spinal fluid, tears, mucus, amniotic fluid or the like.

The terms "SIRPα," "SIRPA," "SIRPα" or "Sirpa" are meant to refer to signal regulatory protein-alpha (SIRPα). SIRPα, also tyrosine-protein phosphatase non-receptor type substrate 1 or CD172A, is a member of the SIRP family and belongs to the immunoglobulin superfamily. SIRPα is a receptor-type transmembrane glycoprotein known to be involved in the negative regulation of receptor tyrosine kinase-coupled signaling processes.

By "SIRPα antagonist" is meant a molecule that does not provoke a biological response. The SIRPα antagonist can prevent or decrease ligand- or agonist-mediated SIRPα responses. The SIRPα antagonist may have affinity for SIRPα and binds the receptor to disrupt the interaction between CD47 and SIRPα, thereby inhibiting SIRPα activation. Other SIRPα antagonists may have affinity for SIRPα ligands or agonists and compete SIRPα receptors to bind the ligands or agonists, thereby preventing or reducing the ability of a ligand or agonist to bind the receptor.

Typically, these SIRPα antagonists have a greater affinity or a lower dissociation constant for the SIRPα ligands or agonists than the receptor.

As used herein, "siRNA" and "small interfering RNA" are used interchangeably and refer to small oligonucleotides of single or double-stranded (ds) RNA used in RNA interference (RNAi). The siRNA can have a length of about 5 to about 50 nucleotides long. The siRNA also may have 3' overhangs at one or both ends. In one embodiment, the siRNA can be used to decrease or eliminate SIRPα gene expression.

As used herein, "shRNA" or "small hairpin RNA" or "short hairpin RNA" are used interchangeably and refer to an RNA molecule with a hairpin turn that can be used in RNA interference (RNAi). The shRNA can have a length of about 10 to about 100 nucleotides long. Expression of the shRNA in cells can be obtained by delivery of plasmids or viral or bacterial vectors. In one embodiment, the shRNA can be used to decrease or eliminate SIRPα gene expression.

By the term "specifically binds," as used herein, is meant a compound, e.g., a protein, a nucleic acid, an antibody, and the like, which recognizes and binds a specific molecule, but does not substantially recognize or bind other molecules in a sample.

The term "subject" is intended to include living organisms that an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

The term "targeting antibody" as used herein refers to an antibody or antibody fragment that binds to an antigen on a target cell. The targeting antibody may recognize an antigen that acts as a cell surface marker on a target cell associated with a particular disease state, such as a viral, bacterial or parasitic infection, an autoimmune disease, or a cancerous cell state.

The term "therapeutic" as used herein means a treatment and/or prophylaxis. A therapeutic effect is obtained by suppression, remission, or eradication of a disease state.

As used herein, the terms "treat," treating," "treatment," and the like refer to reducing or improving a disorder and/or symptom associated therewith. It will be appreciated that, although not precluded, treating a disorder or condition does not require that the disorder, condition or symptoms associated therewith be completely ameliorated or eliminated.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

DESCRIPTION

The present invention relates to compositions and methods that utilize a repressor of protein signal regulatory protein-alpha (SIRPα) to treat cancer.

Phagocytosis is the process in which a cell engulfs a solid particle, forming an internal vesicle called a phagosome. This process enables the immune system to remove pathogens and cell debris. Macrophages, a type of phagocytic cell, are derived from monocytes. Monocytes are recruited to sites of tissue damage or infection, then differentiate into macrophages and dendritic cells that help clear the pathogens and cell debris by phagocytosis. Macrophages discriminate between foreign (pathogens) and self-antigens via receptors on their cell surface.

In some aspects, this invention relates to disrupting the interaction between CD47 and protein signal regulatory protein-alpha (SIRPα). SIRPα, also known as tyrosine-protein phosphatase non-receptor type substrate 1 or CD172A, is a member of the SIRP family and belongs to the immunoglobulin superfamily. SIRP family members are receptor-type transmembrane glycoproteins known to be involved in the negative regulation of receptor tyrosine kinase-coupled signaling processes. CD47, an integrin-associated cell surface glycoprotein protein, has been demonstrated to be a ligand for SIRPα (Oldenborg, 2004, Leuk. Lymphoma 45(7):1319-27) and, upon interaction with SIRPα on phagocytes, provides a "don't eat me" signal, thus acting as a "marker of self."

Furthermore, SIRPα has been shown to be an inhibitory phagocyte receptor, and its interaction with CD47 expressing erythrocytes is the main inhibitory signal of erythrophagocytosis. In other words, CD47 expressed on the surface of self-cells prevents elimination of these cells by binding to the inhibitory receptor SIRP-alpha on the surface of phagocytes. Once it is activated, SIRPα inhibits pro-phagocytic signals from Fc and complement receptors, resulting in inhibition of phagocytosis (de Almeida et al., 2009, Immunopharmacol. Immunotoxicol. 31(4):636-40). Thus, macrophages presenting SIRPα on their surfaces rely on interaction with CD47 to identify the particle as being self or foreign.

Compositions

The present invention includes a phagocytic cell that possesses phagocytic activity against tumor tissue. In one embodiment, a phagocytic cell is modified by a repressor of signal regulatory protein-alpha (SIRPα) and bound to a targeting antibody.

The repressor of SIRPα comprises at least one selected from the group consisting of anti-SIRPα antibody, SIRPα-shRNA, SIRPα-siRNA, SIRPα antagonist, a CRISPR system targeted to SIRPα, and a combination thereof.

In some embodiment, the phagocytic cell is a macrophage modified by a repressor of signal regulatory protein-alpha (SIRPα) and bound to a targeting antibody.

In some embodiments, a bone marrow cell is modified by a repressor of signal regulatory protein-alpha (SIRPα) and bound to a targeting antibody. In one embodiment, the SIRPα repressed bone marrow cell differentiates into a mature SIRPα repressed macrophage. In another embodiment, the differentiated mature SIRPα repressed macrophage has a stronger phagocytic activity than a native macrophage of the mammal.

In one aspect, the invention includes a composition comprising the modified macrophage as described herein. In another aspect, the invention includes a composition comprising a signal regulatory protein-alpha (SIRPα) repressed bone marrow cell bound to a targeting antibody.

The composition also has a therapeutic effect on a tumor tissue. In one embodiment, the therapeutic effect comprises tumor shrinkage of at least about 60% of the tumor. In some embodiments, the tumor tissue comprises a brain cancer, bladder cancer, breast cancer, cervical cancer, colorectal cancer, liver cancer, kidney cancer, lymphoma, leukemia, lung cancer, melanoma, metastatic melanoma, mesothelioma, neuroblastoma, ovarian cancer, prostate cancer, gastric cancer, pancreatic cancer, renal cancer, skin cancer, thymoma, sarcoma, non-Hodgkin's lymphoma, Hodgkin's lymphoma, uterine cancer, and the like.

Repressor of Signal Regulatory Protein-Alpha (SIRPα)

In one aspect, the invention includes a phagocytic cells, such as a macrophage or monocyte, modified by a repressor of signal regulatory protein-alpha (SIRPα).

The repressor includes a molecule or compound that represses SIRPα expression, activity, function, or any combination thereof. The repressor can prevent or interfere with the SIRPα by inhibiting expression or decreasing expression of SIRPα, masking or hiding an activation site on SIRPα, and interfering with one or more functions of SIRPα. Repressors can include, but are not limited to, anti-SIRPα antibody, SIRPα-shRNA, SIRPα-siRNA, SIRPa antagonist, a CRISPR system targeted to SIRPα, and a combination thereof.

In one embodiment, the repressor is an anti-SIRPα antibody. The antibody can prevent or interfere with the interaction between CD47 and SIRPα by sequestering SIRPa protein, masking or hiding the interaction site on SIRPα, and/or interfering with SIRPα function. The antibody may have higher binding affinity for SIRPα protein than the binding affinity SIRPa has for CD47.

In one embodiment, the repressor is a SIRPα-shRNA. The shRNA include RNA molecules with a hairpin turn that can be used in RNA interference (RNAi). The shRNA can have a length of about 10 to about 100 nucleotides long. Expression of the shRNA in cells can be obtained by delivery of plasmids or viral or bacterial vectors. In one embodiment, shRNA can be used to decrease or eliminate SIRPα gene expression.

In one embodiment, the repressor is a SIRPα-siRNA. The siRNA include small oligonucleotides of single or double-stranded (ds) RNA used in RNA interference (RNAi). The siRNA can have a length of about 5 to about 50 nucleotides long. The siRNA also may have 3' overhangs at one or both ends. In one embodiment, the siRNA can be used to decrease or eliminate SIRPα gene expression.

In one embodiment, the repressor is a SIRPα antagonist. The SIRPα antagonist can prevent or decrease ligand- or agonist-mediated SIRPα responses. The SIRPα antagonist may have affinity for SIRPα and bind the receptor to disrupt the interaction between CD47 and SIRPα, thereby inhibiting SIRPα activation. SIRPα antagonists may have affinity for SIRPa ligands or agonists and compete with SIRPα receptors to bind the ligands or agonists, thereby preventing or reducing the ability of a ligand or agonist to bind the receptor. Typically, these SIRPα antagonists have a greater affinity or a lower dissociation constant for the SIRPα ligands or agonists than the receptor.

In one embodiment, the repressor is a CRISPR system. The CRISPR system is a facile and efficient system for inducing targeted genetic alterations. Target recognition by the Cas9 protein requires a 'seed' sequence within the guide RNA (gRNA) and a conserved dinucleotide containing protospacer adjacent motif (PAM) sequence upstream of the gRNA-binding region. The CRISPR system can thereby be engineered to cleave virtually any DNA sequence by redesigning the gRNA in cell lines (such as 293T cells), primary cells, and CAR T cells. The CRISPR system can simultaneously target multiple genomic loci by co-expressing a single CAS9 protein with two or more gRNAs, making this system uniquely suited for multiple gene editing or synergistic activation of target genes.

One example of a CRISPR system used to inhibit gene expression, CRISPRi, is described in U.S. Publication No.: 2014/0068797. CRISPRi induces permanent gene disruption that utilizes the RNA-guided Cas9 endonuclease to introduce DNA double stranded breaks which trigger error-prone repair pathways to result in frame shift mutations. A catalytically dead Cas9 lacks endonuclease activity. When coexpressed with a guide RNA, a DNA recognition complex is generated that specifically interferes with transcriptional elongation, RNA polymerase binding, or transcription factor binding. This CRISPRi system efficiently represses expression of targeted genes.

CRISPR system gene disruption occurs when a guide nucleic acid sequence specific for a target gene and a Cas endonuclease are introduced into a cell and form a complex that enables the Cas endonuclease to introduce a double strand break at the target gene. In one embodiment, the CRISPR system comprises an expression vector, such as, but not limited to, an pAd5F35-CRISPR vector. In one embodiment, a modified T cell is generated by introducing a Cas expression vector and a guide nucleic acid sequence specific for a gene into a T cell. In another embodiment, the Cas expression vector induces expression of Cas9 endonuclease. Other endonucleases may also be used, including but not limited to, T7, Cas3, Cas8a, Cas8b, Cas10d, Cse1, Csy1, Csn2, Cas4, Cas10, Csm2, Cmr5, Fok1, other nucleases known in the art, and any combination thereof.

In one embodiment, the CRISPR system comprises a Cas expression vector, such as an inducible promoter inducible by exposure to an antibiotic (e.g., by tetracycline or a derivative of tetracycline, for example doxycycline). However, it should be appreciated that other inducible promoters can be used. The inducing agent can be a selective condition (e.g., exposure to an agent, for example an antibiotic) that results in induction of the inducible promoter. This results in expression of the Cas expression vector.

In another embodiment, the CRISPR system comprises a guide nucleic acid sequence specific for SIRPα. The guide nucleic acid sequence targets SIRPα for Cas endonuclease-induced double strand breaks. The sequence of the guide nucleic acid sequence may be within a loci of the SIRPα genes. In one embodiment, the guide nucleic acid sequence is at least 10, 11, 12, 13, 14, 15, 16, 17, 18, 19, 20, 21, 22, 23, 24, 25, 26, 27, 30, 31, 32, 33, 34, 35, 36, 37, 38, 39, 40 or more nucleotides in length.

In another embodiment, the CRISPR system comprises a guide nucleic acid sequence specific for CD47 and/or SIRPα. The guide nucleic acid sequence targets CD47 and/or SIRPα for Cas endonuclease-induced double strand breaks. The sequence of the guide nucleic acid sequence may be within a loci of the CD47 and/or SIRPα genes. In one embodiment, the guide nucleic acid sequence is at least 10, 11, 12, 13, 14, 15, 16, 17, 18, 19, 20, 21, 22, 23, 24, 25, 26, 27, 30, 31, 32, 33, 34, 35, 36, 37, 38, 39, 40 or more nucleotides in length.

The guide nucleic acid sequence may be specific for any gene, that encodes a gene product that interferes with CD47-SIRPα interaction, such as a gene product that would modulate expression of the SIRPα gene.

The guide nucleic acid sequence includes a RNA sequence, a DNA sequence, a combination thereof (a RNA-DNA combination sequence), or a sequence with synthetic nucleotides. The guide nucleic acid sequence can be a single molecule or a double molecule. In one embodiment, the guide nucleic acid sequence comprises a single guide RNA.

In another embodiment, the repressor is a TALEN system. TALENS are artificial restriction enzymes generated by fusing a TAL effector DNA binding domain to a DNA cleavage domain. TALENs uses a nonspecific DNA-cleaving nuclease fused to a DNA-binding domain that can be to target essentially any sequence. For TALEN technology, target sites are identified and expression vectors are made. See Liu et al, 2012, J. Genet. Genomics 39:209-215. The linearized expression vectors (e.g., by NotI) is used as template for mRNA synthesis. See Joung & Sander, 2013, Nat Rev Mol Cell Bio 14:49-55.

TALENs and CRISPR methods provide one-to-one relationship to the target sites, i.e. one unit of the tandem repeat in the TALE domain recognizes one nucleotide in the target site, and the crRNA or gRNA of CRISPR/Cas system hybridizes to the complementary sequence in the DNA target. Methods can include using a pair of TALENs or a Cas9 protein with one gRNA to generate double-strand breaks in the target. The breaks are then repaired via non-homologous end-joining or homologous recombination.

Targeting Antibody

The phagocytic cell of the invention is also bound to a targeting antibody. The targeting antibody may bind the phagocytic cell through a Fc receptor on the phagocytic cell, such as a macrophage, monocyte or bone marrow cell. In one embodiment, a macrophage is exposed to the targeting antibody simultaneously, prior to or after modification with the repressor of SIRPα. In another embodiment, a bone marrow cell is exposed to the targeting antibody simultaneously, prior to or after modification with the repressor of SIRPα.

In some embodiments, the targeting antibody binds to an antigen on a target cell. Examples of antigens include cell surface markers that are associated with viral, bacterial and parasitic infections, autoimmune disease, and cancer cells.

The choice of targeting antibody depends upon the type and number of antigens that are present on the surface of a target cell. For example, the targeting antibody may be chosen to recognize an antigen that acts as a cell surface marker on a target cell associated with a particular disease state.

In one embodiment, the targeting antibody binds to a tumor antigen, such as an antigen that is specific for a tumor or cancer of interest. In one embodiment, the tumor antigen of the present invention comprises one or more antigenic cancer epitopes. Nonlimiting examples of tumor associated antigens include CD19; CD123; CD22; CD30; CD171; CS-1 (also referred to as CD2 subset 1, CRACC, SLAMF7, CD319, and 19A24); C-type lectin-like molecule-1 (CLL-1 or CLECL1); CD33; epidermal growth factor receptor variant III (EGFRvIII); ganglioside G2 (GD2); ganglioside GD3 (aNeuSAc(2-8)aNeu5Ac(2-3)bDGalp(1-4)bDGlcp(1-1)Cer); TNF receptor family member B cell maturation (BCMA); Tn antigen ((Tn Ag) or (GalNAca-Ser/Thr)); prostate-specific membrane antigen (PSMA); Receptor tyrosine kinase-like orphan receptor 1 (ROR1); Fms-Like Tyrosine Kinase 3 (FLT3); Tumor-associated glycoprotein 72 (TAG72); CD38; CD44v6; Carcinoembryonic antigen (CEA); Epithelial cell adhesion molecule (EPCAM); B7H3 (CD276); KIT (CD117); Interleukin-13 receptor subunit alpha-2 (IL-13Ra2 or CD213A2); Mesothelin; Interleukin 11 receptor alpha (IL-11Ra); prostate stem cell antigen (PSCA); Protease Serine 21 (Testisin or PRSS21); vascular endothelial growth factor receptor 2 (VEGFR2); Lewis(Y) antigen; CD24; Platelet-derived growth factor receptor beta (PDGFR-beta); Stage-specific embryonic antigen-4 (SSEA-4); CD20; Folate receptor alpha; Receptor tyrosine-protein kinase ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3 (aNeu5Ac(2-3)bDGalp(1-4)bDGlcp(1-1)Cer); transglutaminase 5 (TGS5); high molecular weight-melanoma-associated antigen (HMW-MAA); o-acetyl-GD2 ganglioside (OAcGD2); Folate receptor beta; tumor endothelial marker 1 (TEM1/CD248); tumor endothelial marker 7-related (TEM7R); claudin 6 (CLDN6); thyroid stimulating hormone receptor (TSHR); G protein-coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCRI); adrenoceptor beta 3 (ADRB3); pannexin 3 (PANX3); G protein-coupled receptor (GPR20); lymphocyte antigen 6 complex, locus K 9 (LY6K); Olfactory receptor 51E2 (OR51E2); TCR Gamma Alternate Reading Frame Protein (TARP); Wilms tumor protein (WTi); Cancer/testis antigen 1 (NY-ESO-1); Cancer/testis antigen 2 (LAGE-1a); Melanoma-associated antigen 1 (MAGE-A1); ETS translocation-variant gene 6, located on chromosome 12p (ETV6-AML); sperm protein 17 (SPA17); X Antigen Family, Member 1A (XAGEl); angiopoietin-binding cell surface receptor 2 (Tie 2); melanoma cancer testis antigen-1 (MAD-CT-1); melanoma cancer testis antigen-2 (MAD-CT-2); Fos-related antigen 1; tumor protein p53 (p53); p53 mutant; prostein; surviving; telomerase; prostate carcinoma tumor antigen-1 (PCTA-1 or Galectin 8), melanoma antigen recognized by T cells 1 (MelanA or MART1); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1 (CYP1B1); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RU1); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIR1); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1). In one embodiment, the targeting antibody is a tumor specific antibody.

In one embodiment, the targeting antibody is a fragment of an antibody, such as the antigen binding fragment. The targeting antibody can include any domain that binds to the antigen and may include, but is not limited to, a monoclonal antibody, a polyclonal antibody, a synthetic antibody, a human antibody, a humanized antibody, a non-human antibody, a single chain antibody, a single chain variable fragment, a chimeric antibody, and any fragment thereof. Thus, in one embodiment, the targeting antibody comprises at least a portion of a mammalian antibody.

In some instances, the targeting antibody is derived from the same species in which it will ultimately be used in. For example, for use in humans, the targeting antibody comprises a human antibody, a humanized antibody, or a fragment thereof.

Human Antibodies

It may be preferable to use human antibodies or fragments thereof when using the targeting antibody. Completely human antibodies are particularly desirable for therapeutic treatment of human subjects. Human antibodies can be made by a variety of methods known in the art including phage display methods using antibody libraries derived from human immunoglobulin sequences, including improvements to these techniques. See, also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. For example, it has been described that the homozygous deletion of the antibody heavy chain joining region (JH) gene in chimeric and germ-line mutant mice results in complete inhibition of endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Antibodies directed against the target of choice can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies, including, but not limited to, IgG1 (gamma 1) and IgG3. For an overview of this technology for producing human antibodies, see, Lonberg and Huszar (Int. Rev. Immunol., 13:65-93 (1995)). For a detailed discussion of this technology for producing human antibodies and human monoclonal antibodies and protocols for producing such antibodies, see, e.g., PCT Publication Nos. WO 98/24893, WO 96/34096, and WO 96/33735; and U.S. Pat. Nos. 5,413,923; 5,625,126; 5,633,425; 5,569,825; 5,661,016; 5,545,806; 5,814,318; and 5,939,598, each of which is incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above. For a specific discussion of transfer of a human germ-line immunoglobulin gene array in germ-line mutant mice that will result in the production of human antibodies upon antigen challenge see, e.g., Jakobovits et al., Proc. Natl. Acad. Sci. USA, 90:2551 (1993); Jakobovits et al., Nature, 362:255-258 (1993); Bruggermann et al., Year in Immunol., 7:33 (1993); and Duchosal et al., Nature, 355:258 (1992).

Human antibodies can also be derived from phage-display libraries (Hoogenboom et al., J. Mol. Biol., 227:381 (1991); Marks et al., J. Mol. Biol., 222:581-597 (1991); Vaughan et al., Nature Biotech., 14:309 (1996)). Phage display technology (McCafferty et al., Nature, 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson, Kevin S, and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of unimmunized mice. A repertoire of V genes from unimmunized human donors can be constructed and antibodies to a diverse array of antigens (including self-antigens) can be isolated essentially following the techniques described by Marks et al., J. Mol. Biol., 222:581-597 (1991), or Griffith et al., EMBO J., 12:725-734 (1993). See, also, U.S. Pat. Nos. 5,565,332 and 5,573,905, each of which is incorporated herein by reference in its entirety.

Human antibodies may also be generated by in vitro activated B cells (see, U.S. Pat. Nos. 5,567,610 and 5,229,275, each of which is incorporated herein by reference in its entirety). Human antibodies may also be generated in vitro using hybridoma techniques such as, but not limited to, that described by Roder et al. (Methods Enzymol., 121:140-167 (1986)).

Humanized Antibodies

Alternatively, in some embodiments, a non-human antibody can be humanized, where specific sequences or regions of the antibody are modified to increase similarity to an antibody naturally produced in a human. For instance, in the present invention, the antibody or fragment thereof may comprise a non-human mammalian scFv. In one embodiment, the antigen binding domain portion is humanized.

A humanized antibody can be produced using a variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/5):489-498; Studnicka et al., 1994, Protein Engineering, 7(6):805-814; and Roguska et al., 1994, PNAS, 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Patent Application Publication No. US2005/0042664, U.S. Patent Application Publication No. US2005/0048617, U.S. Pat. Nos. 6,407,213, 5,766,886, International Publication No. WO 9317105, Tan et al., J. Immunol., 169:1119-25 (2002), Caldas et al., Protein Eng., 13(5):353-60 (2000), Morea et al., Methods, 20(3):267-79 (2000), Baca et al., J. Biol. Chem., 272(16):10678-84 (1997), Roguska et al., Protein Eng., 9(10):895-904 (1996), Couto et al., Cancer Res., 55 (23 Supp):5973s-5977s (1995), Couto et al., Cancer Res., 55(8):1717-22 (1995), Sandhu J S, Gene, 150(2):409-10 (1994), and Pedersen et al., J. Mol. Biol., 235(3):959-73 (1994), each of which is incorporated herein in its entirety by reference. Often, framework residues in the framework regions will be substituted with the corresponding residue from the CDR donor antibody to alter, preferably improve, antigen binding. These framework substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature, 332:323, which are incorporated herein by reference in their entireties.)

A humanized antibody has one or more amino acid residues introduced into it from a source which is nonhuman. These nonhuman amino acid residues are often referred to as "import" residues, which are typically taken from an "import" variable domain. Thus, humanized antibodies comprise one or more CDRs from nonhuman immunoglobulin molecules and framework regions from human. Humanization of antibodies is well-known in the art and can essentially be performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816,567; 6,331,415; 5,225,539; 5,530,101; 5,585,089; 6,548,640, the contents of which are incorporated herein by reference herein in their entirety). In such humanized chimeric antibodies, substantially less than an intact human variable domain has been substituted by the corresponding sequence from a nonhuman species. In practice, humanized antibodies are typically human antibodies in which some CDR residues and possibly some framework (FR) residues are substituted by residues from analogous sites in rodent antibodies. Humanization of antibodies can also be achieved by veneering or resurfacing (EP 592,106; EP 519,596; Padlan, 1991, Molecular Immunology, 28(4/5):489-498; Studnicka et al., Protein Engineering, 7(6):805-814 (1994); and Roguska et al., PNAS, 91:969-973 (1994)) or chain shuffling (U.S. Pat. No. 5,565,332), the contents of which are incorporated herein by reference herein in their entirety.

The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987), the contents of which are incorporated herein by reference herein in their entirety). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993), the contents of which are incorporated herein by reference herein in their entirety).

Antibodies can be humanized that retain high affinity for the target antigen and that possess other favorable biological properties. According to one aspect of the invention, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind the target antigen. In this way, FR residues can be selected and combined from the recipient and import sequences so that the desired antibody characteristic, such as increased affinity for the target antigen, is achieved. In general, the CDR residues are directly and most substantially involved in influencing antigen binding.

A humanized antibody retains a similar antigenic specificity as the original antibody. However, using certain methods of humanization, the affinity and/or specificity of binding of the antibody to the target antigen may be increased using methods of "directed evolution," as described by Wu et al., J. Mol. Biol., 294:151 (1999), the contents of which are incorporated herein by reference herein in their entirety.

Sources of Cells

In one embodiment, a source of phagocytic cells used in the compositions and methods described herein is obtained from a subject. Non-limiting examples of subjects include humans, dogs, cats, mice, rats, and transgenic species thereof. Preferably, the subject is a human. The cells can be obtained from a number of sources, including peripheral blood mononuclear cells, bone marrow, lymph node tissue, spleen tissue, umbilical cord, and tumors. In certain embodiments, any number of cell lines available in the art may be used. In certain embodiments, the cells can be obtained from a unit of blood collected from a subject using any number of techniques known to the skilled artisan, such as Ficoll separation. In one embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media, such as phosphate buffered saline (PBS) or wash solution lacks calcium and may lack magnesium or may lack many if not all divalent cations, for subsequent processing steps. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, cells are isolated from peripheral blood by lysing the red blood cells and depleting the lymphocytes and red blood cells, for example, by centrifugation through a PERCOLL™ gradient. Alternatively, cells can be isolated from umbilical cord, bone marrow, spleen, lymph nodes, thymus, ascites fluid, tumor, or other source of phagocytic cells. In any event, a specific subpopulation of cells can be further isolated by positive or negative selection techniques.

The mononuclear cells so isolated can be depleted of cells expressing certain antigens, including, but not limited to, CD34, CD3, CD4, CD8, CD14, CD19 or CD20. Depletion of these cells can be accomplished using an isolated antibody, a biological sample comprising an antibody, such as ascites fluid, an antibody bound to a physical support, and a cell bound antibody.

Enrichment of specific cell populations by negative selection can be accomplished using a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, enrich of a cell population for monocytes, macrophages and/or dendritic cells by negative selection can be accomplished using a monoclonal antibody cocktail that typically includes antibodies to CD34, CD3, CD4, CD8, CD14, CD19 or CD20.

During isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. The use of high concentrations of cells can result in increased cell yield, cell activation, and cell expansion.

In one embodiment, a population of cells include, but are not limited to, peripheral blood mononuclear cells, cord blood cells, a purified population of phagocytic cells, and a cell line. In another embodiment, peripheral blood mononuclear cells comprise the population of phagocytic cells. In yet another embodiment, purified cells comprise the population of phagocytic cells.

The present invention includes the composition further comprising opsonins. Opsonins include any molecule or compound that enhance phagocytosis of a target. Coating a target cell, such as a cancerous, necrotic or other target cell, enhances selective phagocytosis by phagocytic cells, such as macrophages, monocytes, neutrophils, mast cells, and dendritic cells. The phagocytic cell expresses opsonin receptors, such as Fc and complement receptors, that bind the opsonin to activate the phagocytic process. Opsonins include, but are not limited to, IgG antibody, red blood cell (anti-RBC) antibody, IgM, C3b, C4b, iC3b, mannose-binding lectin, C-reactive protein, and any combination thereof.

In another aspect, the invention includes a composition comprising a signal regulatory protein-alpha (SIRPa) repressed bone marrow cell and an opsonin, wherein the composition has a therapeutic effect on a tumor tissue.

In one embodiment, the SIRPa repressed bone marrow cell differentiates into a mature SIRPa repressed macrophage. In another embodiment, the differentiated mature SIRPa repressed macrophage has a stronger phagocytic activity than the native macrophage of the mammal.

In embodiments where the tissue is a tumor tissue, the composition has a therapeutic effect on the tumor tissue. In one embodiment, the therapeutic effect comprises tumor shrinkage of at least about 60% of the tumor. In another embodiment, the tumor shrinkage is at least 20%, 25%, 30%, 35%, 40%, 45%, 50%, 55%, 60%, 65%, 70%, 75%, 80%, 85%, 90%, 95%, or greater or any percentage therebetween.

Methods

In one aspect, the invention includes a method of modifying a phagocytic activity to target a specific tissue in a mammal, the method comprising contacting a phagocytic cell with a repressor of signal regulatory protein-alpha (SIRPα) and a targeting antibody, wherein the phagocytic cell has enhanced phagocytic activity and a therapeutic effect on the tissue in the mammal.

In one embodiment, the phagocytic cell modified is a macrophage or a monocyte. In another embodiment, the phagocytic cell is a bone marrow cell, such as a bone marrow cell that differentiates into a mature macrophage.

In another embodiment, the phagocytic cell is contacted with targeting antibody simultaneously, prior to or after modification with the repressor of SIRPα.

In yet another embodiment, the phagocytic cell is modified to have a stronger phagocytic activity than the native phagocytic cell of the mammal.

In one example of the invention, the method described herein includes a repressor of the interaction between CD47 and SIRPa. The method comprises administering a repressor to prevent or interfere with the interaction between the proteins by inhibiting expression or decreasing expression of one or both proteins, masking or hiding the binding site of one or both proteins, interfering with one or more functions of one or both proteins. Repressors of the CD47-SIRPa interaction include, but are not limited to, anti-CD47 antibody, CD47-shRNA, CD47-siRNA, anti-SIRPa antibody, SIRPa-shRNA, SIRPa-siRNA, CD47 antagonist, SIRPa antagonist, anti-CD47-SIRPa antibody, a CRISPR system targeted to CD47 or SIRPa or both, and a combination thereof.

The method further comprises administering an opsonin in the composition. Examples of opsonins include, but are not limited to, IgG antibody, red blood cell (anti-RBC) antibody, IgM, C3b, C4b, iC3b, mannose-binding lectin, C-reactive protein, and any combination thereof. In one embodiment of the invention, the repressor of the CD47-SIRPa interaction is administered to the mammal prior to administration of the opsonin. In another embodiment, the repressor of the CD47-SIRPa interaction is administered to the mammal with the opsonin. In yet another embodiment, the repressor of the CD47-SIRPa interaction is administered to the mammal after the administration of the opsonin.

In another embodiment, the tissue is a tumor tissue. In embodiments where the tissue is a tumor tissue, the therapeutic effect includes, but is not limited to, the removal or elimination of tumor tissue or a decrease in tumor size or tumor tissue. The effective amount may cause the tumor tissue to be decreased when compared to the original tissue size, the tumor tissue size prior to therapeutic treatment, a reference tissue or any other standard or condition. In one embodiment, the method comprises tumor shrinkage of at least about 60% of the tumor. In another embodiment, the tumor shrinkage is at least 20%, 25%, 30%, 35%, 40%, 45%, 50%, 55%, 60%, 65%, 70%, 75%, 80%, 85%, 90%, 95%, or greater or any percentage therebetween.

In another aspect, the invention includes a method of modulating phagocytic activity to target a specific tissue in a mammal. The method comprises administering to the mammal an effective amount of a composition comprising a signal regulatory protein-alpha (SIRPa) repressed bone marrow cell and an opsonin, wherein the effective amount of the composition modulates phagocytic activity and has a therapeutic effect on the tissue in the mammal.

In one embodiment, the SIRPa repressed bone marrow cell differentiates into a mature SIRPa repressed macrophage. In another embodiment, the differentiated mature SIRPa repressed macrophage has a stronger phagocytic activity than the native macrophage of the mammal. In yet another embodiment, the SIRPa repressed bone marrow cell may be an autologous or allogenic bone marrow cell.

Therapy

The compositions described herein may be formulated as a therapy. The pharmaceutical composition may also include a pharmaceutically acceptable carrier. A therapeutically effective amount of the pharmaceutical composition may be administered.

In one aspect, the invention includes a method of enhancing phagocytic activity of a phagocytic cell toward tumor tissue in a mammal. The method comprises administering to the mammal an effective amount of a composition comprising a signal regulatory protein-alpha (SIRPα) repressed phagocytic cell bound to a targeting antibody, wherein the effective amount of the composition enhances phagocytic activity and has a therapeutic effect in the mammal.

In one example of the invention, the method described herein includes a repressor of SIRPα. The method comprises administering the repressor to prevent or interfere with SIRPα function by inhibiting expression or decreasing expression of SIRPα, masking or hiding a binding site on SIRPα, and interfering with one or more functions of SIRPα. In some embodiments, the phagocytic cell is modified by at least one selected from the group consisting of anti-SIRPα antibody, SIRPα-shRNA, SIRPα-siRNA, SIRPα antagonist, a CRISPR system targeted to SIRPα, and a combination thereof.

In another embodiment, the tissue is a tumor tissue. In embodiments where the tissue is a tumor tissue, the therapeutic effect includes, but is not limited to, the removal or elimination of tumor tissue or a decrease in tumor size or tumor tissue. The effective amount may cause the tumor tissue to be decreased when compared to the original tissue size, the tumor tissue size prior to therapeutic treatment, a reference tissue or any other standard or condition. In one embodiment, the method comprises tumor shrinkage of at least about 60% of the tumor. In another embodiment, the tumor shrinkage is at least 20%, 25%, 30%, 35%, 40%, 45%, 50%, 55%, 60%, 65%, 70%, 75%, 80%, 85%, 90%, 95%, or greater or any percentage therebetween.

In another aspect, the invention includes a method of treating a tumor in a mammal. The method comprises administering to the mammal an effective amount of a composition comprising a signal regulatory protein-alpha (SIRPα) repressed phagocytic cell bound to a targeting antibody, wherein the effective amount of the composition has a therapeutic effect in the mammal, thereby treating the tumor tissue.

In one embodiment, the SIRPα repressed phagocytic cell is a macrophage or a monocyte. In another embodiment, the SIRPα repressed phagocytic cell is a bone marrow cell that differentiates into a mature SIRPα repressed macrophage. In another embodiment, the differentiated mature SIRPα repressed macrophage has a stronger phagocytic activity than the native macrophage of the mammal. In yet another embodiment, the SIRPα repressed phagocytic cell may be an autologous or allogenic to the mammal.

In certain embodiments, the composition of the invention provides a therapeutic effect. Therapeutic effects include, but are not limited to, removal or elimination of target cells, decrease in tumor cells or tumor size or tumor tissue, removal or elimination of necrotic or apoptotic cells, or decrease in necrotic or apoptotic cells by phagocytosis. The effective amount may cause the target cells to be decreased in number when compared to the original tissue size, such as a tumor tissue, the tissue size prior to therapeutic treatment, a reference tissue or any other standard or condition.

In one embodiment, the treatment of the tumor comprises at least one selected from the group consisting of suppression of tumor tissue growth and decrease of the tumor tissue by at least 60%. In another embodiment, the tumor tissue is decreased by at least 20%, 25%, 30%, 35%, 40%, 45%, 50%, 55%, 60%, 65%, 70%, 75%, 80%, 85%, 90%, 95% or greater. In still another embodiment, the tumor tissue is decreased by at least 60% as compared to an original size of the tumor tissue, the tumor tissue size prior to therapeutic treatment, a reference tissue or any other standard or condition. In another embodiment, the tumor tissue is decreased by at least 20%, 25%, 30%, 35%, 40%, 45%, 50%, 55%, 60%, 65%, 70%, 75%, 80%, 85%, 90%, 95%, or greater as compared to an original size of the tumor tissue.

In one embodiment, the target cells include, but are not limited to, tumor cells, such as malignant and metastatic cells, necrotic cells, apoptotic cells, infected cells, such as bacterial or viral infected cells, and other target cells. In one embodiment, the target cells are in a tumor tissue, such as a brain cancer, bladder cancer, breast cancer, cervical cancer, colorectal cancer, liver cancer, kidney cancer, lymphoma, leukemia, lung cancer, melanoma, metastatic melanoma, mesothelioma, neuroblastoma, ovarian cancer, prostate cancer, gastric cancer, pancreatic cancer, renal cancer, skin cancer, thymoma, sarcoma, non-Hodgkin's lymphoma, Hodgkin's lymphoma, uterine cancer, and the like.

The composition of the invention can be administered in dosages and routes and at times to be determined in appropriate pre-clinical and clinical experimentation and trials. The compositions may be administered multiple times at dosages within these ranges.

In certain embodiments, the composition of the invention provides a therapeutic effect. Therapeutic effects include, but are not limited to, removal or elimination of target cells, decrease in tumor cells or tumor size or tumor tissue, removal or elimination of necrotic or apoptotic cells, or decrease in necrotic or apoptotic cells by phagocytosis. The effective amount may cause the target cells to be decreased in number when compared to the original tissue size, such as a tumor tissue, the tissue size prior to therapeutic treatment, a reference tissue or any other standard or condition.

In one embodiment, the treatment of the tumor comprises at least one selected from the group consisting of suppression of tumor tissue growth and decrease of the tumor tissue by at least 60%. In another embodiment, the tumor tissue is decreased by at least 20%, 25%, 30%, 35%, 40%, 45%, 50%, 55%, 60%, 65%, 70%, 75%, 80%, 85%, 90%, 95% or greater. In still another embodiment, the tumor tissue is decreased by at least 60% as compared to an original size of the tumor tissue, the tumor tissue size prior to therapeutic treatment, a reference tissue or any other standard or condition. In another embodiment, the tumor tissue is decreased by at least 20%, 25%, 30%, 35%, 40%, 45%, 50%, 55%, 60%, 65%, 70%, 75%, 80%, 85%, 90%, 95%, or greater as compared to an original size of the tumor tissue.

In one embodiment, the target cells include, but are not limited to, tumor cells, such as malignant and metastatic cells, necrotic cells, apoptotic cells, infected cells, such as bacterial or viral infected cells, and other target cells. In one embodiment, the target cells are in a tumor tissue, such as a brain cancer, bladder cancer, breast cancer, cervical cancer, colorectal cancer, liver cancer, kidney cancer, lymphoma, leukemia, lung cancer, melanoma, metastatic melanoma, mesothelioma, neuroblastoma, ovarian cancer, prostate cancer, gastric cancer, pancreatic cancer, renal cancer, skin cancer, thymoma, sarcoma, non-Hodgkin's lymphoma, Hodgkin's lymphoma, uterine cancer, and the like.

In yet another aspect, the invention includes a method of treating a mammal with a tumor. The method comprises administering to the mammal an effective amount of a composition comprising a repressor of CD47-signal regulatory protein-alpha (CD47-SIRPa) interaction and opsonin, thereby treating the tumor.

In another aspect, the method includes a method of treating a mammal with a tumor. The method comprises administering to the mammal an effective amount of a composition comprising a signal regulatory protein-alpha (SIRPa) repressed bone marrow cell and opsonin, thereby treating the tumor.

The composition of the invention can be administered in dosages and routes and at times to be determined in appropriate pre-clinical and clinical experimentation and trials. The compositions may be administered multiple times at dosages within these ranges.

Administration of the composition of the invention may be combined with other methods useful to treat the desired disease or condition as determined by those of skill in the art.

The administration of the composition of the invention may be carried out in any convenient manner known to those of skill in the art. The composition of the present invention may be administered to a mammal by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In other instances, the composition of the invention is injected directly into a target site in the mammal, a local disease site in the mammal, a lymph node, an organ, a tumor, and the like. In one embodiment, the composition described herein is administered intravenously to the mammal.

In one embodiment, SIRPa repressed bone marrow cell is administered intravenously to the mammal. The SIRPa repressed bone marrow cell may be administered prior to administration of the opsonin, with the opsonin or after the administration of the opsonin. In another embodiment, the repressor of the CD47-SIRPa interaction is intravenously to the mammal. The repressor of the CD47-SIRPa interaction may be administered to the mammal prior to the opsonin, with the opsonin or after the administration of the opsonin.

Pharmaceutical Compositions

Pharmaceutical compositions of the present invention may comprise the composition as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

It can generally be stated that a pharmaceutical composition comprising the repressed macrophages described herein may be administered at a dosage of $10^4$ to $10^9$ cells/kg body weight, preferably $10^5$ to $10^6$ cells/kg body weight, including all integer values within those ranges. The compositions may also be administered multiple times at these dosages. The composition can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer the repressed phagocytic cells to a subject and then subsequently reinfuse the patient with additional repressed phagocytic cells. This process can be carried out multiple times every few weeks. In certain embodiments, repressed phagocytic cells can be obtained from blood draws of from 10 ml to 400 ml. In certain embodiments, repressed phagocytic cells are obtained from blood draws of 20 ml, 30 ml, 40 ml, 50 ml, 60 ml, 70 ml, 80 ml, 90 ml, or 100 ml. Not to be bound by theory, using this multiple blood draw/multiple reinfusion protocol, may select out certain populations of cells.

In certain embodiments of the present invention, methods of treatment using the compositions described herein, or other methods known in the art where composition are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or other treatments for PML patients. In further embodiments, the compositions of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993). In a further embodiment, the compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

In certain embodiments, the compositions described herein may be used for the manufacture of a medicament for the treatment of response disease or condition in a subject in need thereof. In yet other embodiments, the compositions described herein may be used for the manufacture of a medicament for the treatment of a cancer in a subject in need thereof.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

It should be understood that the method and compositions that would be useful in the present invention are not limited to the particular formulations set forth in the examples. The following examples are put forth so as to provide those of ordinary skill in the art with a complete disclosure and description of how to make and use the cells, expansion and culture methods, and therapeutic methods of the invention, and are not intended to limit the scope of what the inventors regard as their invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Polymerase Chain Reaction: Principles, Applications and Troubleshooting", (Babar, 2011); "Current Protocols in Immunology" (Coligan, 2002).

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

The materials and methods employed in the experiments disclosed herein are now described.

Materials. For washing or antibody staining of cells, PBS without $Ca^{2+}$ or $Mg^{2+}$ (Invitrogen) was supplemented with 2% FBS (Invitrogen). For cell culture, Ham's F-12 growth media, penicillin-streptomycin, and FBS were all purchased from Invitrogen. For flow cytometry, 7-Amino-actinomycin D (7-AAD) was purchased from Sigma and Hoechst 33342 was purchased from Invitrogen.

Antibodies. Receptor blocking was done with anti-hSIRPA antibody (SIRP-A1, clone: SE7C2, from Santa Cruz, sc-23863) and with anti-mSIRPA antibody (rat anti-mouse CD172a, clone P84, BD Pharmingen). Opsonization of human cells was done with anti-human Ab (rabbit polyclonal IgG from Rockland, 109-4139). Primary antibodies used for flow cytometry and imaging include anti-human CD41-FITC (Biolegend), CD47(B6H12)-APC (Biolegend), CD47(B6H12)-AF647 (BD Pharmingen), CD235a-PE (Biolegend), CD11b-APC (Biolegend). Primary anti-mouse F4/80-APC/Cy7 (Biolegend), CD11b-PE/Cy7 (Biolegend). Secondary antibodies include donkey anti-rabbit Alexa 488 (Invitrogen), or donkey anti-rabbit Alexa 647 (Invitrogen).

F(ab')2 Production. Anti-h F(ab')2 were produced using Thermo Scientic Pierce™ F(ab')2 Preparation Kit. Briefly, immobilized pepsin was used to cleave full length anti-h antibody. After 3 hour incubation pepsin was removed by centrifugation at 5000 g for 1 min. A SDS-PAGE was used to assess complete digestion. Follow successful cleavage, Fc fragments were removed using an Amicon Ultra centrifugal filter device with a 50,000 molecular weight cut-off. F(ab'2) product from above was centrifuged in filter at 5000 g for 30 mins. After centrifugation F(ab')2 was collected and filter membrane was washed with PBS. To verify Fc fragments were removed, the recovered F(ab')2 was ran on a SDS-PAGE along with the filtrate.

Other Cell lines. EC4-isolated primary mouse liver carcinoma from a transgenic mouse that has an inducible human C-myc. IPS-MSC—Inducible human pluripotent stem cells that were differentiated into mesenchymal stem cells; obtained from the Progeria Research Foundation cell and tissue bank.

Development of A549 CD47-KD Cell Lines. A549 cells originally obtained from ATCC were previously made to stably express tdTomato and cultured in Ham's F-12 growth media supplemented with 10% FBS and 1% pen-strep.

Stable CD47-KD cell lines were established using a standard transduction protocol. Briefly, human CD47 shRNA lentiviral transduction particles (#NM_00177) were purchased from Sigma. tdTomato-A549 cells were transduced with viral particles and stable clones were generated by puromycin selection. The CD47 knockdown efficiency was determined by antibody staining (B6H12) using flow cytometry. Two stable A549 cell lines were selected based on CD47 knockdown efficiency. The KD+ cell line (#TRCN0000007837) was further refined by successive rounds of flow sorting to establish a 90% CD47 knockdown (CD47 KD++). The shCtl (#TRCN0000007835) displayed a level of CD47 expression similar to that of untransduced cells. These cells were further transduced with GFP– lentiviral particles and sorted to obtain a homogeneous WT cell line stably expressing GFP.

Development of THP-1 SIRPA-KD Cell Lines. THP-1 cells were purchased from ATCC and cultured in RPMI growth media supplemented with 10% FBS and 1% pen-strep. Stable SIRPA-KD cell lines were established using a standard transduction protocol. Briefly, human SIRPA shRNA lentiviral transduction plasmid were purchased from Santa Cruz (sc-44106-SH). Plasmid was transfected into bacteria, allowed to replicate, and harvested using maxi plasmid isolation kit. Activated lentiviral particles were produced from plasmid. THP-1 cells were transduced with viral particles and stable clones were generated by puromycin selection. The SIRPA knockdown efficiency was determined by antibody staining using flow cytometry.

Immunofluorescence. A549 cells were seeded on 18 mm$^2$ circular microscope cover slips in a 6 well plate and allowed to adhere overnight in F-12 growth media supplemented with 10% FBS and 1% antibiotics. Cells were briefly fixed with 4% paraformaldehyde for 5 min at RT followed by three PBS washes. Next, cells were blocked using 3% BSA+0.05% Tween-followed by antibody incubation in blocking buffer. Primary antibodies were used at 1:100 and incubated for 1 hour at RT. After incubation, cells were washed three times with PBS. All donkey secondary antibodies (Alexa Fluor 488 and 647) were stained for 1 hour at RT at 1:400 dilution in PBS. Hoescht 33342 was used to stain DNA at 1 µg/mL for 5 minutes at RT. Cover slips were washed a final three times with PBS before mounting on slides using ProLong Gold Antifade Reagent (Life Technologies), sealed with nail polish, and cured for 24 hours before imaging Images were acquired using an Olympus IX71 inverted microscope with a 300 W Xenon lamp illumination using 40×, 60×, or 150× objectives with or without 1.6× multiplication. Further image analysis was done using ImageJ (National Institutes of Health).

Flow Cytometry of In Vitro Cultured Cells. A549 cells were dissociated using 10 mM EDTA in PBS, washed, and resuspended in 2% FBS in PBS. Antibody (B6H12-AF647 1:50) incubation was done at RT for 1 hour followed by washing and resuspension in 2% FBS. Samples were run on a BD LSRII.

Phagocytosis Assay (Flow Cytometry). THP-1 was incubated in RPMI medium with 100 ng/mL phorbol myristate acetate (PMA), for 2 days. In assays including anti-hSIRPA antibody (SE7C2 clone), macrophages were pre-incubated at 5.32 nM at 37 C for 1 hour prior to addition of A549. All conditions were supplemented non-specific IgG ~30 ug/mL from FBS. A549 were prepared by using cell dissociation buffer Hanks from Invitrogen to remove cells followed by incubation with anti-h and B6H12 antibodies at 1 µM and 83 nM respectively. Following A549 were incubated at a ratio of 5 A549s per THP-1, cells were incubated for 75 min at 37 C then rinsed with PBS. Three minute Trypsin incubation was used to remove non-ingested A549s. The remaining cells were scraped off the plate and stained with CD11b (label THP-1s) and anti-rabbit-AF488 antibody (to distinguish non-ingested A549). The cells were then washed 2× with PBS and resuspended in 5% FBS/PBS, then analyzed by a BD LSRII cytometer. Phagocytosis of human red blood cells followed the same protocol as described in (Sosale et al., (2015) Blood 125:542-552).

Establishment of A549 tumors In Vivo. CD47 knockdown and control cells were dissociated from tissue culture flasks using 10 mM EDTA in PBS. $10^6$ cells per injection were suspended in 100 µL ice cold PBS and 25% Matrigel (BD) and injected subcutaneously in the flank of non-obese diabetic/severe combined immunodeficient (NOD/SCID) mice with null expression of interleukin-2 receptor gamma chain (NSG mice). Treatment groups were a mix of male and female mice. All animal experiments were planned and performed according to IACUC protocols.

In Vivo Tumor Imaging. Mice were anesthetized via inhalation of isoflurane at 3 L/min and maintained at 1.5 L/min. Images were acquired using a Perkin Elmer IVIS Spectrum with excitation and emission filters set at 535 nm and 580 nm respectively optimized for tdTomato imaging. Images of each face of the sagittal plane were taken to capture both left and right flanks. Mouse fur was soaked with ethanol to reduce auto fluorescence prior to imaging. Three Fluorescent standards were used to subtract background fluorescence and calibrate imager. Images were analyzed in Image J where the length and width of the td tomato tumor was measured. Analysis of tdTomato intensity was done using Living Image from Perkin Elmer which involved spectral unmixing of 10-13 images to sufficiently remove any tdTomato auto-fluoresces from the mice.

Antibody Treatment. Mice were warmed under a heat lamp prior to tail vein injection to dilate the vein. Rabbit anti-human IgG made against human red blood cells (anti-hum) from Rockland Immunochemicals and serum purified rabbit IgG from Sigma-Aldrich was reconstituted per manufacturer's direction and further diluted using sterile PBS. Mice were injected with 600 µg/animal (~20 mg/kg) twice a week. Anti-human IgG (H+L) (Sigma Aldrich) was injected at 8 µg/animal (~0.3 mg/kg) daily for one week. Mouse anti-human Mucin 1 was purchased from ThermoFisher (MA5-15131) and given to mice as 10 ug per animal twice a week. Cetuximab was purchased from Invivogen and given to mice as 10 ug per animal twice a week.

Generation of Drug Loaded Polymer Worms. Polyethyleneoxide (PEO)—Polybenzylcaprolactone (PBCL) diblock copolymer was obtained from Alberta Research Chemicals Inc. (ARCI), Edmonton, AB, Canada. Aggregates were formed in water by solvent evaporation of the copolymer dissolved in chloroform with the final concentration of polymer in water being 30 mg/ml. The aggregates were mixed with PKH 26 hydrophobic red dye, and morphology confirmed by imaging using an Olympus IX71 microscope with a 60× objective (oil, 1.25 NA) and Cascade CCD camera (Photometrics, Tucson, Ariz.). Paclitaxel dissolved in methanol, and was added to the aggregates at a concentration of 30 µg of drug per mg of polymer in dispersion. The mixture was stirred overnight, and the unincorporated drug was removed by dialyzing using a Slide-A-Lyzer Dialysis cassette with a Molecular Weight Cut-Off (MWCO) of 3000 (Thermo Scientific). The dialyzed mixture was centrifuged at 2000 rpm for 8 minutes prior to injection. The drug loading was measured via Shimadzu prominence HPLC (High Performance Liquid Chromatography) with Pinnacle DBC18 Column (4.6×150 mm, 5 µm particles). In vitro cytotoxicity was assayed as described in Cai et al., 2007.

Adoptive Transfer of NSG Bone Marrow. Femurs and tibias of donor NSG mice were removed, and bone marrow flushed with 4% FBS/PBS. Red cells were lysed by incubating for 10 min at room temperature with 3 parts RBC lysis buffer (Sigma) per 1 part 4% FBS/PBS. Cells were washed 2× and resuspended in warm 2% FBS/PBS. CFDA-SE (Invitrogen) was added 1:1000 and incubated for 15 min at 37° C., then spun, resuspended in warm complete DMEM, and incubated for an additional 30-40 min at 37° C. When applicable, anti-mSIRPA antibody was added during this incubation period. Cells were then washed, resuspended in 0.1% FBS/PBS, counted and volume adjusted to allow injection of 106 cells. Remaining cells were analyzed by flow cytometry to establish initial composition.

Preparation of Engineered Human Marrow. Fresh human bone marrow (cat #: ABM001-1 from AllCells) was incubated with equal volume of 3 mL red blood cell lysing buffer hybrid-Max (R7757 Sigma-Aldrich) for 10 mins in a 15 mL conical tube. Cells were placed in a centrifuge at 2000 rpm for 2.5 min immediately after incubation. Lysate was removed and remaining cells were suspended in 1 mL of red blood cell lysis buffer for a second lysis phase for 4 mins. Cells were spun down at 2000 rpms for 2.5 mins and resuspended in 500 uL of PBS. To this, 1 uL of 10 mM (prepared according to kit instructions) of CFDA SE solution from Invitrogen (V12883) was added and incubated with cells for 40 mins at 37° C., inverted 2-3 times every 5 mins. After this incubation period, SIRPA blocking (SE7C2) and Fc priming with anti-human (Rockland, 109-4139) antibodies were added to cells at 4 ug/mL and 100 ug/mL respectively. After incubation cells were spun down at 2000 rpms for 2.5 mins and resuspended in 1 mL of 5% FBS in PBS (wash). Cells were spun down again at 2000 rpms for 2.5 mins and resuspended in 100 uL of 5% FBS in PBS. Cell count was performed using a hemocytometer and cells were diluted to 40k cells per uL (8M cells total per mouse) for intravenous tail vein injection in tumor bearing mice. Mice that were treated with unprimed cells were injection intravenously with 600 ug (6 ug/uL) of human red blood cell antibody from Rockland 4-6 hrs prior to injection of engineered marrow cells.

Confocal Imaging. Confocal imaging was done in Leica TCS SP8 system with a 63×/1.4 NA oil-immersion objective, and Amira (FEI) was utilized for the 3D image reconstruction.

Ex Vivo Tumor Flow Cytometry Analysis. On the day of analysis mice belonging to the treatment cohort were injected with the standard antibody dose as described herein. Mice were euthanized 1.5-2 hours following injection by cervical dislocation. Tumors and spleens were removed, placed in 20% FBS, and tumor core and periphery tissue was segregated. Tumor tissue was cut into 1-3 mm pieces, transferred to 15 mL centrifuge tubes and spun to remove media. Tissue was then resuspended in 3 mL warm Dispase (STEMCELL Technologies) supplemented with 3 mg/mL Collagenase (Sigma) and 200 uL of 1 mg/mL DNase I (Roche). Samples were pipetted for 1-3 minutes until cloudy, but not stringy. Dissociation was quenched by addition of 10 mL room temperature PBS and suspension was filtered using a 70 µm cell strainer. Filtrate was spun, supernatant discarded, and pellet resuspended in 2% FBS for antibody incubation. Spleens were prepared by mechanical dissociation, filtration, and red blood cell lysis using Red Cell Lysing Buffer (Sigma). Lysed samples were washed and resuspended in 2% FBS for antibody incubation. Prior to antibody incubation samples were blocked with Fc Block (BD Pharmingen) (1:500) for at least 5 min at RT. CD47-AF647 (1:25), donkey anti-rabbit AF488 or AF700 (1:400), donkey anti-rat AF647 (1:400), F4/80 APC-Cy7 (3:50), CD11b PE-Cy7 (1:25), Gr-1 APC (1:25), hCD47 AF647 (1.5:50), and Hoescht 33342 (1:1250) were incubated at RT for 1 hour. After incubation, cells were washed and resuspended in 2% FBS.

Analysis of Mouse Blood Profiles. 100 uL of blood was isolated from anesthetized mice by Retro-orbital bleeds. Blood was collected in eppendorf tubes containing EDTA. Blood was kept at room temperature and immediately analyzed using a Drew Scientific Hemovet (HV950).

3D Migration Assay. Migration assays were performed using 24-well inserts with 3-µm, 5-µm, and 8-µm pore filters with $2 \times 10^6$, $4 \times 10^5$, and $1 \times 10^5$ pores per cm, respectively. Lung tumor cells were mixed with engineered marrow cells in a 10:1 ratio; $3 \times 10^5$ total cells were seeded in the top wells. The same 1:1 mixture of DMEM and F-12, supplemented with 15% FBS and 1% penicillin-streptomycin, was added to both top and bottom wells such that there was no nutrient gradient across the filter. After incubating for approximately 24 hours at 37° C. and 5% $CO_2$, cells were harvested from the top wells using Trypsin and from the bottom wells using both Trypsin and scraping.

RNA Isolation and Sequencing. For RNA isolation RNeasy plus Mini Kit (Qiagen) was used. Libraries for RNA-Seq were made by using TruSeq Stranded mRNA Library Prep kit (Illumina) per manufacturer's instruction, followed by 100 bp paired-end sequencing with HiSeq 2500 (Illumina). 10 cDNA libraries were pooled together, resulting in ~16,000,000 reads for each sample.

Mass spectrometry to determine antibody target list. Mass spectrometry (MS) samples were prepared using the same procedures outlined in (Swift et al., (2013) Science 341.6149: 1240104). Briefly, ~1 $mm^3$ gel sections were excised from SDS-PAGE gels and were washed in 50% 0.2 M ammonium bicarbonate (AB), 50% acetonitrile (ACN) solution for 30 min at 37° C. The washed slices were lyophilized, incubated with a reducing agent [20 mM TCEP in 25 mM AB solution], and alkylated [40 mM iodoacetamide (IAM) in 25 mM AB solution]. The gel sections were lyophilized again before in-gel trypsinization [20 mg/mL sequencing grade modified trypsin, Promega] for 18 hours at 37° C. with gentle shaking. The resulting tryptic peptides were extracted by adding 50% digest dilution buffer (60 mM AB solution with 3% formic acid) and injected into a high-pressure liquid chromatography system coupled to a hybrid LTQ-Orbitrap XL mass spectrometer (Thermo Fisher Scientific) via a nano-electrospray ion source.

Raw data from each MS sample was processed using MaxQuant (version 1.5.3.8, Max Planck Institute of Biochemistry). MaxQuant's built-in Label-Free Quantification (LFQ) algorithm was employed with full tryptic digestion and up to 2 missed cleavage sites. Peptides were searched against a FASTA database compiled from UniRef100 (June 2011) human, plus mouse and contaminants. The software's decoy search mode was set as 'reverse' and a MS/MS tolerance limit of 20 ppm was used, along with a false discovery rate (FDR) of 1%. The minimum number of amino acid residues per tryptic peptide was set to 7, and MaxQuant's 'match between runs' feature was used for transfer of peak identifications across samples. All other parameters were run under default settings. The MaxQuant output tables were then fed into its custom bioinformatics suite, Perseus (version 1.5.2.4), for protein annotation and sorting.

Synthesis of soft and stiffpolyacrylamide gels. Round glass coverslips (18 mm, Fisher Scientific) were cleaned in boiling ethanol and RCA solution (H2O:H2O2:NH4OH=2:1:1 in volume) for 10 min each, and then functionalized in ATCS solution (Chloroform with 0.1% allytrichlorosilane (Sigma) and 0.1% triethylamine (Sigma)) for an hour. Fresh precursor solution for 0.3 kPa soft gels (3% acrylamide+ 0.07% bis-arylamide in DI water) and 40 kPa stiff gels (10% acrylamide+0.3% bis-arylamide in DI water) were prepared respectively. Afterwards, 0.1% N,N,N',N'-tetramethylethylenediamine (Sigma) and 1% ammonium persulphate (Sigma) were added to each precursor solution and pipetted 20 ul of this mixture onto each coverslip to allow gel polymerization. To coat collagen-I on the gel, crosslinker sulpho-sanpah (50 µg/ml in 50 mM HEPES, G-Biosciences) was applied to cover the whole gel surface and photoactivated under 365 nm UV light for 7 min. Excess amount of sulpho-sanpah were washed after UV and collagen-I solution (100 µg/ml in 50 mM HEPES) was added for coating. The coating process usually takes overnight on shaker at room temperature to ensure saturation.

Additionally, human red blood cell samples were prepared each day for flow cytometry as an internal calibration and normalization standard for hCD47 expression.

Statistical Analysis. All statistical analyses were performed using GraphPad Prism 4. Unless otherwise noted, all statistical comparisons were made by unpaired two-tailed Student t test and were considered significant if P<0.05.

The results of the experiments are now described in the following examples.

Example 1: Engorge and Accumulate: Donor MΦ in Tumors are More Phagocytic than TAMs Two key issues addressed in the present invention were: (i) whether tail-vein injected marrow monocytes and macrophages (MΦ) accumulated measurably in a human solid tumor, and (ii) whether such cells could efficiently phagocytose human tumor cells. NSG mouse marrow cells were fluorescently labeled with the green dye CFDA, their SIRPα receptors were blocked, and their Fc receptors were primed with a targeting Ab (FIG. 1A—left). The targeting Ab's are all human specific (FIGS. 9A-9H), and included monoclonal Ab's against MUC1 and EGFR (Cetuximab) as well as a polyclonal anti-hum IgG that minimized selection of cancer cells lacking one specific antigen. The "Antibody-primed Plus SIRPα Blocked macrophages," A'PB MΦ, were tail vein injected into NSG mice bearing large solid tumors (8-wk old) of a human lung carcinoma cell line (A549) expressing tdTomato (FIG. 1A—middle). Three days after cell injections and a systemic boost of targeting Ab in amounts used in therapy or lower (FIG. 15), mice were sacrificed. Tumors were quickly isolated and disaggregated with collagenase for analysis by flow cytometry with a particular focus on non-cancer cells that were tdTom$^+$ (FIGS. 10A-10H). Surface markers F4/80 and CD11b identified most tissue macrophages, but tdTom$^+$ served as a marker for functional phagocytosis.

Figures 1B, 1C, 1D:
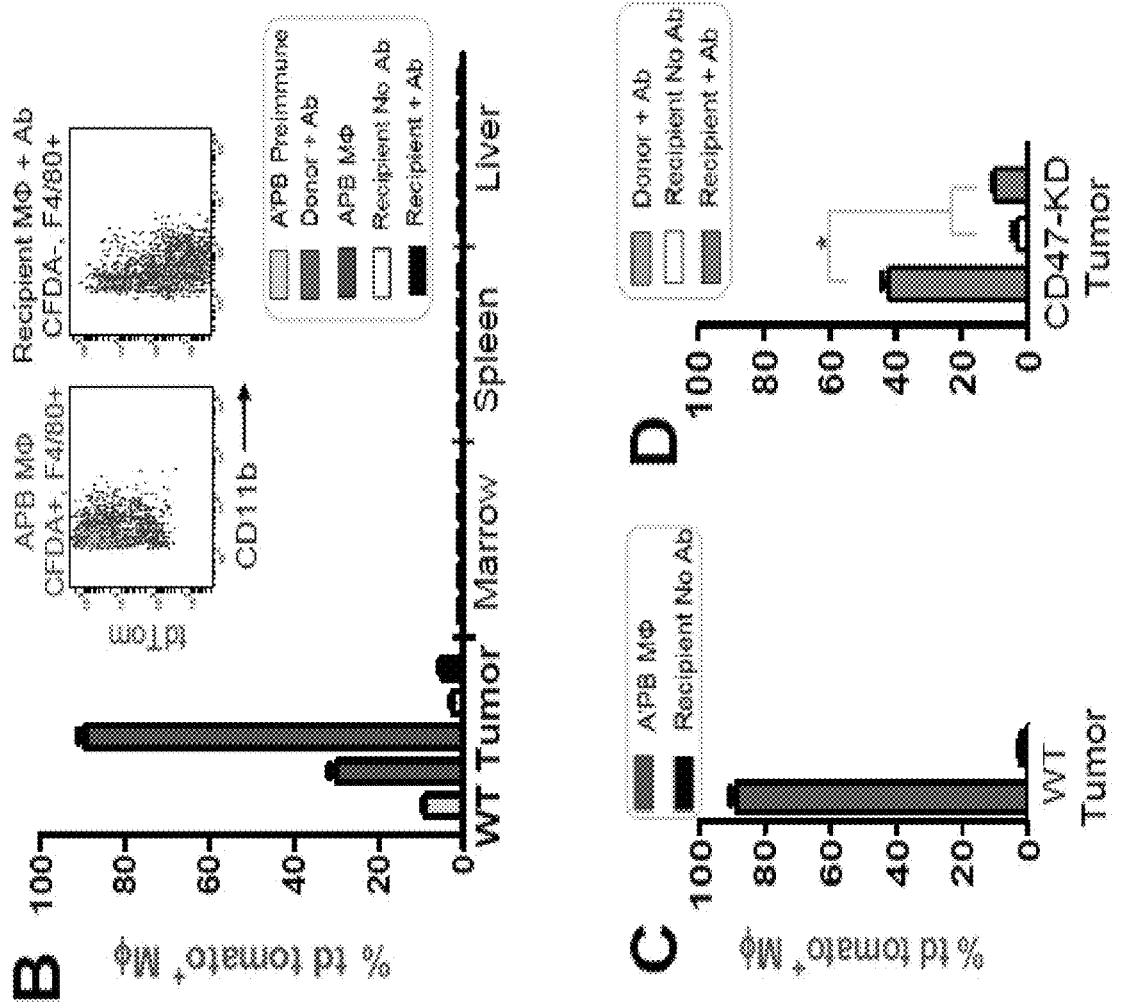

Phagocytic donor macrophages were detected in tumors but not marrow, spleen, or liver (FIG. 1B and FIGS. 11A-11G for knockdown tumors). This finding began to suggest that donor macrophages traffic into tumors and once they engorge they do not traffic elsewhere. Maximum phagocytic activity was found for the A'PB MΦ and the 'unprimed' version (APB MΦ), with 90% of these donor macrophages in the tumors phagocytosing cancer cells (respectively: FIG. 1B—inset left panel, FIG. 1C). No difference in phagocytic activity of donor macrophage subpopulations was detected as nearly all CD11b$^+$, F4/80$^+$, and CFDA$^+$ cells were also tdTom$^+$. Donor MΦ without SIRPα blockade, but with systemic anti-hum Ab were phagocytic, with 30% of these donor cells in the tumors phagocytosing cancer cells. Donor MΦ with SIRPα blockade combined with pre-immune Ab primed on the Fc receptors were much less phagocytic, with only 10% of MΦ in the tumors phagocytosing cancer cells despite systemic injections of the pre-immune Ab. Tumor associated macrophages (TAMs) were the least phagocytic of these WT tumors, with <5% of recipient MΦ in the tumors showing phagocytosis of cancer cells (FIG. 1B—inset right panel). This decreased by more than half in the absence of tail-vein injections of anti-hum Ab, but TAMs were clearly phagocytic toward CD47 knockdown tumors, with 12% in these KD tumors phagocytosing cancer cells after injections of anti-hum Ab (FIG. 1D). In the same KD mice, donor MΦ (without SIRPα blockade) were 40% phagocytic upon tail-vein injection plus opsonizing Ab. Compared to TAMs, donor macrophages were thus more phagocytic.

Figure 1E:
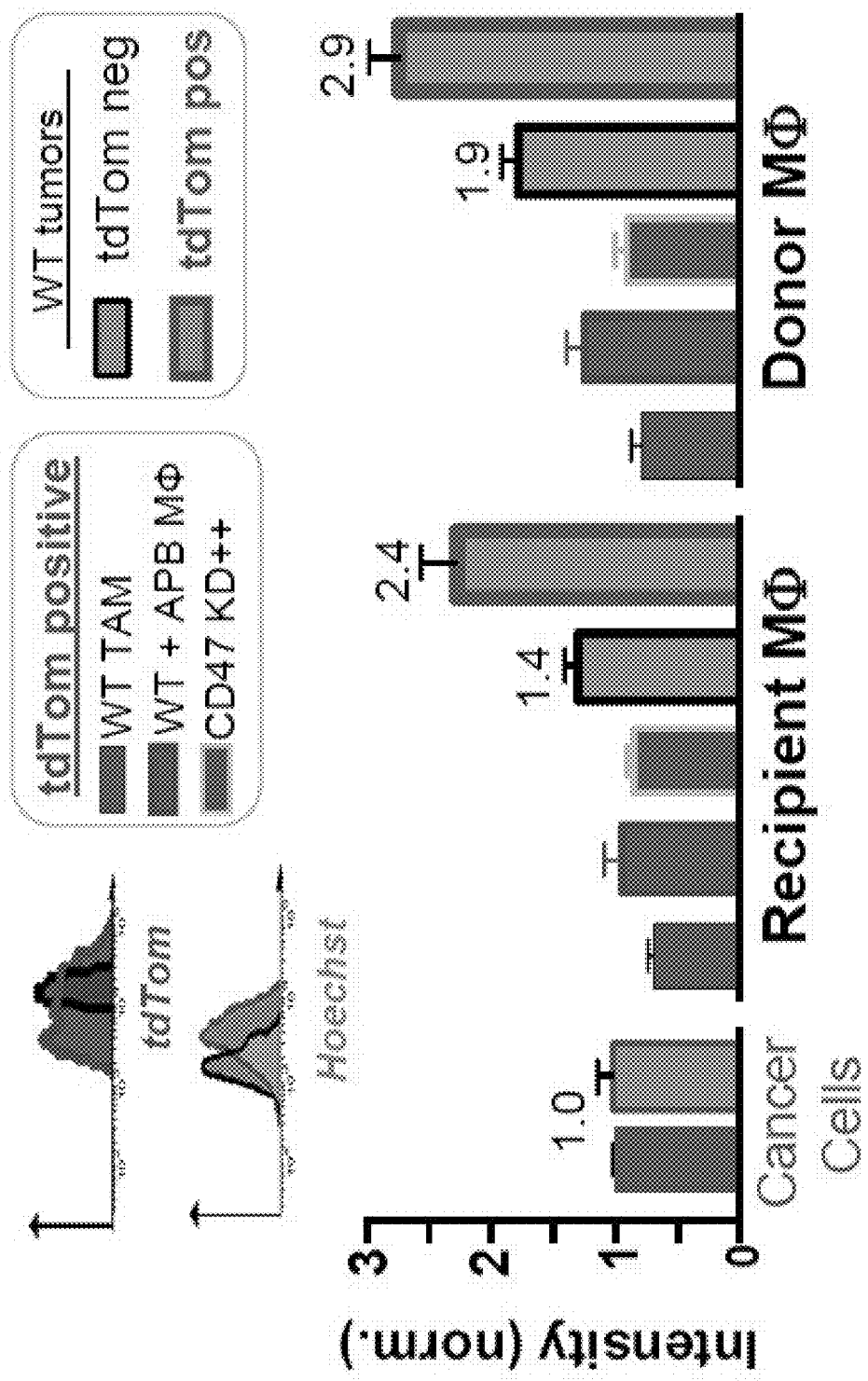
Figure 1F:
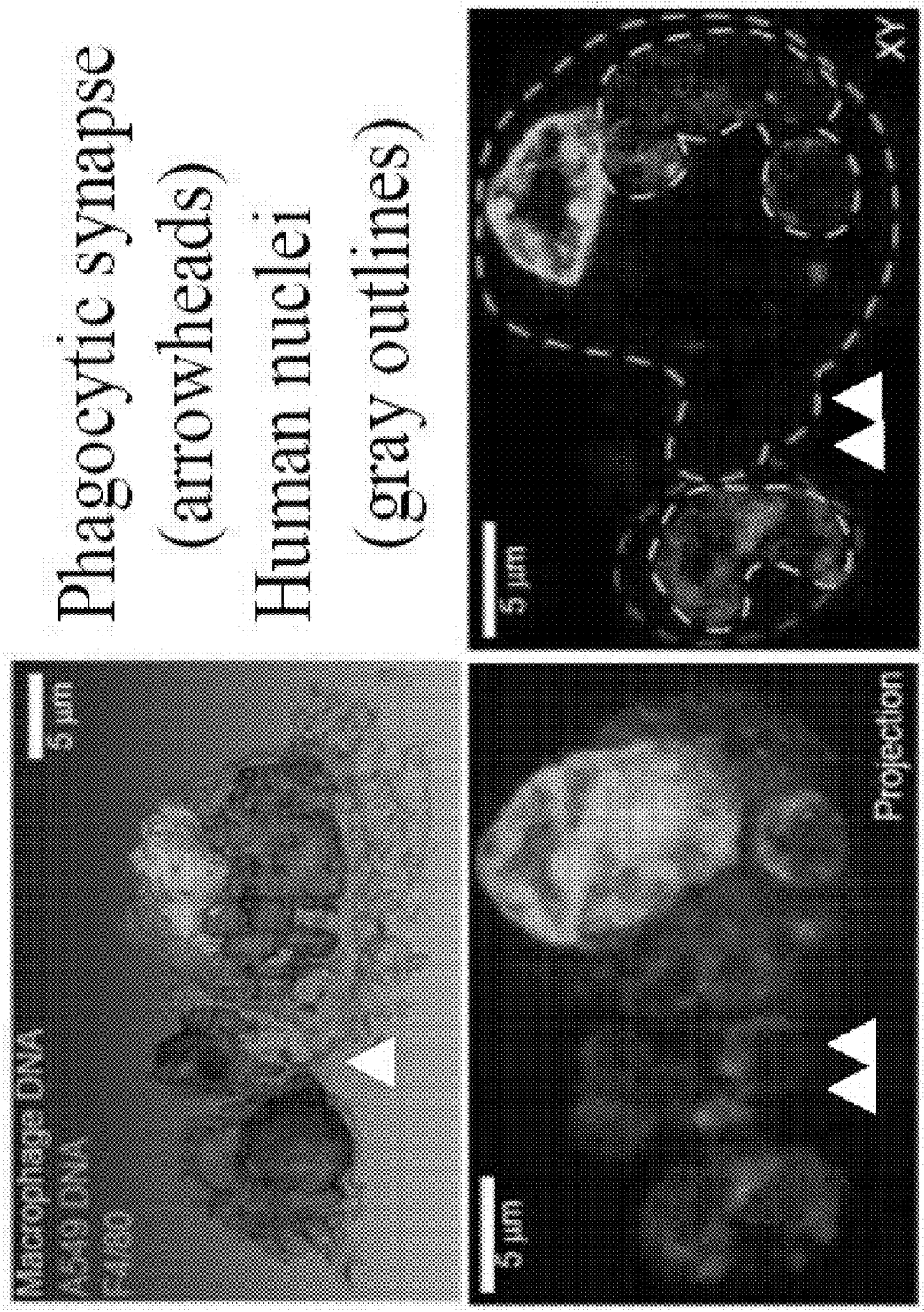

Complete engulfment of a tdTom$^+$ cancer cell by a macrophage was evident from an absence of secondary stain for anti-hum Ab which is abundant on tdTom$^+$ A549 cells (FIGS. 10A-10H). This suggested macrophages are internalizing Ab with Fc receptor as they eat. All tdTom$^+$ macrophages showed a similar average tdTom intensity as the A549 cells (FIG. 1E), with the most phagocytic cells (Sirpα blockade) showing higher intensity at a single cell level than the least phagocytic cells (TAMs eating WT tumors). The distribution of tdTom intensities in macrophages was much broader and skewed to lower signal than the tight distribution for cancer cells (FIG. 1E, histogram), consistent with degradation of the cancer cell after engulfment. Confocal imaging (FIG. 1F) of a disaggregated tdTom A549 tumor from a mouse treated with mouse A'PB MO's confirmed internalization of cancer cells into phagosomes that also display an abundance of F4/80 surface marker. The human nuclei were particularly prominent, and of course eliminating cancer cells in a tumor requires such engulfment. DNA-Hoechst stain intensities were therefore analyzed for recipient and donor macrophages from tumors that were tdTom positive or negative. Normalization to cancer cells showed recipient and donor tdTom positive macrophages had higher DNA intensity by about one cancer cell nucleus compared to tdTom negative macrophage (FIG. 1E). As with tdTom intensity distributions, the DNA intensity for tdTom positive macrophages showed greater variation than that in tdTom negative macrophages (FIG. 1E, histogram). Macrophages were thus consuming the entire cancer cell, which is consistent with higher Forward and Side Scatter for tdTom positive macrophages compared to tdTom negative macrophages (FIGS. 10A-10H). Confocal imaging of these samples also showed engulfment of cancer cells and their nuclei (FIG. 1F).

Figure 1G:
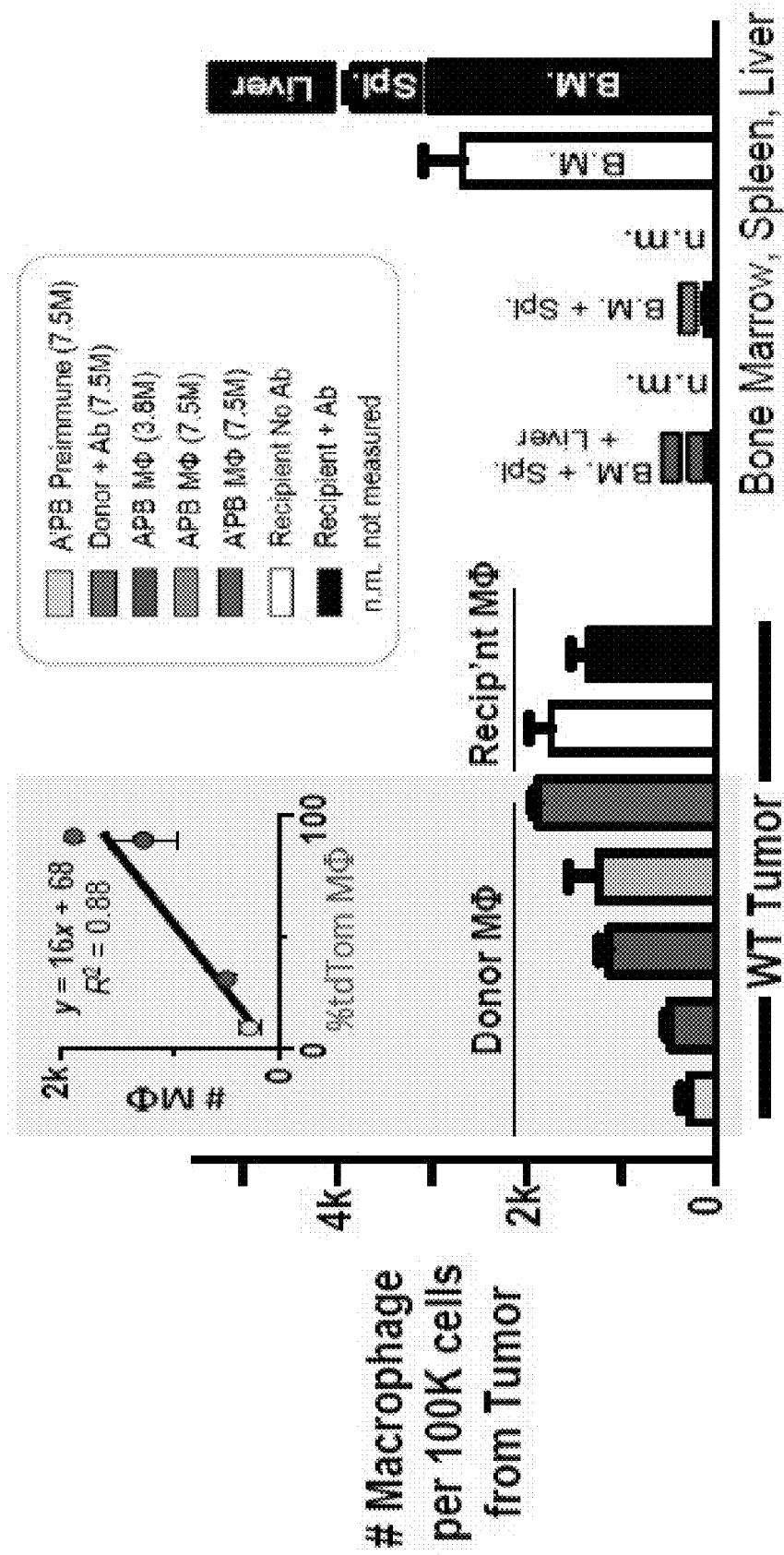

Although tdTom positive macrophages were detected only in wildtype tumors and not in marrow, spleen, or liver, these latter tissues did harbor some donor macrophages in addition to the expected recipient macrophages (FIG. 1G and FIGS. 11A-11G for knockdown tumors). Bone marrow had 2-3K macrophages per 100K cells, which makes this a reasonable source of donor macrophages (FIGS. 10A-10H). The spleen and liver are known to filter out injected cells and particles, and bone marrow homing of at least some marrow-derived macrophages seemed sensible. Nonetheless, donor macrophages injected shortly after systemic anti-hum Ab accumulated more so in tumors (per 100K cells) than the other tissues (FIG. 1G). Regardless of whether 6M or 12M of the highly phagocytic donor cells were tail-vein injected, about ~1.5K donor macrophages were detected in tumors. Without wishing to be bound by any specific theory, excess donor macrophages not in the tumor may disperse widely in other tissues and/or die. The tumor thus seemed saturated, consistent with a crowded solid tumor with only small pores to squeeze through. Donor neutrophil accumulation in the tumor was 30-fold less than donor macrophages, and therefore neutrophils likely contributed little to tumor shrinkage (FIGS. 10A-10H).

Importantly, tumor accumulation increased linearly by almost 10-fold as donor cells were made more phagocytic (i.e. SIRPα-blocked plus anti-hum Ab) (FIG. 1G, upper inset plot). Highest in abundance were the APB and A'PB macrophages that achieved tumor numbers similar to the resident TAMs. The abundance of TAMs was unaffected (or perhaps decreased slightly) with tumor opsonization and with the low level of phagocytosis by TAMs.

Example 2: Macrophages Engorge and Accumulate Above Small Pores In Vitro

Figure 2A:
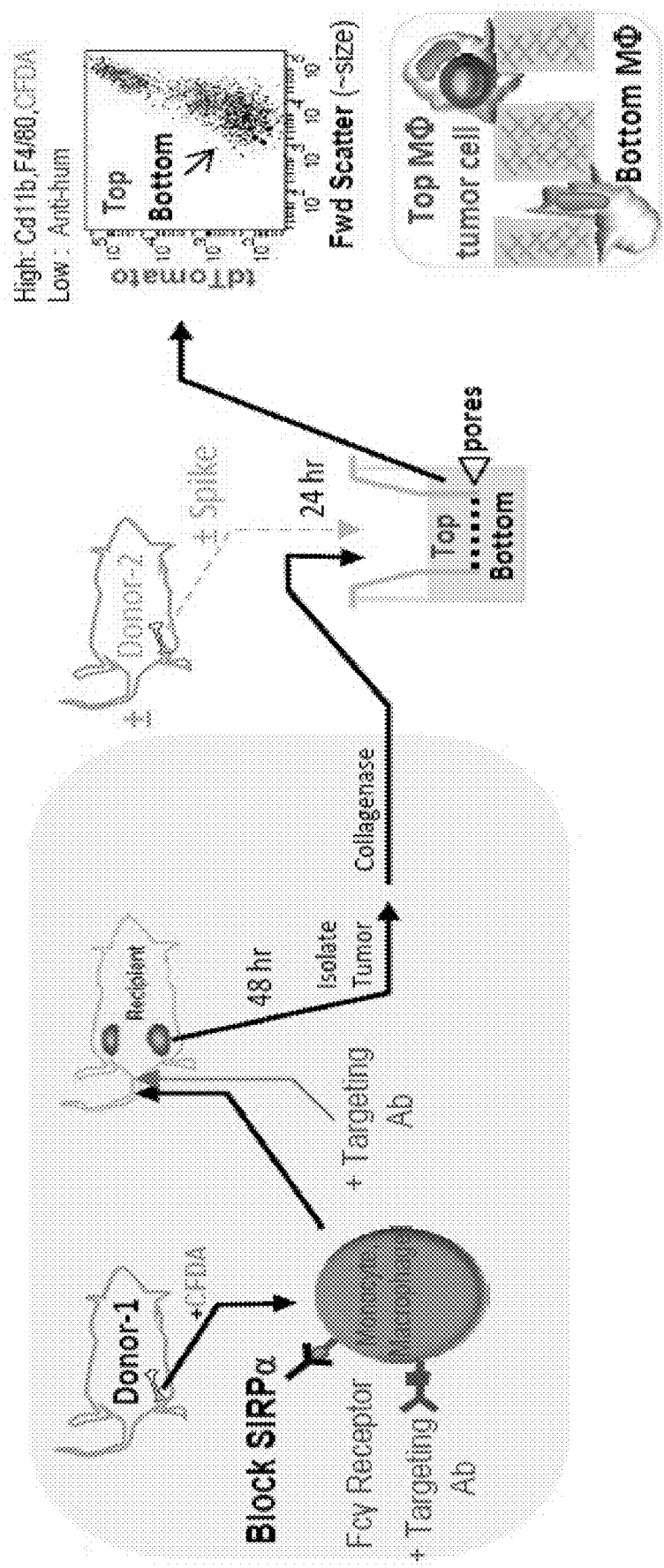
FIGS. 2A-2C are a series of graphs and images showing engineered donor macrophages in recipient tumors assayed for phagocytosis and 3D-Motility.

Macrophages that have engorged an entire A549 cancer cell could be physically impeded in 3D-migration as nuclear size and stiffness hindered both the 3D migration of hematopoietic cells and migration of A549 cancer cells in these same tumors. To assess an 'engorge and accumulate' mechanism in which macrophages eat more and thereby migrate less, tumors were disaggregated once again and all tumor-derived cells were plated for 24 hrs on the tops of transwells with small or large pores (FIG. 2A—right). Transwells with 3 μm pores or larger were used as they have similar micro-pore diameters as the solid tumors here and they recapitulated key trends for 3D-migration. Flow cytometry scatterplots (FIG. 2A flow scatterplot and FIGS. 12A-12E) showed macrophages on top of a transwell had far higher tdTom intensity and were much larger in size compared to macrophages on the bottom. The large size of macrophages relative to the smallest pores used here was confirmed by the scale bar in confocal imaging (FIG. 1F).

Figures 2B, 2C:
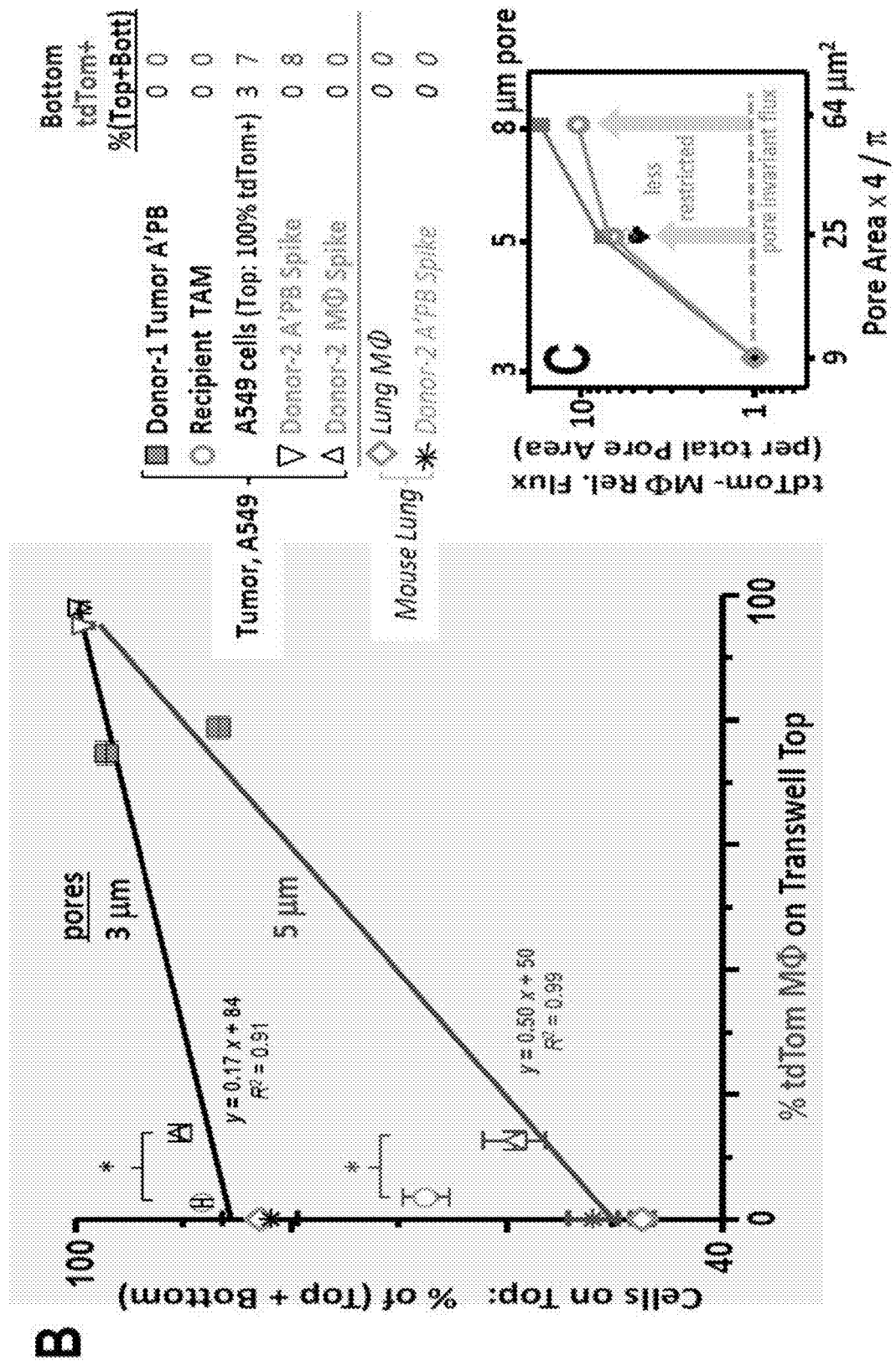

Macrophages were focused on, including the recipient's tumor associated macrophages (TAMs) because macrophages showed the highest level of engulfment of tdTom+ cancer cells compared to monocytes and neutrophils (FIG. 1B and FIGS. 12A-12E). Spike-in of fresh marrow cells from a second donor (Donor-2) was added to the disaggregated tumor cells in order to make direct comparisons to fresh macrophages that had not trafficked in vivo. Much more migration of TAMs and spiked marrow macrophages (without blockade or targeting) was found relative to A'PB MΦ (spiked or injected), with the large-pore transwells showing the greatest differences (FIG. 2B and FIGS. 12A-12E). Spiked A'PB MO did not show a dependence on pore size, with nearly 100% of cells on top phagocytosing cancer cells for both pore sizes. The A'PB MO pulled directly from the tumor were similar with ~80% on top phagocytosing cancer cells. Spiked marrow macrophages without SIRPα block were far less phagocytic with only 12% on top phagocytosing cancer cells. However, TAMs from the recipient were even less phagocytic than any donor macrophages, with only ~3% on top phagocytosing cancer cells. This >30-fold range of phagocytosis occurred despite the fact that all cells were mixed together with the same Ab opsonized cancer cells. Importantly, macrophage flux—which is calculated by dividing by both pore area and pore number—was by far smallest for 3 μm pores with little difference between 5 and 8 μm pores (FIG. 2C).

Phagocytosis on bottom was detected only for the most phagocytic A'PB MΦ that were spiked in and only for the more permissive large pore transwell (FIG. 2B table and FIGS. 12A-12E); the result could reflect phagocytosis of the small number of tdTom cancer cells that migrate to bottom. To verify that the A'PB MO could indeed squeeze efficiently through pores if they had not engulfed a lung cancer cell, these MΦ's were spiked into disaggregated NSG lung tissue on top of a transwell. No phagocytosis was observed, and more than 50% of all macrophages migrated, including both spiked A'PB and lung MΦ (FIG. 2B and FIGS. 12A-12E). The various ex vivo studies confirmed the higher phagocytic activity of donor cells versus TAMs, consistent with the hypothesis that phagocytic engorgement of cancer cells impedes 3D-migration within tumors to favor marrow macrophage accumulation.

Example 3: Donor MΦ with Sirpα Block and Primed Fc Receptor Shrink Tumors

Figures 3A, 3B:
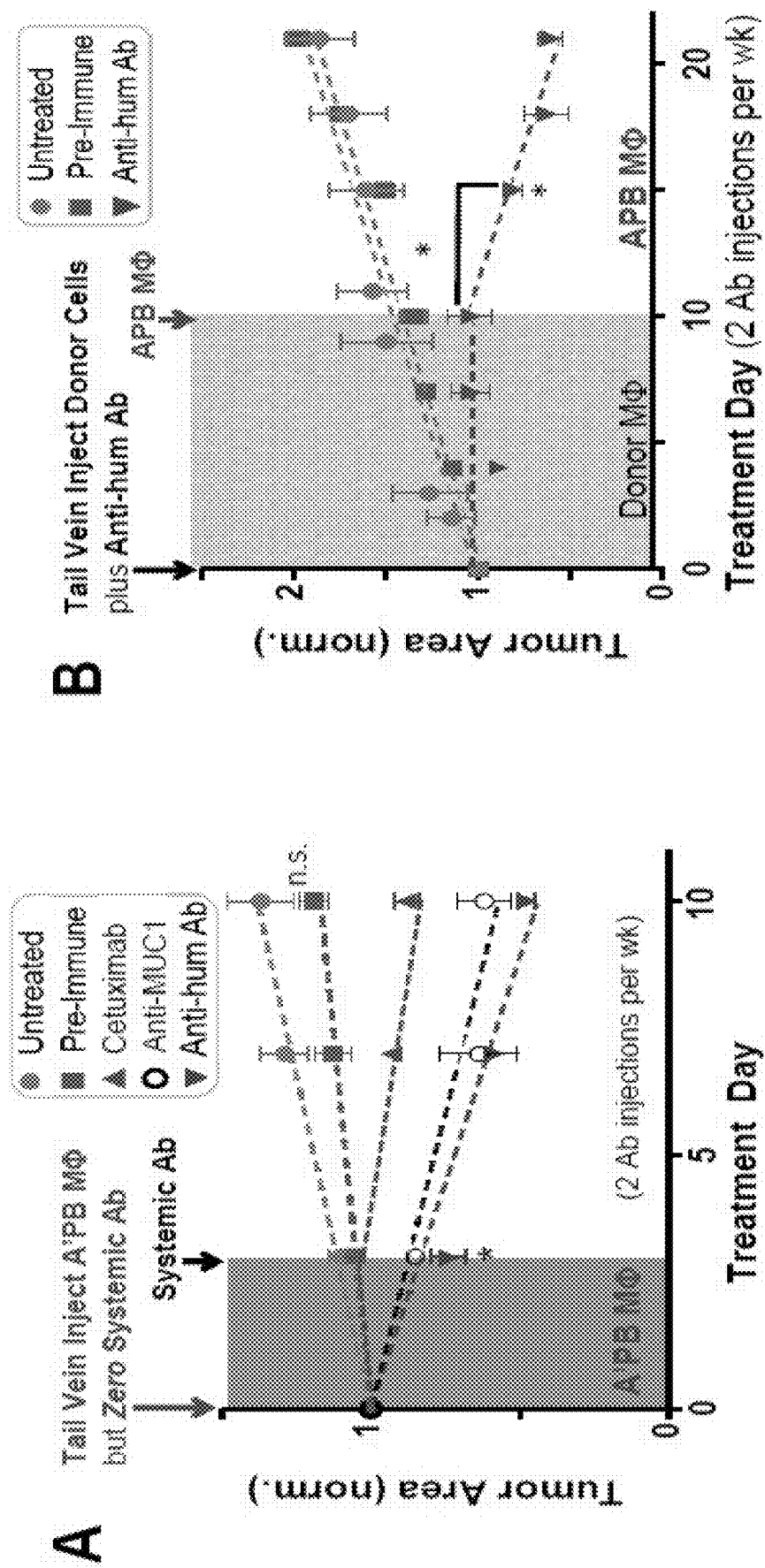
FIGS. 3A-3F are a series of graphs and images showing SIRPA block on donor macrophages enhances tumor shrinkage while tumor associated macrophages selectively clear only CD47 knockdown tumor cells in WT/CD47 KD mosaic tumors.

Tumor size measurements following tail-vein injection of A'PB MΦ were made from the total tdTom signal from the cancer cells which was also used for the cross sectional area of the tumor. For the first three days, no targeting Ab was injected systemically because A'PB was loaded directly with the targeting antibody. Tumors shrank −25% with anti-hum A'PB and −15% with anti-MUC1 A'PB, but in the same time period Cetuximab (anti-EGFR) A'PB and pre-immune A'PB gave similar ~10% tumor growth as untreated tumors (FIG. 3A). Anti-MUC1 is a mouse IgG that bound very strongly to Fc receptors on mouse MΦ compared to the humanized IgG Cetuximab (FIGS. 9A-9H). Tumor shrinkage was accompanied by decreases in tdTom intensity, which was consistent with phagocytosis and degradation of tdTom protein (FIG. 1E) on a timescale faster than days (FIGS. 10A-10H). Since the strongly bound targeting Ab on the A'PB was engulfed during eating (FIG. 1F and FIGS. 10A-10H), supplemental tail-vein injections of targeting Ab began after day-3, with twice per week injections being typical for multi-week chemotherapy. Untreated and pre-immune treated tumors grew 15-30% larger by day 10 while treated tumors continued to shrink almost linearly, by more than −50% with anti-hum, −38% with anti-MUC1, and −15% with Cetuximab. Binding of Cetuximab to A549 cells was strong after systemic injection (FIGS. 9A-9H), which provided for successful opsonization even though the A'PB lost their weakly associated Cetuximab before or shortly after injection. Anti-MUC1 injections at >10-fold higher doses have been found completely ineffective at treating tumors (Kufe, (2009) Nat. Rev. Cancer 9, 874-85), which makes the findings here unique. Cetuximab injections at 50-fold higher doses only delayed growth of A549 tumors by about half (Hsu et al., (2010) Mol. Cancer 9, 139). Paclitaxel treatments of the same tumor model also shrank almost linearly and shrank by day 10 to −25% (Nair et al., (2016) Nanomedicine), which demonstrates that the engineered macrophage treatments might be even more effective than a standard chemotherapeutic.

To assess the effect of SIRPα blockade, donor cells without SIRPα blockade were tail-vein injected with systemic anti-hum Ab which resulted in inhibition of tumor growth for 10 days (FIG. 3B and FIGS. 10A-10H). Subsequent injection of donor cells with SIRPα blockade (APB MΦ D) decreased tumor size and tdTom intensity by almost −50% over 10 days (FIG. 3B—right half of plots and FIGS.

10A-10H). Mice treated with donor cells but only a pre-immune, non-specific Ab continued to grow at the untreated rate. Ab opsonization of cancer cells is thus essential for engulfment of cancer cells in vivo, and SIRPα blockade will synergize to drive tumor shrinkage.

Example 4: Tumor Associated Macrophages (TAMs) can Only Shrink CD47 Knockdown Tumors Because in vitro and in vivo data indicated TAMs were minimally phagocytic of wildtype tumors (FIGS. 1B and 2B) but could engulf cancer cells with CD47 knockdown (FIGS. 1D and 1E), mosaic tumors were generated with ~2:1 control cells (sh-Control) expressing GFP (FIGS. 10A-10H and FIG. 16). No significant difference in tumor growth rate was observed between Mosaic, WT/shCtl and CD47 KD tumors for moderate knockdown (FIG. 3C and FIGS. 10A-10H). Deep knockdown of CD47 did, however, increase tumor growth rates (FIGS. 10A-10H), which hints at re-programming and potential dangers of knockdown thera-pies. Tail-vein injection of anti-hum Ab was sufficient to shrink mosaic tumors to a small, stable size with (untreated/treated) tumor sizes at day-18 of (1.5/0.7)=2.1. To determine which cancer cells were engulfed, tumors were analyzed by flow cytometry. Untreated tumors averaged 2:1 KD:WT (as GFP$^+$:GFP$^-$) versus treated tumors 0.4:1 KD:WT. The change in ratio agreed with the in vivo imaging results: for every 3 cancer cells in untreated tumors, only 1.4 are present after treatment, i.e. (3/1.4)=2.1. More importantly, the results showed KD cancer cells were selectively phagocy-tosed (5-fold more) compared to WT.

Figures 3C, 3D:
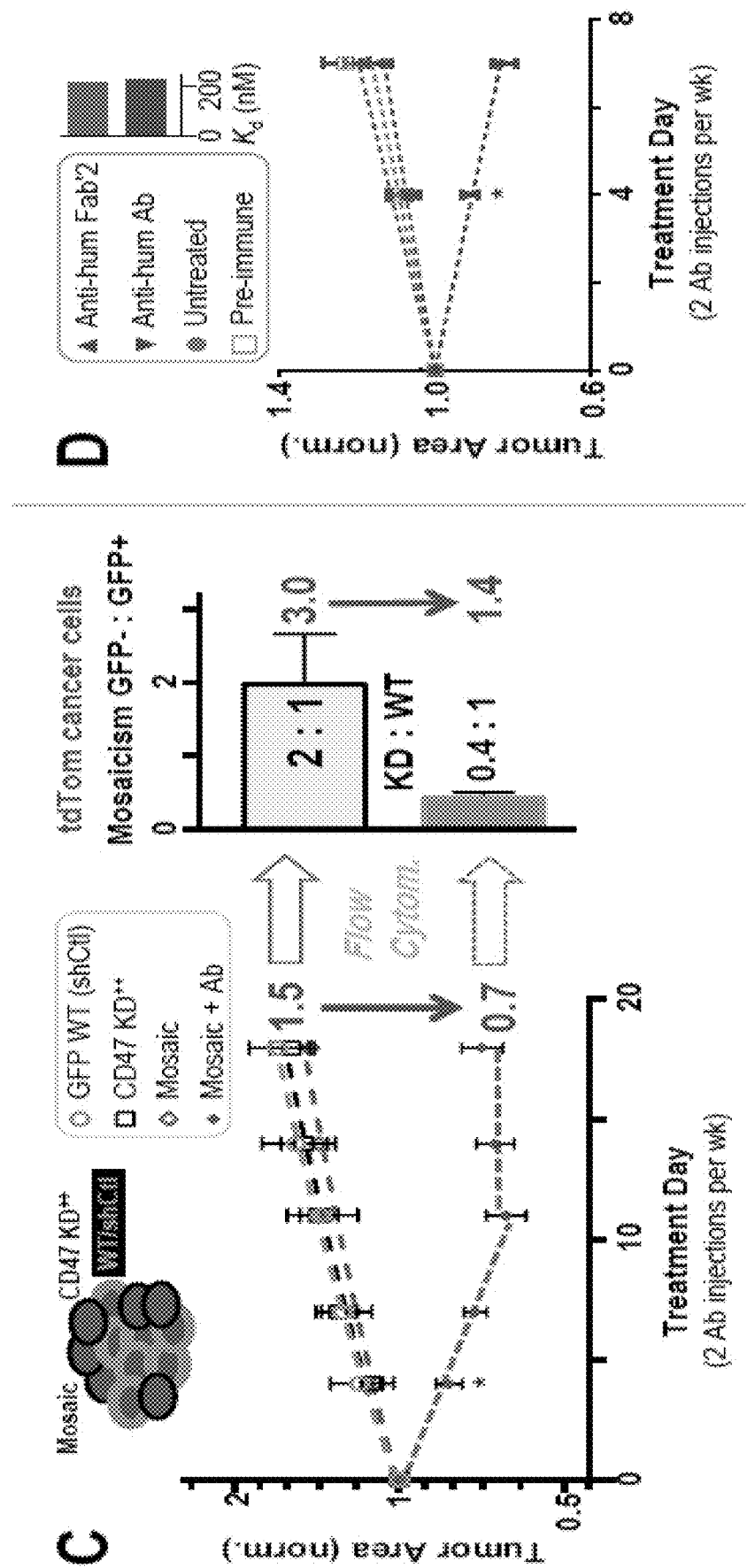

The Fc part of a targeting Ab is expected to not only bind to Fc receptors on macrophages (FIGS. 9A-9H and FIGS. 10A-10H) but also activate the receptors when they cluster on cancer cells, thereby driving phagocytosis and tumor shrinkage. On the other hand, calreticulin opsonization of cancer cells has been described as contributing to macro-phage-driven tumor shrinkage upon CD47 inhibition. To test the pathway here, the Fc fragment was cleaved off of the anti-hum Ab to generate a F(ab')2 with similar binding affinity as the intact Ab (FIG. 3D inset). Neither F(ab')2 nor the pre-immune Ab affected growth of CD47 knockdown tumors (FIG. 3D). The result is consistent with a key role for Fc receptor activation and suggests binding of anti-hum Ab alone has no anti-tumor effect.

Figures 3E, 3F:
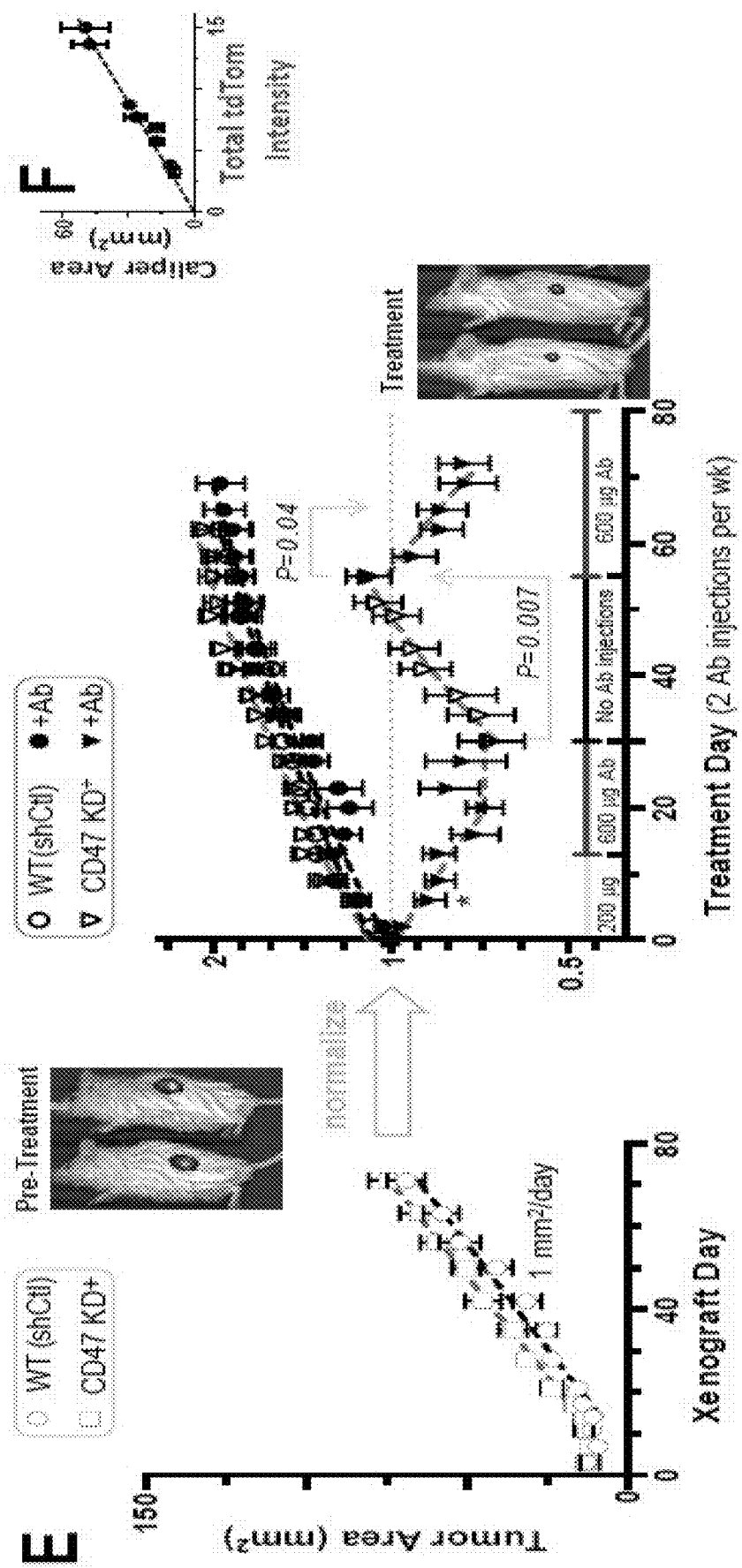

Treatment of WT/shCtl tumors and KD tumors with varying doses of anti-hum Ab could provide more definitive evidence that anti-hum Ab shrinks only KD cells. WT tumors and KD tumors grew at similar rates over 10 weeks (FIG. 3E), consistent with the mosaic tumors. Tail-vein injected anti-hum Ab with dose escalation had no effect on WT tumors but caused CD47 KD tumors to shrink 30% over three weeks (FIG. 3E—right plot). When anti-hum Ab treatment was stopped, tumors re-grew at a rate similar to pre-treatment. After 25 days of regrowth, tail-vein injection of more Ab once again caused tumors to shrink, with shrinkage occurring at rates similar to the first round of treatment.

Example 5: Engorge and Accumulate as a Mechanism for Tumor Shrinkage

Figures 4A, 4B:
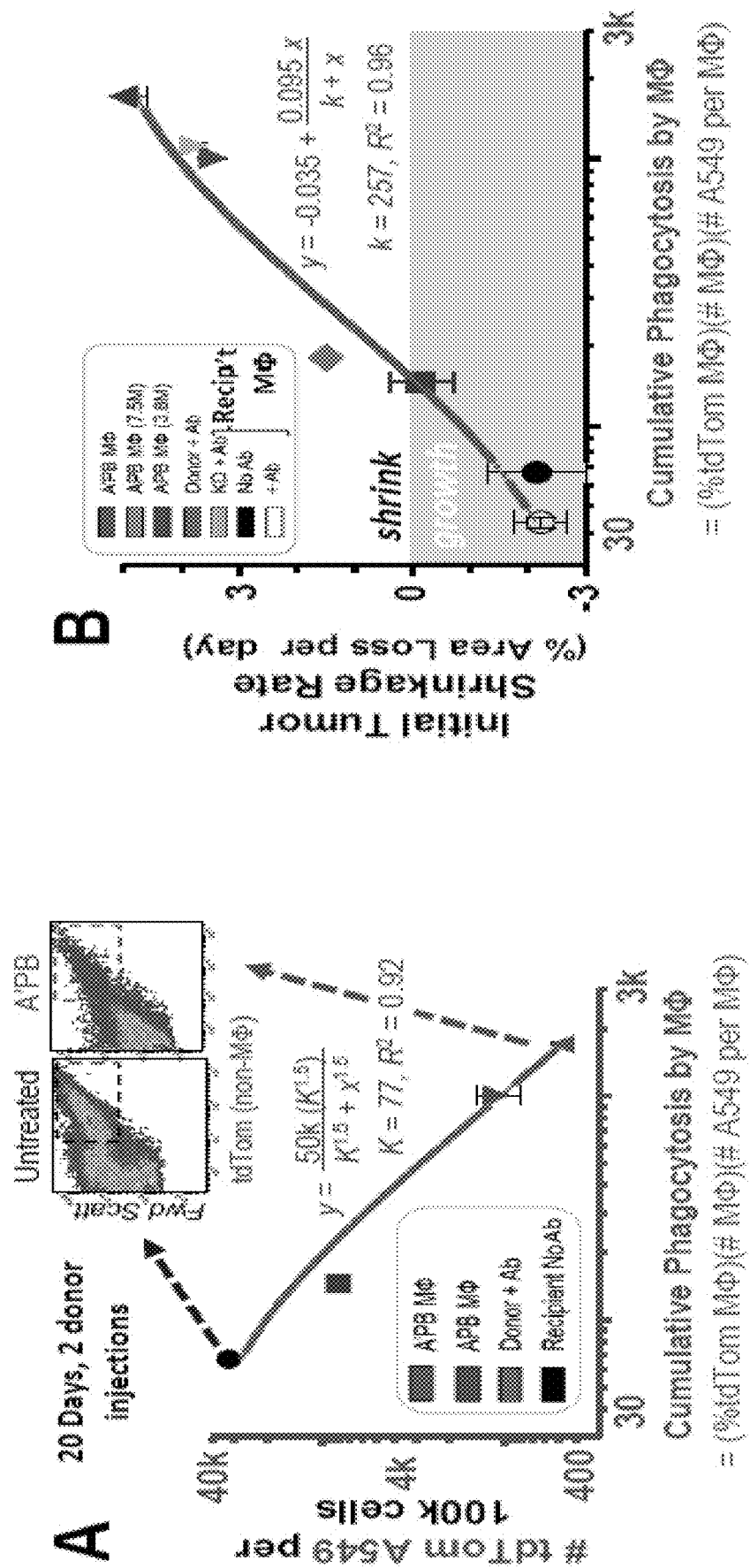
FIGS. 4A-4H are a series of graphs and images showing phagocytic capacity of donor and recipient macrophages.

Based on the findings described herein for a given con-dition, a "cumulative phagocytosis index" was defined by multiplying the percentage of tdTom positive macrophages (FIGS. 1B-1D) by the number of macrophages in the tumor (FIG. 1G) and by the number of cancer cells engulfed per macrophage (FIGS. 1E-1F). The number of tdTom A549 cells per 100k cells that remained in the tumor under different phagocytic treatments decreased when plotted ver-sus cumulative phagocytosis by macrophages (FIG. 4A). Thus, untreated tumors consisted of ~40% cancer cells (FIG. 4A, left inset scatterplot), but A'PB MΦ treatment decreased cancer cell number by ~100-fold (FIG. 4A, right inset scatterplot). Such selective clearance of the tdTomato cancer cells was not only consistent with the selective eating in mosaic tumors with CD47 knockdown cancer cells (FIG. 3C) but also with overall shrinkage of WT tumors by the engineered donor macrophages (FIGS. 3A-3B).

Figure 4C:
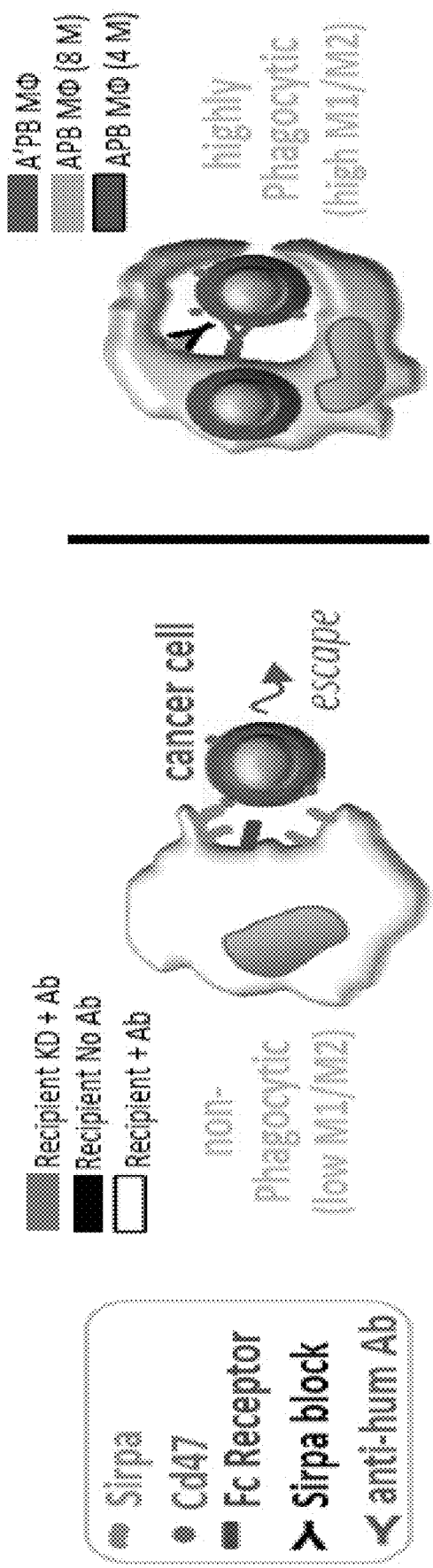
Figure 6:
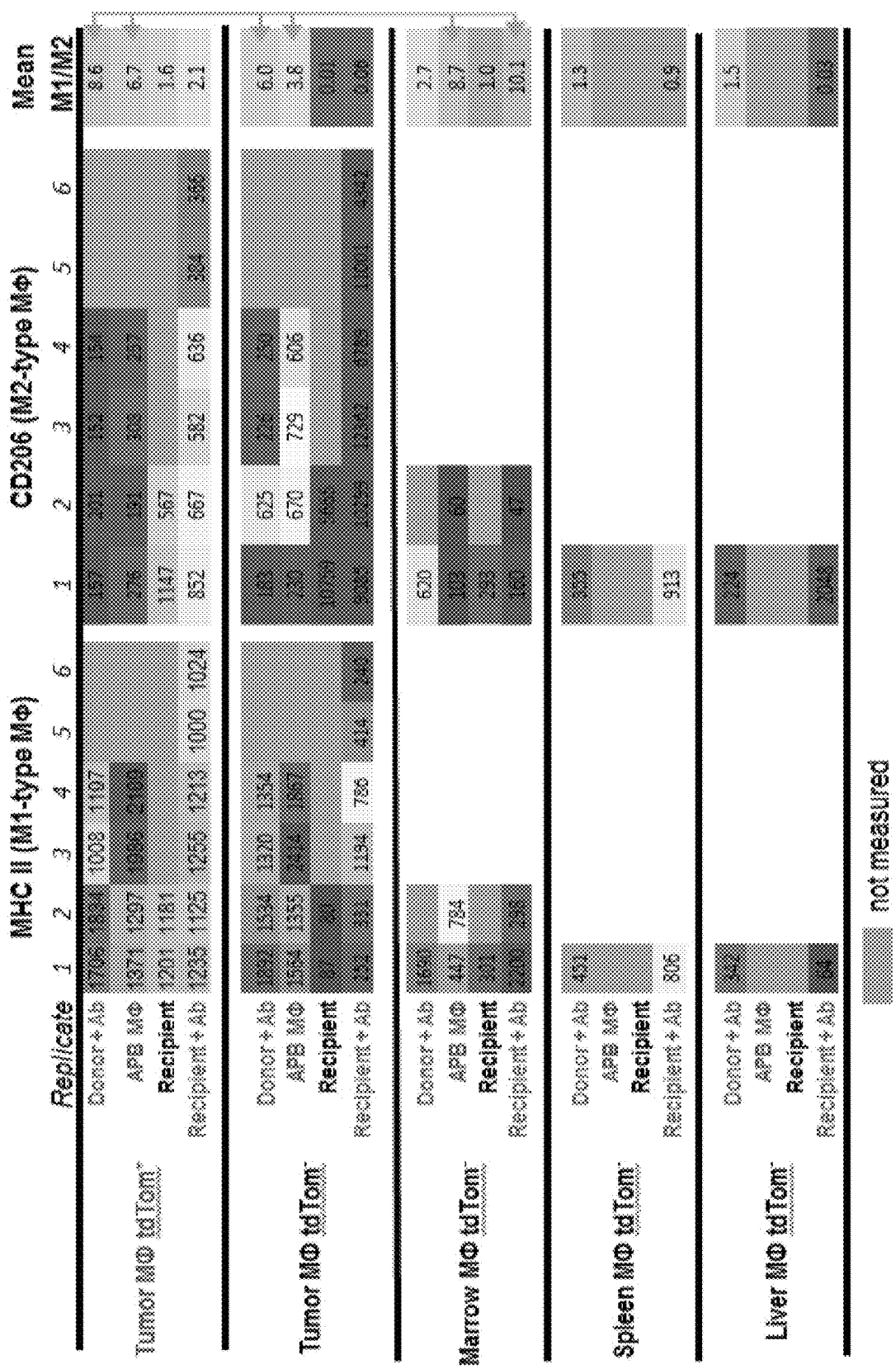
FIG. 6 is a table showing M1 and M2 analysis of eating macrophages. Donor and recipient macrophages isolated from different tissues were stained for M1 (MHC II) and M2 (CD206) markers. Donor cells, regardless of SIRPA blocking, had a high M1 to M2 ratio as did marrow macrophages. Recipient macrophages from the tumor were split depending if they were tdTomato positive (M1) or negative (M2).
Figures 9A, 9B:
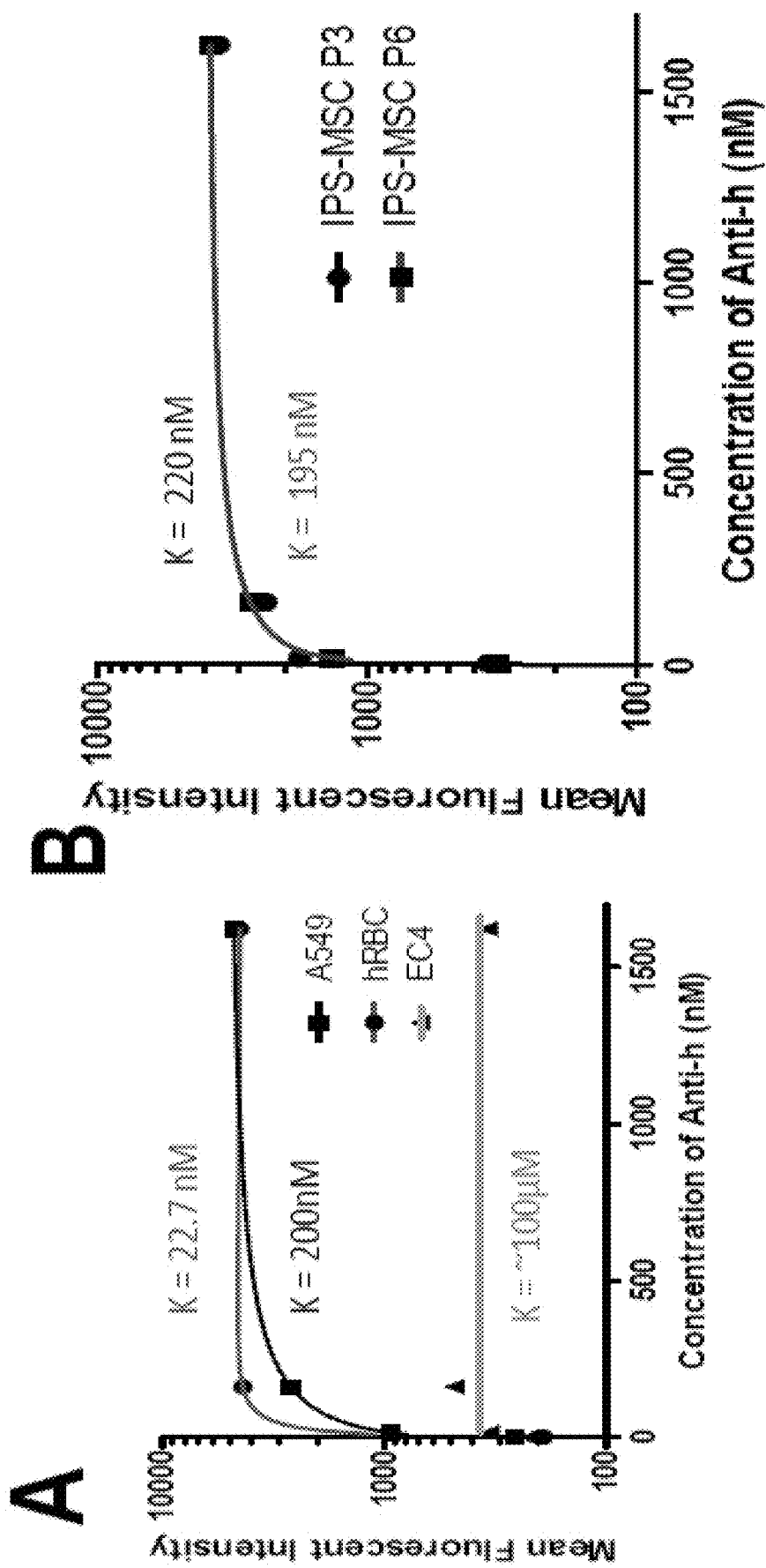
FIGS. 9A-9H are a series of graphs and images showing targeting antibodies bind mainly to human cells and mouse macrophage, causing no evident toxicity in mice.
Figure 9C:
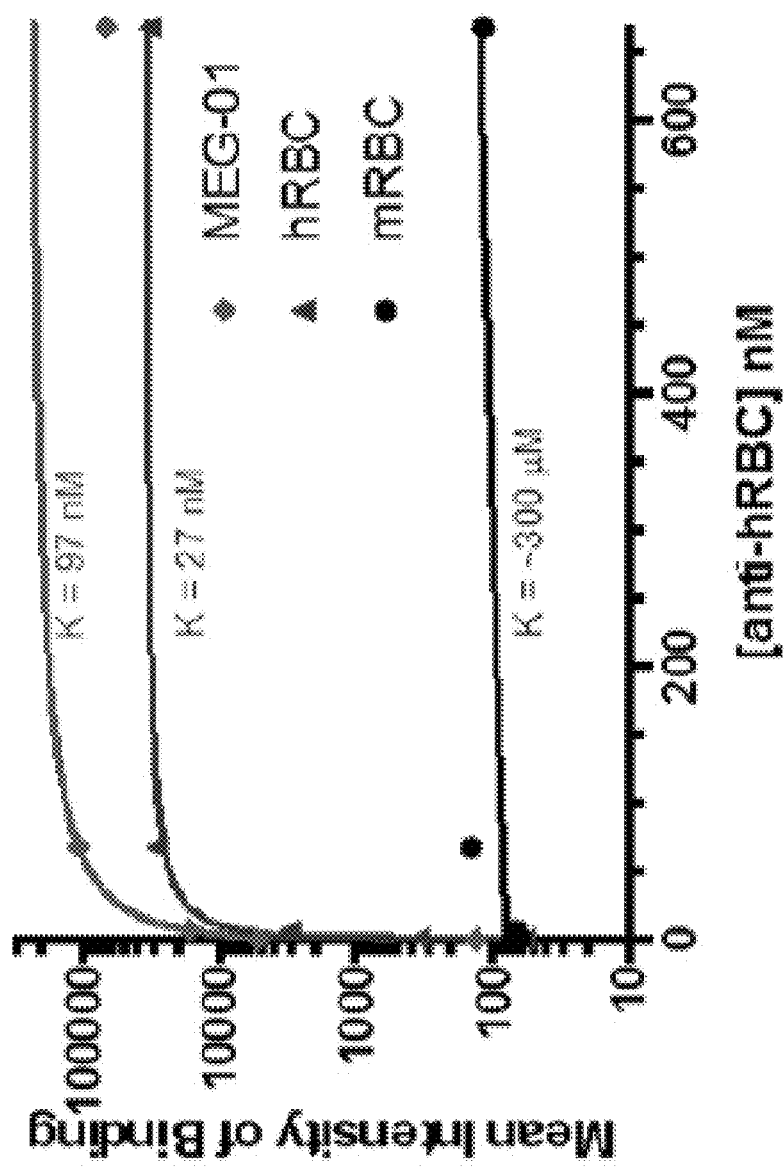
Figure 9D:
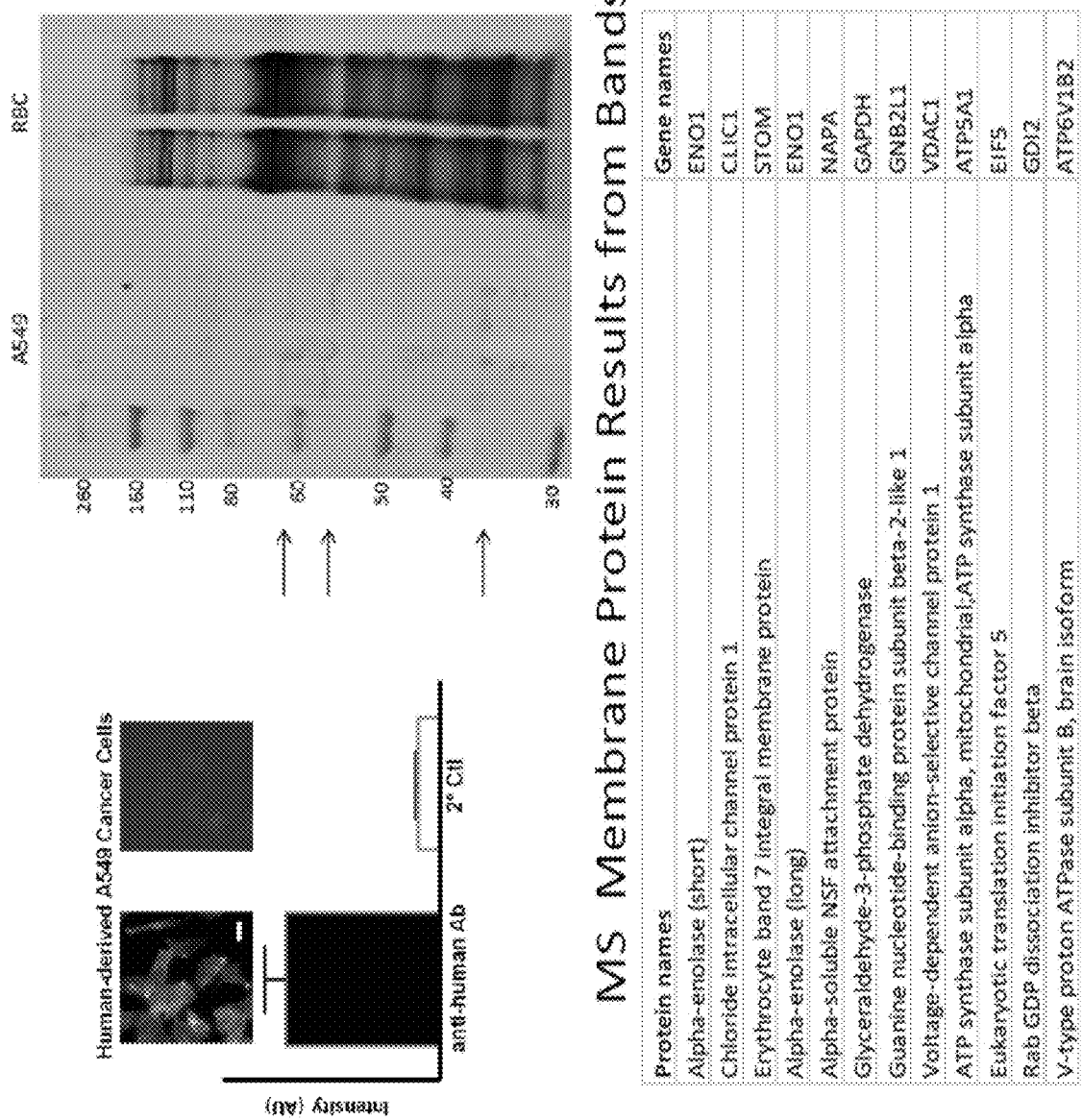
Figure 9E:
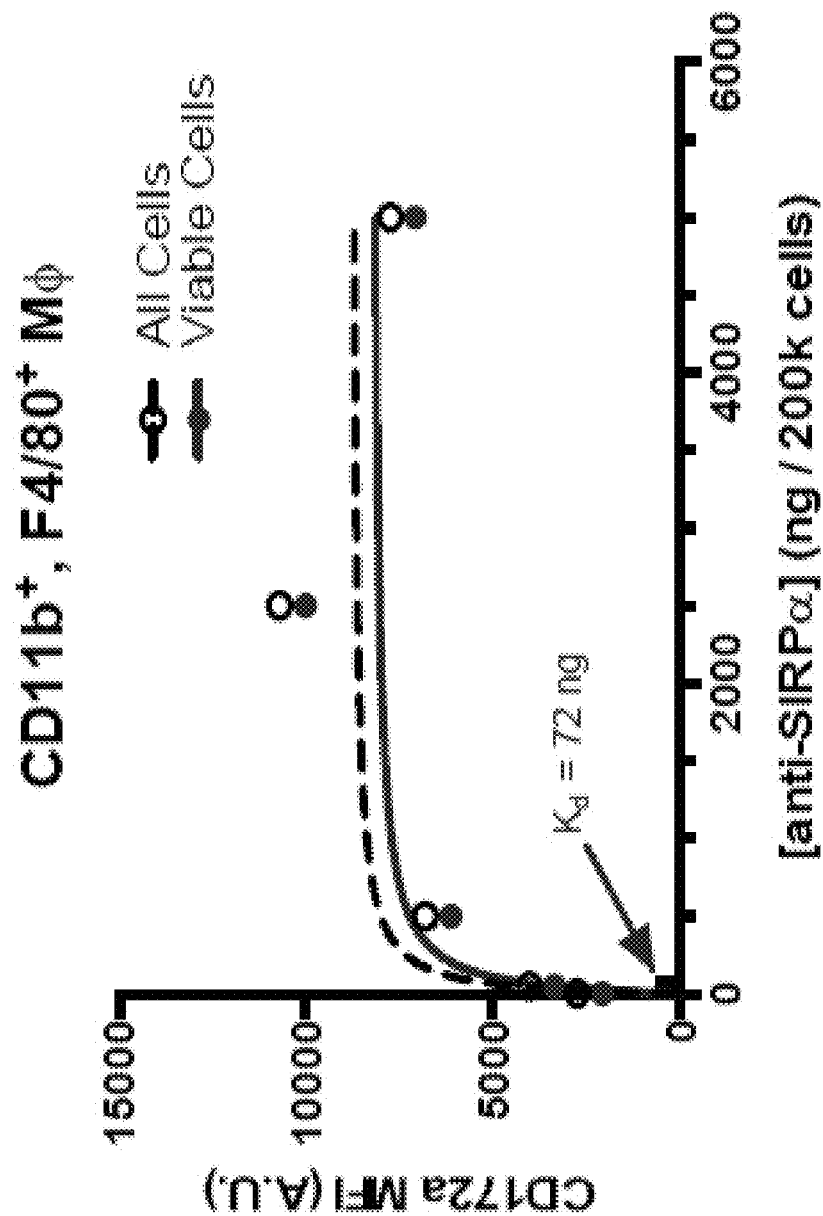
Figure 9F:
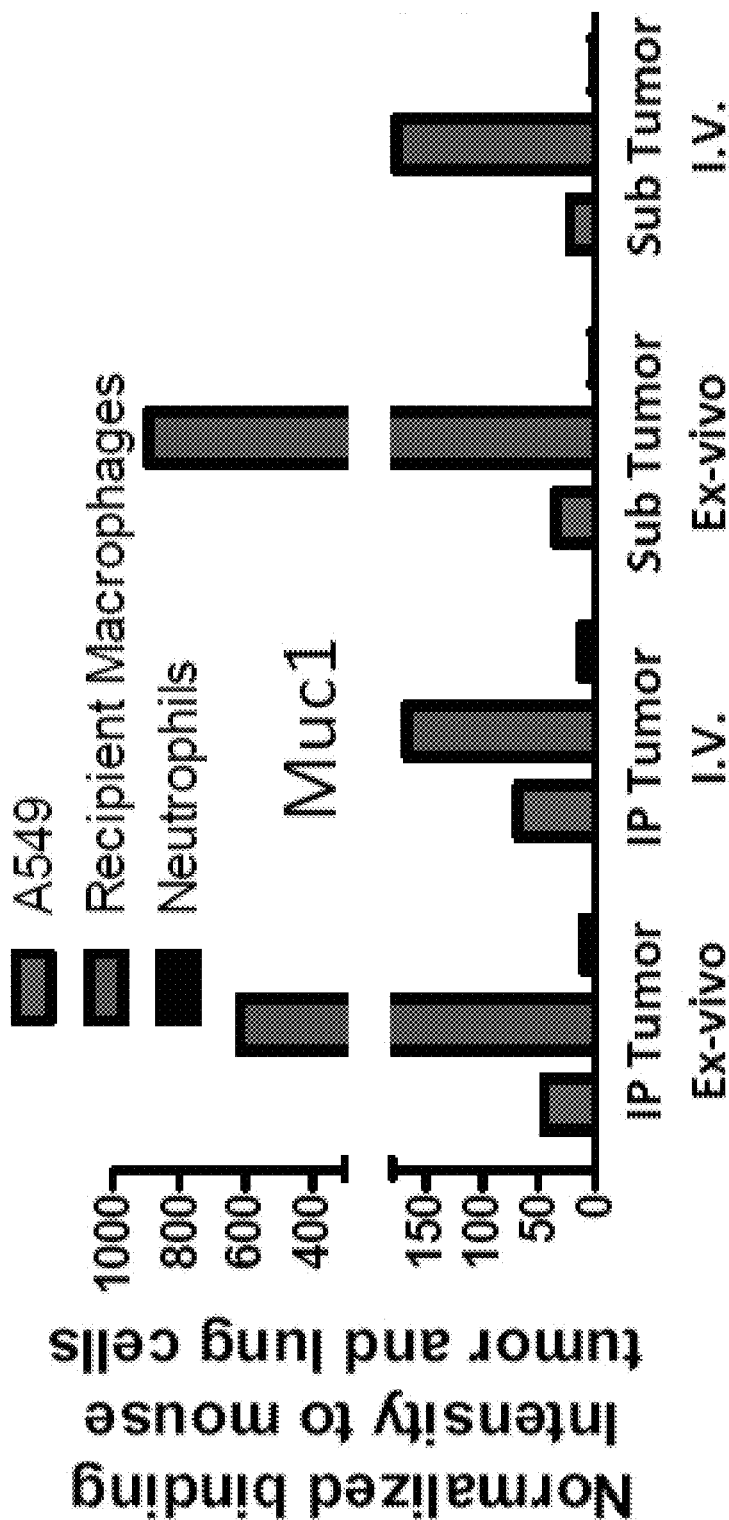
Figures 9G, 9H:
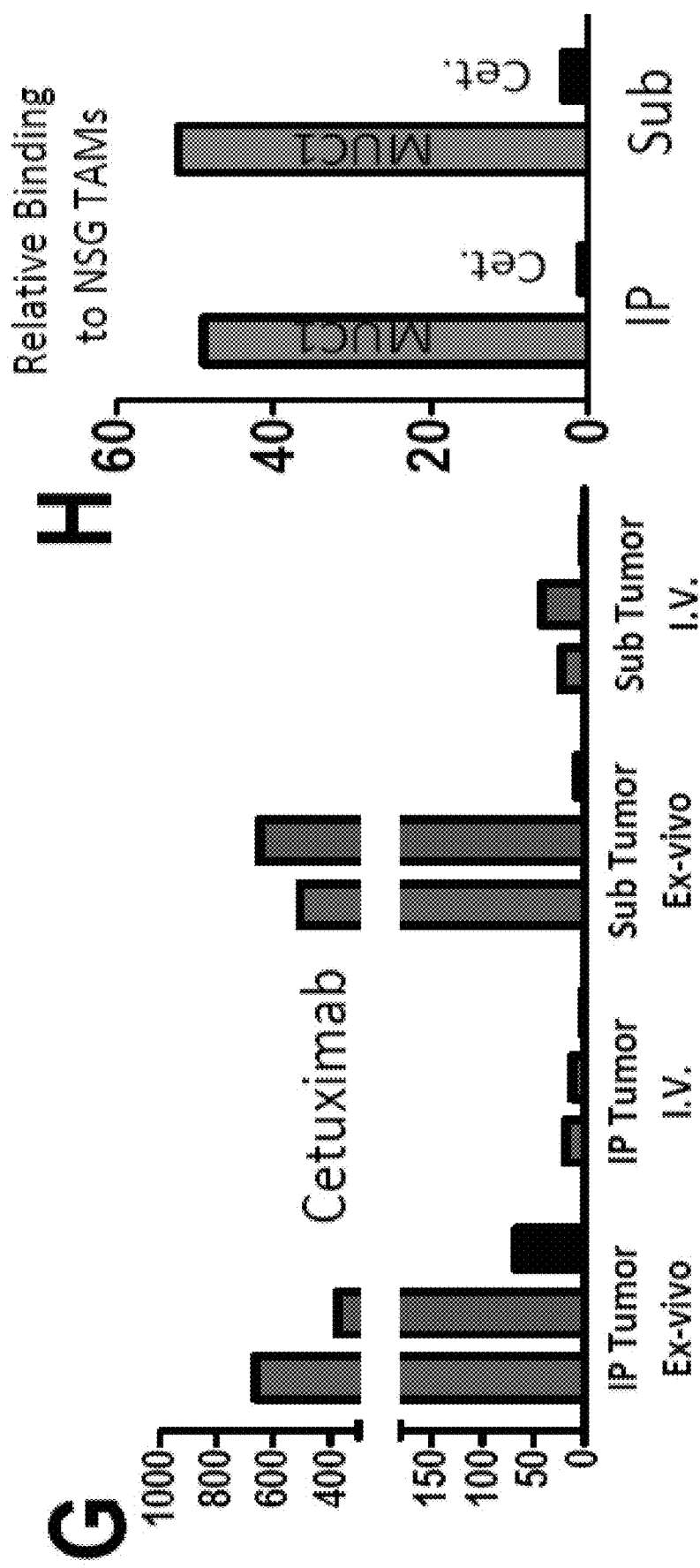
Figure 10A:
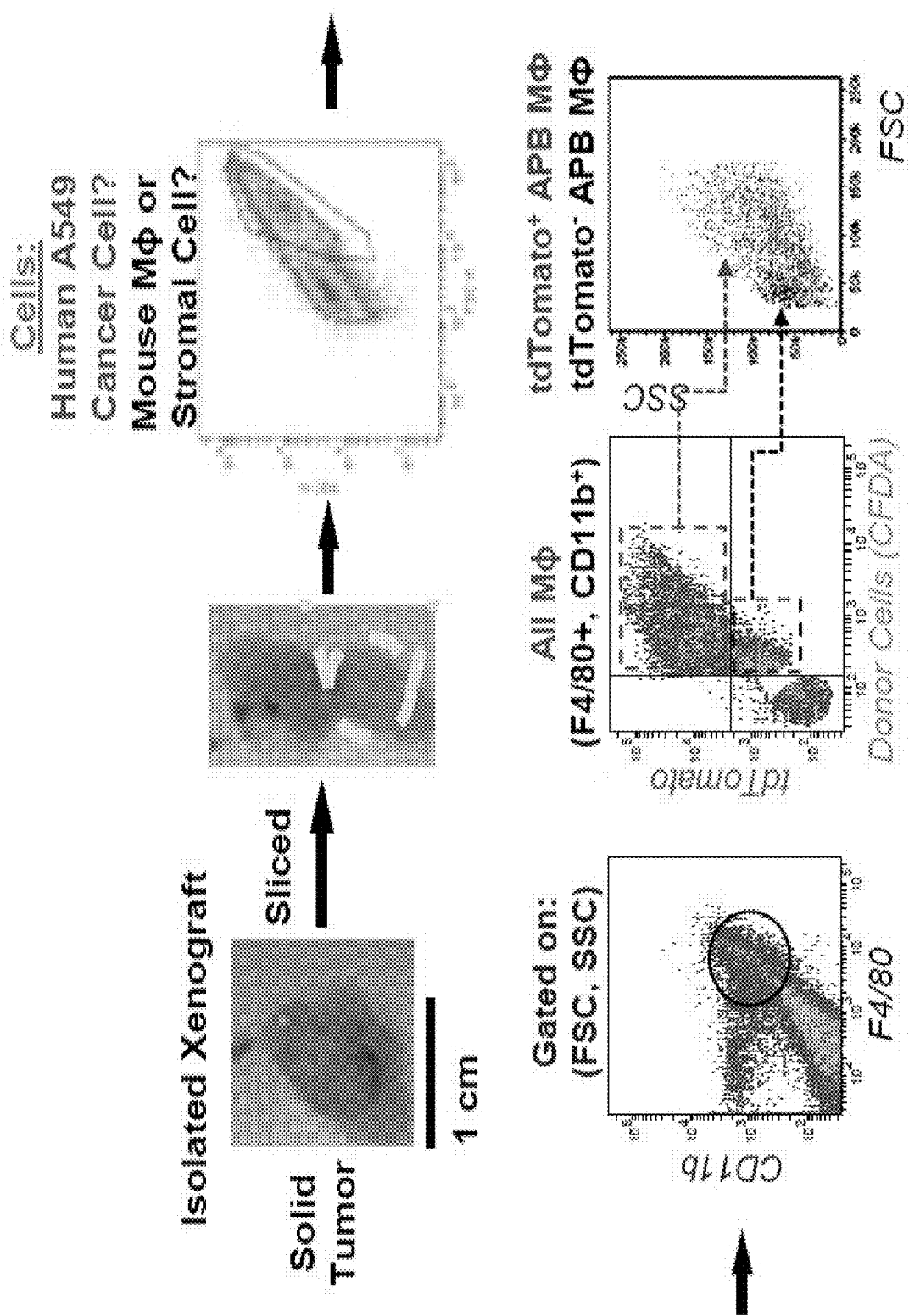
FIGS. 10A-10I are a series of graphs and images showing donor cells alone inhibit tumor growth, but priming FCY receptor on APB MO yields the most effective anti-tumor response.
Figure 10B:
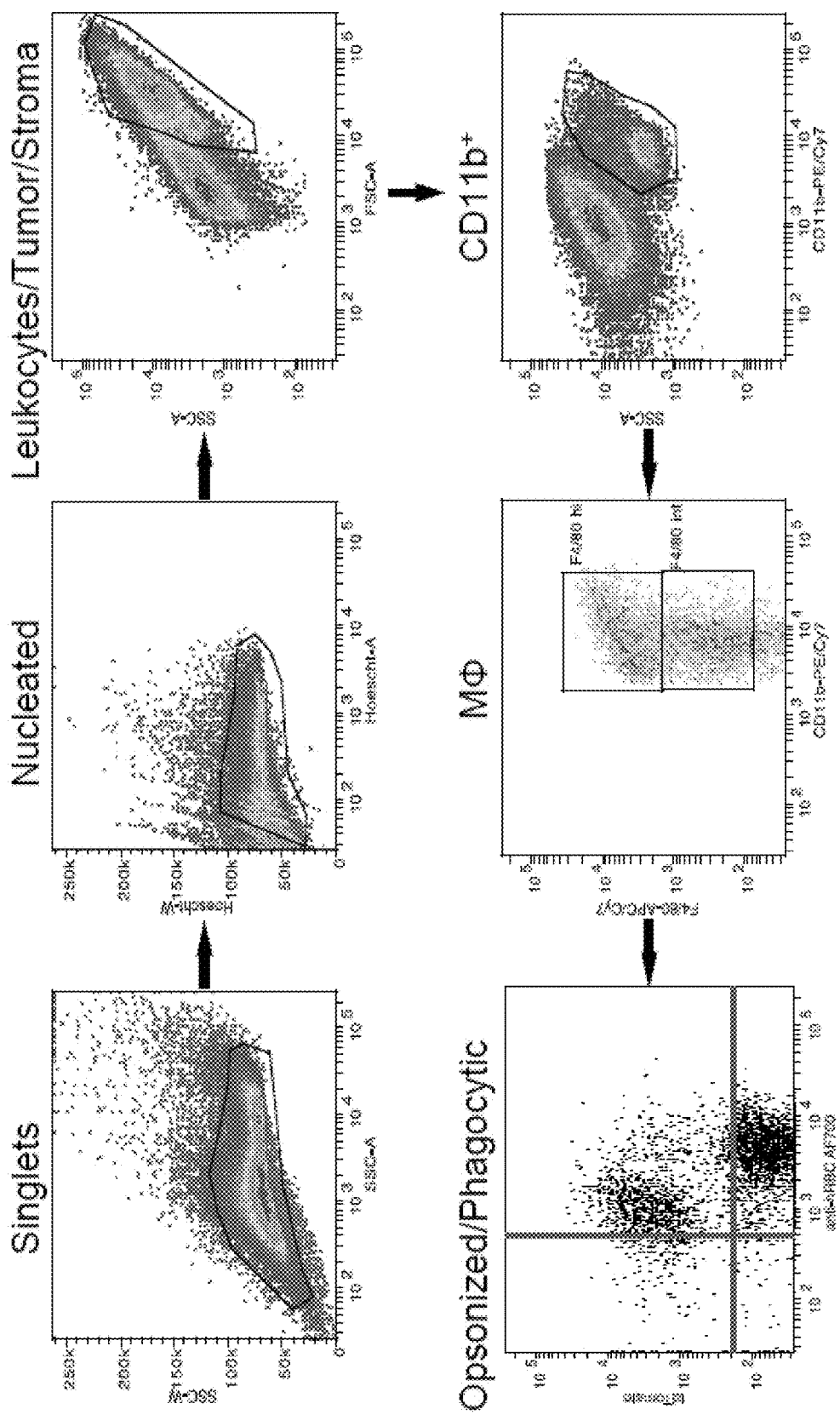
Figure 10C:
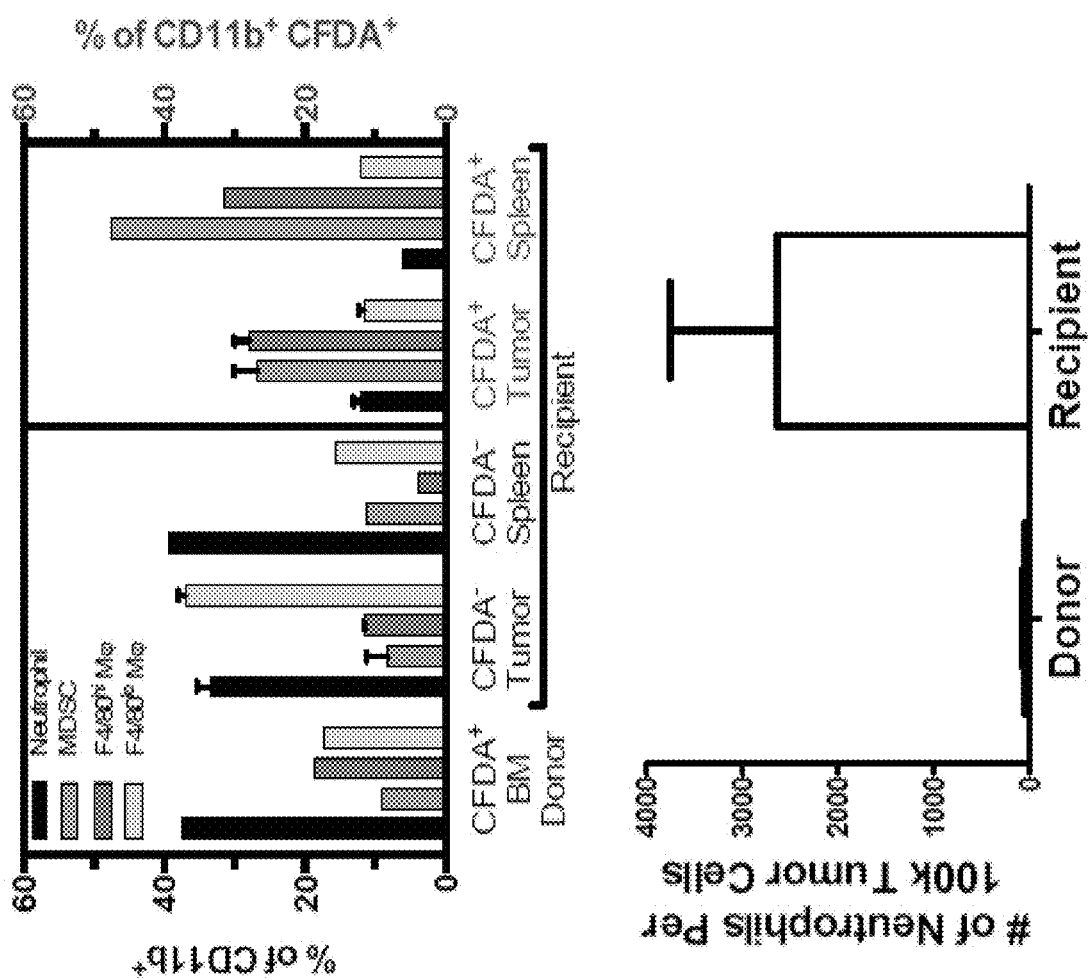
Figures 10D, 10E:
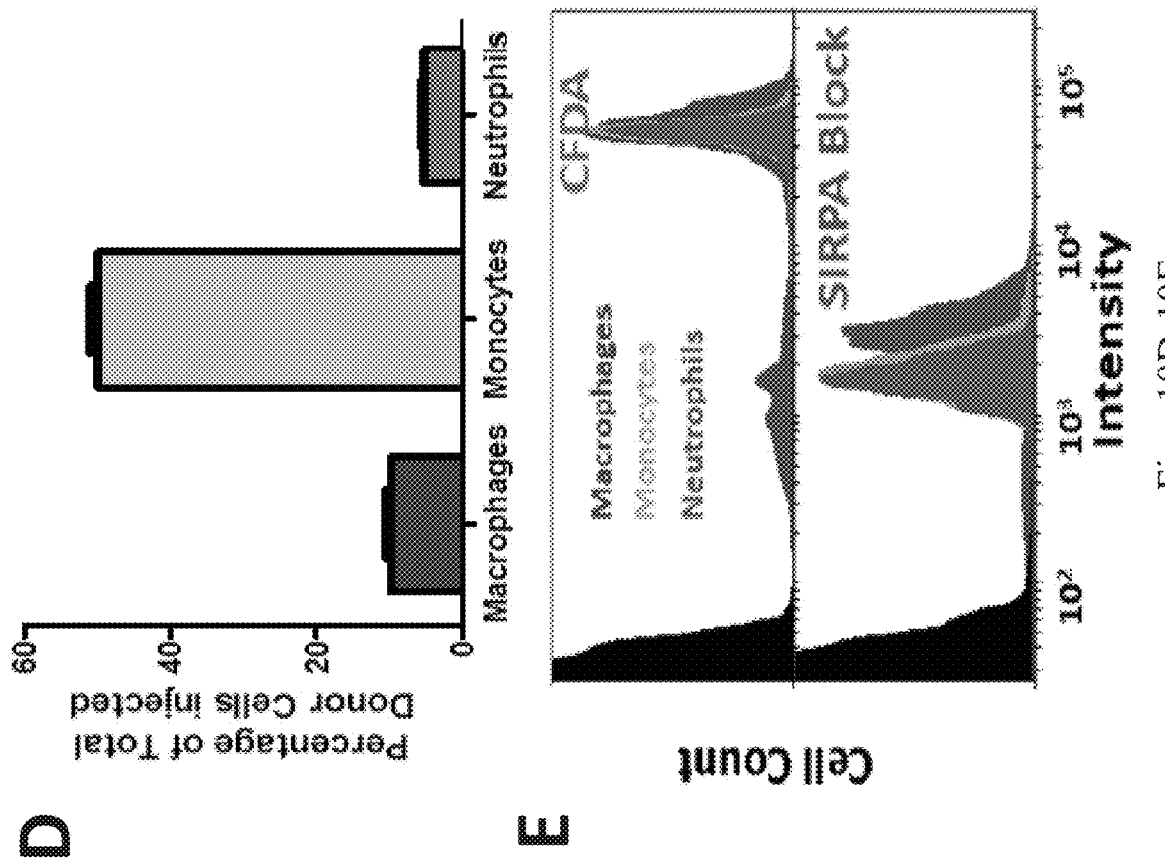
Figure 10F:
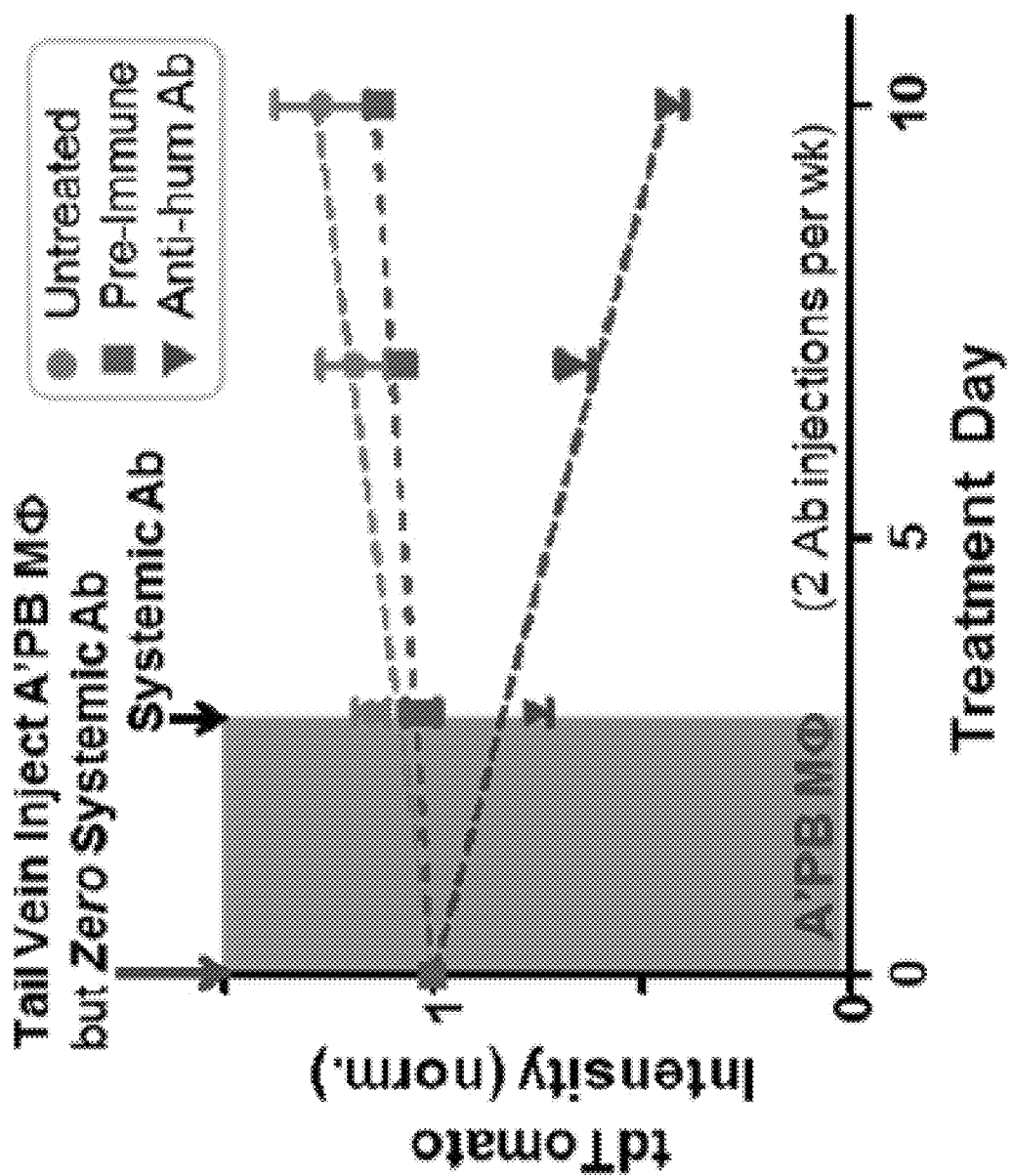
Figure 10G:
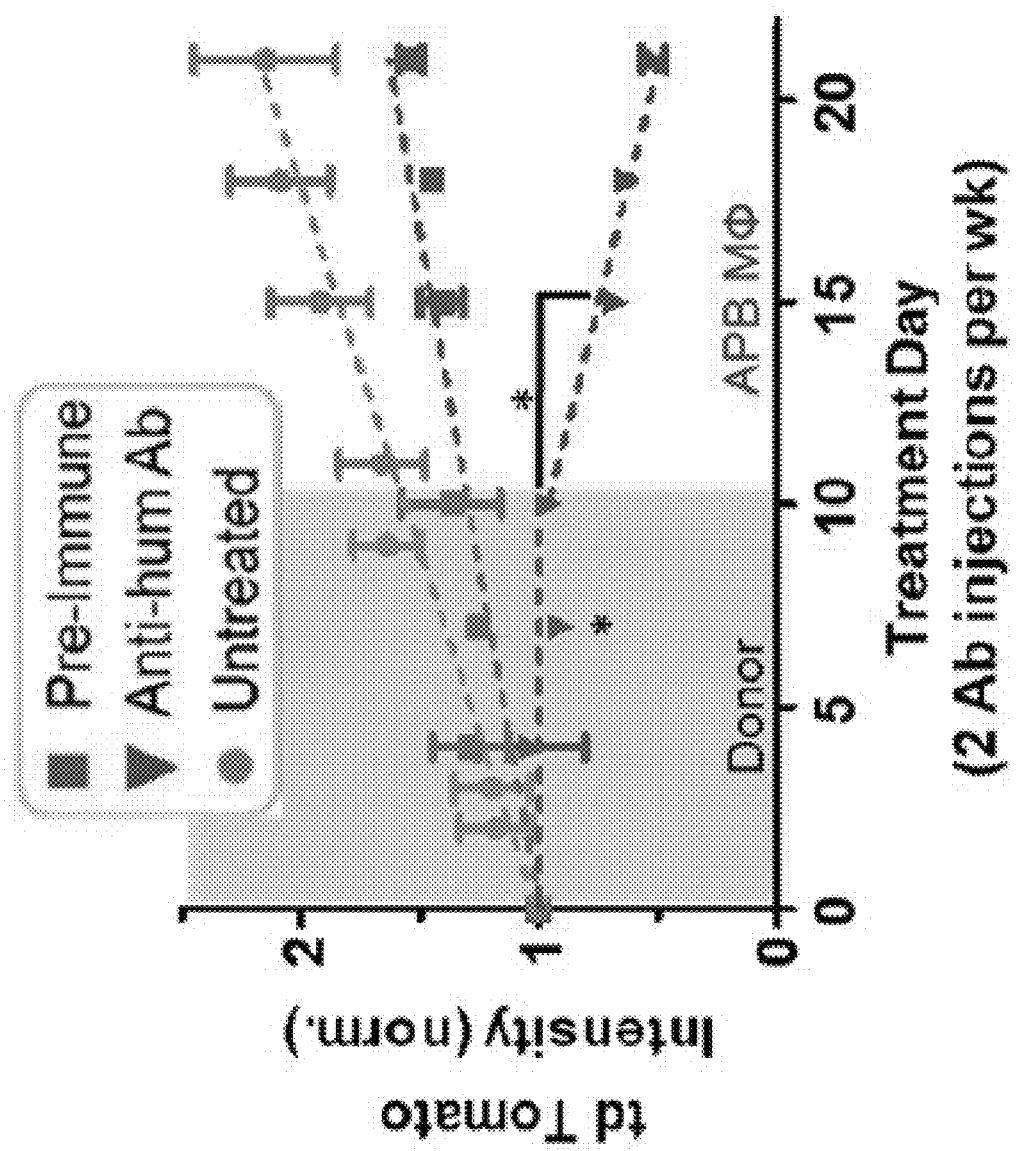
Figure 10I:
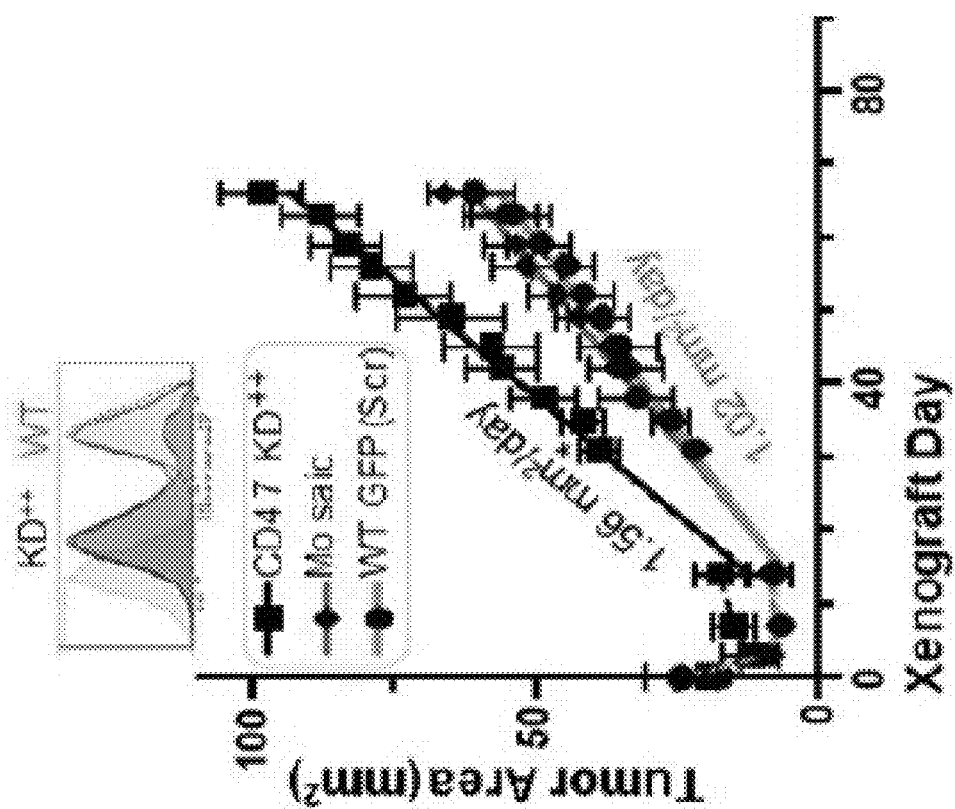
Figure 10H:
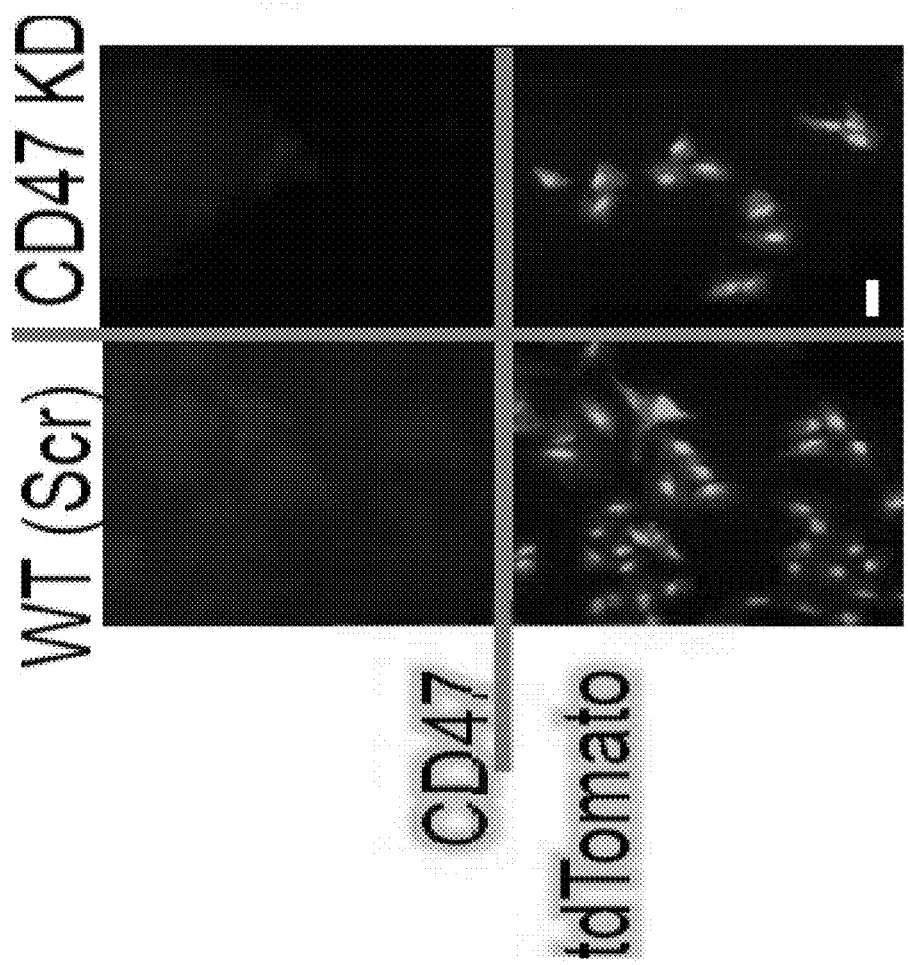
Figures 11A, 11B:
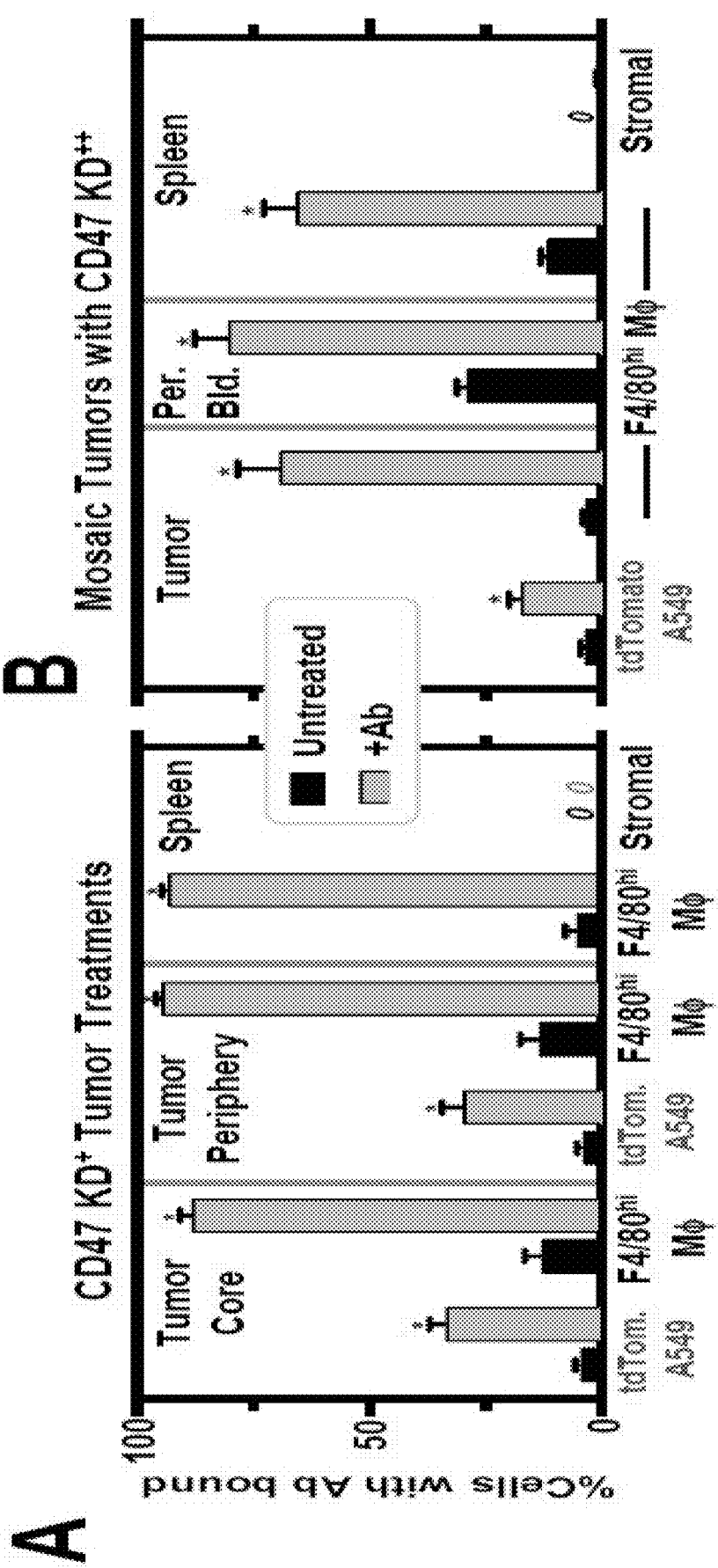
FIGS. 11A-11G are a series of graphs showing Ab binding to cell populations and phagocytic activity.
Figures 11C, 11D:
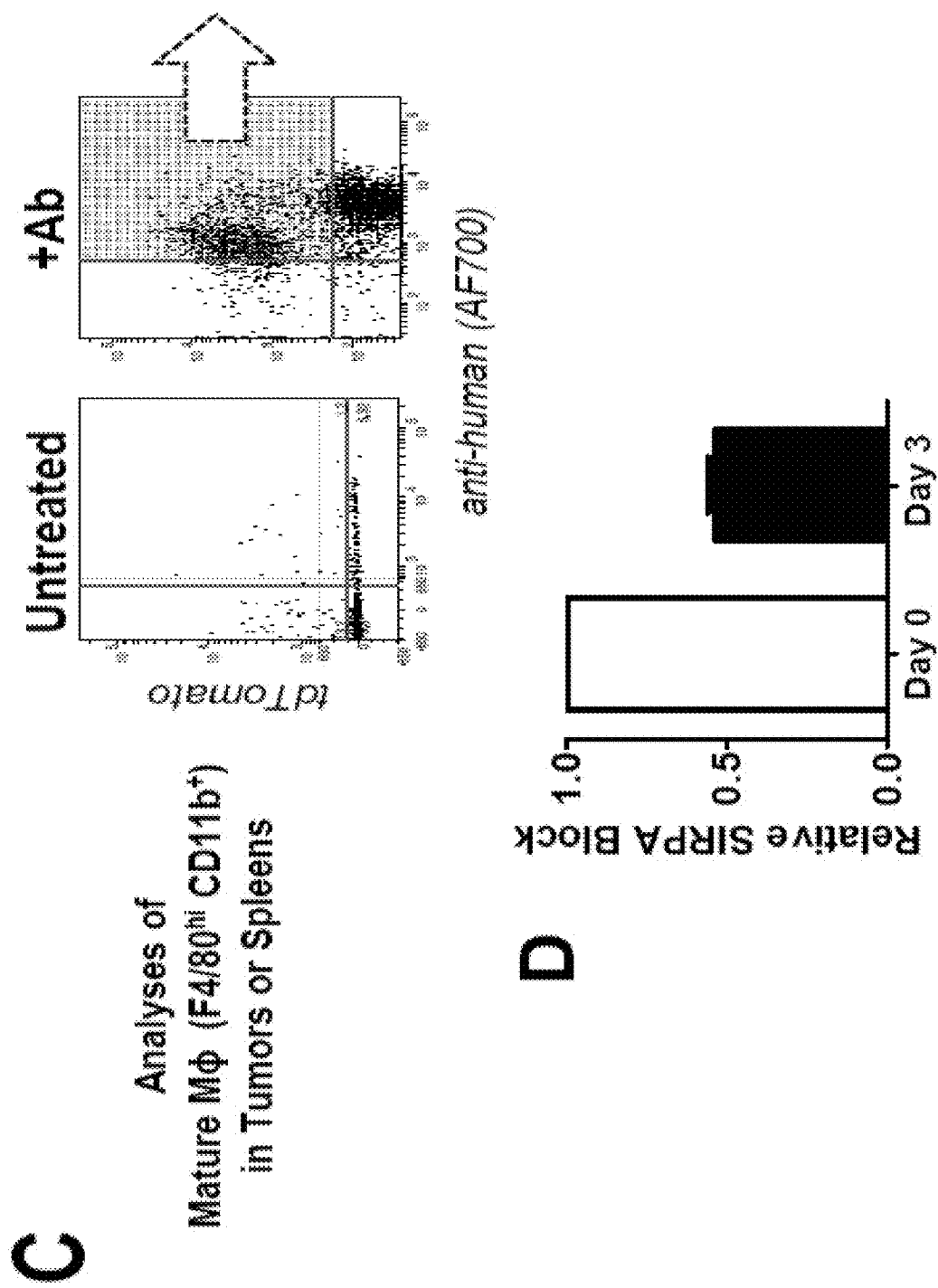
Figure 11E:
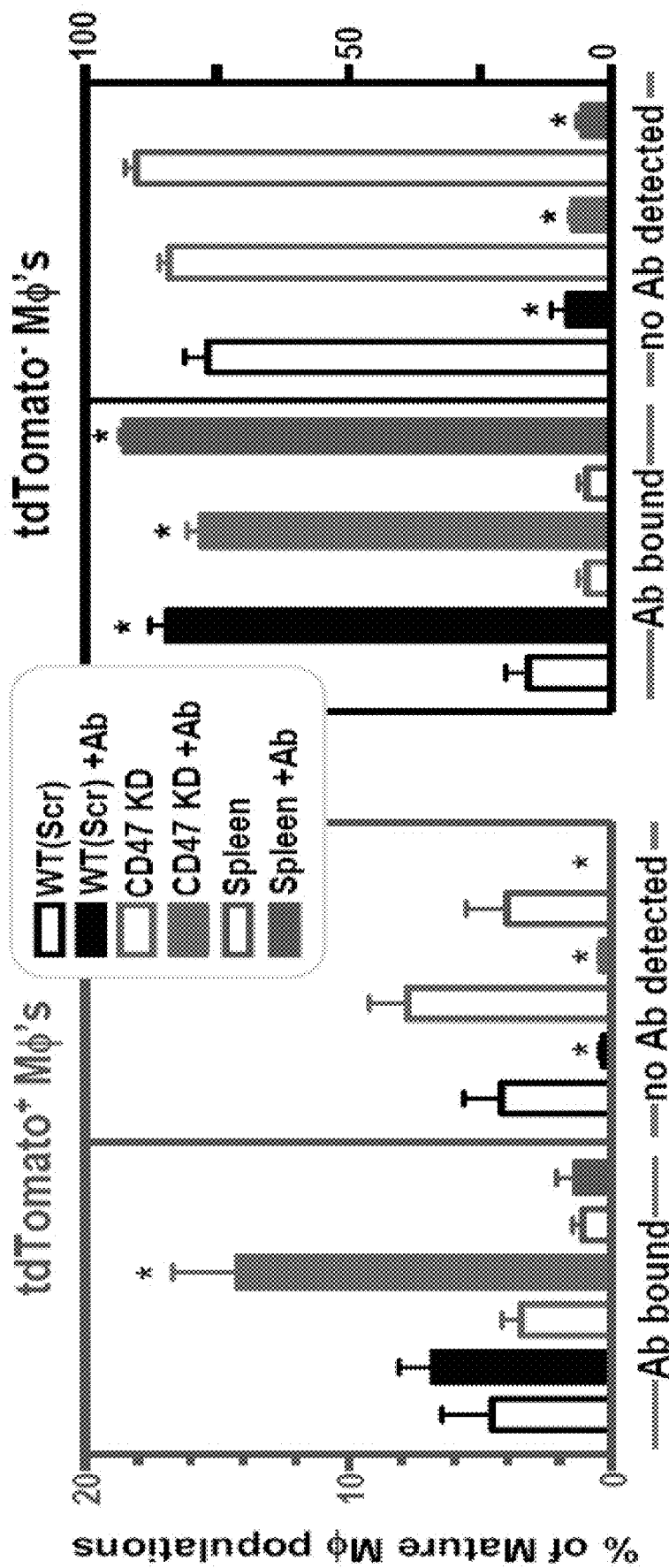
Figure 11F:
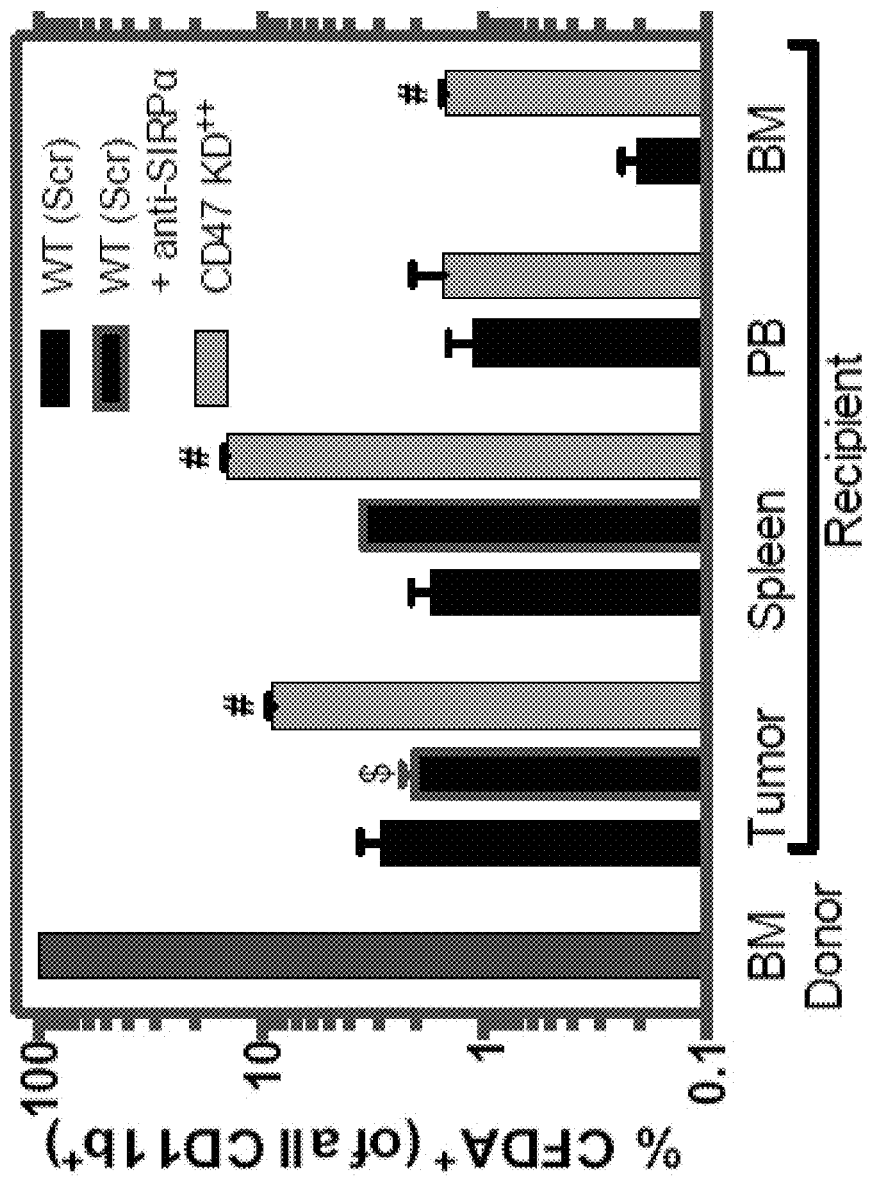
Figure 11G:
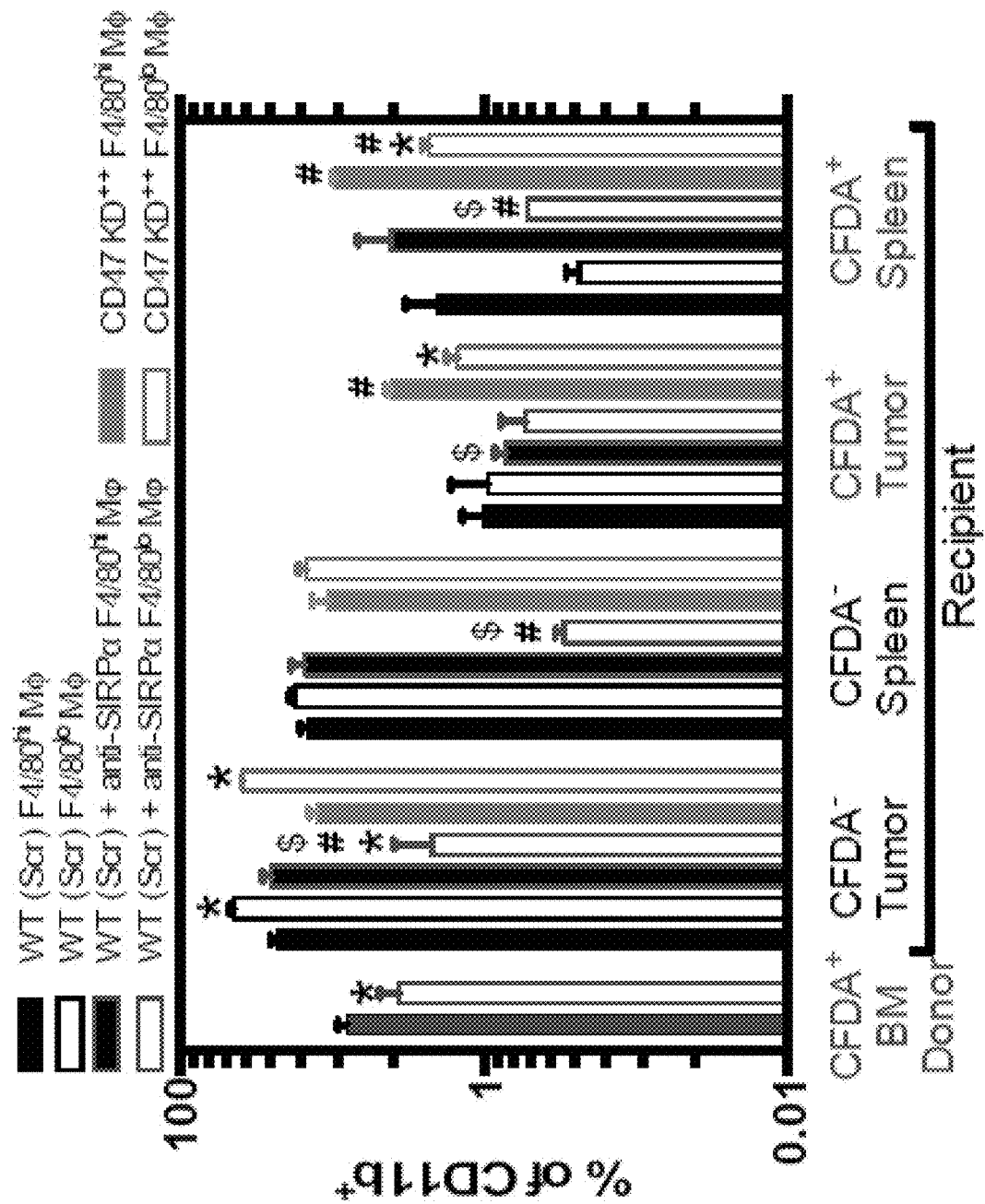
Figure 12A:
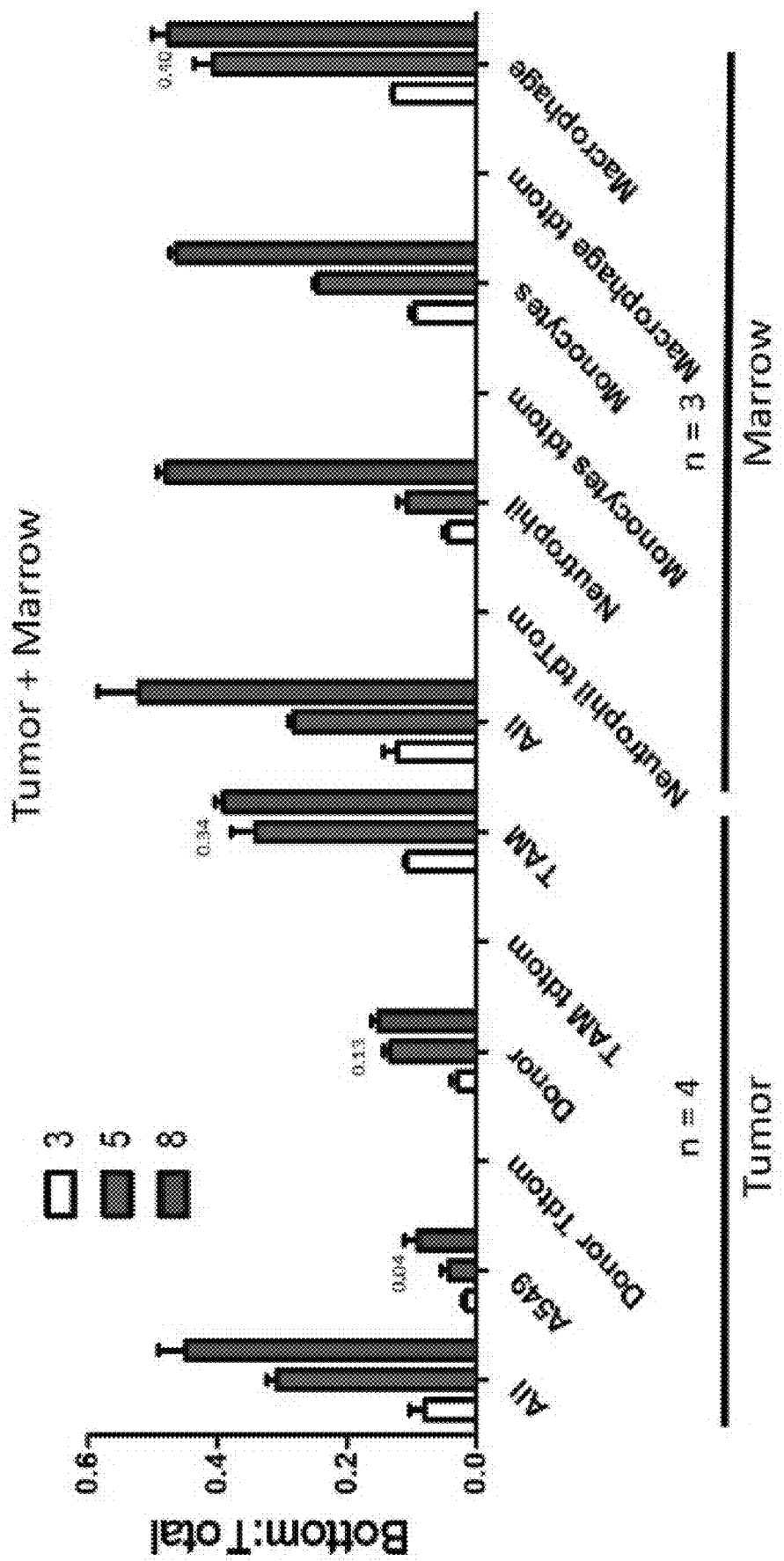
FIGS. 12A-12E are a series of graphs showing transwell analysis of phagocytosis and 3D-Motility of all cell types. Plots of 3D migration and phagocytic activity of tumor tdTomato A549 cells on 3 um, 5 um, and 8 um pores of donor marrow, lung, and tumor cells. All conditions have n>3, but tumor only has n=1 (mean±SEM).
Figures 12B, 12C:
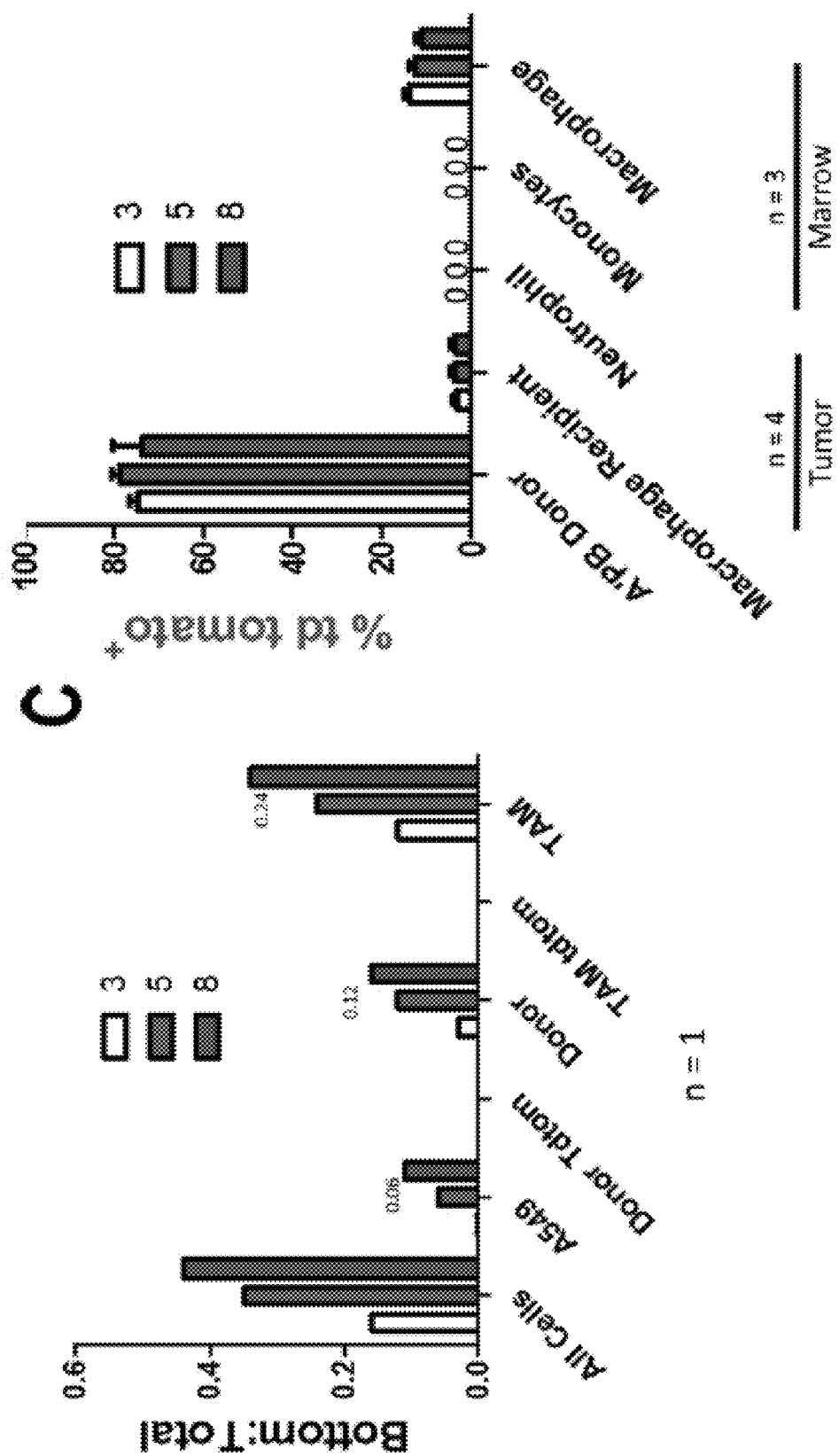
Figure 12D:
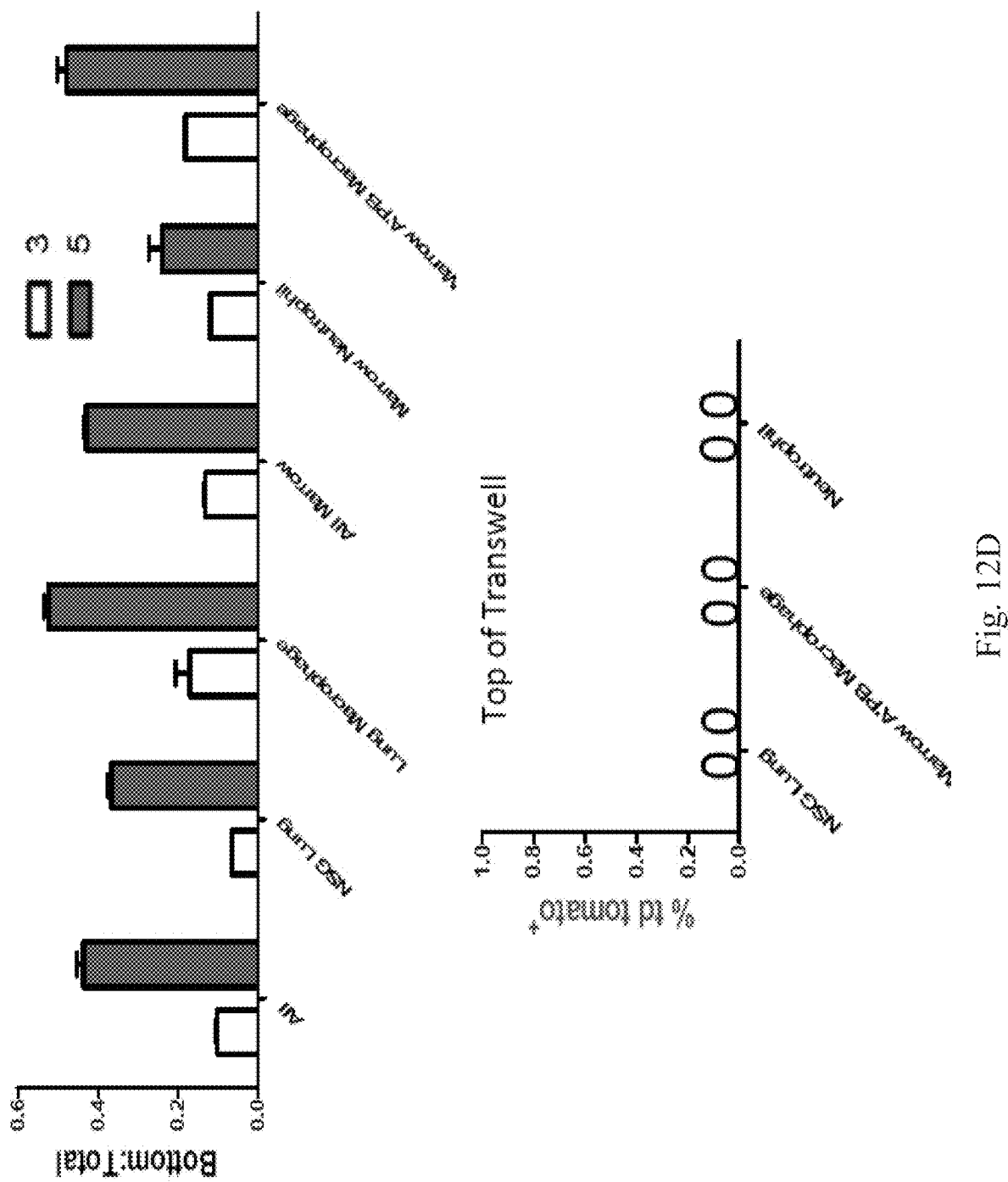
Figure 12E:
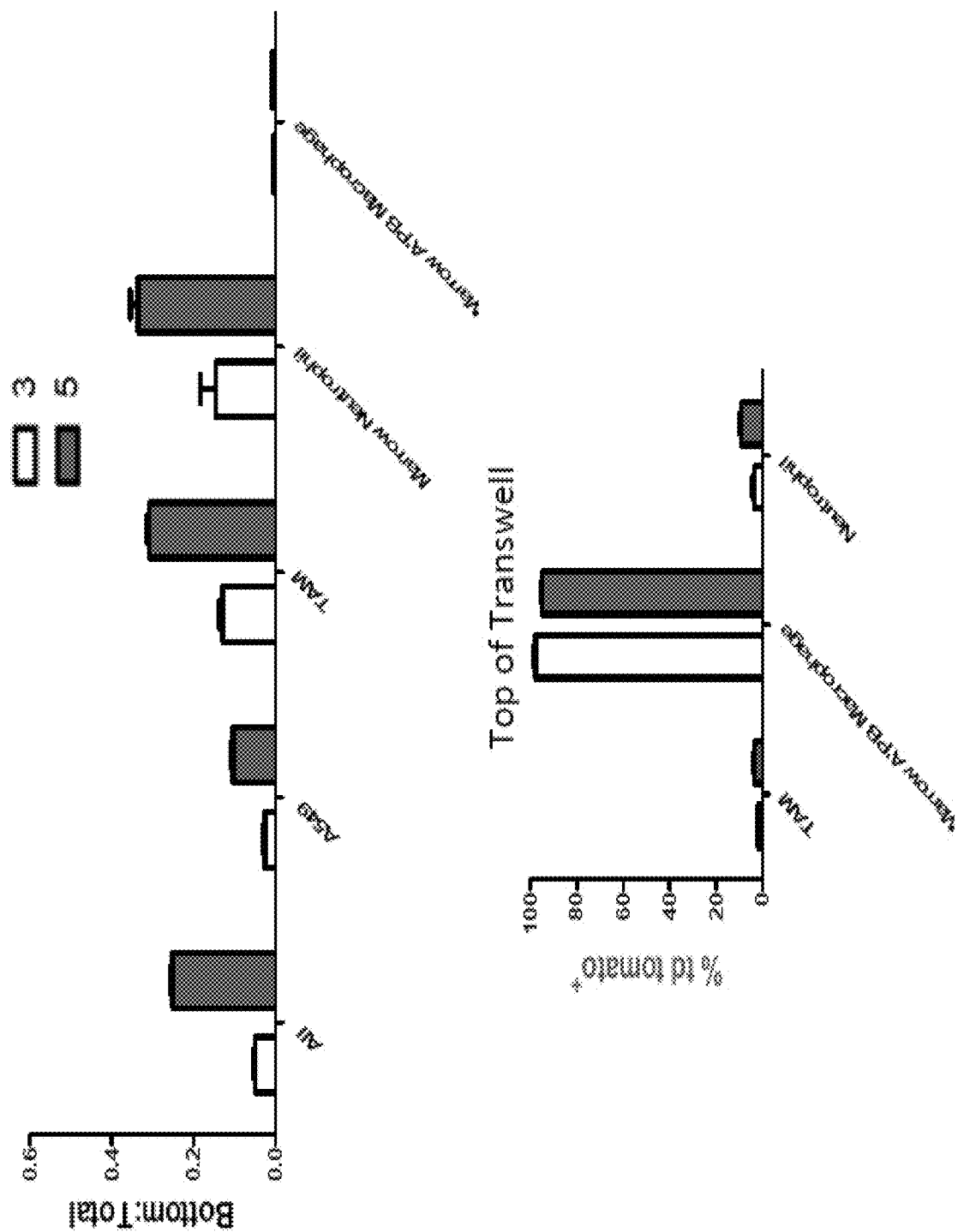

Tumor shrinkage rate increased with cumulative phago-cytosis by all of the different macrophage types injected into mice with WT and with CD47-KD tumors (FIG. 4B). Tumor growth equated to a negative shrinkage rate, even though tumor cells remained at 40%. Treatments that relied on TAMs were all in the lower half of this plot, even with CD47 blockade. To begin to clarify some of the differences between donor macrophages and recipient TAMs, tumors were isolated 3 hours after treatment and stained for the so-called M1-marker major histocompatibility complex II as a 'phagocytic phenotype', and also the M2-marker mannose receptor (Mrc1 or Cd206) indicating a relatively non-phago-cytic phenotype. Recipient TAMs that were tdTom negative had a comparatively low M1/M2 ratio as were macrophages in spleen or liver, whereas recipient TAMs that had engulfed cancer cells as tdTom positive showed a much higher M1/M2 ratio (FIG. 4C, FIG. 6 last column). Fresh marrow-derived macrophages as well as the tumor-extracted donor and APB macrophages always showed the highest M1/M2 ratio regardless of whether a cancer cell was phagocytosed. Furthermore, high MHCII expression in dendritic cells increases migration of dendritic cells enhancing presentation and activation of T cells and B cells. A'PB MΦ would therefore be effective in such processes.

Example 6: Donor MΦ in Tumors Differ from Marrow MΦ and TAMs that have Highest SIRPα

Figure 4D:
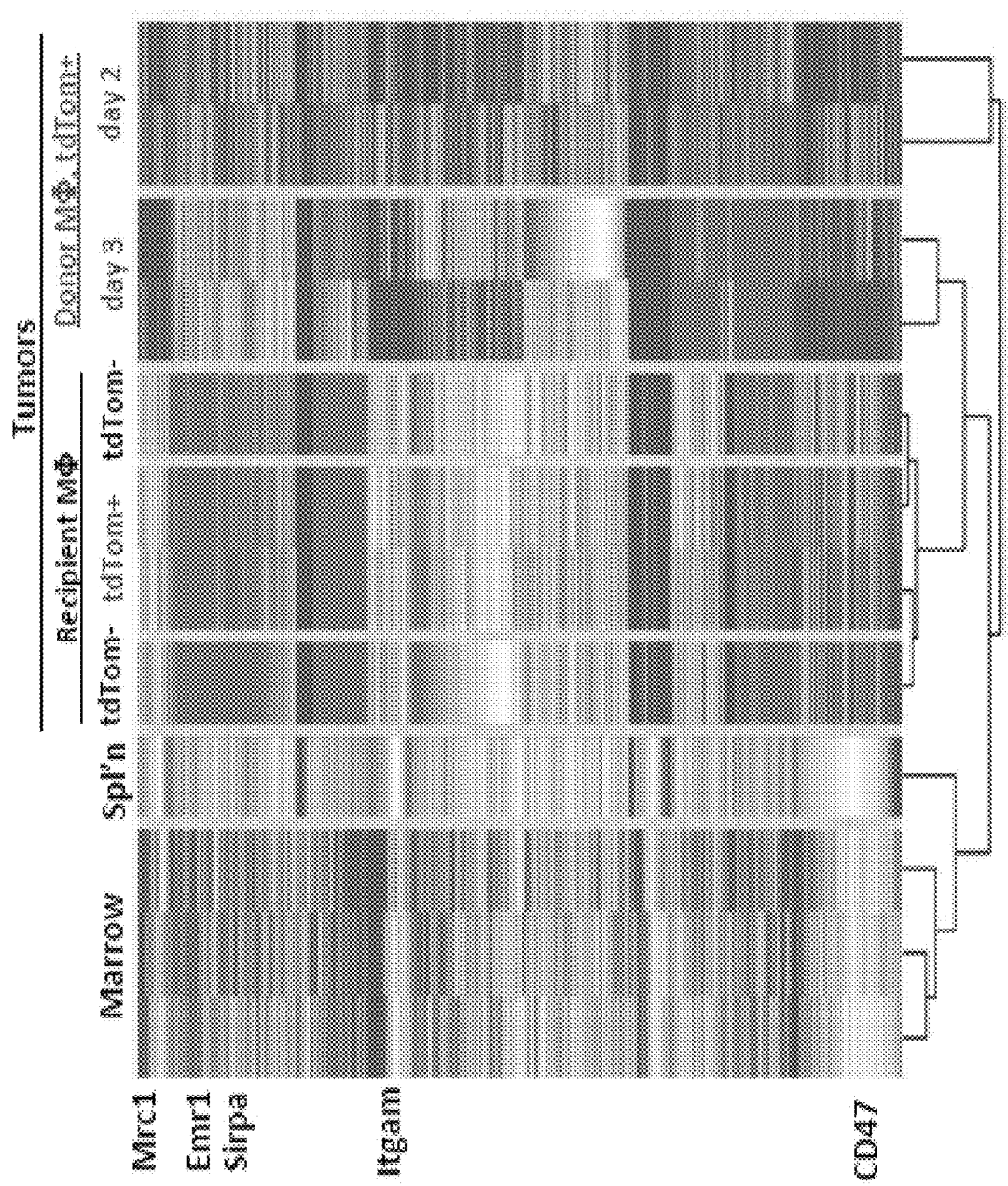

Macrophages are increasingly understood to be highly plastic cells, so that characterization by a few surface molecules cannot adequately describe macrophage pheno-type in different tissue microenvironments. RNA-Seq was therefore done on marrow macrophages and tumor-extracted donor macrophages (tdTom positive) as well as splenic macrophages and TAMs that were tdTom positive and negative. Hierarchical clustering of expression data showed donor macrophages from tumors clustered between splenic macrophages and TAMs (FIG. 4D).

Figure 4E:
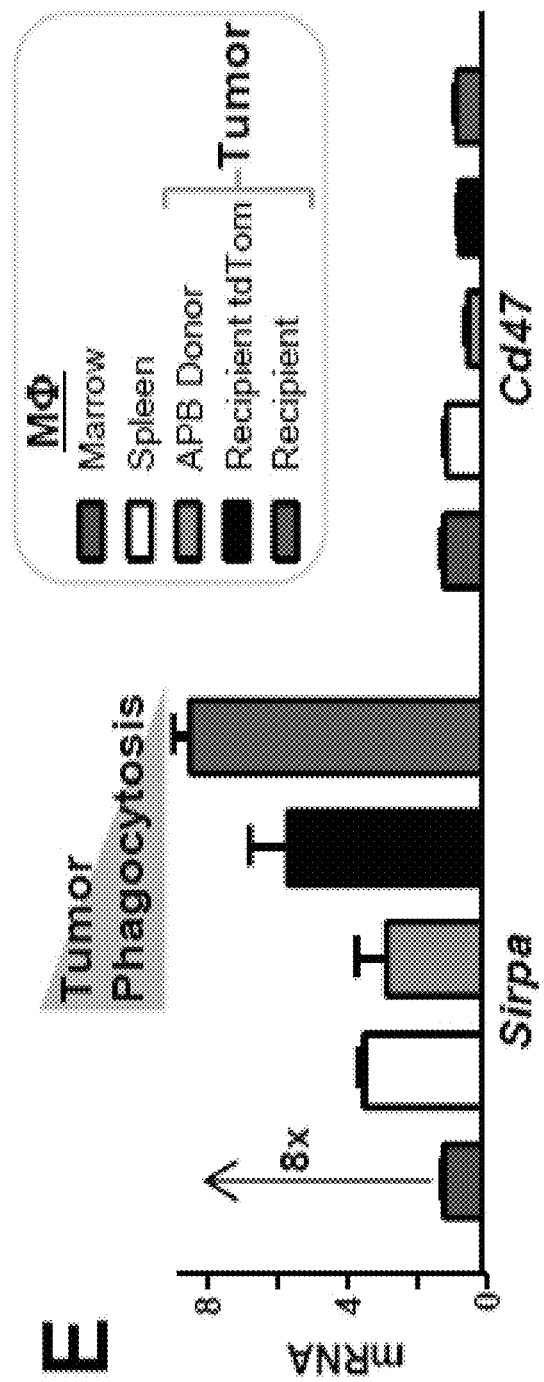
Figure 4F:
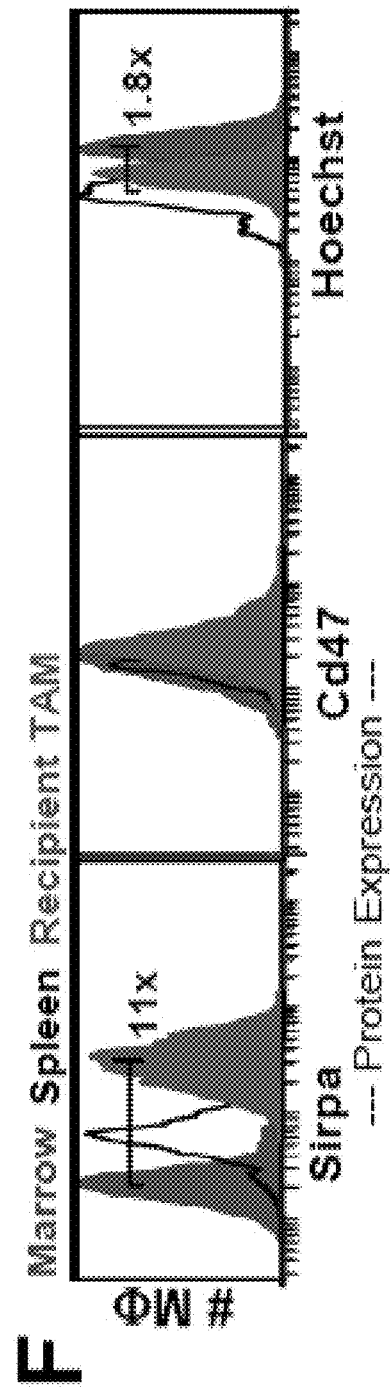

Among transcripts most relevant to phagocytic activity, Sirpa increased 8-fold with decreasing phagocytic pheno-type. Fresh marrow-derived macrophages had the lowest Sirpa, donor macrophages in tumors had intermediate Sirpa similar to splenic macrophages, and TAMs had the highest Sirpa (FIG. 4E). Cd47 varied little between the different macrophages. Flow cytometry for surface protein confirmed the trend for Sirpa with Marrow<Spleen<TAMs, whereas Cd47 did not vary (FIG. 4F). Without wishing to be bound by any specific theory, high Sirpa will increase the sensi-tivity to cells expressing even low levels of CD47 and will therefore tend to passivate macrophages, just as blocking Sirpa (or knocking down CD47) does the opposite in favor-ing phagocytosis. The increased SIRPα in donor macro-phages relative to marrow macrophages also equals or exceeds the loss of anti-SIRPα blocking antibody with dissociation in the tumor (FIGS. 11A-11G). Consistent perhaps with an important role for macrophage differentiation and with the Hoechst staining of DNA in phagocytosis studies (FIG. 1F), marrow macrophages exhibited higher Hoechst staining of DNA than TAMs.

Figure 7:
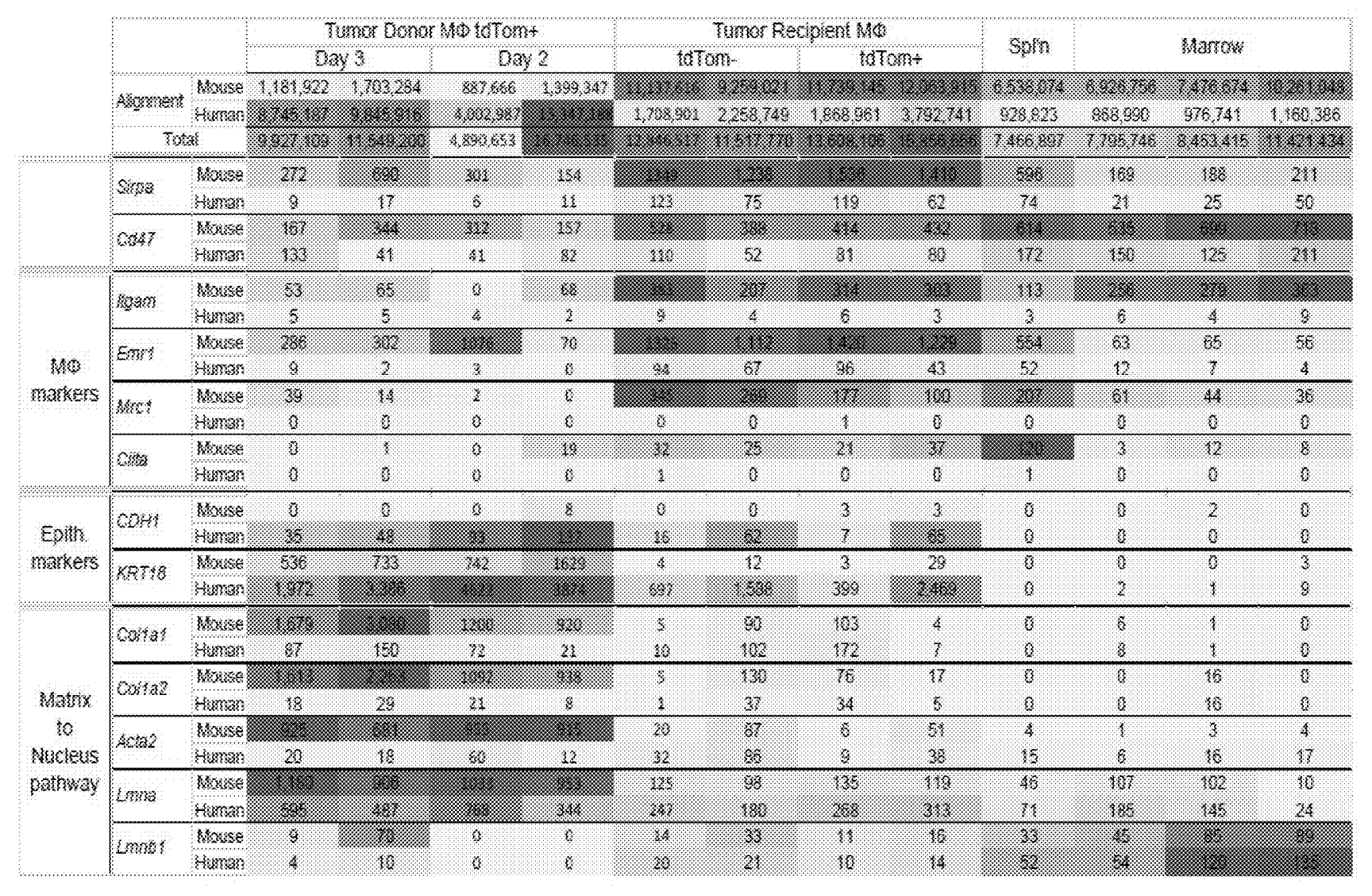

By aligning RNA-Seq data with the human transcriptome (rather than mouse), human RNA was most abundant in donor macrophage taken from tumors, which was consistent with phagocytosis of human cancer cells (FIG. 7). For the fresh marrow and spleen macrophages, a mouse:human alignment ratio of ~8:1 was inverted to ~1:7 for donor macrophage taken from tumors. Whereas macrophage markers were dominated by mouse sequence reads in all samples, epithelial markers (E-cadherin, keratin-18) typical of a lung cancer line were human and detected only in the tumor macrophages, both donor macrophages and TAMs.

Figures 4G, 4H:
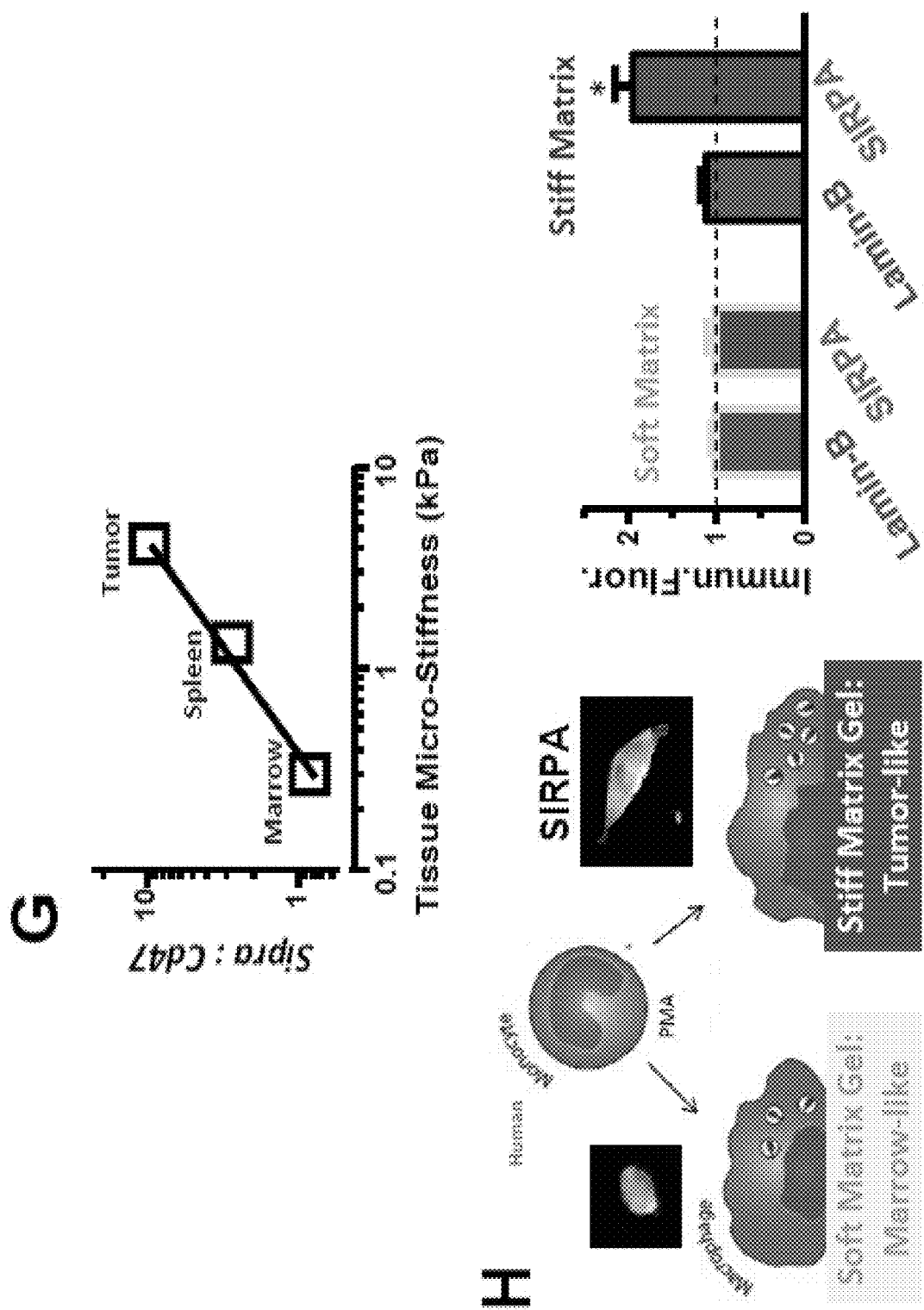

A solid tumor's highly collagenous microenvironment is very different from the very soft, low matrix microenvironment in marrow. Marrow-derived macrophages that engorge on cancer cells and accumulate in solid tumors can therefore be anticipated to differentiate. Among the transcripts that increased the most were those for collagen-1 (FIG. 7), which is a heterotrimer (of Col1a1 and Col1a2) that self-assembles into fibers that determine the solidity of tissue. Collagen also contributes to the small size of matrix pores in a tissue as well as the stiffness of tissues including tumors and scars. Matrix stiffness often alters cell phenotype and affects phagocytosis. One intriguing mechanosensor is the nuclear structure protein lamin-A, and Lmna was indeed highest in donor macrophages from the solid tumors tested herein (FIG. 7). Combining the transcriptome results with those of others from many other tissues (Lavin et al., (2014) Cell 159: 1312-1326) revealed a consistent increase in the ratio Lamin-A:Lamin-B versus tissue or tumor solidity as a micro-stiffness (FIGS. 13A-13F). Lamin-B isoforms are relatively constant compared to the increased collagen with tissue solidity. Profiling showed Sirpa: Cd47 followed the same trend versus tissue or tumor solidity (FIG. 4G).

The in vivo results prompted an in vitro study of lamin and SIRPα changes in human-derived THP1 macrophages adhering either to a gel that is soft like marrow or a gel that is much stiffer like a tumor. Not only did the ratio lamin-A:lamin-B increase with stiffness but so did SIRPA (FIG. 4H and FIGS. 13A-13F). The latter was statistically the same as the ~300%±100% increase in SIRPα RNA in the donor macrophages in comparing tumor to marrow (FIG. 4E). SIRPα was also functional on THP1 macrophages attached to rigid substrates because SIRPα blockade increased whole-cell engulfment of opsonized A549 cancer cells in vitro just as effectively as CD47 blockade on these cancer cells, and RNAi knockdown of SIRPα had a similar effect (FIGS. 13A-13F). Tumor solidity thus relates not only to small matrix pores that restrict migration of engorged and accumulating donor macrophages but also to mechanisms of differentiation that passivate these macrophages and clusters them phenotypically closer to TAMs.

Figure 5A:
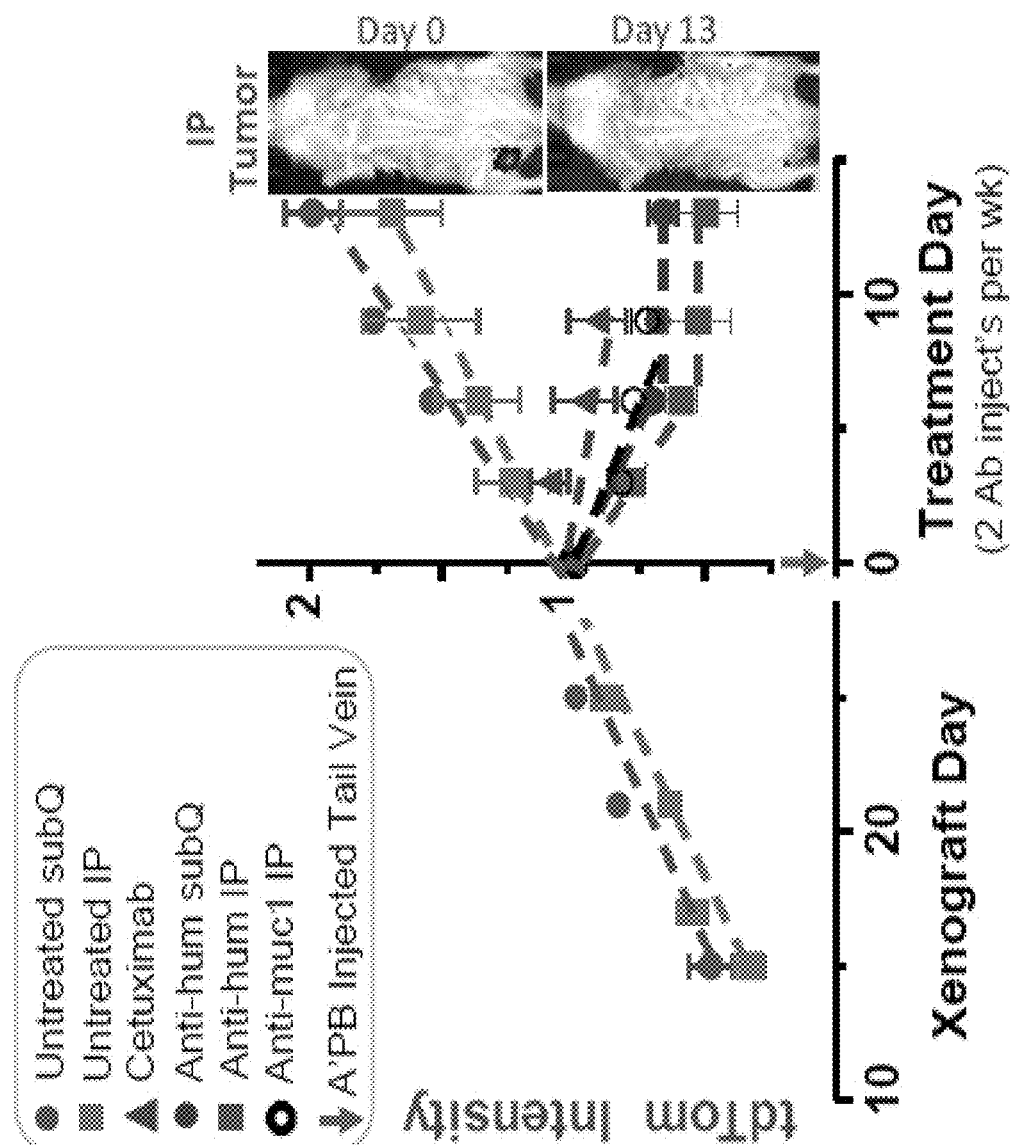
FIGS. 5A-5E are a series of graphs and images showing single and multiple injections of mouse and human A'PB or APB MO cause rapid shrinkage of subcutaneous and intraperitoneal tumors.
Figure 5B:
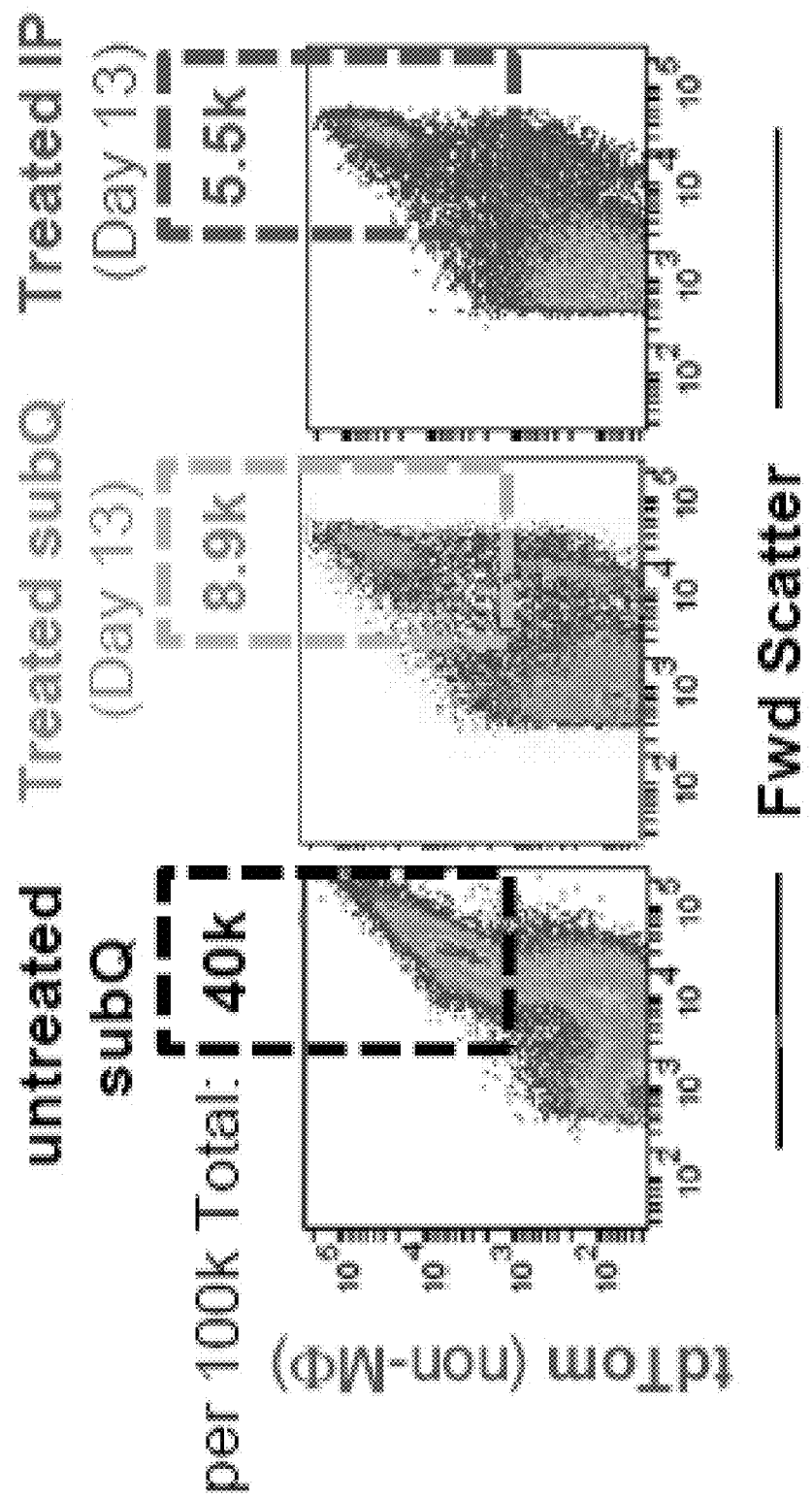

Example 7: Plateaus in Tumor Shrinkage can be Corrected by Multiple Injections of Donor Macrophages Intraperitoneal (IP) tumors of the lung cancer derived A549 cells model the distal invasiveness of lung tumors and thus provide an opportunity to challenge the trafficking, phagocytosis, and perhaps differentiation of donor marrow macrophages after tail vein injection. An IP tumor and a subcutaneous tumor on the opposite side of the same mouse were treated with intravenous A'PB MΦ which resulted in shrinkage of both tumors at approximately the same rates (FIG. 5A). Decreases in tdTom intensities in vivo by day-13 with anti-hum Ab matched the proportional decreases in the number of cancer cells measured (per 100K cells) by flow cytometry (FIG. 5B). This agreement added confidence to a plateau in IP shrinkage apparent from day-9 to day-13 and prompted additional long term studies.

Figure 5C:
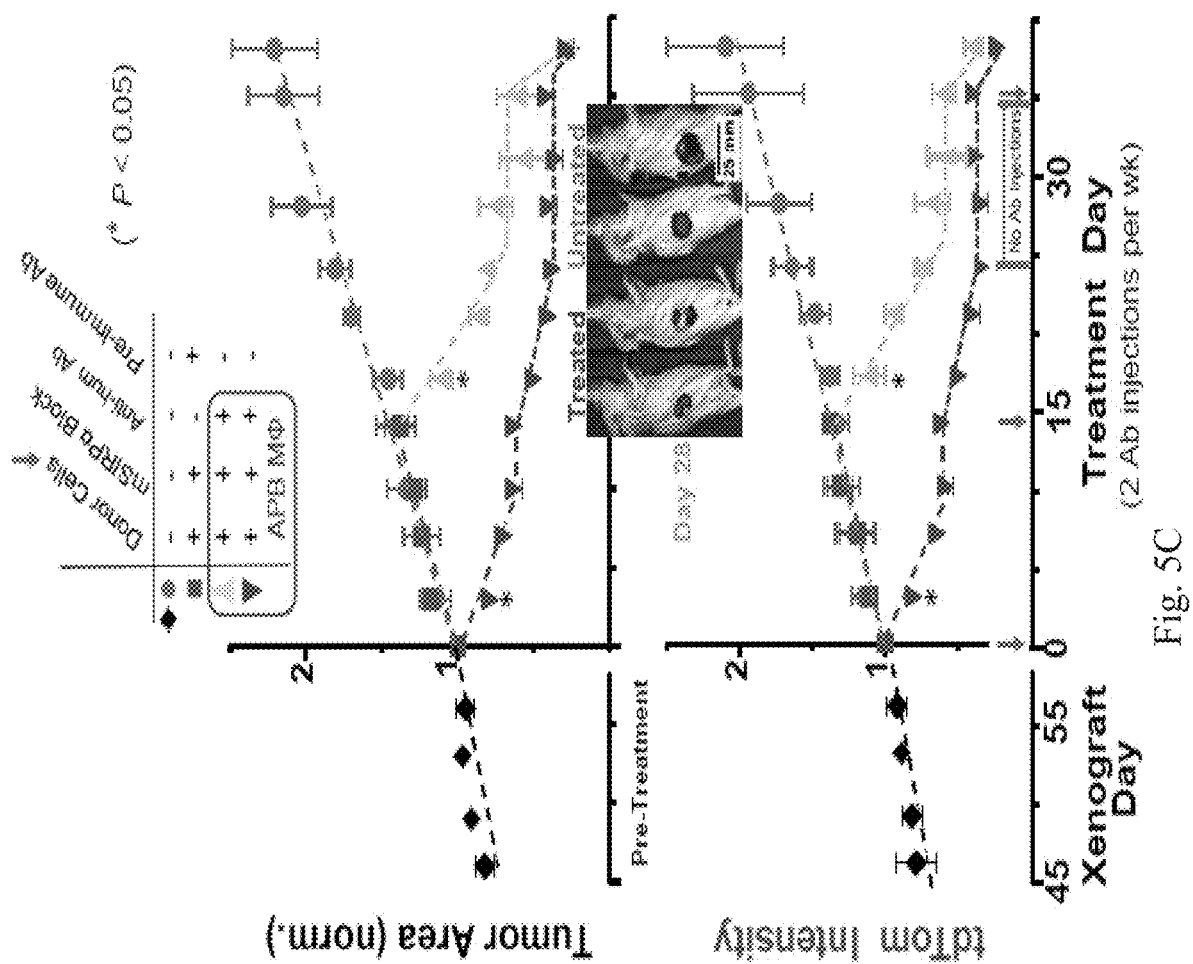

Treatment of subcutaneous tumors in both male and female NSG mice began once tumors reached ~80 mm$^2$ (~8 wks). Untreated tumors continued to grow linearly in terms of both projected area and tdTom intensity. Injection of anti-hum Ab plus APB MΦ caused a 20% loss of both tdTom intensity and tumor size by day 3 whereas a pre-immune Ab plus APB MΦ (i.e. SIRPα blocked) had no effect (FIG. 5C). With time, shrinkage of treated tumors slowed and reached only 40% by day 10 with a plateau up to day 14. Biweekly injections of anti-hum Ab continued, but a treatment plateau confirmed the observations in the IP studies.

To ensure that plateaus following shrinkage were not due to resistance of anti-hum Ab (eg. down-regulation of epitopes), mice were given on day 14 a second injection of APB MΦ. The additional macrophages produced a rapid decrease in tumor size and tdTom intensity (FIG. 5C). Pre-immune controls also responded to the same treatment and had to be treated because the tumors reached the maximum size allowed by our animal facility. Systemic injections of anti-hum Ab stopped at day 24, and tumors stopped shrinking until a cell treatment at day 35, at which time tumors began shrinking again.

Example 8: Human MΦ s Shrink Human Tumors & Multiple Injections Drive Shrinkage

Figure 5D:
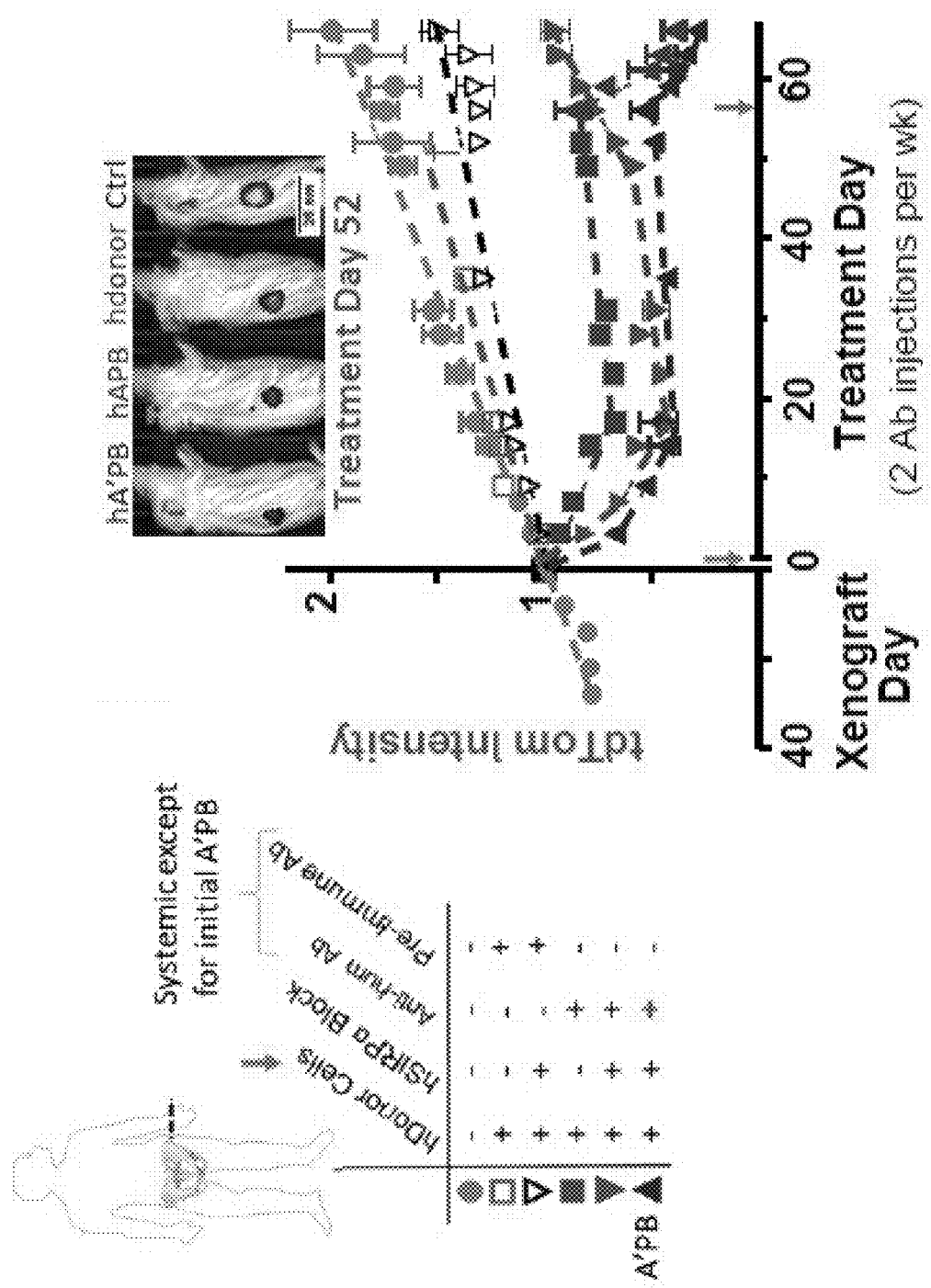

Fresh marrow macrophages from a diverse pool of human donors (FIG. 8) were surface engineered per macrophages from mouse donors except a human-specific anti-hSIRPα antibody was used (FIG. 5D). Tail vein injections of human donor cells (~12M) were followed by biweekly injections of either anti-hum or pre-immune Ab. Tumors shrunk within days after human APB and A'PB MΦ treatments, decreasing by ~40% within the first week (FIG. 5D), which was similar to mouse donor results (FIG. 5C). No significant effect on tumor growth resulted from pre-immune injections combined with either APB MΦ or human donor MΦ's lacking SIRPα blockade (FIG. 5D). However, human donor injection with anti-hum Ab (and no SIRPα blockade) did shrink tumors to a small extent (FIG. 5D), which had a slightly more positive effect than analogous treatments with mouse marrow which stopped growth (FIG. 3B). Flow cytometry analyses of the CD14$^+$ CD33$^+$ CD66b$^-$ human macrophages isolated from tumors showed human macrophages were larger than mouse macrophages, and each typically engulfed two to three tdTom cancer cells (FIGS. 14A-14F). This exceeded the ~1:1 result for mouse macrophages:human cancer (FIGS. 1E-1F) and was therefore consistent with more human engorgement of more human cancer cells and more accumulation which causes greater shrinkage.

Beyond the initial phases of tumor shrinkage following treatment, plateaus in tumor size were again evident by ~day 15 despite continuous biweekly injections of anti-hum Ab. No significant tumor growth was measured up to 55 days after donor cell injection but shrinkage could be re-initiated with additional injections of human donor cells. Sustained breaks in treatment with mouse marrow macrophages also led to periods of no regrowth. Eventually tumors re-grew at rates approximating those of untreated tumors (FIGS. 14A-

14F). Human marrow macrophage injections thus caused similar tumor shrinkage and had similar limits as injections of APB and A'PB mouse macrophages.

To assess whether hSIRPα blockade on human donor macrophages was as effective as blocking CD47, tumors with CD47 KD were treated with hAPB MΦ or human donor both with anti-hum Ab. Tumors treated with hAPB MΦ and human donor without SIRPα shrunk at the same rate signifying that the SIRPα blockade has no additive effect to CD47 blockade (FIGS. 14A-14F). Furthermore, consistent with treatment by engineered mouse marrow macrophages, engineered human marrow macrophages shrunk tumors significantly more effectively than TAMs, with 12% tumor shrinkage per day versus 2%, respectively.

Figure 5E:
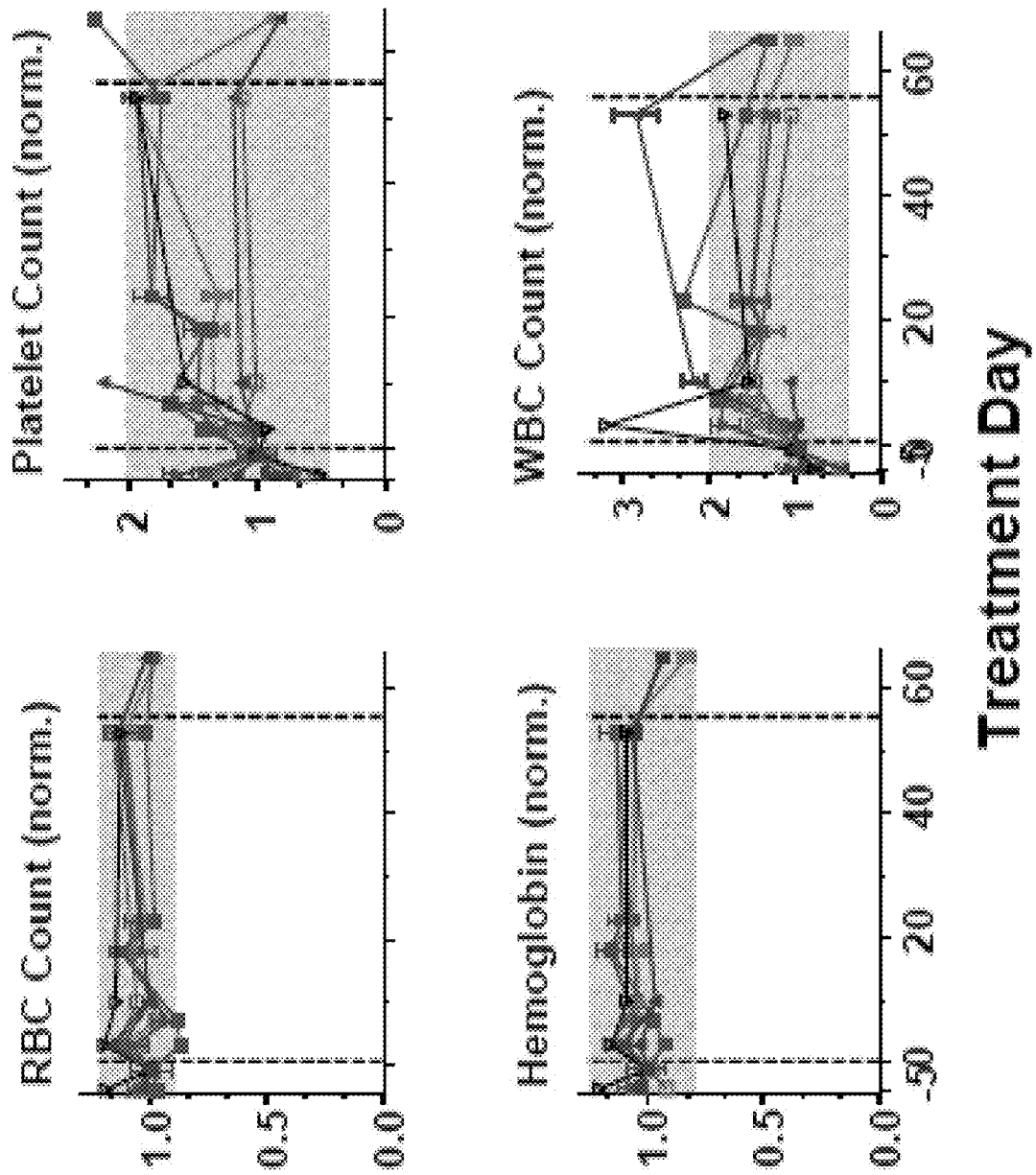

Example 9: Blood Profiles Remain Normal with Engineered Marrow Treatments of Tumors Safety is a concern whenever inhibiting macrophage recognition of 'self' based on past findings that systemic injections of anti-CD47 rapidly clear some blood cells and can lead to an adaptive immune response. CD47-knockout mice can also exhibit auto-immunity, anemia, and premature death. Blood was therefore drawn periodically from the various treated mice and collected using the same methods for studies of both human donors and NSG donors, but with protracted studies for human donor cells. Blood was isolated one and four days before treatment to establish pretreatment variation in blood profiles (FIG. 5E). After multiple treatments with engineered human donor cells, blood was collected once or twice per week along with any observations of anomalous mouse behavior (there were none). RBC count, hemoglobin levels, percent hematocrit, platelet count, and WBC count all remained within the normal range for all treated mice over the ~9 wk experiment (FIG. 5E). For all mice, a slight upward increase in WBC count was observed and could reflect inflammation associated with retro orbital bleeds. Safety results for NSG mouse donors are similar (FIGS. 14A-14G). Intravenous injections of engineered donor macrophages thus appeared safe at the same time that these injections rapidly and effectively shrank solid tumors.

Example 10: Discussion

Phagocytes are often considered highly motile as well as phagocytic, but there is also evidence from modern methods that tissue resident macrophages do not exchange (much) with blood monocytes. Disease and injury could sometimes differ from homeostasis. For example, with hardening of arteries, blood monocytes enter the disease site, engorge as infiltrating macrophages, and fail to egress. In the present study, marrow-derived monocytes and macrophages squeezed through capillary-size pores unless they phagocytosed. Spiking the most phagocytic marrow macrophages that could be engineered (A'PB MΦ) into normal mouse lung tissue that is not phagocytosed by these macrophages showed in 24 hours that half of these MΦ's migrated from top to bottom of a minimally restrictive transwell (FIGS. 2B-2C). Spiking these same cells into a disaggregated human lung tumor xenograft ex vivo showed nearly 100% of cells phagocytosed and almost 100% were retained on top of the same transwell. Engorging on large cells such as cancer cells certainly made the macrophage much larger than the pores (FIGS. 1F and 2A). Without wishing to be bound by any specific theory, engorgement can be a steric mechanism for infiltrating macrophage accumulation, although it is also possible that cells turn off their motility machinery when they are phagocytosing (and/or digesting).

For efficient engulfment of cancer cells in vivo, at least three features of a macrophage can be optimized. First, a macrophage should have high phagocytic potential. Second, the CD47-SIRPα self-recognition system should be blocked such as with anti-SIRPα blocking Ab. Third, the cancer cell should be specifically opsonized. Both NSG mouse marrow macrophages and human marrow macrophages infiltrated large solid tumors after intravenous injection of marrow-derived cells, and these macrophages fully engulfed human cancer cells (FIGS. 1B-1G). RNAi knockdown of SIRPα also increased phagocytosis of Ab-opsonized cells (FIGS. 13A-13F), but such a permanent engineering of cells—versus blockade with an Ab that is slowly lost—can be problematic because injection of SIRPα-knockdown macrophages can promote tumor growth. Phagocytosis also required a targeting antibody such as anti-hum IgG, anti-MUC1, or Cetuximab that bound and opsonized the tumor cells (FIGS. 3A, 3C, 3E, and 9A-9H) and that also bound (via its Fc domain) to the macrophages (FIG. 3D). Monoclonal IgG's beyond the anti-MUC1 and Cetuximab used here have previously been successfully used to shrink tumors after CD47 blockade, but the most widely used and successful antibody therapies today is likely polyclonal IgG of anti-RhD, which has been injected in countless pregnant women since the 1960's to clear maternal blood of any fetal blood bearing foreign RhD antigen. Given the large molecular heterogeneity of tumors and their ability to evolve (perhaps even lose MUC1), polyclonal Ab mixtures can help minimize selection and survival of cancer cell sub-populations.

Tumor shrinkage by mouse macrophages required simultaneous inhibition of self-recognition, which was most readily achieved by blocking SIRPα on macrophages prior to cell injection (FIGS. 1A-1C, 3A-3B). APB macrophages showed the largest amount of phagocytosis with nearly all macrophages eating tdTom A549 cells (FIG. 1B). Knockdown of CD47 on the cancer cells also worked (FIG. 3C, 3E) even though shrinkage depended on TAMs that are far less phagocytic than marrow derived macrophages (by ~30-fold FIGS. 1B, 1D). This finding is consistent with past reports showing the density of TAMs in tumors correlates with poor clinical outcomes, based in part on TAMs being relatively non-phagocytic. For human and mouse marrow derived macrophages, tumor shrinkage here was enhanced by blocking SIRPA on macrophages prior to injection, and tumor shrinkage was greatest when macrophages were also pre-loaded or primed with the antibody that opsonizes the tumor cells (FIGS. 1C, 2B, 5A). On the other hand, systemic injections of just the opsonizing antibody had zero effect on tumor growth in the absence of cell injections (FIG. 3C, 3E), and pre-immune antibody never showed significant effect with engineered cells (FIGS. 3B, 5C, 5D). For all of the many treatment and control conditions, the extent of macrophage phagocytosis of tumor cells as measured at the single cell level showed depletion of cancer cells as well as initial rates of shrinkage or growth of tumors (FIGS. 4A, 5B).

No detectable impact on mouse health resulted from the cell therapy treatments described herein, which drove phagocytosis and tumor shrinkage. Blood profiles and body weight (FIGS. 5E and 14A-14F), as well as many observations of mouse activity, all supported the safety of the protocols. Past studies of tumor shrinkage using systemic injection of anti-CD47 led to decreases in blood cells and platelets as well as increased reticulocytes, which are all a consequence of ubiquitous expression of CD47. Careful attention to species specificity of anti-CD47 is of course needed in such studies, but CD47 blockade in a clinical setting will likely sensitize all healthy cells to macrophage clearance, particularly by macrophages in the spleen but also probably the liver and marrow among other tissues. Combination of systemic anti-CD47 with tumor opsonizing antibodies nonetheless engaged a small number of phagocytic TAMs (confirmed here in FIG. 1D, with quantitation of tumor cell uptake), and this is sufficient to cause shrinkage of established solid, ortho topic tumors. CD47 knockdown studies described herein showed selective eating of cells with low CD47, enriching for CD47-high cancer cells (FIGS. 3C-3E). Without wishing to be bound by any specific theory, this might explain why cancer patients tend to have CD47-high cancer cells even if TAMs have limited efficacy. In comparison to systemic injections of anti-CD47, the donor marrow macrophages that were engineered here to selectively phagocytose cancer cells as foreign appear safe as they traffic, reside, and phagocytose less in the spleen and more so in the tumor (FIG. 1B, 1G).

Collagen in solid lung tumors is sufficiently rigid to impede infiltration of T-cells. For blood cells leaving the marrow, the idea that matrix barriers and porosity can limit migration was postulated years ago with the hypothesis that deformability of the marrow cell and its nucleus would restrict entry into the blood stream. Nuclear deformability is set by lamin levels which indeed controls hematopoietic cell migration through small pores. Across tissues and tumors, lamin-A:B increased in macrophages in the stiffer tissues (FIGS. 13A-13F), so that the stiffer nucleus will make it physically more difficult for the phagocyte to egress as will engulfment of another cell with a stiff nucleus (FIGS. 1E-1F). The resulting accumulation and eventual differentiation of infiltrating marrow macrophages towards a TAM phenotype (FIGS. 1B, 1G, and 4D-4H) is accompanied by many changes in gene expression, and these including upregulation of SIRPα. Higher SIRPα equates to more opportunity to bind and be passivated by 'marker of self' CD47, so that phagocytosis by donor macrophages will be slowly suppressed, and tumors will eventually re-grow. Multiple injections of marrow cells can address this and are already done in the clinic with marrow and leukocytes. The findings here thus provide insight into mechanisms and utility of engineering: (i) a highly phagocytic and motile phenotype, with (ii) inhibition of 'self signaling by SIRPα blockade, combined with (iii) robust target opsonization.

Example 11: Antibody Stimulated Tumor Shrinking is Dependent on CD47 Expression

Figure 24A:
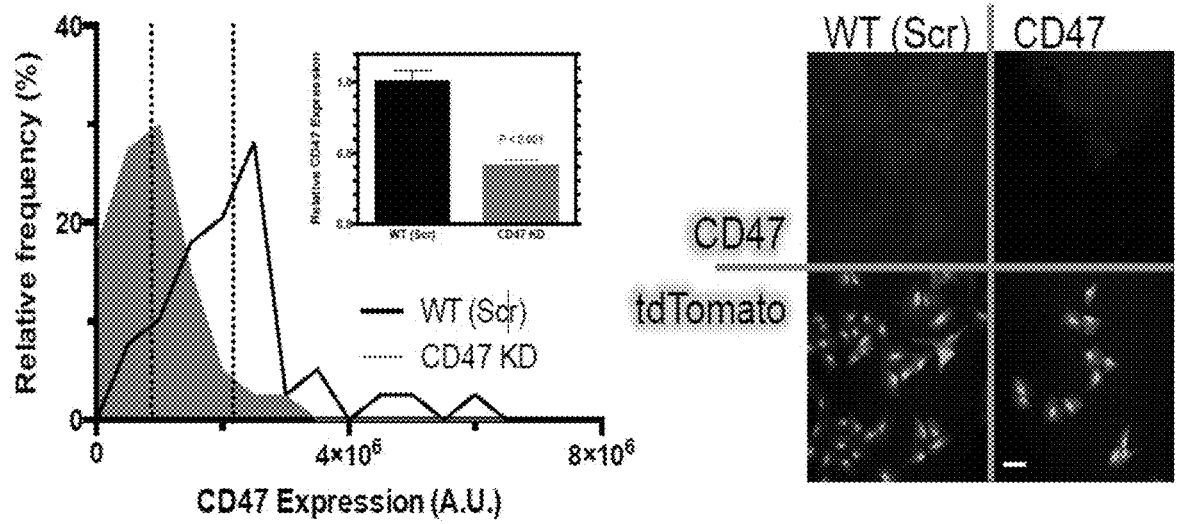
FIGS. 24A-24D are a series of graphs and images showing preliminary studies of CD47 knockdown in vitro and in vivo.
Figure 24B:
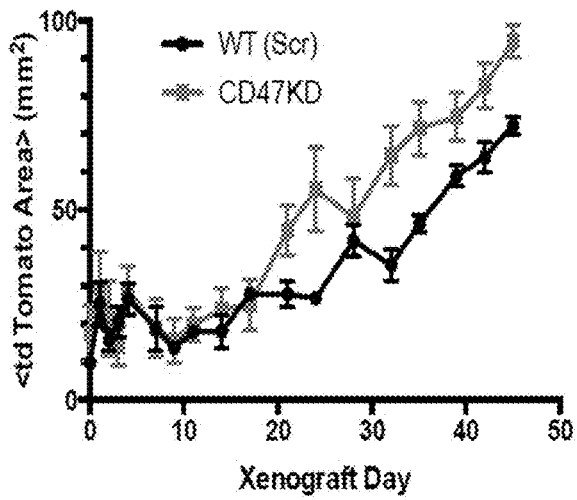

A human lung cancer cell line expressing the fluorescent protein, tdTomato was previously established (Harada et al., J. Cell Biol. 204, 669-82 (2014)). Transduction and antibiotic selection resulted in both a stable "scramble" tdTomato-A549 (WT Scr) cell line and a stable CD47 knockdown tdTomato-A549 (CD47 KD) cell line. Approximately 60% knockdown was confirmed by immunofluorescence (FIG. 24A, right). Both WT Scr and CD47 KD were used in a preliminary in vivo study in which subcutaneous xenograft tumors were grown on each flank of NOD/SCID/IL-2Rγ-/- (NSG) mice. Tumor progression was monitored in this and all subsequent in vivo studies by live animal imaging to detect tdTomato fluorescence. No significant difference in tumor growth rate was observed between WT Scr and CD47 KD (FIG. 24B).

Figure 24C:
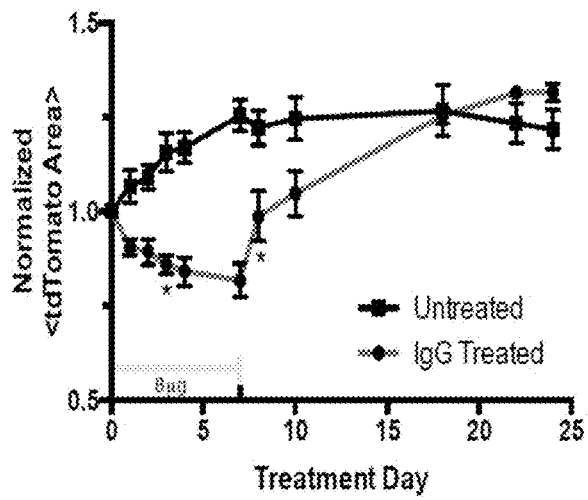

Recent work has shown tumor shrinking by blocking the CD47-SIRPα interaction with injection of a high affinity SIRPα variant in combination with a chemotherapeutic antibody (Weiskopf 2014) and the well-established use of Rho(D) antibodies in suppression of isoimmunization. To test if opsonizing antibody could be used in combination with CD47-SIRPα disruption, the following experiments were performed. Indeed, when mice bearing CD47 KD xenograft tumors were treated with anti-human IgG antibody, tumors shrank to ~60% of the size at treatment initiation by 7 days (FIG. 24C).

Figure 17A:
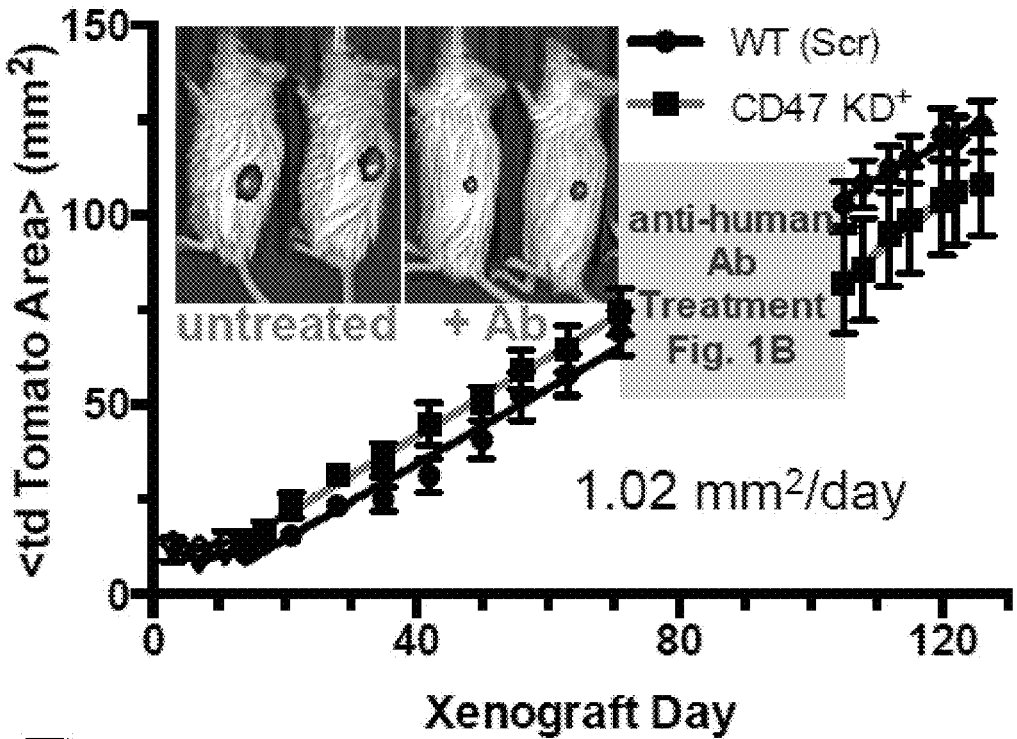
FIGS. 17A-17F are a series of images, graphs and histograms showing in vivo tumor growth and anti-hrbc treatment.
Figures 25A, 25B, 25C:
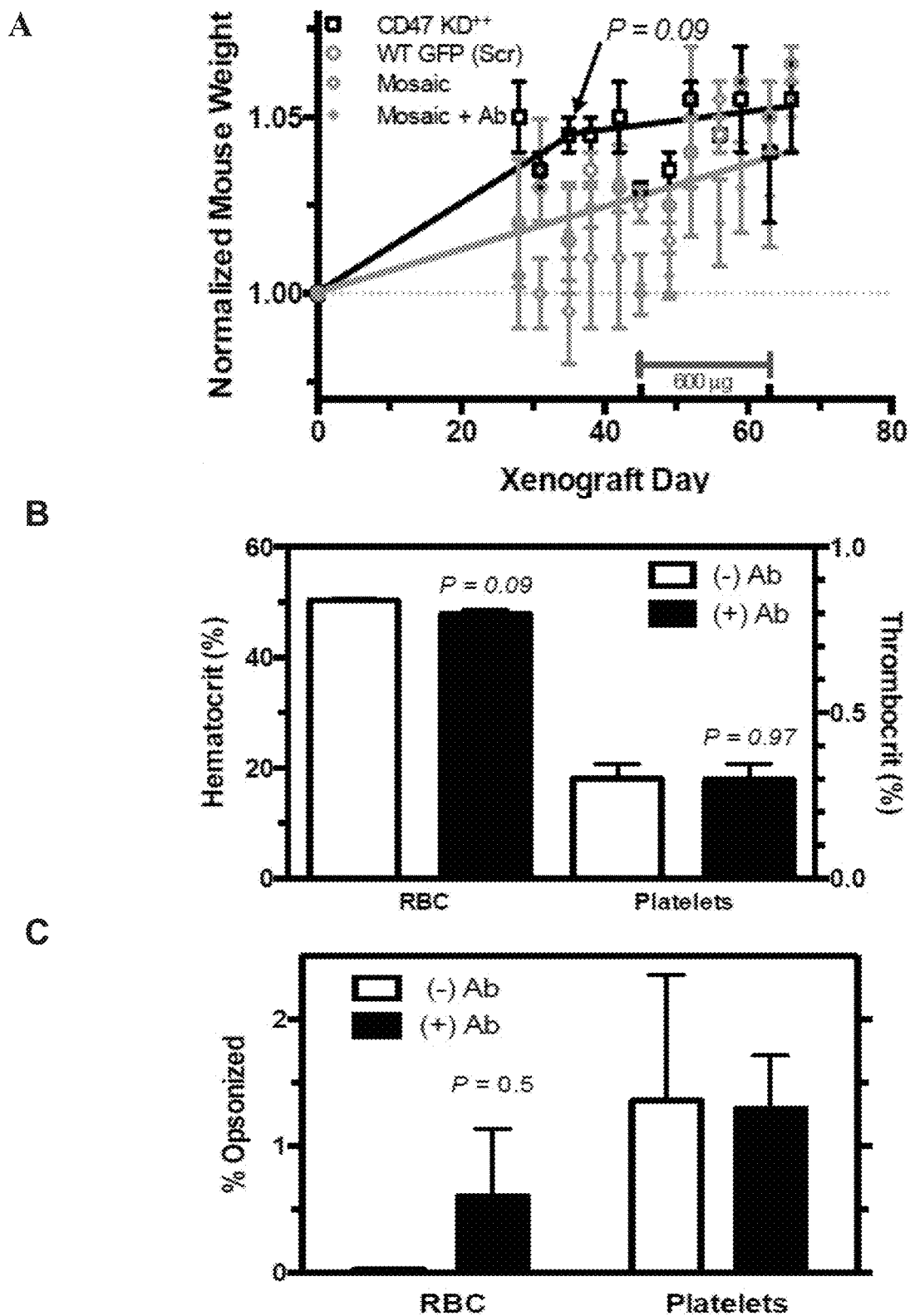
FIGS. 25A-25C are a series of graphs showing antibody treatment does not cause adverse side effects.

The CD47 KD cell line was further enriched by 2 rounds of cell sorting to purify for CD47 knockdown cells (CD47 KD+) and confirmed by flow cytometry (FIG. 25C). Subcutaneous xenograft tumors grown on the flank of NSG mice showed no significant difference in growth rate between WT Scr and CD47 KD+(FIG. 17A).

Figure 17B:
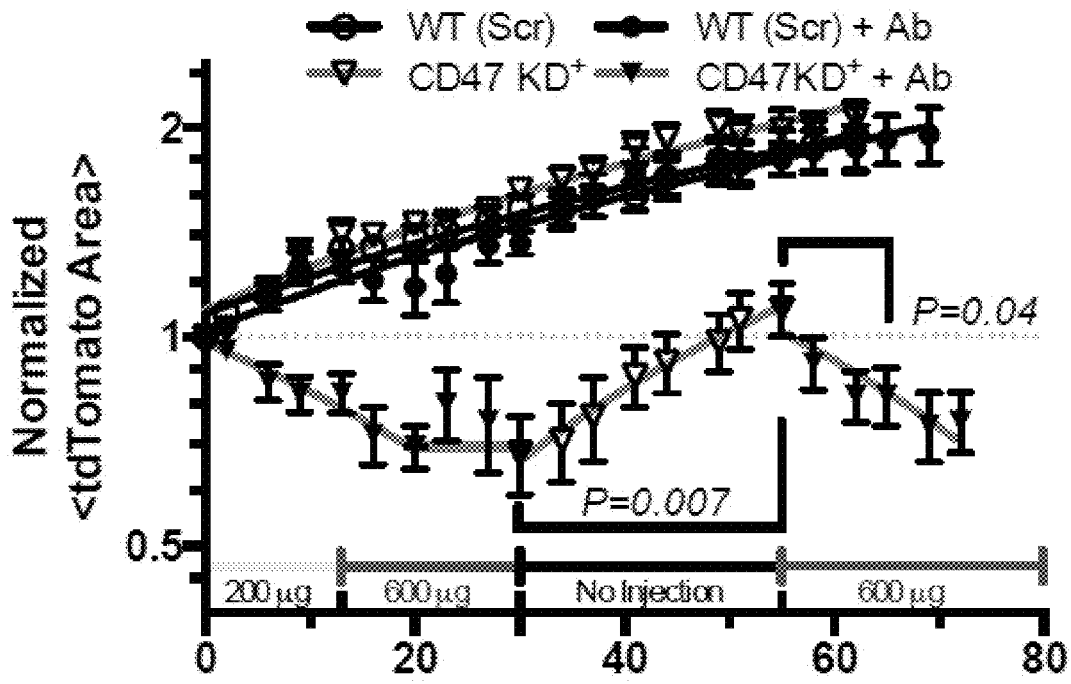
Figure 17C:
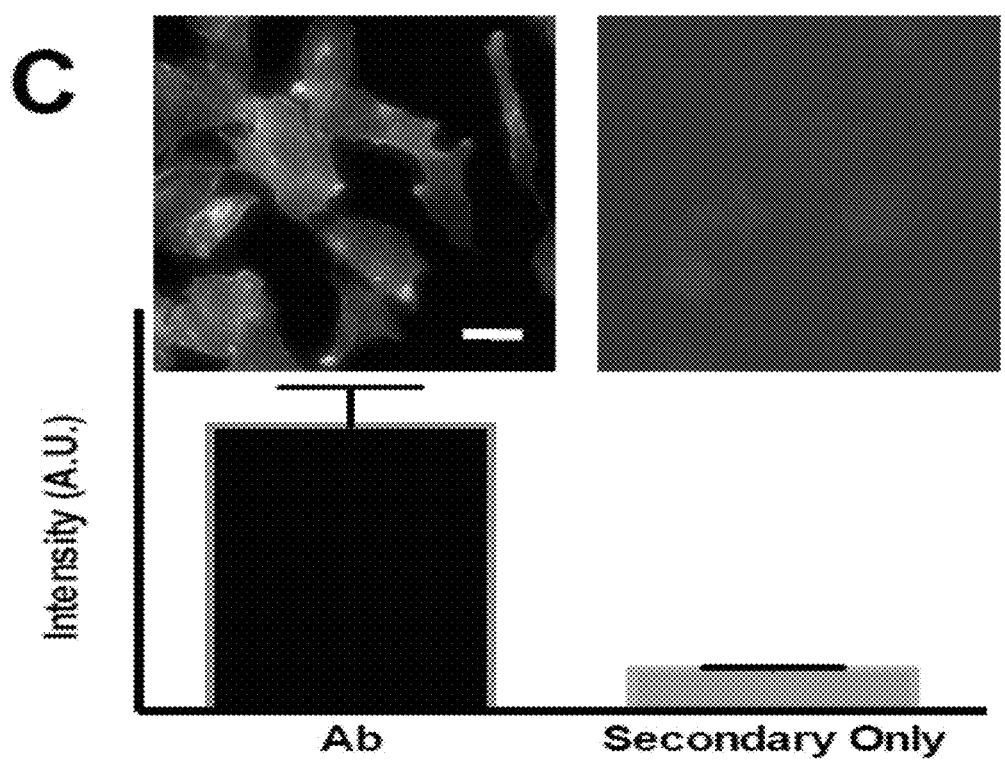
Figure 21A:
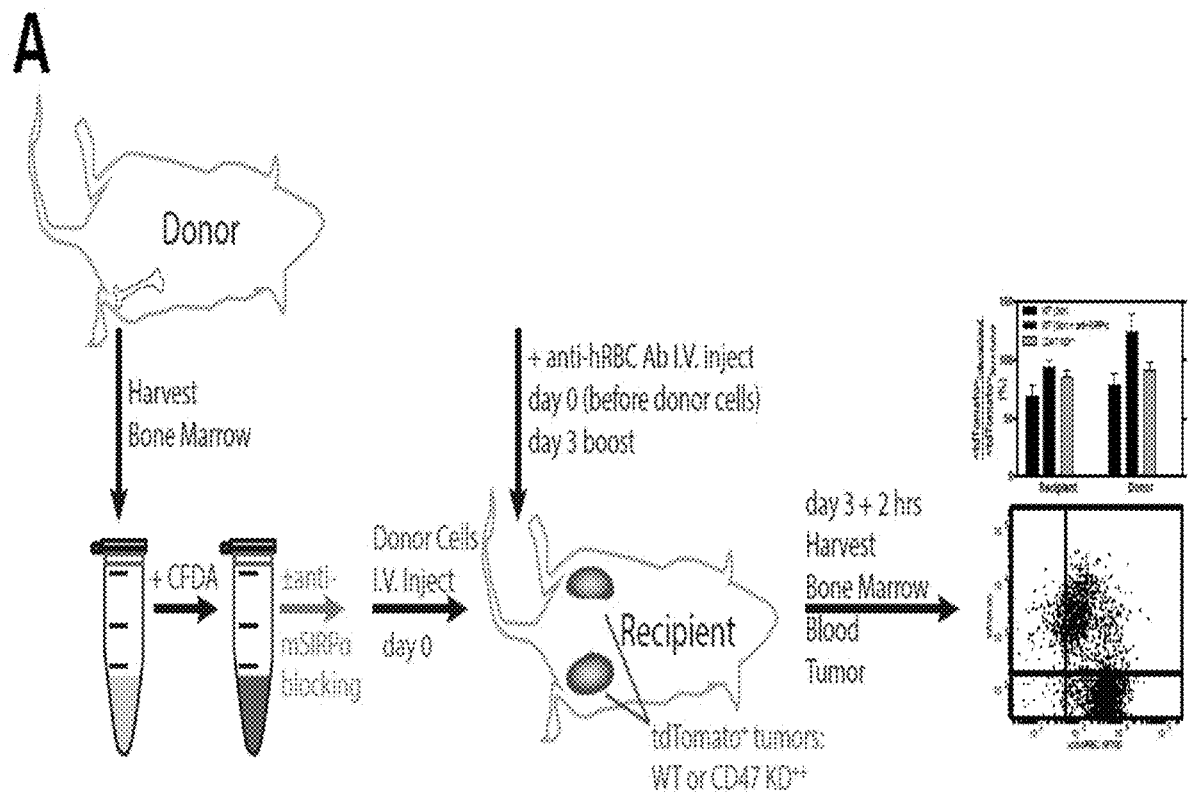
FIGS. 21A-21E are a series of plots and histograms illustrating the adoptive transfer of labeled NSG bone marrow.

To show that antibody-mediated tumor shrinking of CD47 knockdown tumors is truly independent of one particular antibody, mice were treated with an anti-human RBC antibody (Ab) that was the purified IgG fraction from antiserum. Ab binding to A549's was confirmed by immunofluorescence (FIG. 17C). Nearly 50% reduction in tumor size was observed after 4 weeks of biweekly treatment (FIG. 17B). The highest dosage of Ab was equivalent to ~20% of serum IgG levels in fully immunocompetent C57BL/6 mice and ~150% of serum IgG levels reported for humanized NSG mice (FIG. 22). When antibody treatment was discontinued, tumors continued growing at a similar rate as observed prior to treatment and independent of CD47 expression (FIGS. 17A-17B). Surprisingly, after this period of uninterrupted regrowth, reapplication of antibody was again capable of shrinking CD47 KD+ tumors (FIG. 17B) with similar apparent kinetics as the first round of treatment.

Figures 28A, 28B:
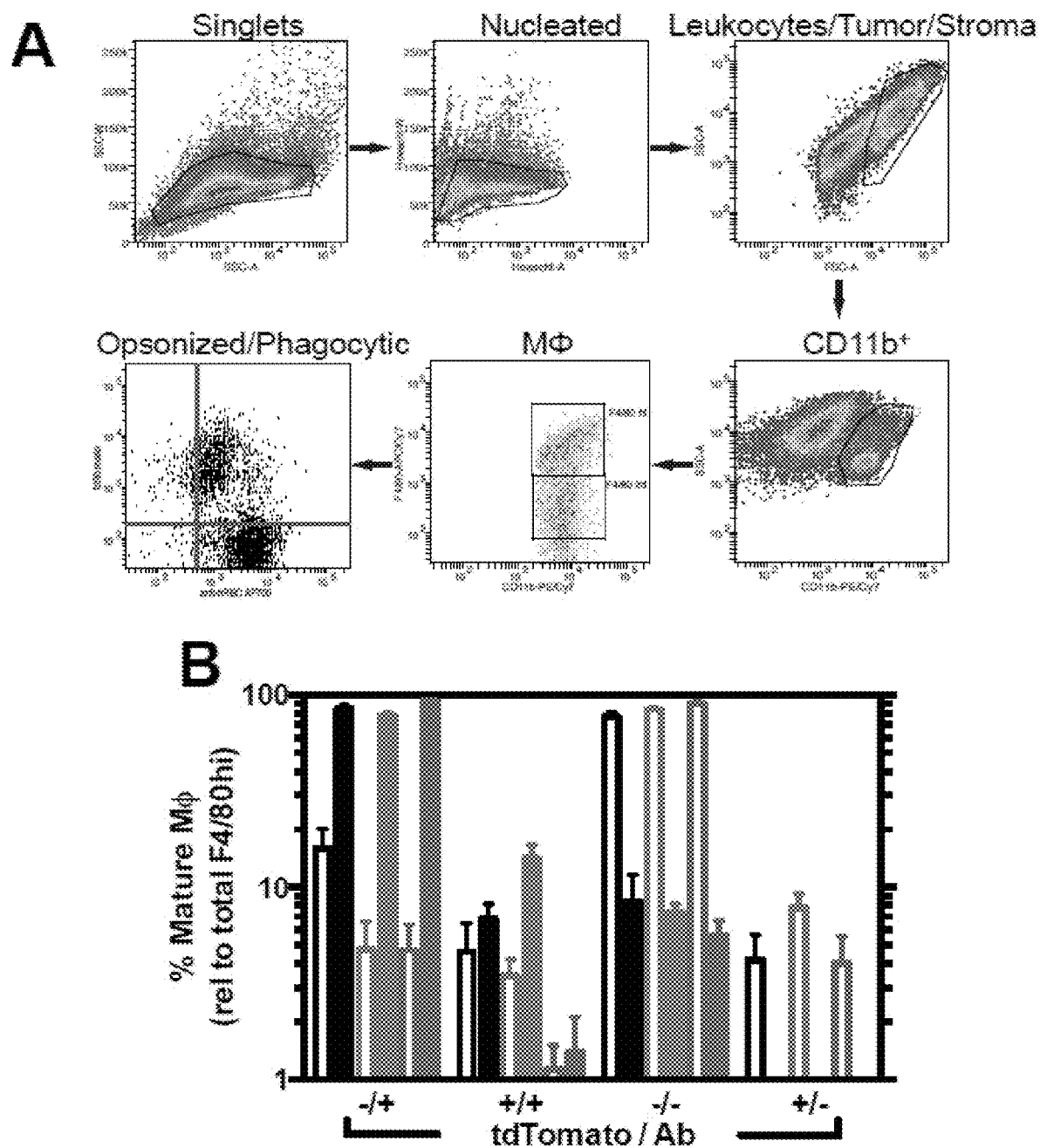
FIGS. 28A-28E are a series of plots and graphs showing macrophage localization and population breakdown.
Figures 28C, 28D, 28E:
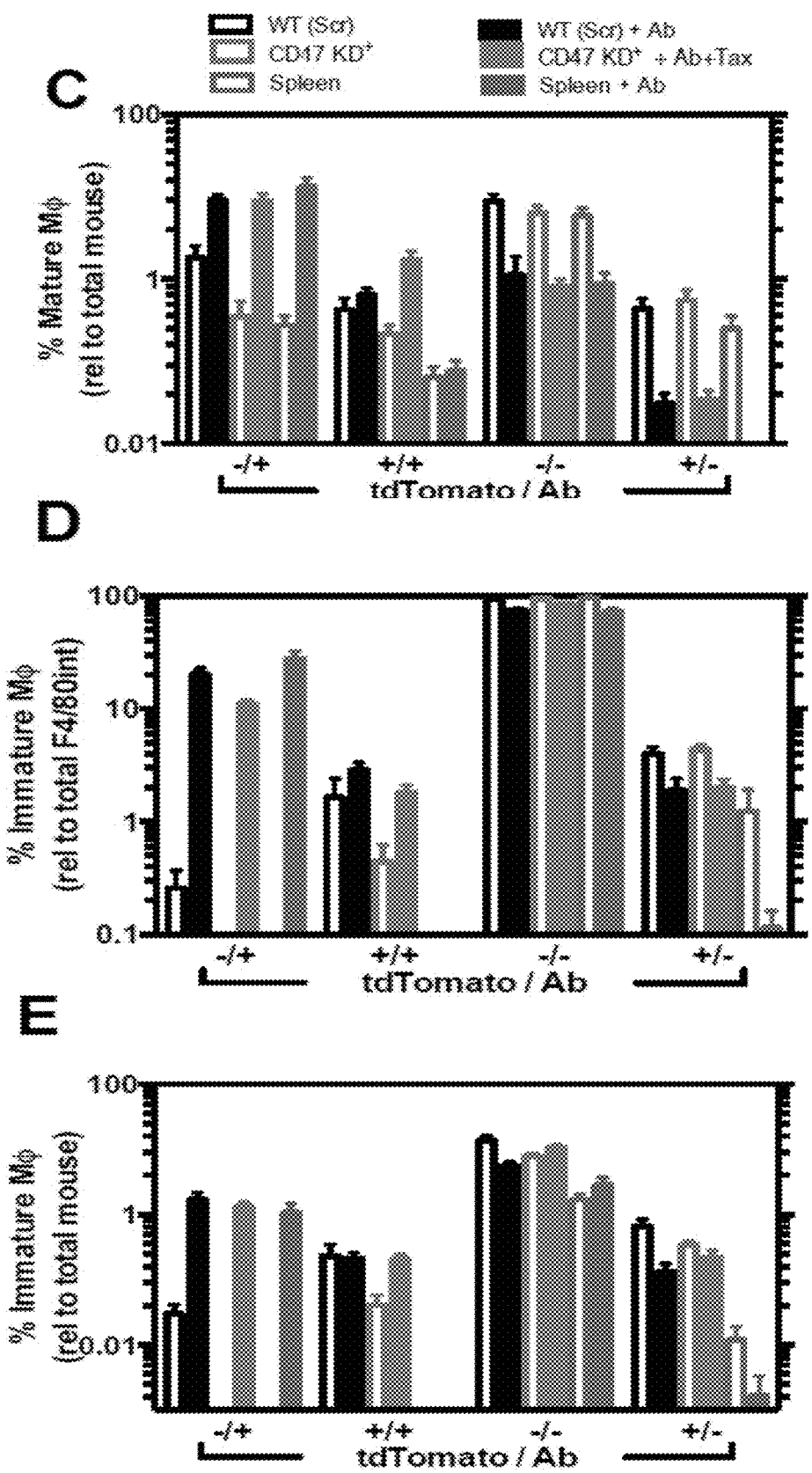

Although the CD47 KD+ had been cell sorted it still contained a small subpopulation of cells expressing normal levels of CD47. To determine that it was the low CD47 expressing cells that are being cleared, the CD47 KD+ cell line was enriched by additional cell sorting (CD47 KD++) and also transfection of the WT Scr cell line with GFP (GFP WT Scr). Flow cytometry confirmed GFP expression and CD47 KD++ knockdown of 93% (FIG. 28B). Despite multiple rounds of cell sorting, the CD47 KD++ cell line still contained a minor population expressing normal CD47 levels, but this was determined to be minor (~10%) and distinct (by flow cytometry) from the true CD47 knockdown majority.

Figure 17D:
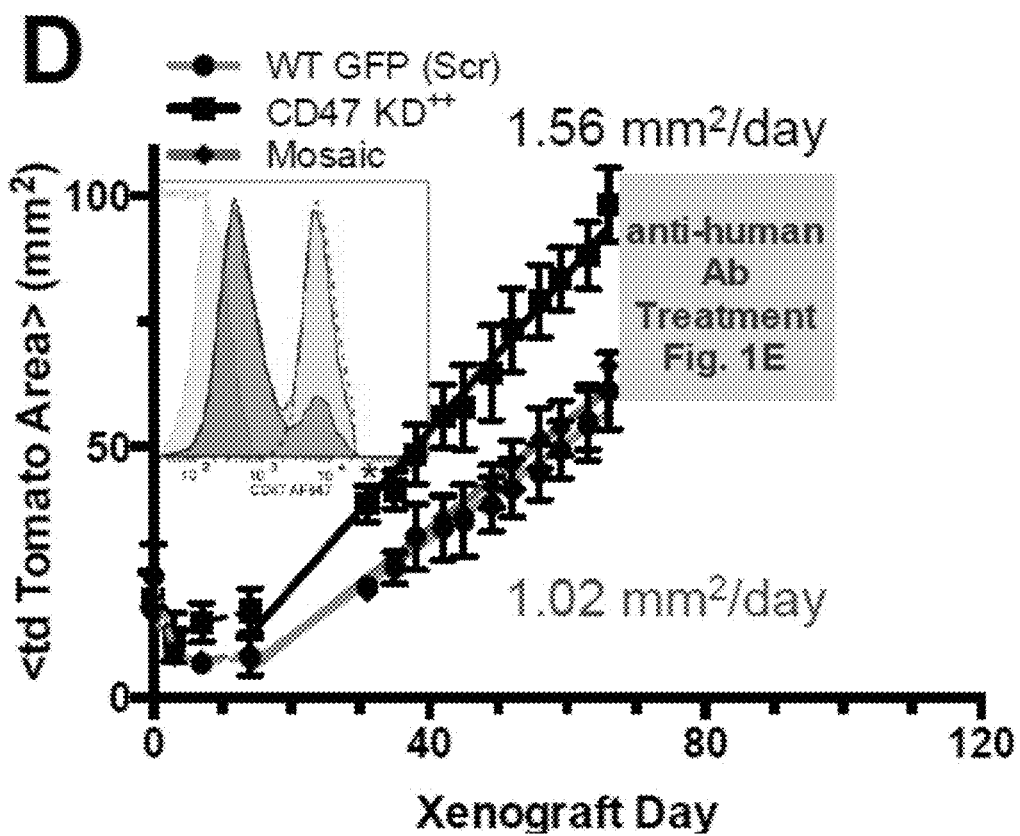

NSG mice were split into the following 3 cohorts: 1) WT GFP Scr, 2) CD47 KD++, 3) Mosaic (WT GFP Scr/CD47 KD++ injected 1:3). The mosaic tumors were subsequently determined to be comprised of a 1:2.7 ratio of WT GFP Scr: CD47 KD++ by flow cytometry (FIG. 17E and FIGS. 28A-28E). Xenografts were again grown subcutaneously on each flank. CD47 KD++ tumors showed an enhanced growth rate compared to tumors containing WT CD47 expression levels (FIG. 17D), perhaps consistent with previous observations of the loss of thrombospondin-1 signaling through CD47 increasing stemness (Kaur et al., Sci. Rep. 3, 1673 (2013)).

Figure 17E:
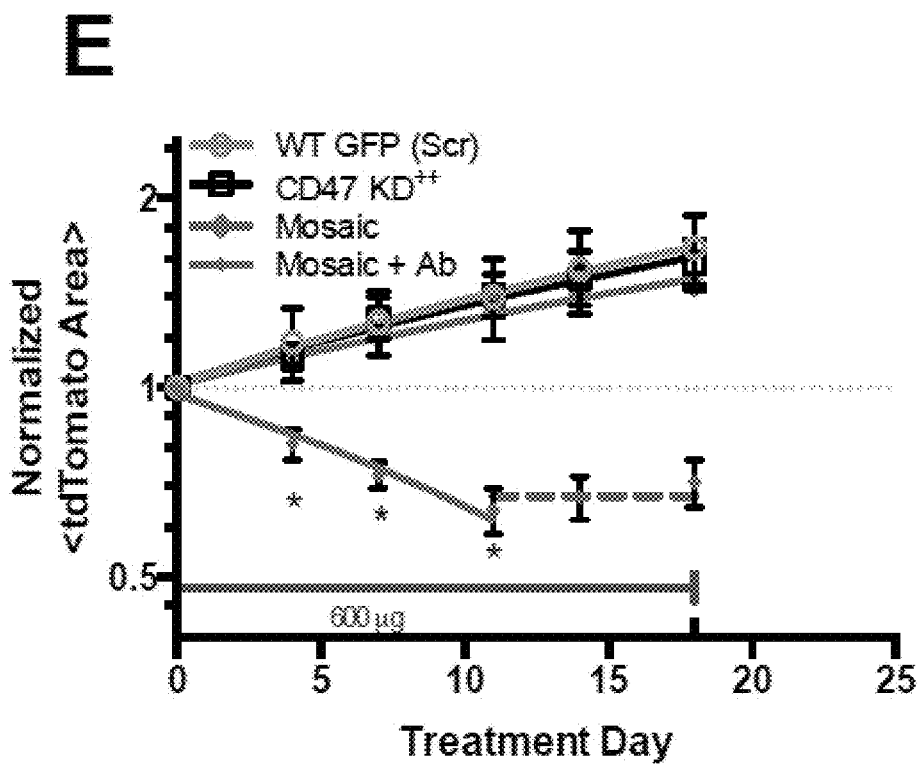
Figure 17F:
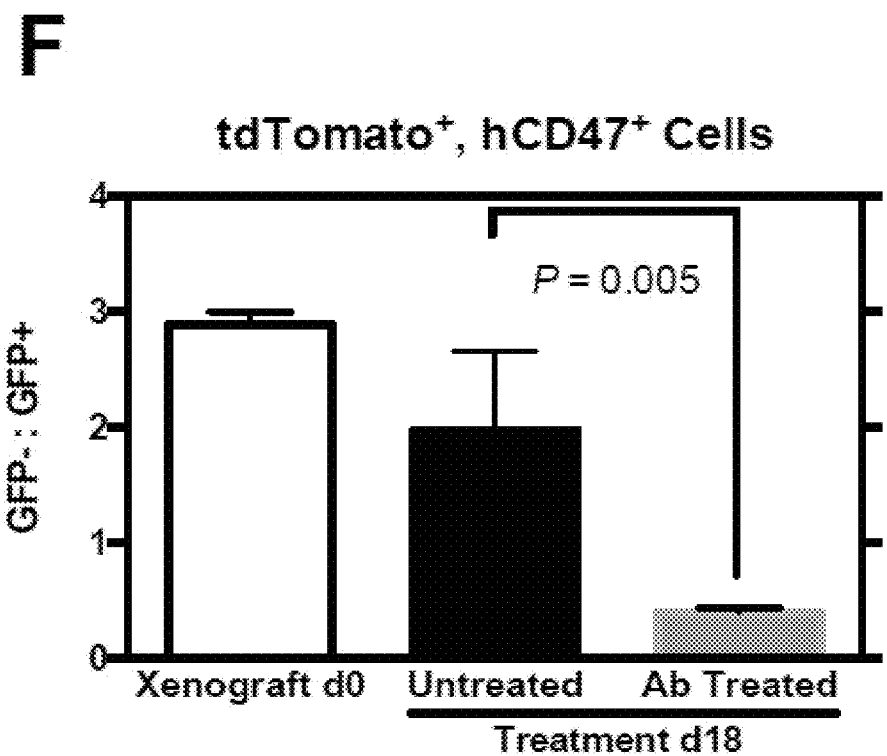

Mosaic tumors treated with anti-hRBC showed a slightly enhanced responsiveness as CD47 KD+ reached a 40% reduction in tumor size by 10 days following biweekly dosing (FIG. 17E). Tumors excised from euthanized mice at the termination of treatment showed an inversion of GFP+: GFP− ratio (FIG. 17F). The initial ratio of 1:2.7 was not significantly changed in untreated Mosaic tumors while the antibody treated Mosaic tumor ratio was 3.3:1, indicating that tumor shrinking was due to selective clearance of GFP-CD47 KD++ cells.

Figure 13A:
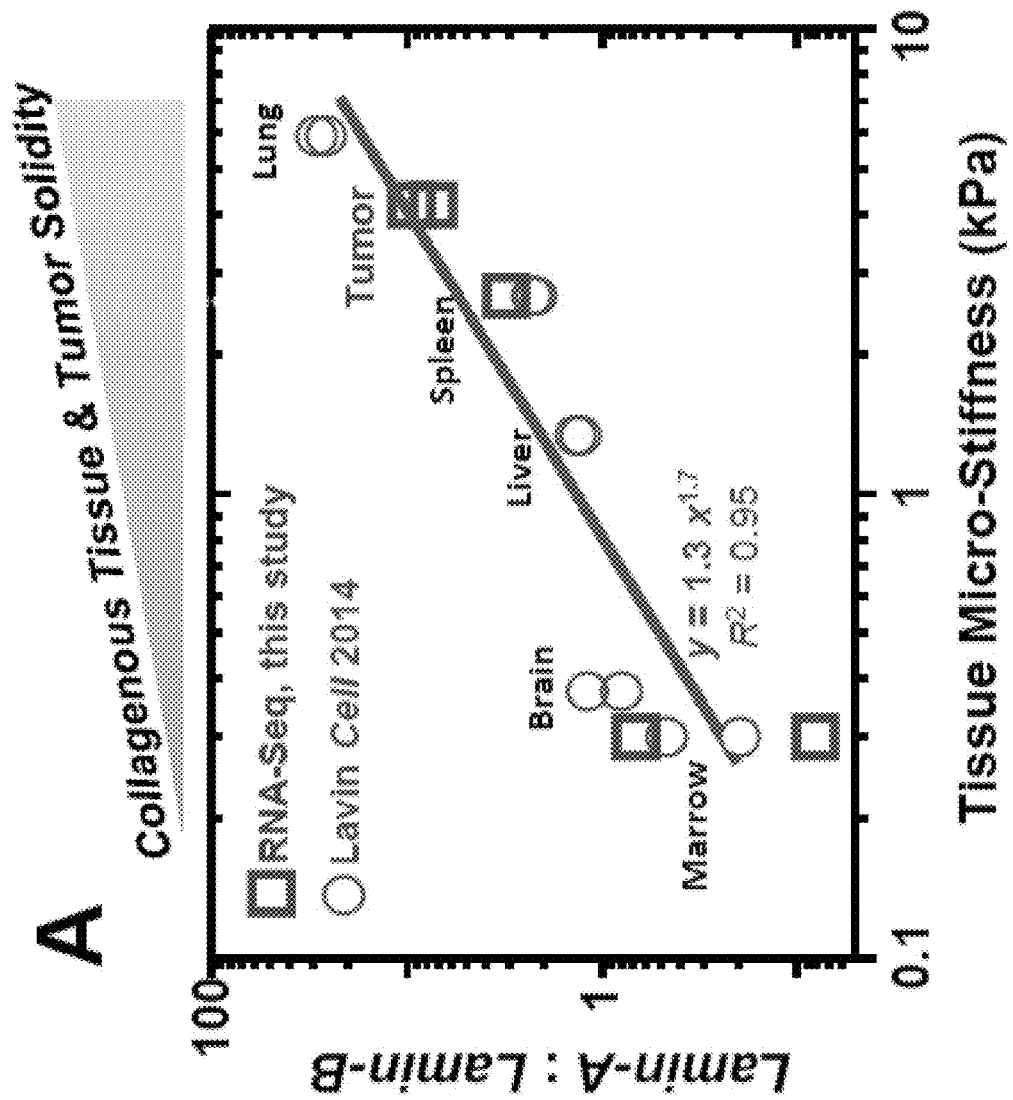
FIGS. 13A-13F are a series of graphs showing stiff matrix regulation of SIRPA and phagocytosis of a lung cancer cell line enhanced by blocking hSIRPA.
Figures 13B, 13C:
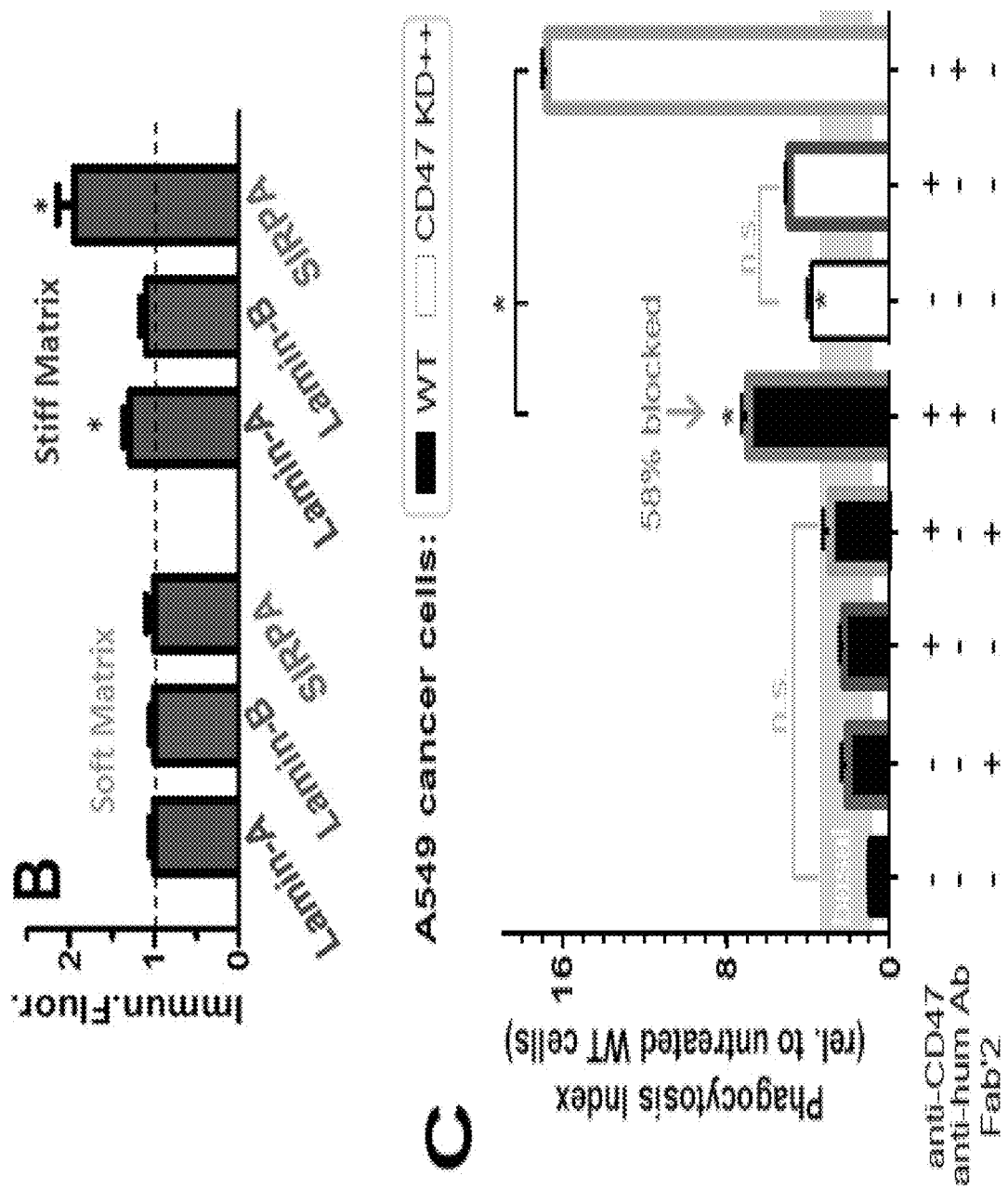
Figures 13D, 13E, 13F:
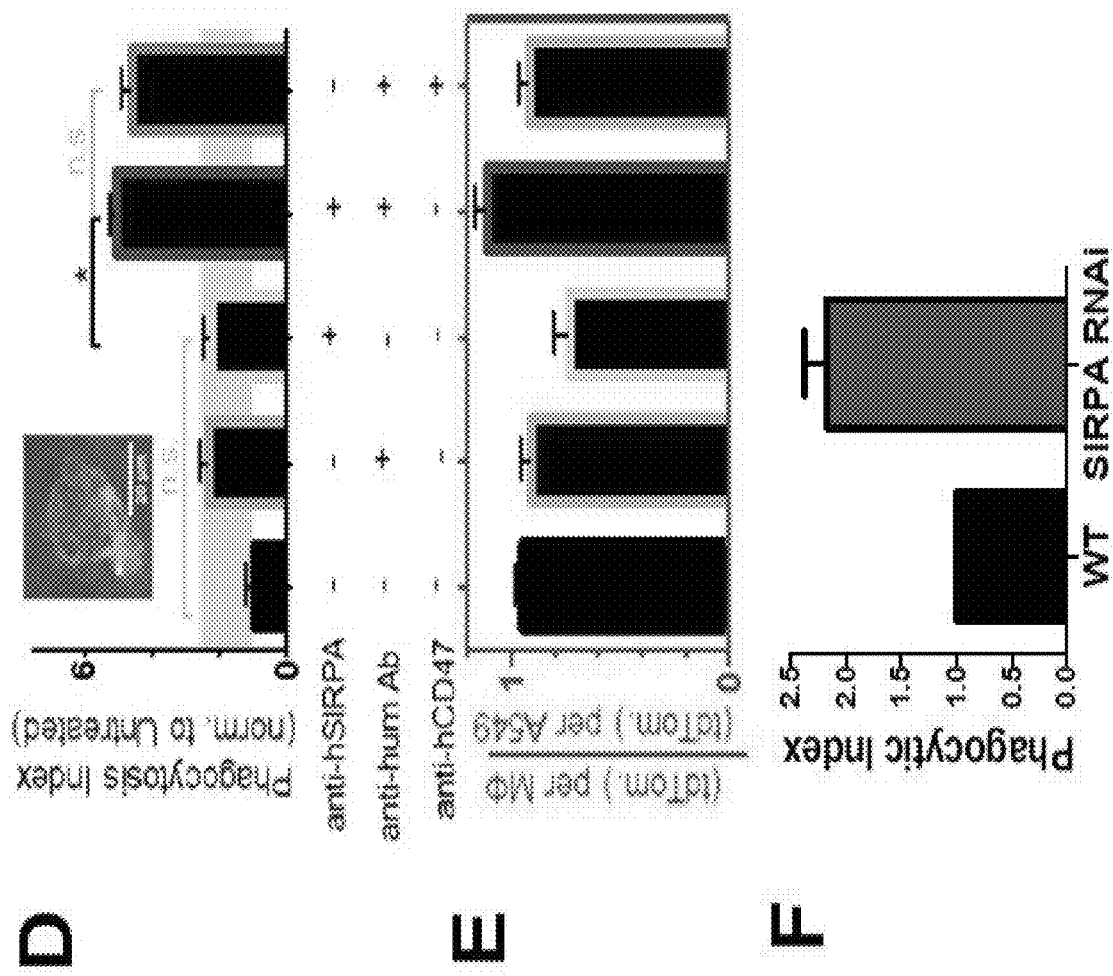
Figure 14A:
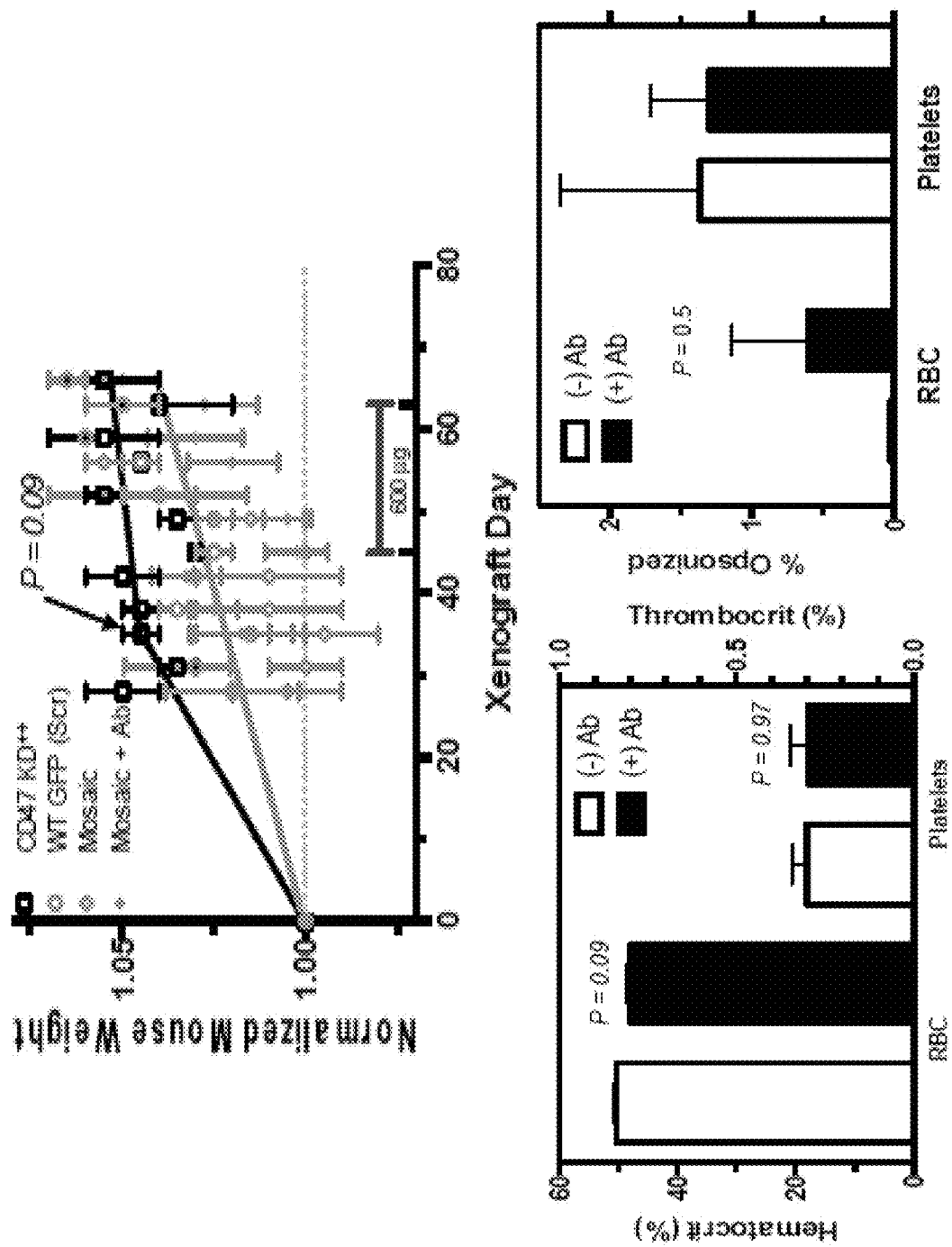
FIGS. 14A-14H are a series of graphs showing safety and in vivo confirmation of human donor efficacy.
Figures 14B, 14C, 14D:
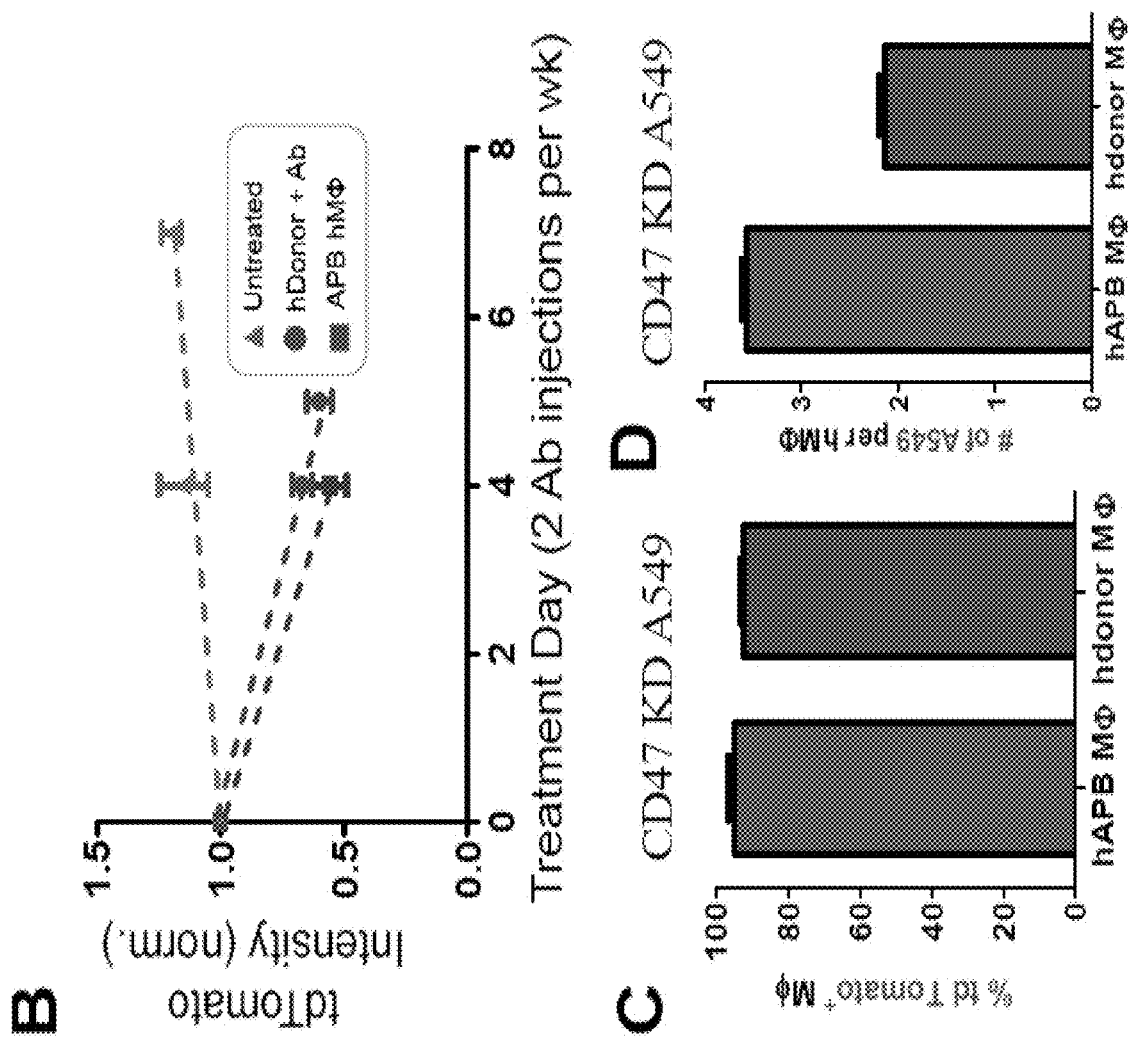
Figures 14E, 14F:
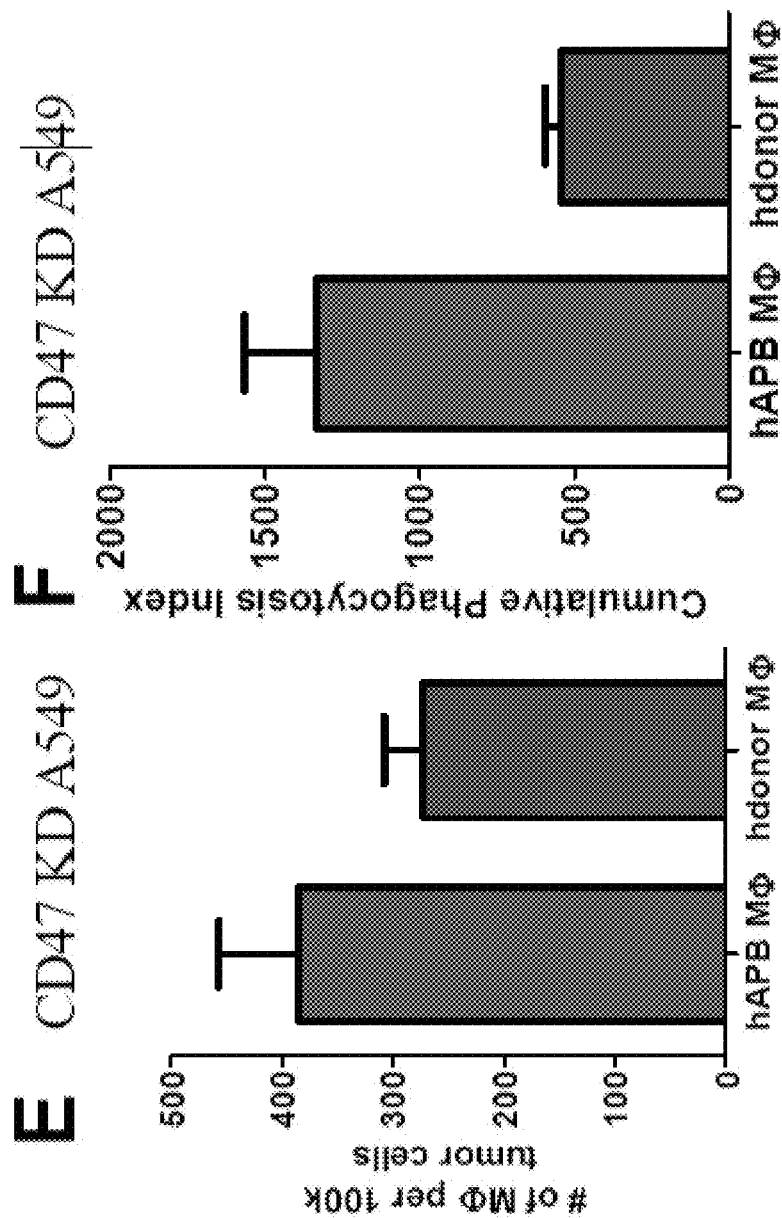
Figure 14G:
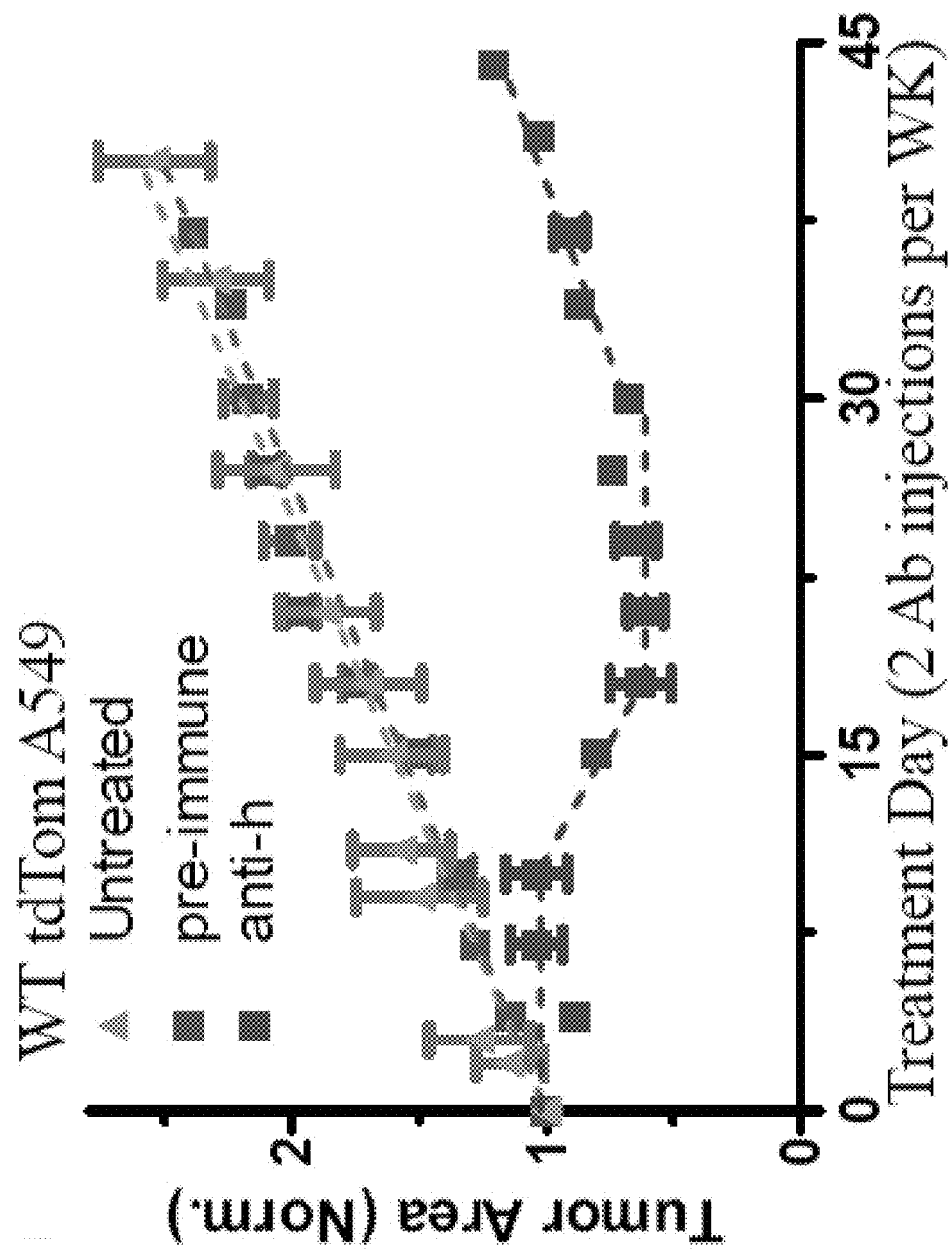
Figure 14H:
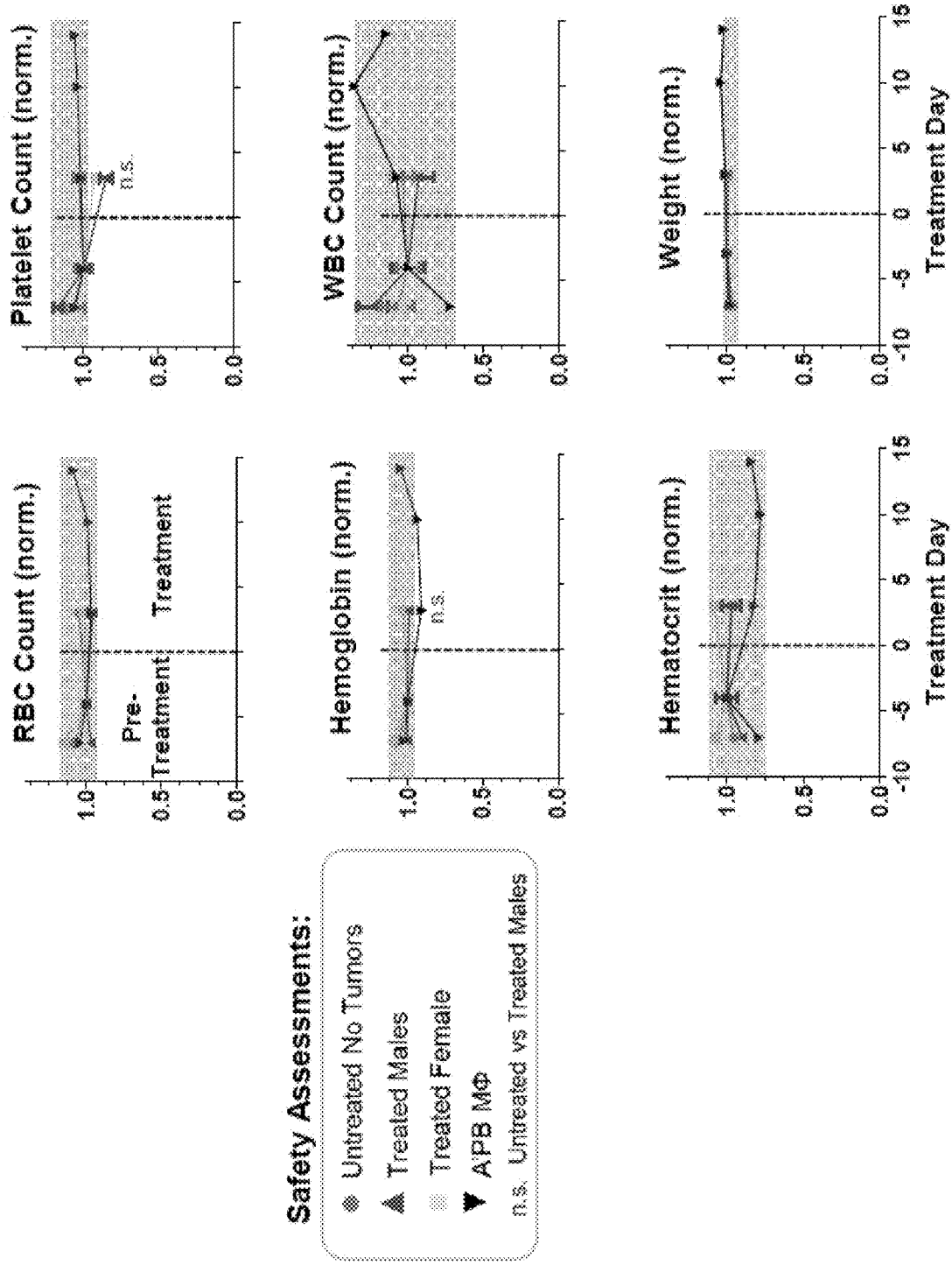
Figures 29A, 29B:
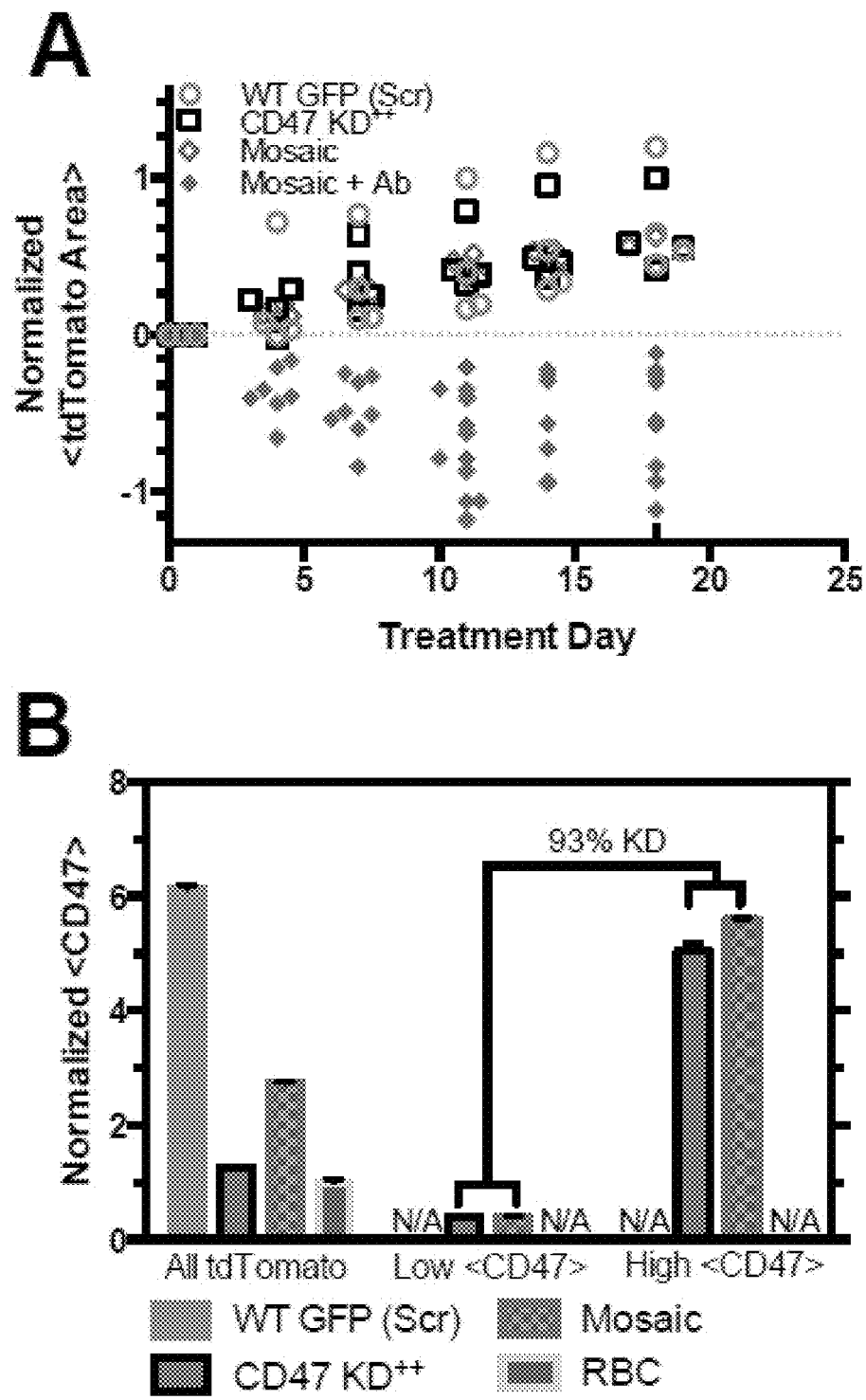
FIGS. 29A-29F are a series of plots and bar graphs showing WT GFP Scr/KD++ mosaic tumor analysis.
Figures 29C, 29D:
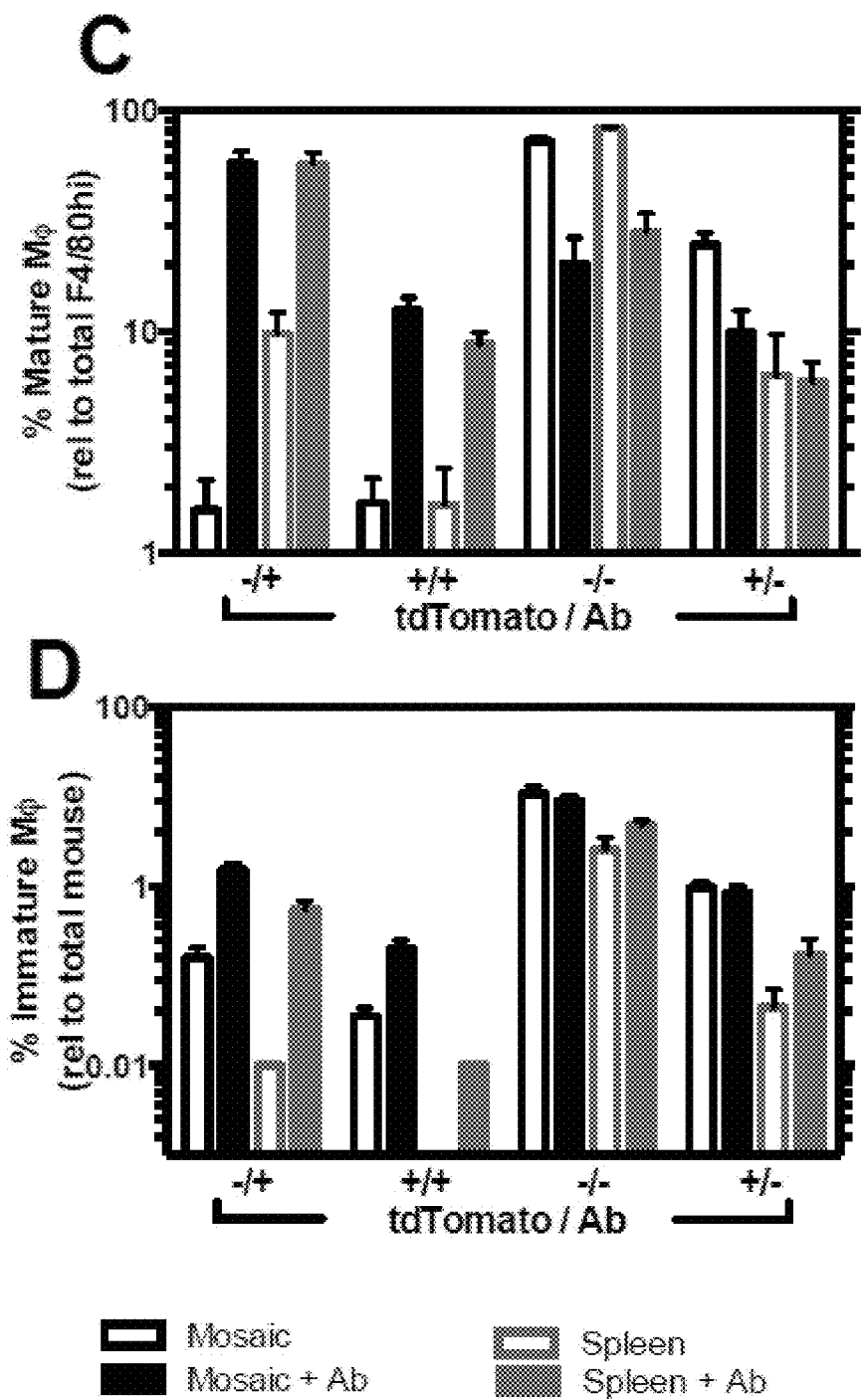
Figures 29E, 29F:
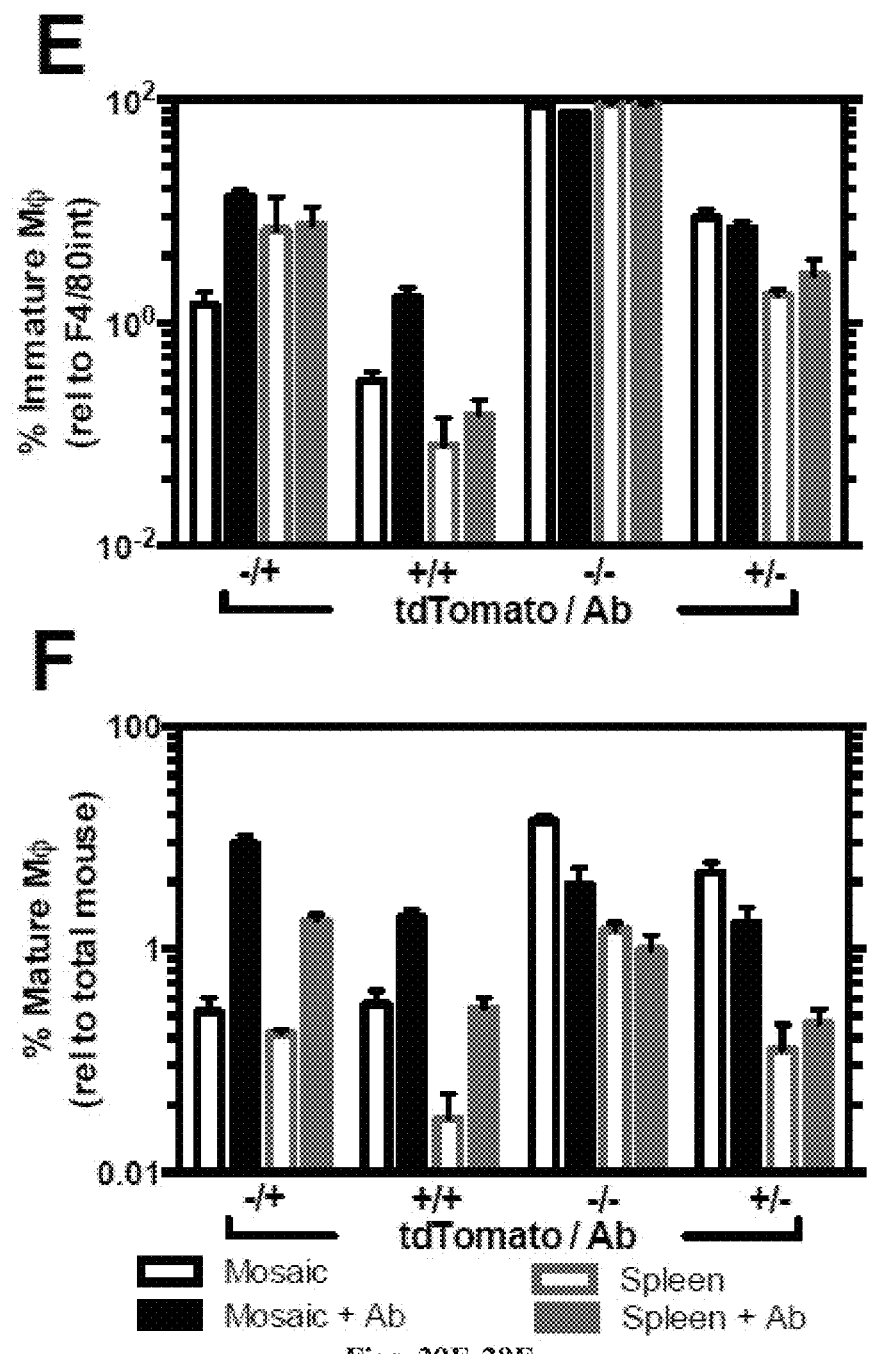

Macrophage subpopulations were analyzed from the tumors. The percentage of immature macrophages relative to the total number of murine cells in a given tissue/spleen is shown in FIG. 29C. The percentage of immature macrophages relative to the total number of immature macrophages in a given tissue/spleen is shown in FIG. 29D. The percentage of mature macrophages relative to total number of mature macrophages in a given tissue/spleen is shown in FIG. 13E. The percentage of mature macrophages relative to total number of murine cells in a given tissue/spleen (n=4 tumors/spleens per group. mean±SEM) is shown in FIG. 29F.

Figure 26A:
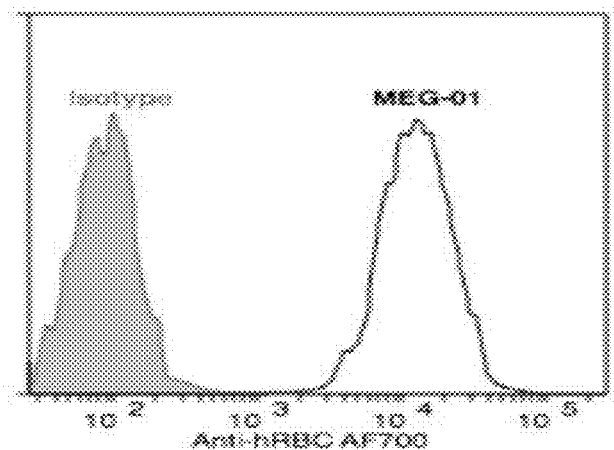
FIGS. 26A-26F are a series of graphs showing anti-human RBC antibody binding and initial treatment.
Figure 26B:
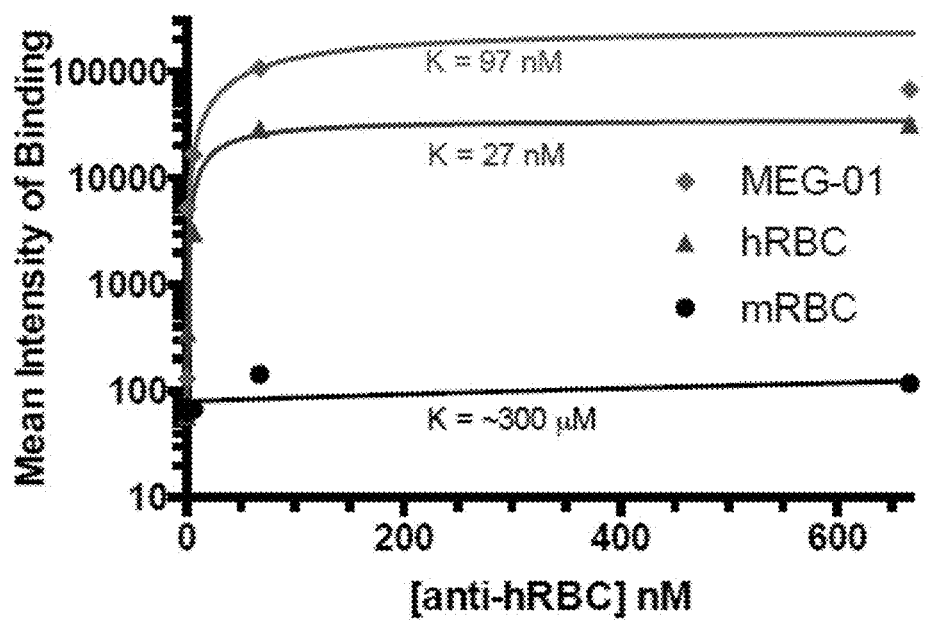
Figure 26C:
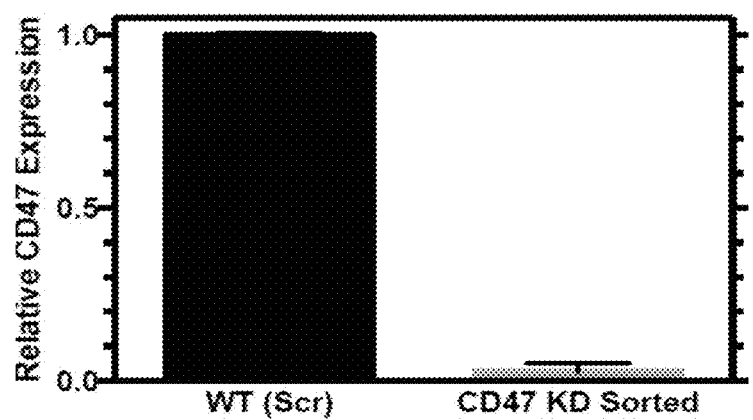
Figure 26D:
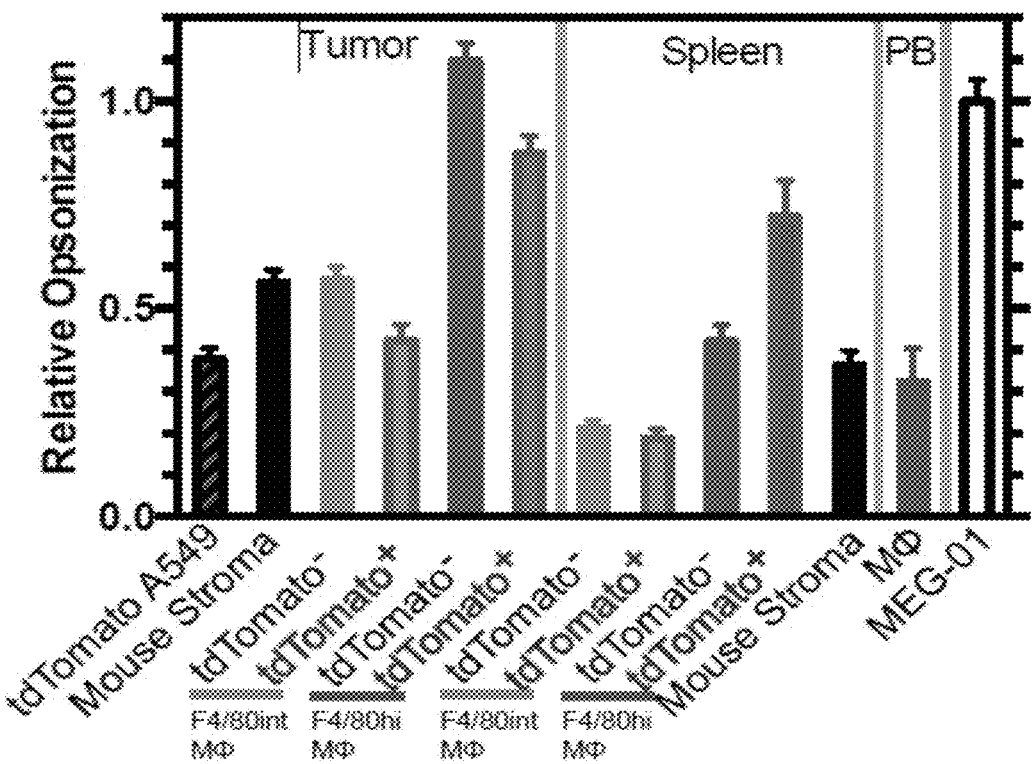
Figure 26E:
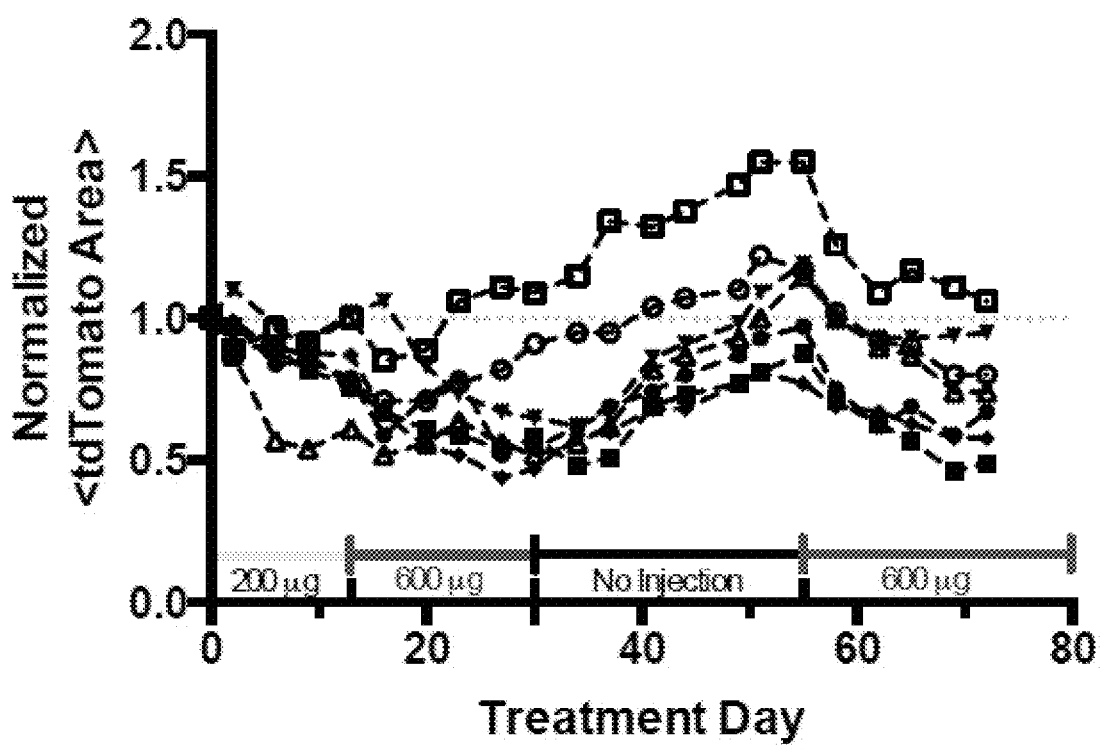
Figures 26F, 27A, 27B:
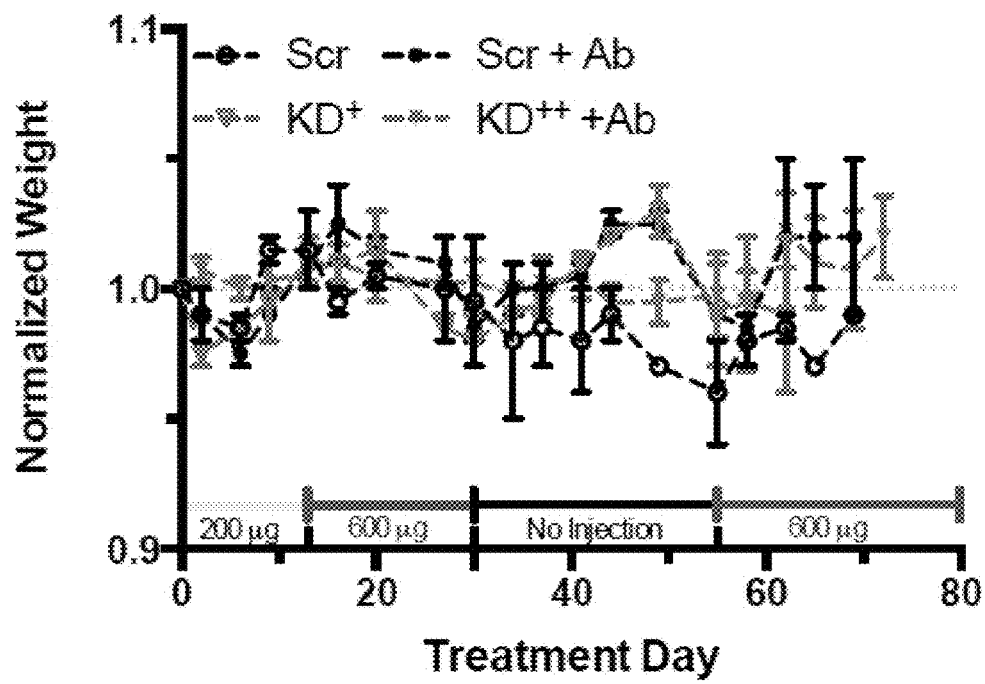
FIGS. 27A-27F are a series of tables and graphs showing antibody+Taxol treatment cytotoxicity, animal monitoring, and tumor assessment.

Several previous studies disrupting the CD47-SIRPα interaction in mice by treatment with anti-CD47 antibody (Willingham et al., Proc. Natl. Acad. Sci. U.S.A 109, 6662-7 (2012)) or a high affinity SIRPα variant-human IgG fusion (Weiskopf et al., Science 341, 88-91 (2013)) showed significant loss of red blood cells and development of chronic anemia. Animals treated with anti-hRBC did not show a loss of weight, as is common with chemotherapeutic strategies, and, in fact, most treated animals gained weight throughout the study (FIG. 25A and FIG. 26F).

Contrary to these other similar approaches, the treatment strategy did not significantly affect peripheral blood cells. Platelet counts remained relatively unchanged, however, there was a slight reduction in hematocrit following antibody treatment (FIG. 25B). These trends in cell number reduction were mirrored by the tendency of antibody opsonization of RBCs and platelets (FIG. 25C). In vitro binding of anti-hRBC to mouse RBCs (mRBC), human RBCs (hRBCs), or MEG-01 (a human megakaryocytic cell line) showed that the affinity of antibody for mRBC was ~300 μM (FIGS. 26A-26E), which is ~10-4 weaker than for human cells. Despite this dramatically reduced affinity, local concentrations of Ab at the injection site briefly approximated the affinity for mRBC, thereby opsonizing a fraction of mRBC. Such an effect could explain the slight reduction in observed hematocrits.

Example 12: Antibody Treatment as Efficacious as Chemotherapy in CD47 Knockdown Tumors Recent clinical advances have used a combination therapy comprised of a highly specific monoclonal antibody, such as rituximab, with chemotherapy. To test if the addition of chemotherapy has an efficacious effect, paclitaxel was combined with anti-hRBC treatment.

Paclitaxel (Tax) loaded polymer filomicelles were shown to have the capacity of shrinking A549 and U251 xenograft tumors in the flank of mice (Christian et al., Mol. Pharm. 6, 1343-52 (2009) and Baumann et al., Oncotarget 4, 64-79 (2013)). Tax loaded filomicelles were created and shown to be capable of killing A549 cell in vitro regardless of CD47 expression (FIG. 18B) as each cell type had a similar Hill Coefficient (FIG. 27A). Cytotoxicity was quantified using the MTT assay as previously described (Cai et al., Pharm. Res. 24, 2099-109 (2007)).

Figure 18A:
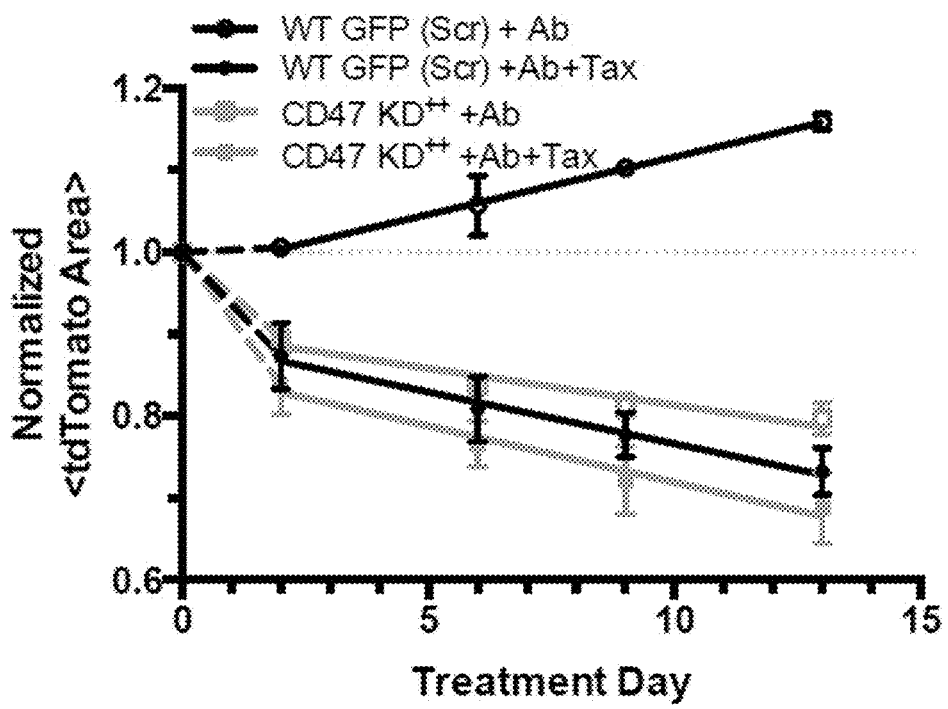
FIGS. 18A-18E are a series of graphs and histograms depicting the combined Ab+chemotherapy treatment of CD47 knockdown tumors.
Figure 18B:
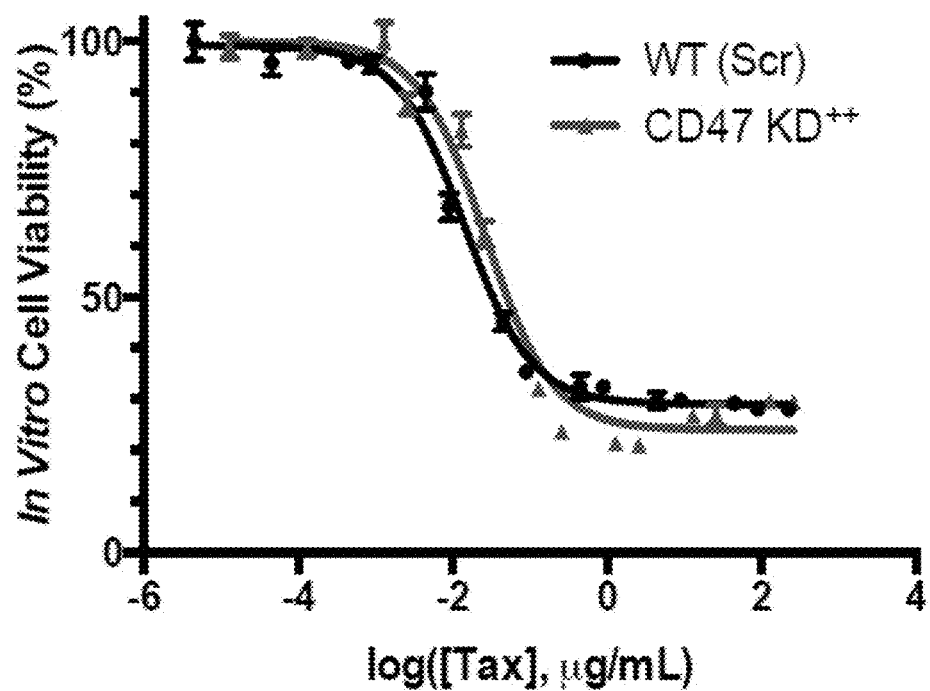
Figures 27C, 27D, 27E, 27F:
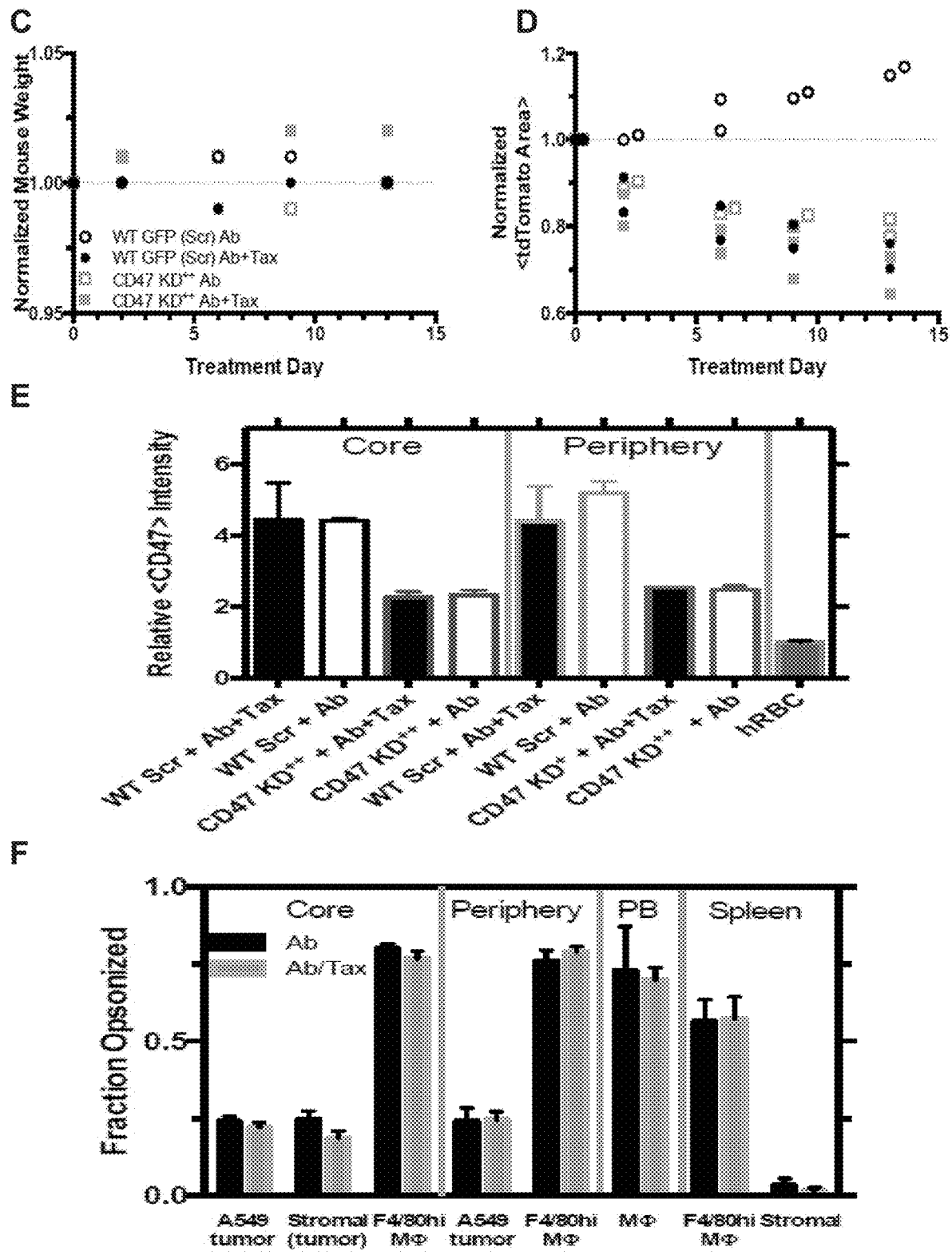

As expected, CD47 KD++ tumors responded to either Ab alone or Ab+Tax, while normal CD47 tumors responded to combination treatment only (FIG. 18A and FIG. 27D). Tumor shrinkage by Tax displayed a similar rate and magnitude of shrinking as previously reported (Christian et al., Mol. Pharm. 6, 1343-52 (2009)). While the addition of chemotherapy to antibody treatment was not synergistic, there was a slight additive effect, but this additional response was not significantly different than Ab treatment alone.

Figure 18C:
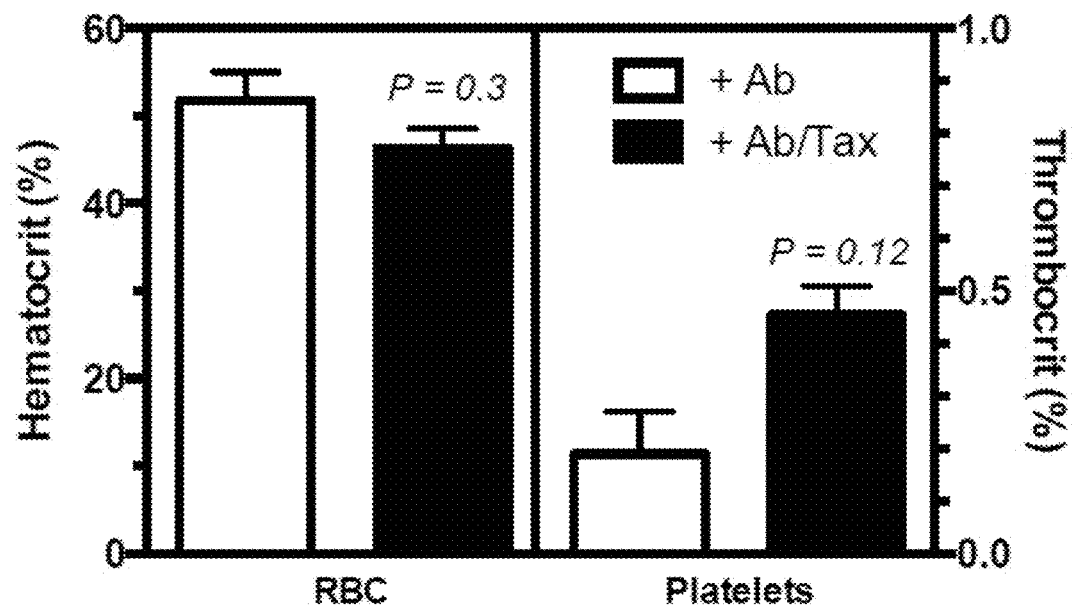
Figure 18D:
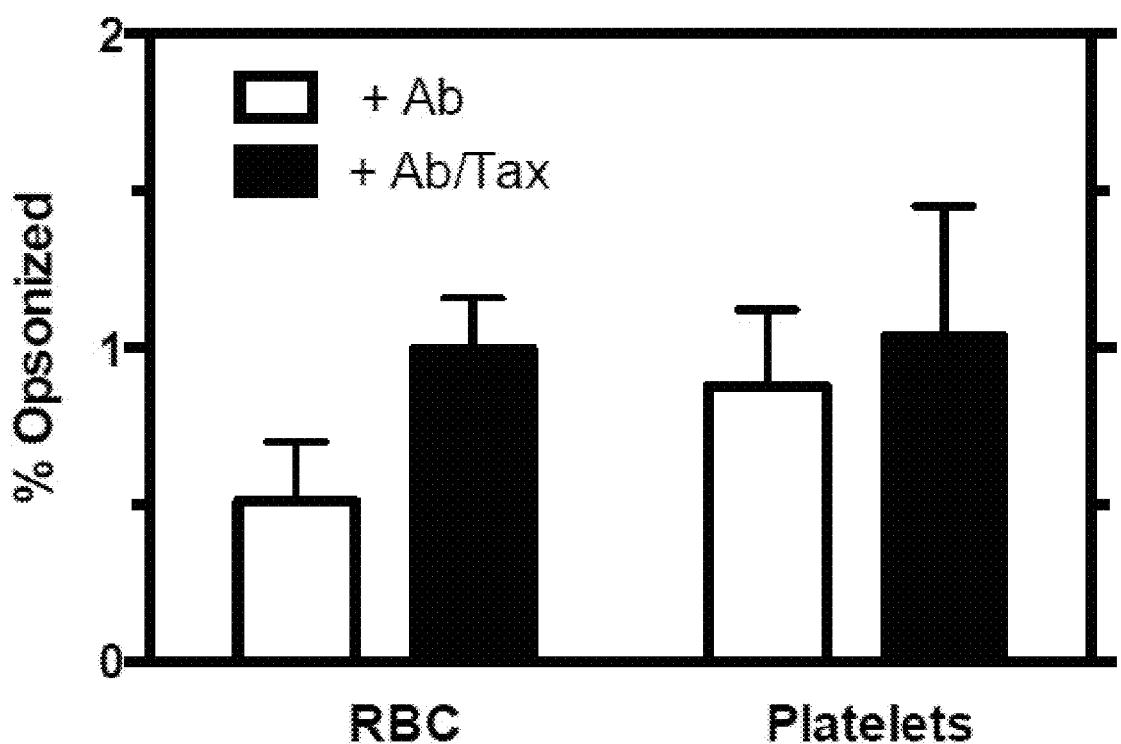
Figure 18E:
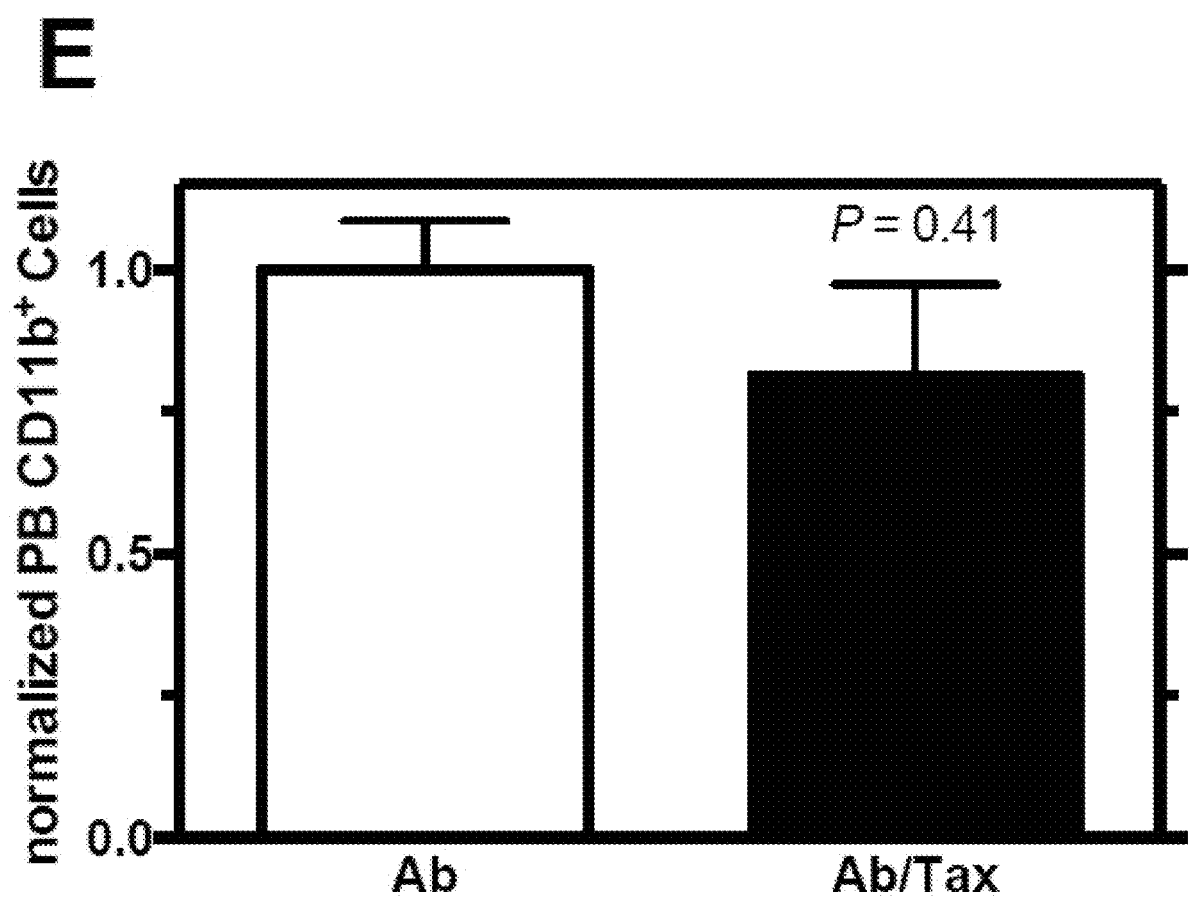

HPLC quantification of Tax concentration in filomicelles revealed that the average Tax dose delivered was ~4.4 mg/kg (FIG. 27B). The addition of Tax to the antibody treatment resulted in further reduction in hematocrit and a slight elevation in thrombocrit (FIG. 18C) without significantly altering antibody binding (FIG. 18D). None of the mice from any treatment arm experienced weight loss during the treatment period (FIG. 27C), but a slight reduction in CD11b+ leukocytes was observed upon application of Tax (FIG. 18E). These results indicate that similar tumor shrinkage can be achieved by CD47-SIRPα disruption and antibody rather than a chemotherapeutic approach.

Figure 19A:
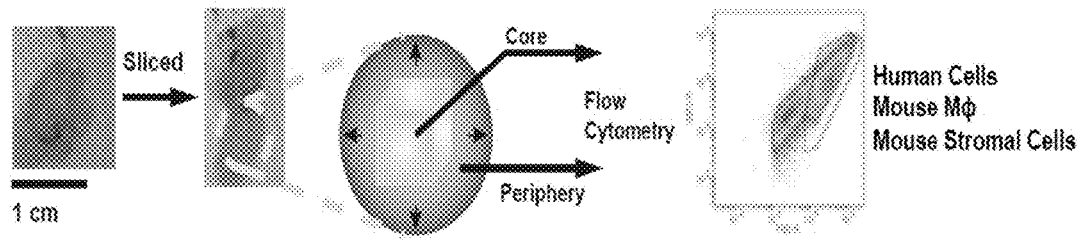
FIGS. 19A-19F are a series of images, graphs and histograms depicting the ex vivo analysis of mouse tissue following treatment.
Figure 19B:
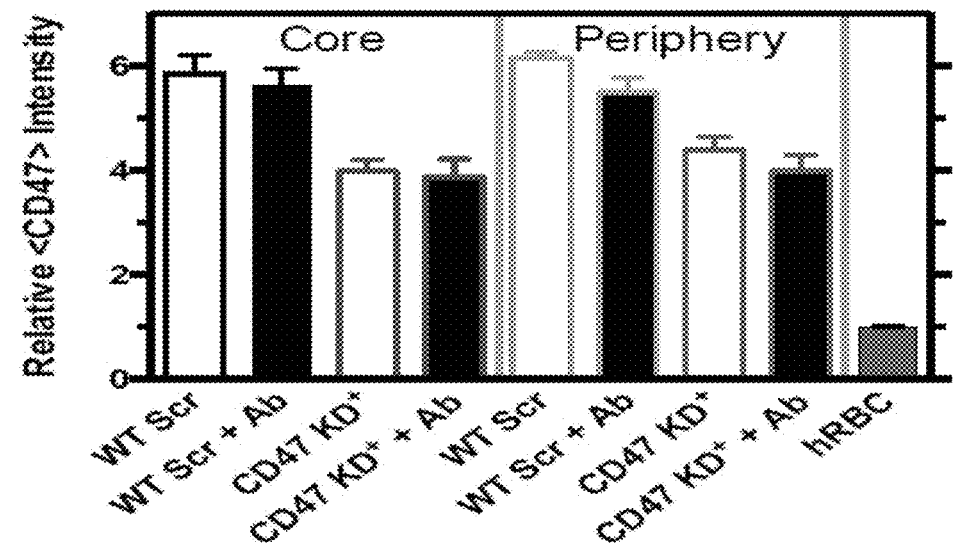

Example 13: Antibody Treatment Shrinks Tumors by Macrophage Phagocytosis of CD47 Knockdown Cells At the completion of each treatment regimen, mice were euthanized, xenograft tumors removed, and when possible, core and periphery tumor tissue kept separated, and analyzed by flow cytometry (FIG. 19A). Flow cytometry of tumor tissue showed similar CD47 expression levels regardless of antibody treatment (FIG. 19B). GFP expression in the mosaic tumors helped in determining a more granular view of CD47 expression and this strategy again revealed similar CD47 levels between untreated and Ab treated within a specific population.

A closer examination of the CD47 surface density on the A549 tumor cells, revealed that each knockdown cell type displayed <200 molecules/m$^2$ at the time of tumor inoculation (FIG. 23). These values are likely conservative overestimates due to an underestimation of A549 surface area determined by imaging well spread cells.

Figure 19C:
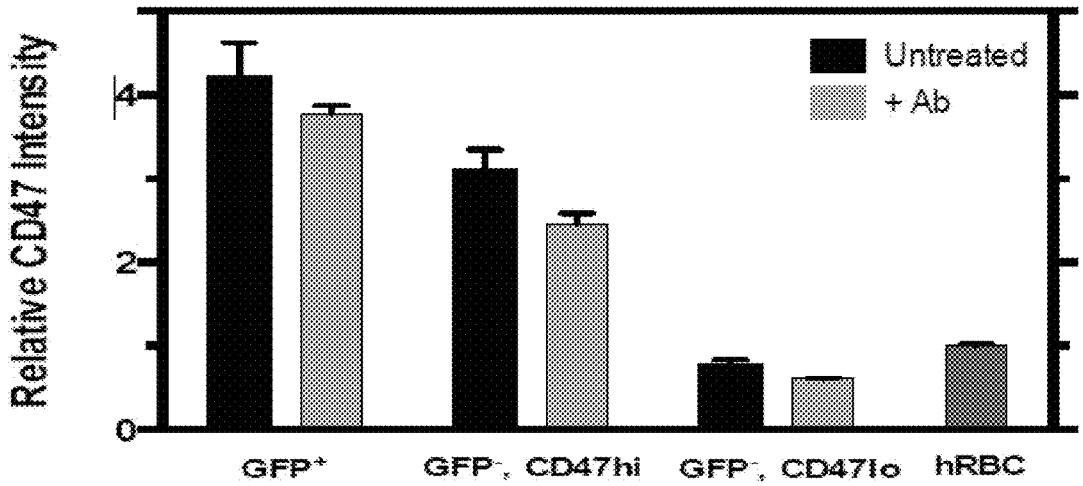
Figure 19D:
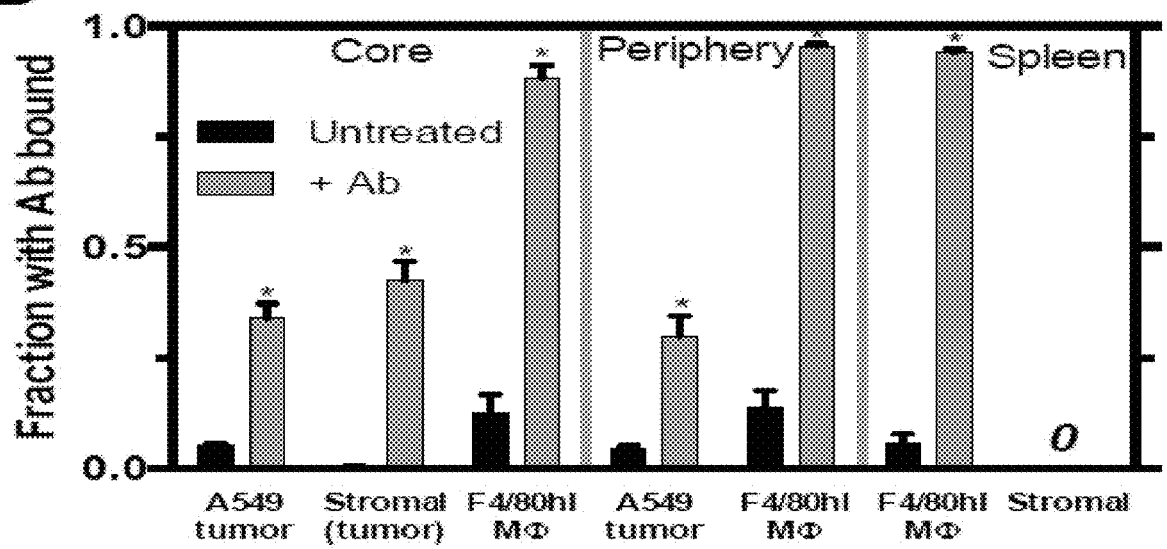

Periphery and core tumor tissue were similarly opsonized and this level of opsonization was matched in mouse stromal cells (FIG. 19D). Likewise, mature macrophages in tumor core and periphery showed bound Ab. However, the level of Ab binding to macrophage was much higher than in either tumor or stromal tissue, and macrophages of the periphery had slightly more bound Ab than those of the core. Tissue from mice used in the mosaic tumor studies recapitulated the trends in Ab binding by showing similar levels of antibody binding in tumor xenograft and mouse stroma and a higher level of antibody binding in tumor and splenic macrophages. Additionally, macrophages in the peripheral blood (PB) were similarly bound by Ab.

Figure 19E:
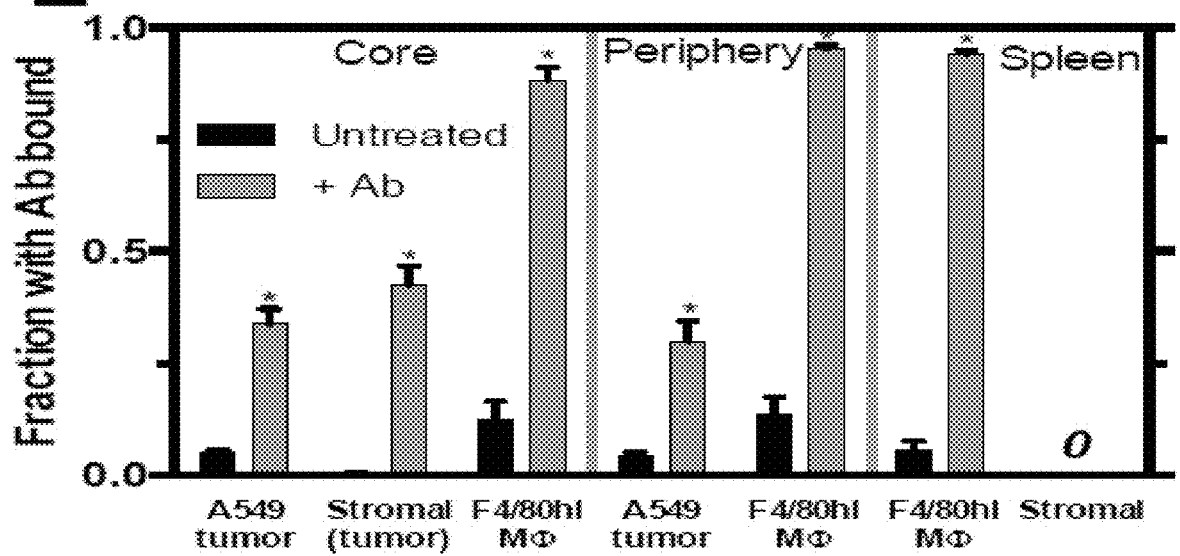
Figure 19F:
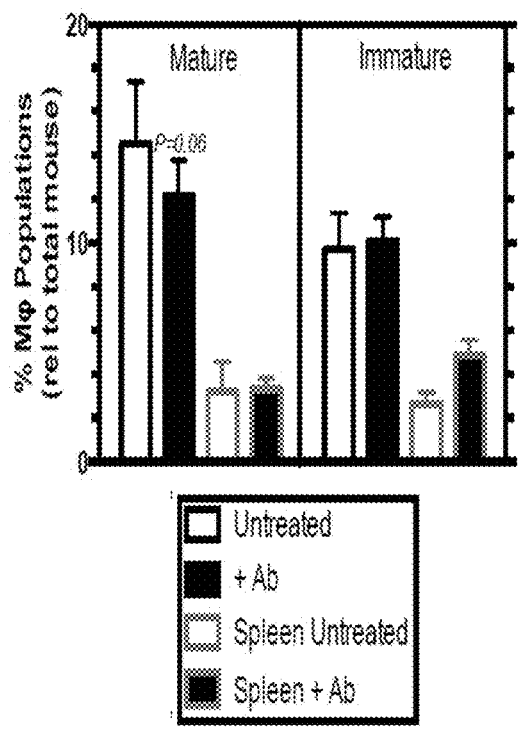
Figure 19F:
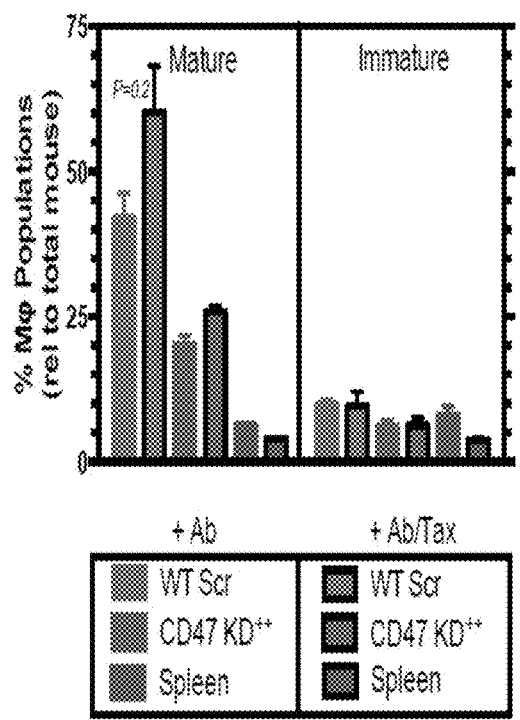

These data provide evidence of a direct interaction of the antibody with macrophages and that macrophages in the circulation retain and/or bind antibody. Analysis of total macrophage numbers as a percent of total mouse cells within a given tissue revealed significantly higher numbers of mature macrophages and that neither subpopulation significantly changed after antibody treatment (FIG. 19F, left). Addition of Tax to antibody treatment showed similar macrophage numbers in CD47 KD++ and spleen (FIG. 19F, right) compared with CD47 KD+ and mosaic studies. However, the number of mature macrophages found in WT Scr tumors was elevated with Tax, perhaps a response to chemotherapeutic induced tumor apoptosis.

Figure 20A:
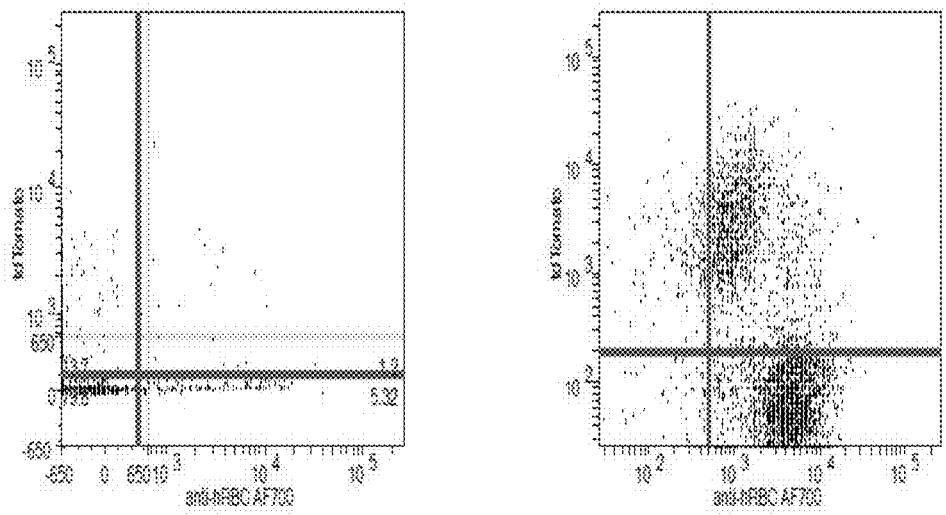
FIGS. 20A-20D are a series of plots and histograms depicting the assessment of phagocytic activity of mature macrophage subpopulation.

To assess whether Ab binding to macrophage was providing a phagocytic stimulus, macrophages were analyzed by flow cytometry using a modified gating scheme (FIG. 28A) (Rose et al., Cytometry. A 81, 343-50 (2012)). This method allows discrimination between immature (CD11b$^+$ F4/80$^{lo}$) and mature (CD11b$^+$ F4/80$^{hi}$) macrophages. In general, the immature macrophage subpopulation was much less Ab bound and was very infrequently tdTomato+(FIGS. 28D-28E and FIGS. 29D-29E). Mature macrophages from untreated mice were infrequently tdTomato+, but mature macrophages from treated animals showed a drastic increase in tdTomato, treatment antibody, or both (FIG. 20A).

Figure 20B:
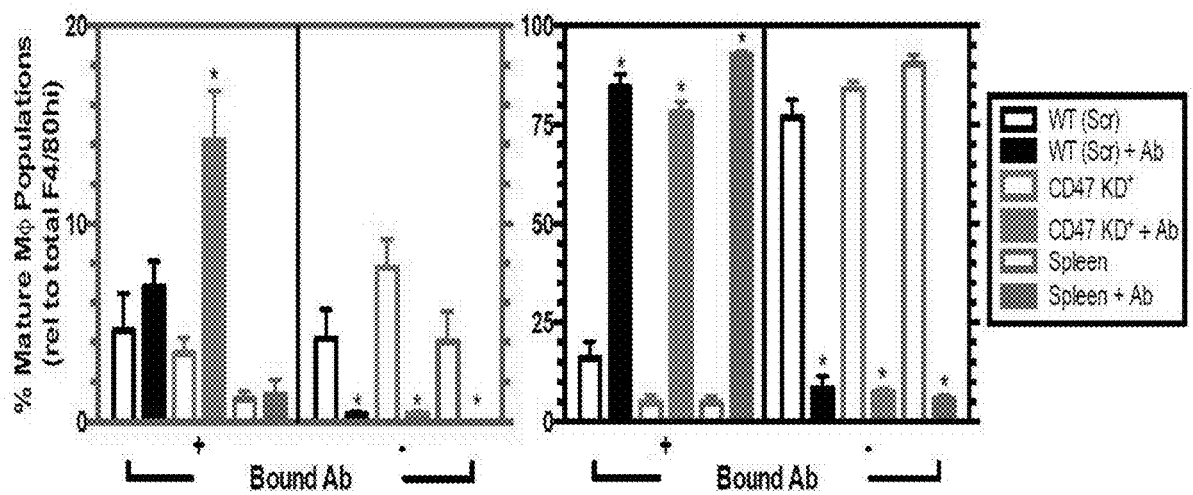
Figures 20C, 20D:
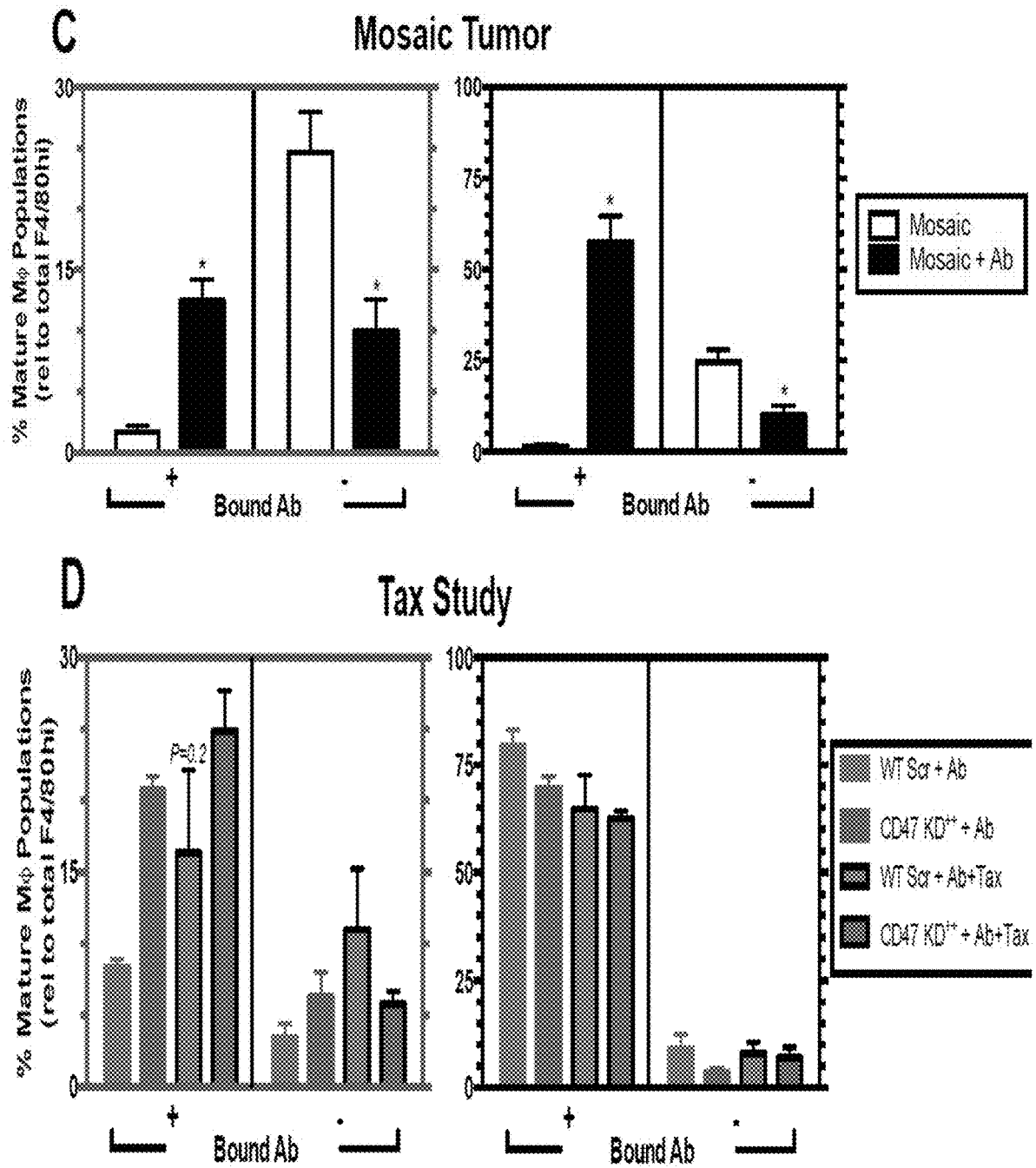

Macrophages that were tdTomato− from the CD47 KD+ study were equally Ab bound regardless of tissue source (FIG. 20B, right), however, tdTomato+ macrophages showed a marked increase when bound to antibody and such macrophages were more frequent from CD47 KD+ tumors (FIG. 20B, left; compare bars 2 & 4 with 8 & 10). Similar trends were seen from mosaic tumors. Specifically, treatment with antibody resulted in an increase in tdTomato+ in antibody bound macrophages (FIG. 20C). The addition of Tax with the antibody treatment showed similar Ab binding to macrophage in the tdTomato− fraction (FIG. 20D, right; compare with FIG. 21B, right filled bars) and antibody treatment alone recapitulated the tdTomato+Ab bound percentages seen in the CD47 KD+ study (compare FIG. 21D left, bars with black outline versus FIG. 21B left, solid bars).

Interestingly, supplementing antibody treatment with Tax resulted in an increase in tdTomato+Ab bound macrophages as compared to antibody alone for WT Scr and CD47 KD++ tumors (FIG. 20D, left; compare black outlined bars with bars without outline). The likely cause of such an increase may be due in part to an increase in calreticulin expression on chemotherapy induced apoptotic cells, which would provide an additional "eat me" signal. Such an increase has been reported in leukemic cells as soon as 72 hours following cyclophosphamide treatment (Pallasch et al., *Cell* 156, 590-602 (2014)) and shown to be sufficient to induce phagocytosis (Gardai et al., *Cell* 123, 321-34 (2005)).

These results provide a mechanism of antibody mediated tumor clearance, whereby disruption of the CD47-SIRPα, in this case by CD47 knockdown, provides for removal of the normally present "don't eat me" signal, while antibody opsonization provides a phagocytic stimulation to mature macrophages effectively delivering an "eat me" signal.

Example 14: Adoptive Transfer of Bone Marrow Cells is a Potential Cell-Based Treatment Strategy for Cancer Cell-based treatments, particularly of macrophages, afforded the benefit of the invasive nature of such cells, permit access to under-vascularized regions of solid tumors which would otherwise be inaccessible to antibodies or chemotherapeutics. Using the fluorescent tdTomato xenograft model provided herein, the feasibility, practicality, and efficacy of using bone marrow cells in homing to tumor sites were assessed.

Bone marrow from a donor NSG mouse was collected, labeled with CFDA-SE, and transferred into a CD47 KD++ or WT Scr tumor bearing recipient mouse. The recipient mouse was also injected with Ab on the morning of bone marrow transfer. Three days later, the recipient mouse was sacrificed and tumor, spleen, peripheral blood, and bone marrow were analyzed by flow cytometry (FIG. 21A).

Figure 21B:
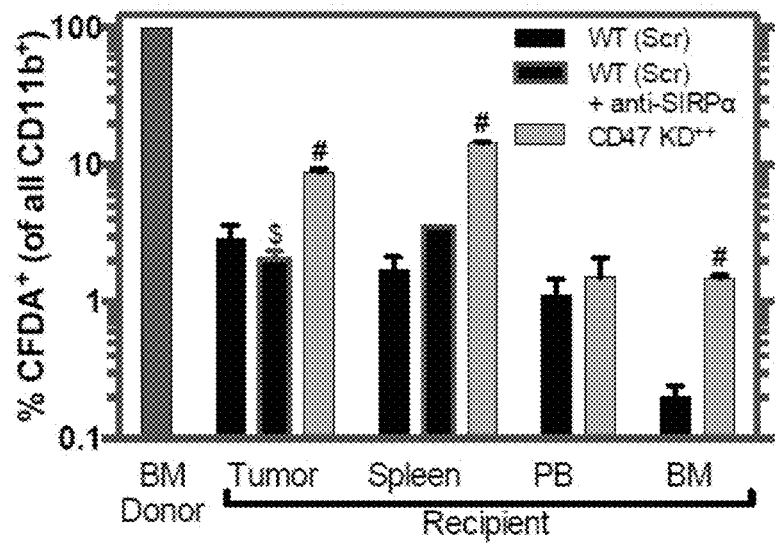

Flow cytometry revealed that >99% of CD11b+ cells from the original donor marrow were labeled (FIG. 21B). More importantly, donor derived CFDA+CD11b+ cells were found in the tumor and spleen of the recipient mouse (FIG. 21B) indicating the capability of injected cells to not only survive, but also traffic to the tumor sites.

Figure 21C:
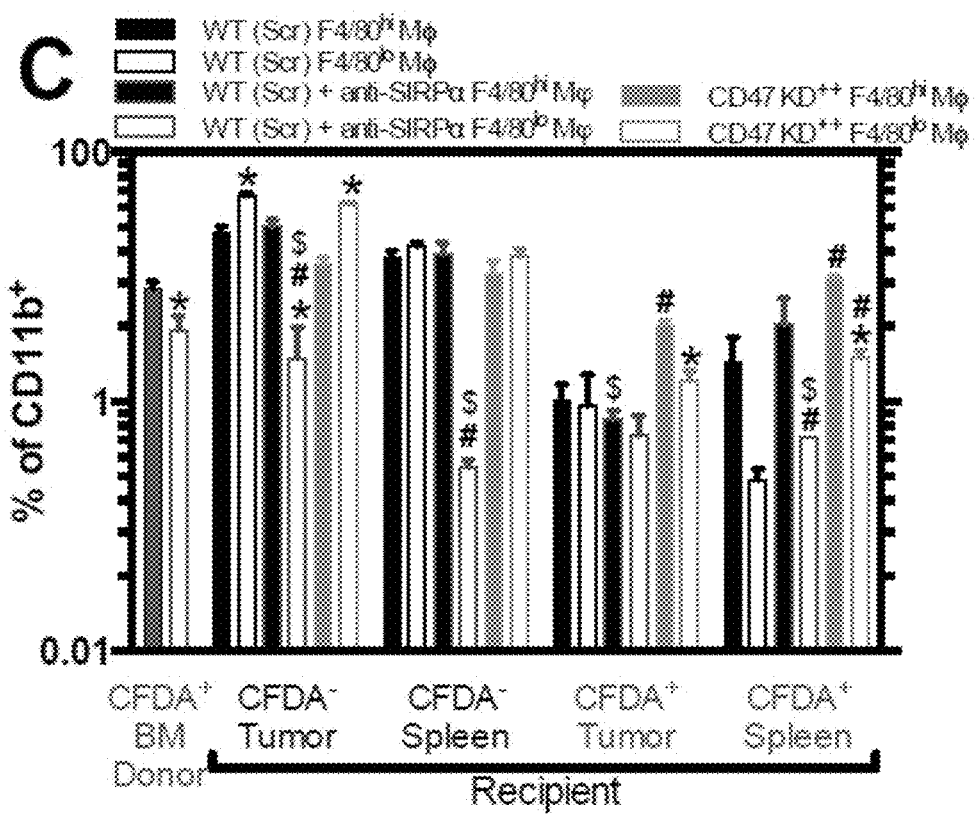

A further identification of the cells present in these tissues showed an expansion of donor-derived mature macrophages relative to immature macrophages in the tumor (FIG. 21C). This effect has beneficial therapeutic implications since the mature macrophages are highly phagocytic.

Figure 30A:
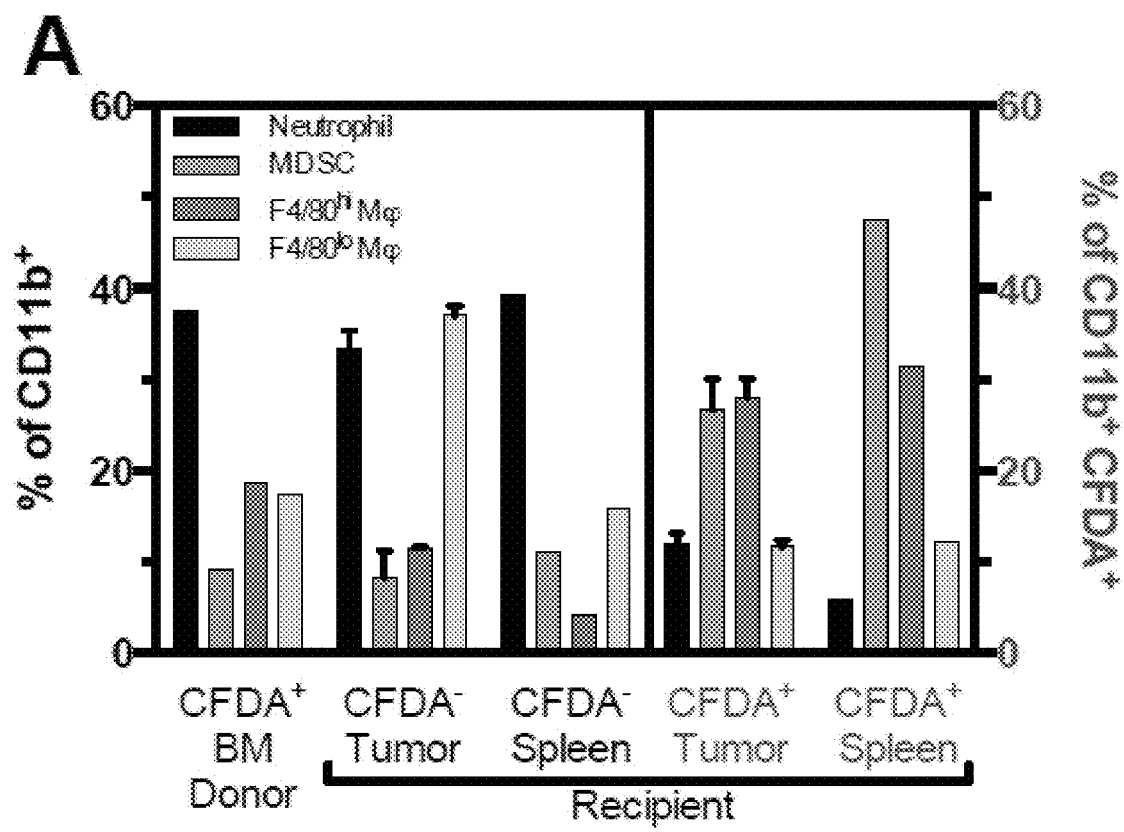
FIGS. 30A-30F are a series of graphs showing detailed analysis of phagocytic cells following labeled bone marrow adoptive transfer.
Figure 30B:
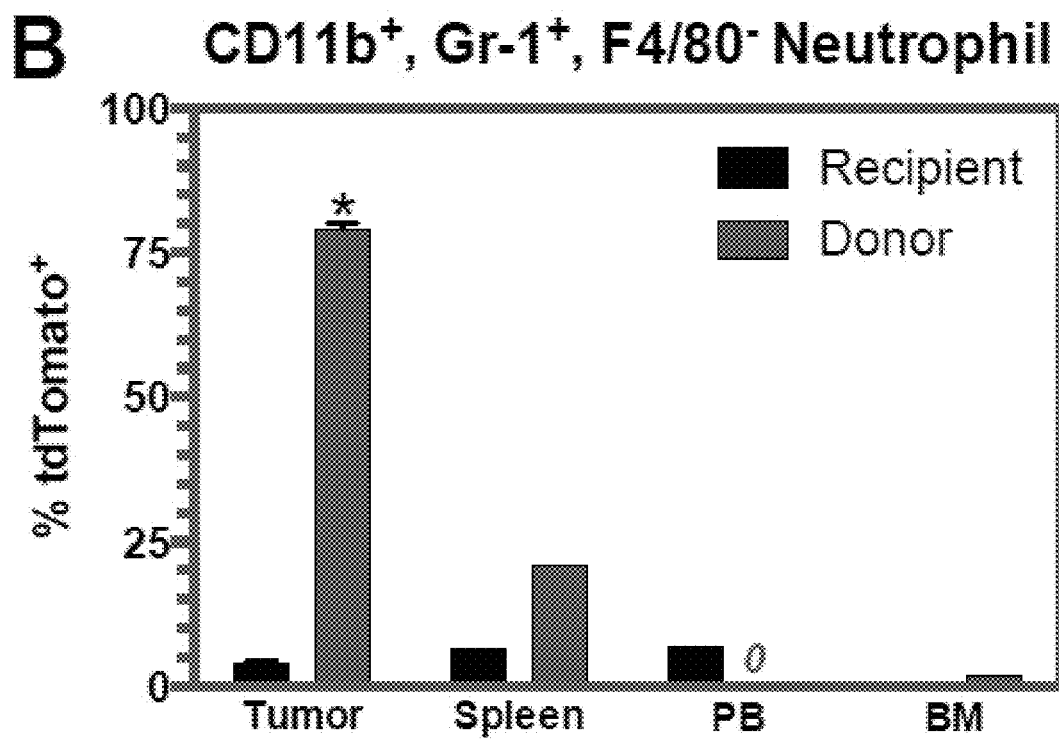
Figures 30C, 30D:
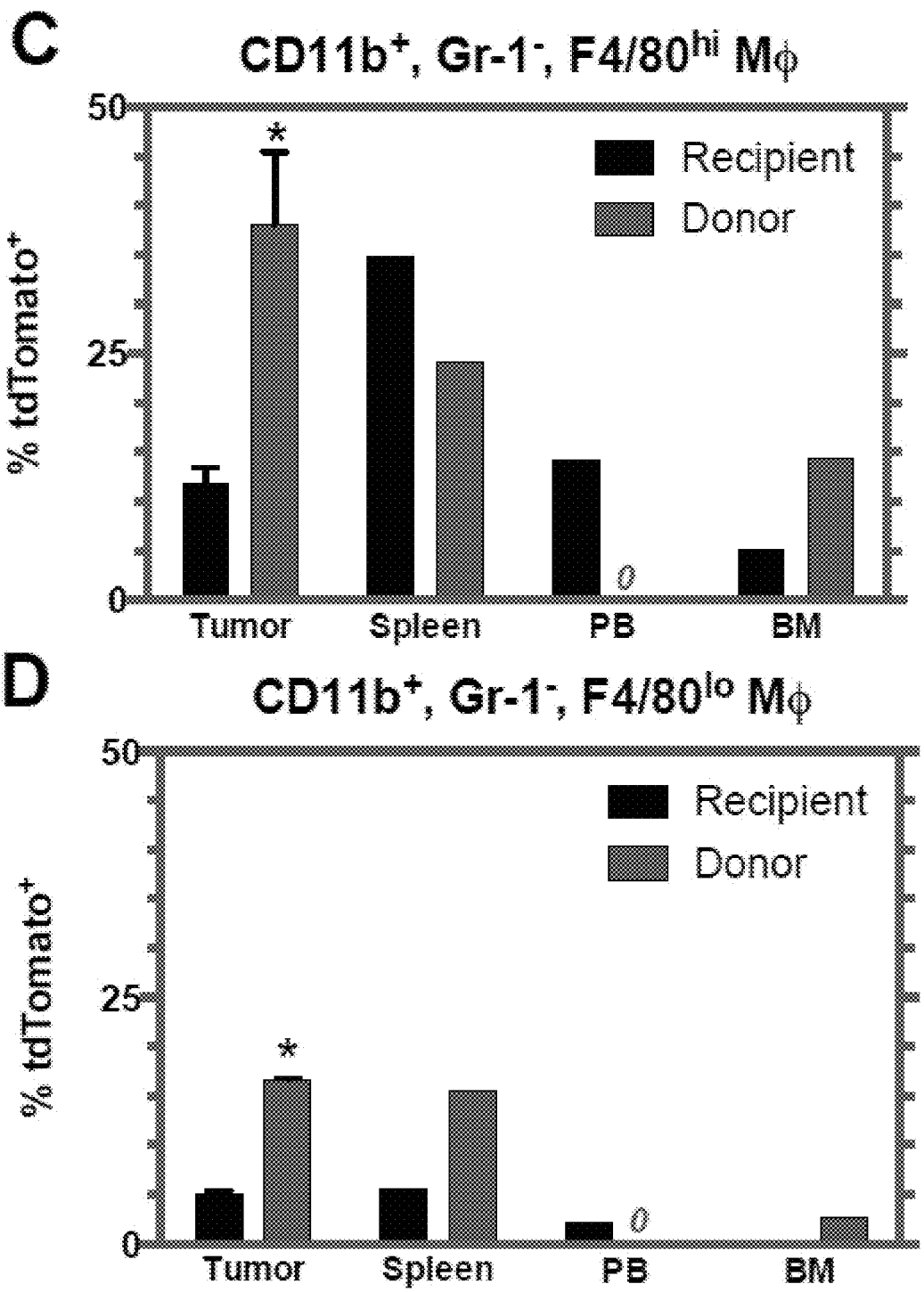
Figure 30E:
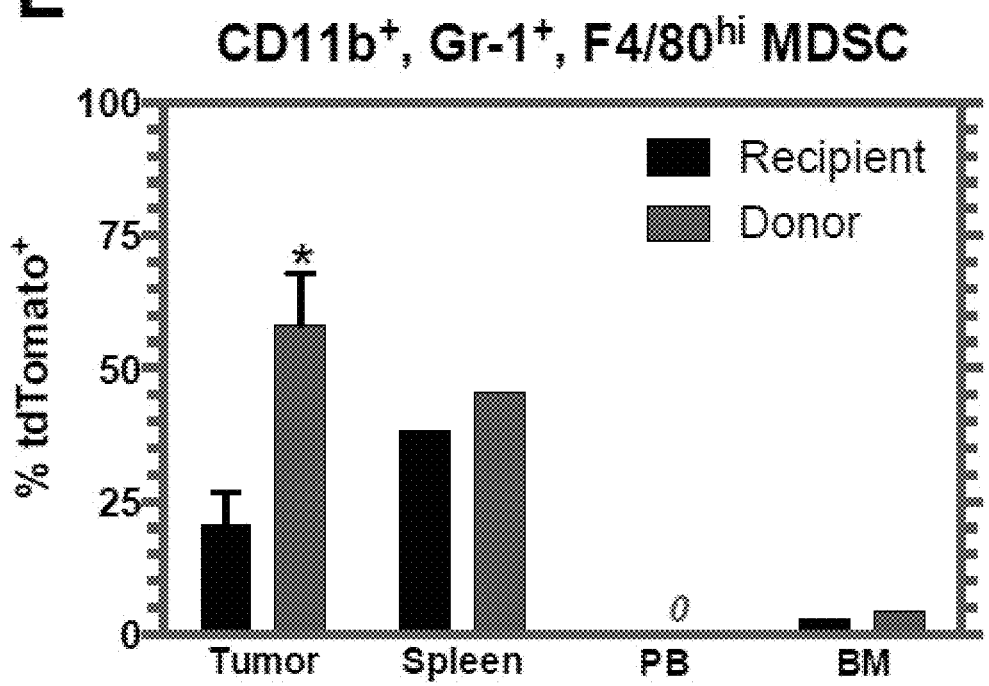
Figure 30F:
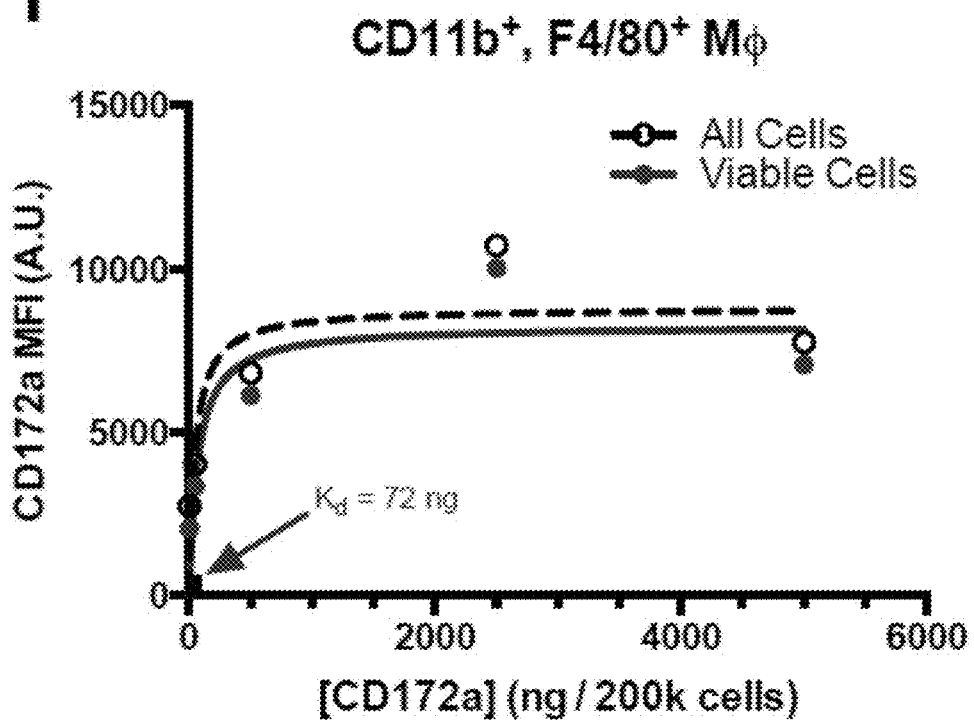

The addition of the granulocyte marker, Gr-1, showed that the increase in the number of mature macrophage in CFDA+ donor cells was accompanied by a decrease in neutrophils, indicating that either neutrophils were at a growth disadvantage compared to macrophages or the tumor environment provided an inflammatory milieu that drove macrophage differentiation and/or expansion (FIG. 30A).

Treating donor cells with anti-mSIRPα did not significantly affect total CD11b+ donor cell (FIG. 21B) or macrophage counts in either tumor or spleen as compared to unblocked cells (FIG. 21C). Tumor analysis by flow cytometry showed the sustained presence of anti-mSIRPα on donor cells, indicating successful SIRPα blocking for the duration of in vivo circulation.

Figure 21D:
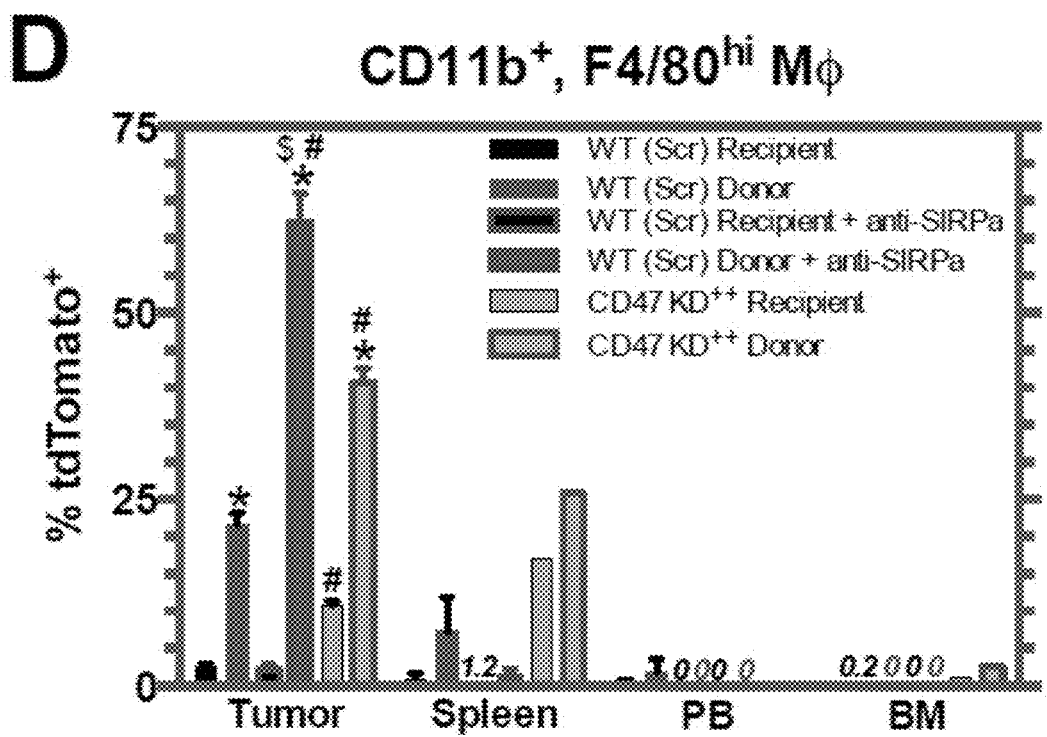
Figures 21E, 22, 23:
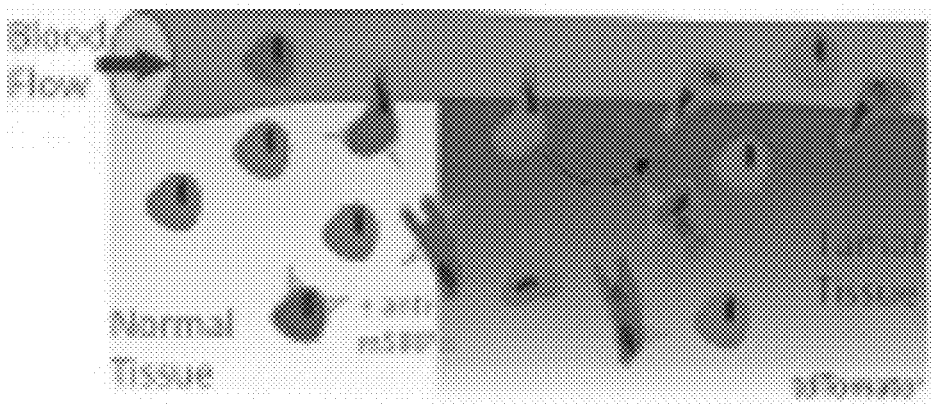
FIG. 22 is a table summarizing the relative IgG supplementation. Calculated estimate of the IgG percent in immunocompetent mouse strains. Calculation assumes a 30 g mouse and 0.6 mg Ab injection. % of IgG is calculated as 0.6 mg injected Ab/total mg IgG*100%. This value provides a magnitude of the Ab dosage for comparison with what is present in immuncompetent animals. Also as a comparison, a typical 300 μg dose of Rhogam represents 0.0006% of total human IgG. Literature values: mouse blood volume1 from Mitruka et al., (Clinical, biochemical and hematological reference values in normal experimental animals and normal humans, Masson Publishing, New York, 1981, p. 413). C57BL/6 IgG concentration2 from Klein-Schneegans et al. (J. Autoimmun. 2, 869-75 (1989)), humanized NSG IgG concentration3 from Rajesh et al. (Hum. Immunol. 71, 551-9 (2010)).
FIG. 23 is a table listing CD47 cell surface density. In vitro (cells used for xenotransplant) and in vivo (cells recovered from excised tumors) CD47 surface density determined by flow cytometry and immunofluorescence. A549 cell area was determined by measuring area of well spread cells imaged by immunofluorescence. This value was multiplied by two assuming negligible height for well spread cells. This method underestimates cell area and the calculated values for CD47/µm2 are thus likely overestimates. CD47 intensity was determined by flow cytometry mean fluorescence intensity and normalized to human red blood cells. Arrows indicate IgG treatment responsive cells. The CD47 surface density value for hRBCs was previously reported (Tsai et al., J. Cell Biol. 180, 989-1003 (2008)). Multiplying this value by the normalized CD47 intensity and scaling by the ratio of A549 area to hRBC area previously reported (Engström et al., Blood 91, 3986-91 (1998)), results in the values presented in this table (FIG. 23).

Next, phagocytosis was assessed in a similar manner as presented above herein. Not only were the donor derived mature macrophages phagocytic, but they appeared to be more aggressively phagocytic (FIG. 21D). Indeed, labeled cells injected into a WT Scr tumor were more phagocytic compared to the recipient mouse's own macrophages and phagocytosis was also elevated in all four donor-derived phagocytic cell types identified (FIGS. 30B-30F).

About 21% of the donor macrophages phagocytosed WT Scr tumors compared to recipient macrophages (3%). In contrast, about 41% of the donor macrophages phagocytosed the CD47 KD++ tumors as compared to recipient macrophages (11%). However, when donor cells were treated with anti-mSIRPα ex vivo prior to delivery to WT Scr bearing mice, 62% of recovered donor macrophages were phagocytic as compared to just 2% of recipient cells.

These data are suggestive of a greater fitness for donor cells compared to recipient cells that have been affected by chronic inflammation due to the presence of the tumor. The results presented herein provide a promising potential for a cell therapy approach using taking advantage of the CD47-SIRPα interaction. Such therapy would be based on a model of phagocytic clearance of solid tumors, wherein circulating macrophages can infiltrate tumor tissues, phagocytose tumor cell(s), then intra-vacate back into circulation, and based on the observations provided herein, be filtered from circulation by the spleen (FIG. 21E).

Figure 31A:
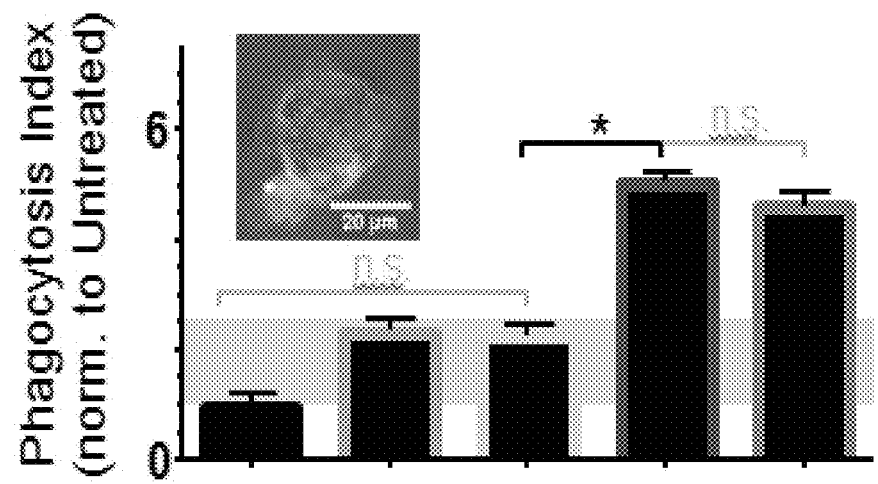
FIGS. 31A-31E is a panel of images showing phagocytosis of lung cancer line A549 after blocking hSIRPA.
Figure 31B:
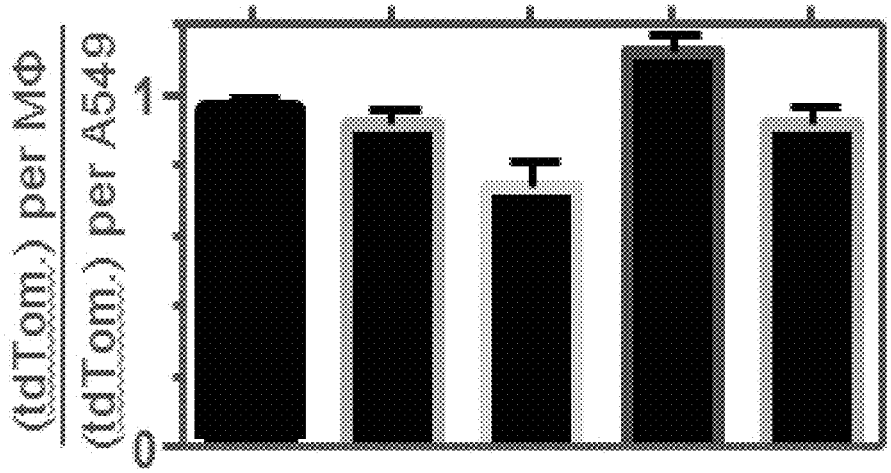
Figure 31C:
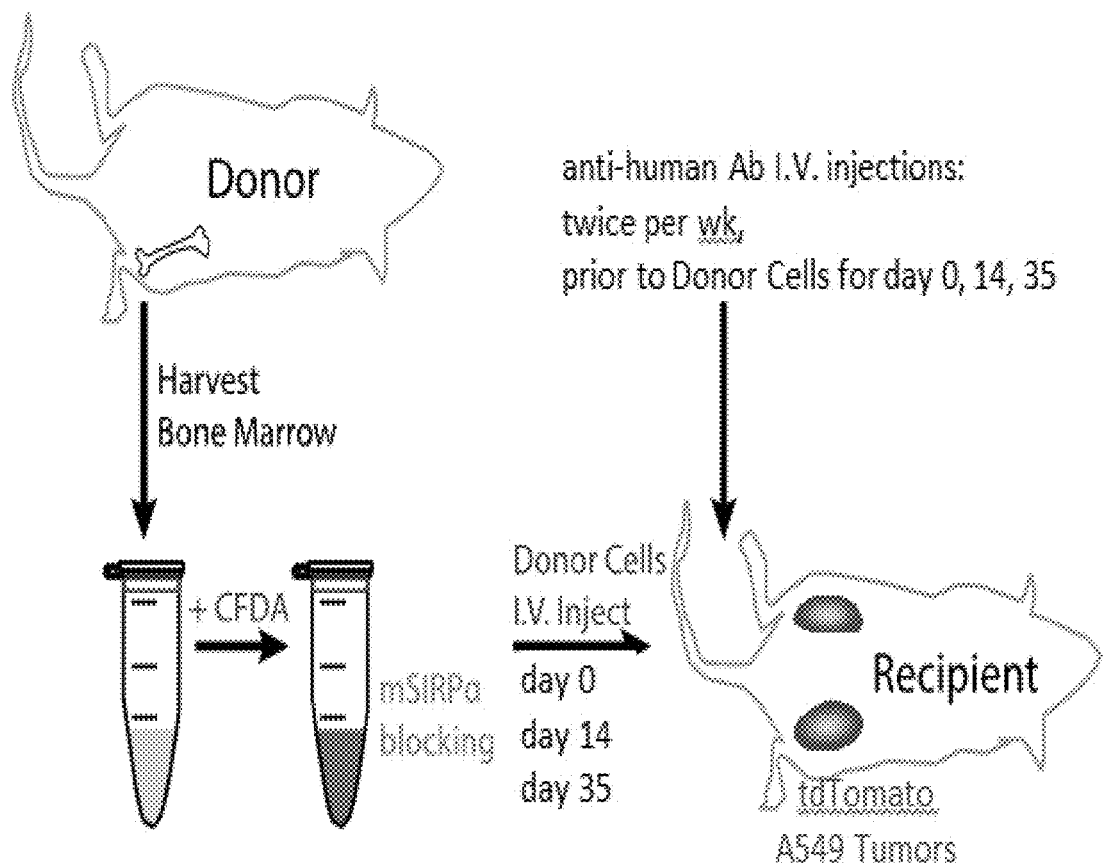
Figure 31D:
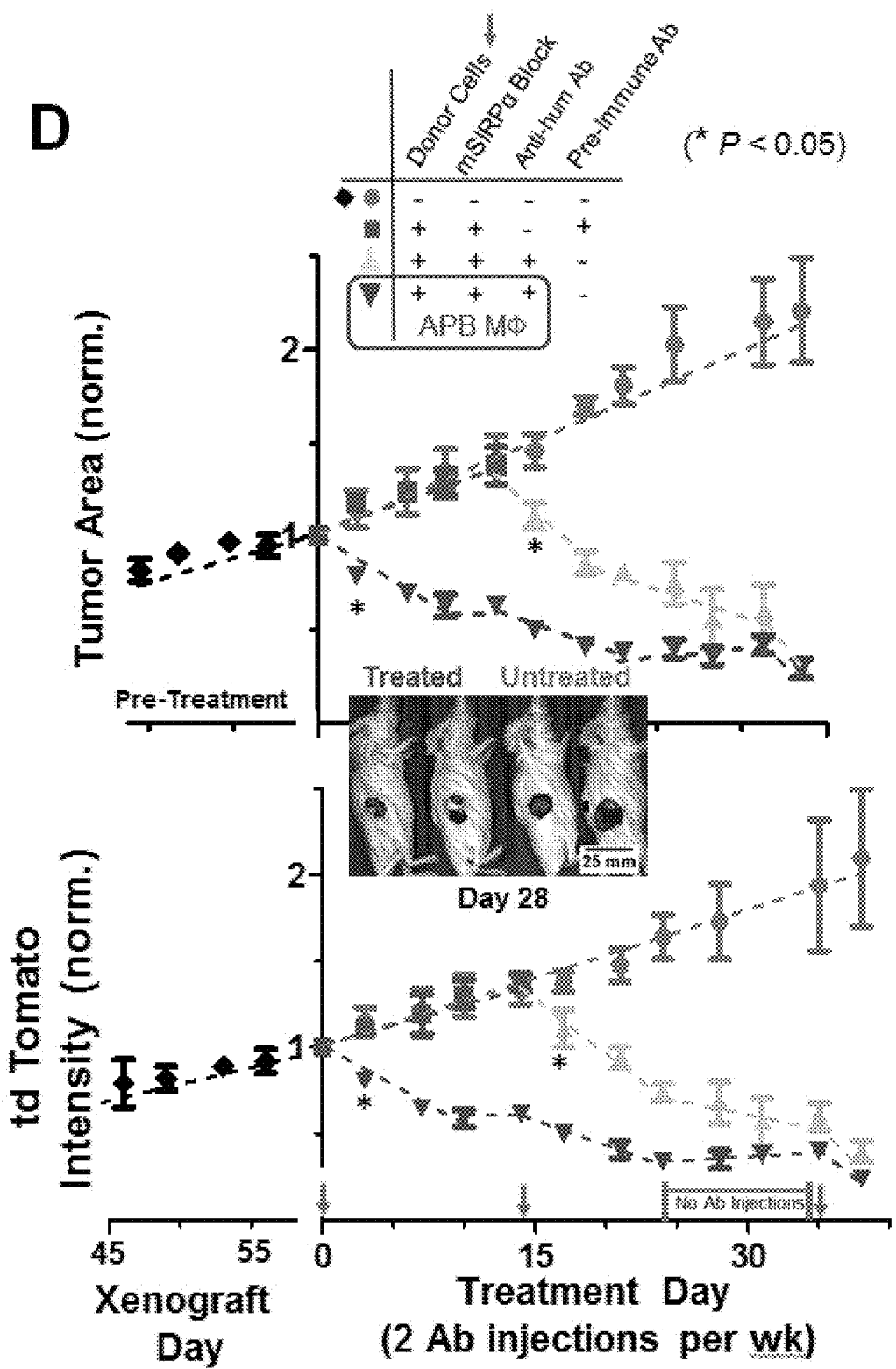
Figure 31E:
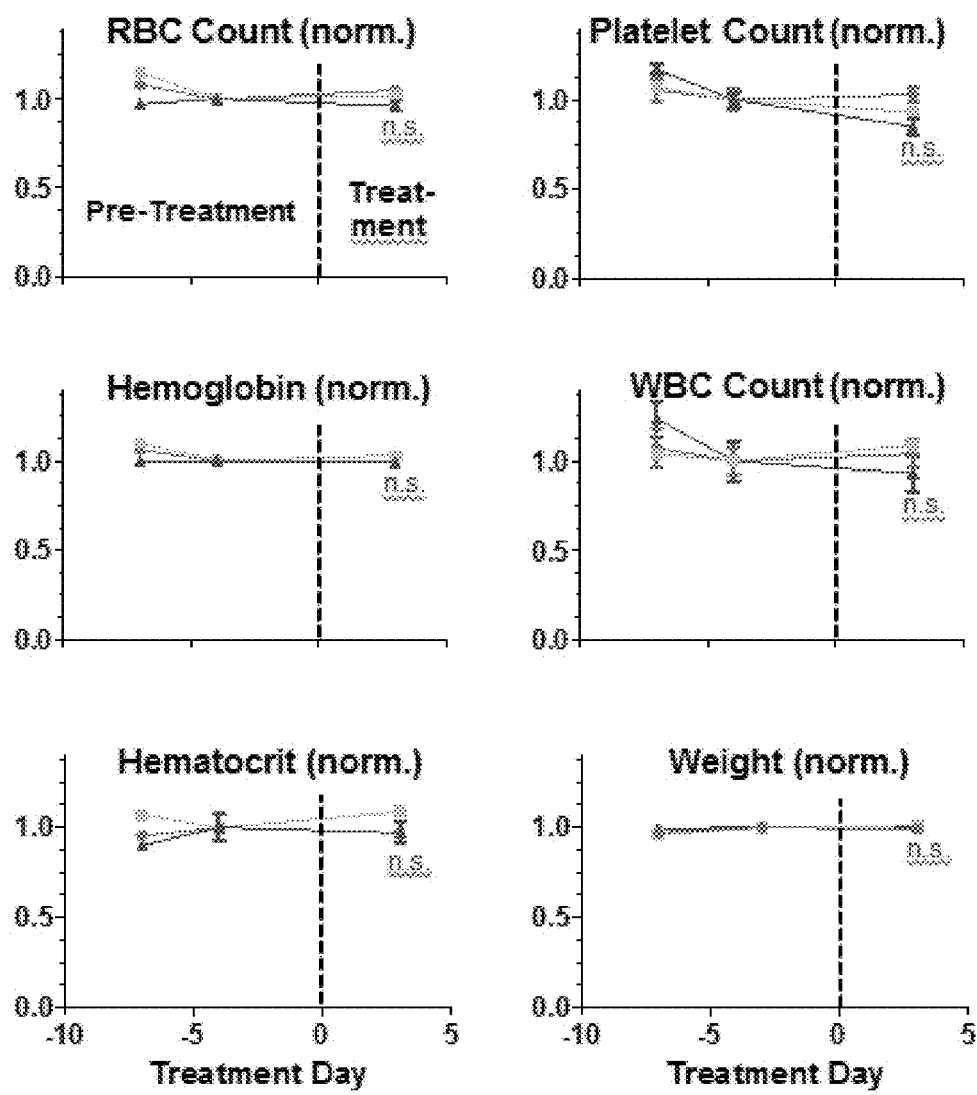

Phagocytosis of lung cancer line, A549, was also enhanced when hSIRPA was blocked, seethe graphs in FIGS. 31A-31B. FIG. 31C diagrams the cell therapy approach for A549 solid tumors by blocking SIRPA on donor marrow cells in systemic injections. Large solid tumors shrank when SIRPA was blocked on donor marrow cells and injected with anti-human antibody, FIGS. 31D-31E. Neither blood parameters nor body weight were significantly affected as the tumors shrank.

Figures 32A, 32B:
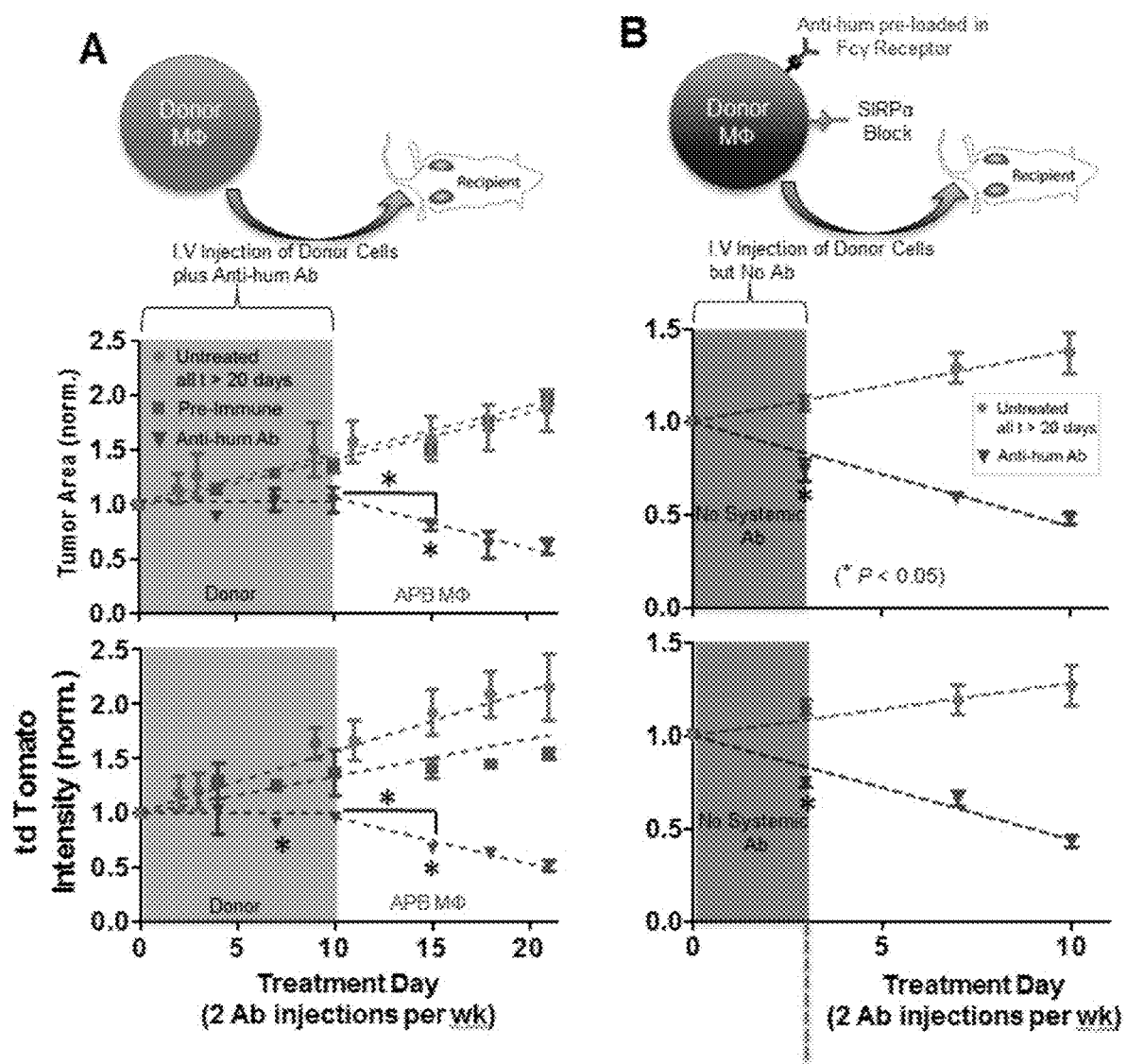
FIGS. 32A-32B are a series of schematics and graphs showing that administration of anti-human antibody and donor cells do not shrink tumors, and that anti-human antibody on donor cells plus blocking SIRPA shrinks tumors effectively without systemic antibody.

In contrast, administration of anti-human antibody and donor cells did not shrink tumors, see FIGS. 32A-32B, while anti-human antibody on donor cells plus blocking SIRPA shrank tumors effectively without systemic antibody.

Example 15: Adoptive Transfer of Human Bone Marrow Cells as a Potential Cell-Based Treatment Strategy for Cancer Three milliliters of fresh human bone marrow (AllCells, cat #: ABM001-1) was incubated with 3 mL of red blood cell lysing buffer (hybrid-Max R7757) for 10 mins in a 15 mL conical. Cell were place in a centrifuge at 2000 rpms for 2.5 mins immediately after incubation. Lysate was removed and the remaining cells were suspended in 1 mL of red blood cell lysis buffer for a second lysis phase for 4 mins.

Cells were spun down at 2000 rpms for 2.5 mins and resuspended in 500 uL of PBS. To the resuspended cells, 1 uL of 10 mM (prepared according to kit instructions) of CFDA SE solution (Invitrogen V12883) was added and incubated with the cells for 40 mins at 37° C. During the incubation, the cells were inverted 2-3 times every 5 mins. During this same incubation period, SIRPA blocking (SIRP-α1, clone: SE7C2, from Santa Cruz, sc-23863) and Fc priming (human red blood cell antibody made in rabbit (Rockland, 109-4139) antibodies were added to cells at 4 ug/mL and 100 ug/mL respectively.

After incubation, the cells were spun down at 2000 rpms for 2.5 mins and resuspended in 1 mL of 5% FBS in PBS (wash). Cells were spun down again at 2000 rpms for 2.5 mins and resuspended in 100 uL of 5% FBS in PBS. Cell counts were obtained using a hemocytometer and cells were diluted to 40k cells per uL (8M cells total per mouse) for intravenous tail vein injection in tumor bearing mice. Mice that were treated with unprimed cells were injected intravenously with 600 ug (6 ug/uL) of human red blood cell antibody 4-6 hrs prior to injection of engineered marrow cells.

Figure 33A:
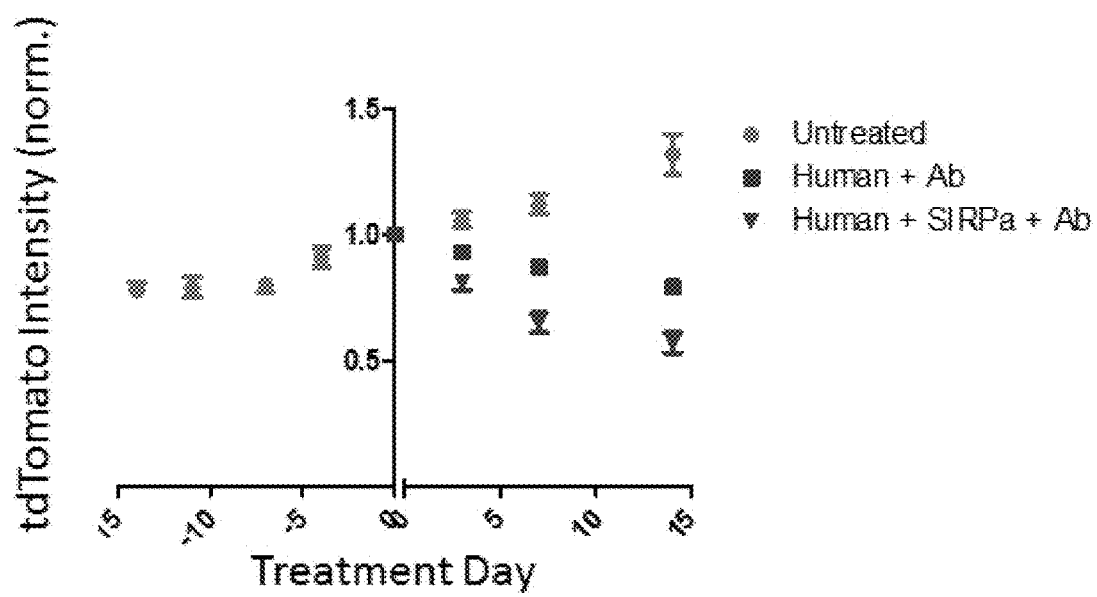
FIGS. 33A-33B are a series of graphs showing human marrow injected into tail veins of NSG mice bearing A549 tumors.
Figure 33B:
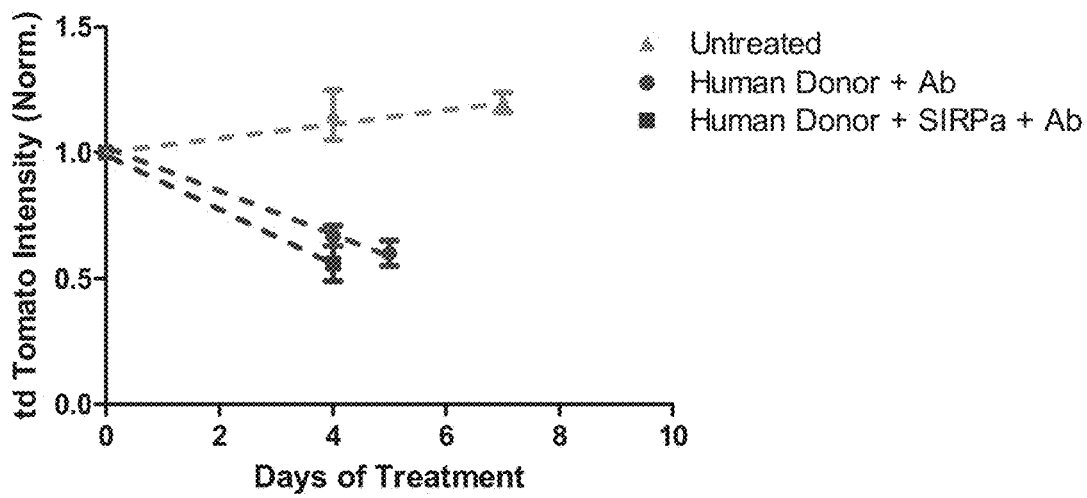

Human marrow cells and antibody plus blocking SIRPA injected into NSG mice bearing A549 tumors were capable of shrinking the tumors, see FIG. 33A. However, CD47KD A549 tumors were treated more efficiently with treatment of human donor marrow and antibody plus blocking SIRPA, see FIG. 33B. This indicates that blocking both CD47 and SIRPA is also an effective mechanism in human cells.

Example 16: Discussion

The present invention provides a mechanistic view of antibody-dependent cellular cytotoxicity (ADCC) amplified by the loss of CD47 expression without adverse effects to anucleated peripheral blood cells. Compared with CD47 knockdown tumors, growth of tumors displaying normal levels of CD47 was unaffected by antibody treatment. Additionally, treated tumors resumed growing at rates similar to those before treatment and were responsive to reapplication of antibody after allowing to regrow to sizes similar to those at the onset of the initial treatment period (FIG. 17A).

Response to a second round of treatment shows similar efficacy as the initial treatment period indicating the presence of an antibody responsive low CD47 expressing component. Treatment with IgG did not directly impact CD47 expression of tumor cells as seen by comparing tissue samples ex vivo (FIGS. 19B-19C). Flow cytometry of A549 cells at the time of xenotransplant showed that CD47 surface density of knockdown cell types was estimated to be much lower (FIG. 23) than what was previously reported for normal human red blood cells (Tsai et al., J. Cell Biol. 180, 989-1003 (2008)). Also, an inhibition constant of ~20 molecules/m$^2$ for human THP-1 cells phagocytosing human CD47 coated beads was previously reported (Tsai et al., J. Cell Biol. 180, 989-1003 (2008)). Considering that the values determined in FIG. 22 are likely overestimates and that the affinity of mouse SIRPα for human CD47 is likely less than that of human SIRPα for human CD47, the CD47 surface density of the knockdown cell agreed remarkably well with the dissociation constant (Ki) previously reported in the art (Tsai et al., J. Cell Biol. 180, 989-1003 (2008)).

The use of a mosaic tumor composed of GFP+ cells that have normal CD47 levels and CD47 knockdown GFP- cells support the view that tumor clearance after antibody treatment was dependent on the disruption of the CD47-SIRPα interaction. Particularly, the GFP+: GFP- ratio was unchanged in the absence of Ab, but the ratio was inverted after Ab treatment (1:2.7 vs 3.3:1, FIG. 17F).

Surprisingly, CD47 KD++ cells were shown to grow more rapidly than WT Scr cells (FIG. 17C). The expression of the pro-phagocytic surface protein calreticulin has been shown to be highly correlated with CD47 expression for a number of cancers and provides a means of selective clearance when treated with anti-CD47 antibody. It would seem that CD47 knockdown would affect calreticulin levels, resulting in an increase in phagocytosis which would limit or prevent tumor progression. However, the accelerated growth rate of CD47 KD++ tumors in the present invention could be a result of concomitant reduction in calreticulin following CD47 knockdown to maintain the WT calreticulin:CD47 ratio as has been seen in colorectal cancer (Steinert et al., Cancer Res. 74, 1694-704 (2014)). Alternatively, high levels of calreticulin have been found to be a poor clinical prognostic in numerous malignancies (Chao et al., Sci. Transl. Med. 2, 63ra94 (2010)).

Figure 24D:
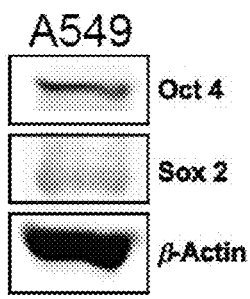

The transfection of vasostatin, the N-terminal domain of calreticulin, also results in downregulation of tumor suppressor genes, including p53, nm23, Rb, and vinculin as well as enhancement of cell spreading, adhesion, and invasion. Each of these factors could be a driver in accelerating tumor growth. Moreover, A549 cells have the capacity for some plasticity as they express key stem cell transcription factors, which has been confirmed herein (FIG. 24D). CD47 loss from endothelial cells promotes stemness and proliferation with a role for altered adhesion (Kaur et al., Sci. Rep. 3, 1673 (2013)).

Combination of the chemotherapeutic drug paclitaxel with Ab treatment, while slightly additive, did not significantly improve CD47 knockdown tumor shrinkage. Interestingly, taxol treated tumors showed an increase in total mature macrophages at the expense of immature macrophages in the spleen (FIG. 19F), as well as an increase in phagocytosing, opsonized mature macrophages in the tumor (FIG. 20D). These results may be an effect of macrophage mobilization in response to a taxol induced inflammatory signal, or may be evidence of a larger effect of taxol on upstream hematopoiesis (FIG. 18C), as a slight increase in thrombocrit, decrease in hematocrit, and decrease in peripheral blood CD11b+ leukocytes was also observed (FIG. 18E) when mice were treated with taxol. Since taxol induces apoptosis by inhibition of microtubule depolymerization, it would be meaningful that megakaryocytes, which normally divide without cytokinesis, would be less sensitive than other lineages.

The invention presented herein demonstrates that an antibody used to stimulate macrophage phagocytosis merely needs to be capable of binding tumor cells. Both anti-human IgG antibody and anti-hRBC antibody showed similar tumor shrinking capacity when treating CD47 knockdown tumors (FIG. 17B, FIG. 17E, FIG. 24C and FIGS. 29A-29B). Clinical antibodies used to treat malignancies are often highly specific to an epitope upregulated in a specific cancer, but also present on normal cells resulting in opsonization of tumor and normal tissue and thus destruction of both. The ability to use any polyclonal antibody, as done herein, could provide a cost effective means of treatment if combined with selective CD47 expression modulation.

The analysis of macrophages harvested from tumors and spleen provided insight into the mechanism of CD47 dependent ADCC. These data showed that mature macrophages bound Ab at higher rates than immature macrophages. These opsonized mature macrophages also showed an increase in phagocytosis, as indicated by tdTomato+ by flow cytometry (FIGS. 20B-20D). The anti-hRBC antibody opsonized human tumor and mouse stroma to a similar level (FIG. 19D and FIG. 19E), however no significant anemia, thrombocytopenia, or weight loss was observed (FIG. 25) in mice treated with this antibody. With the observation that CD47 low expressing cells were selectively eliminated upon antibody treatment, the selective phagocytosis might be due to a combination of suppression of a "don't eat me" signal (CD47-SIRPα disruption) and the addition of an "eat me" signal (FcR engagement by opsonizing antibody).

One of the limitations of many chemotherapeutic drugs is that they are large molecules dependent on the vasculature for delivery to the tumor. This limitation is particularly problematic in treating metastases of the brain, as the blood-brain barrier is notoriously difficult to traverse as demonstrated previously by the use of Tax loaded polymer filomicelles. Subcutaneous flank tumors were responsive to treatment, but cranial xenograft tumors of the same cell type were not responsive (Baumann et al., Oncotarget 4, 64-79 (2013)). Cell based means of tumor shrinkage can avoid vascular dependence since. For example, macrophages are highly motile and capable of invading multiple tissue types. Despite the tumor core being undervascularized, and commonly necrotic, similar macrophage and tumor opsonization levels was seen in core versus periphery, indicating that the antibody freely permeated the tumor. In addition, similar numbers of phagocytic macrophages were seen, regardless of tumor site. This supports the view that macrophages are highly invasive. Tumor associated macrophages (TAMs) are known to polarize to either anti-tumor M1 type or pro-angiogenic, and thus pro-tumor, M2 type. Thus, CD47 targeted antibody treatment might provide an environment that favors M1 programs.

Recent efforts have readdressed decades old methods of treating cancer with tumor-derived vaccines. Anti-cancer vaccines in clinical trials (e.g. NCT01995227 and NCT00459069 per ClinicalTrials.gov) take advantage of a diversity of complex antigens as indicated by proteomic analyses of tumor-derived cells and/or lysates used for such vaccines (53). As a consequence, tumor cell sub-populations that down-regulate a particular antigen are likely to retain other antigens capable of attracting and antagonizing key immune cells, including macrophages, to attack the tumor. These broader approaches, thus, seem robust compared to single antigen approaches.

Ultimately, the present invention inspires investigating tumor reduction where CD47 expression is attenuated, perhaps by treatment with a CD47 siRNA followed shortly thereafter with antibody. Such a scheme of CD47 siRNA delivery has already been shown to inhibit tumor growth and metastasis without systemic organ damage or anemia (Wang et al., Mol. Ther. 21, 1919-29 (2013)), however there was no treatment of established tumors and no treatment with an additional antibody.

Furthermore, anti-CD47 antibody can be generated with a protective linker that is cleaved by proteases typically found in the tumor microenvironment, like the "probody" of the monoclonal antibody, cetuximab (Desnoyers et al., Sci. Transl. Med. 5, 207ra144 (2013)). With such protection, the anti-CD47 antibody can selectively bind tumor tissue, and then a polyclonal opsonin treatment could be supplemented. Alternatively, the CD47-SIRPα signal could be manipulated in macrophage by modulating SIRPα. A potential strategy is naturally motivated by the bone marrow transfer results provided above herein. SIRPα on donor bone marrow cells could be blocked by antibody, or removed through transduction with a SIRPα shRNA. Such engineered cells could be used in combination with a monoclonal antibody to provide a selective immunotherapy.

Thus the present invention demonstrates a mechanism of macrophage stimulation and infiltration that has shown to be efficacious in the treatment of solid tumors in which the CD47-SIRPα interaction has been disrupted. Demonstration of the efficacy of a polyclonal antibody, followed by CD47 expression reduction, could open up a number of potentially cheaper, safer, and more efficient means of treating cancer.

The disclosures of each and every patent, patent application, and publication cited herein are hereby incorporated herein by reference in their entirety. While the present invention has been disclosed with reference to specific embodiments, it is apparent that other embodiments and variations of the present invention may be devised by others skilled in the art without departing from the true spirit and scope of the invention. The appended claims are intended to be construed to include all such embodiments and equivalent variations.

What is claimed is:

1. A composition comprising a modified macrophage comprising a repressor of signal regulatory protein-alpha (SIRPα), and a pharmaceutically acceptable carrier;
   wherein the repressor of SIRPα is selected from the group consisting of a SE7C2 antibody and a P84 antibody; and
   wherein the macrophage is bound to a MA5-15131 targeting antibody and possesses phagocytic activity against tumor tissue.

2. The modified macrophage of claim 1, wherein the targeting antibody is bound to a Fc receptor on the macrophage.

3. The composition of claim 1, wherein the composition has a therapeutic effect on tumor tissue.

4. A composition comprising a signal regulatory protein-alpha (SIRPα) repressed bone marrow cell bound to a targeting antibody; and a pharmaceutically acceptable carrier;
   wherein the repressor of SIRPα is selected from the group consisting of a SE7C2 antibody and a P84 antibody; and
   wherein the bone marrow cell is bound to a MA5-15131 targeting antibody and possesses phagocytic activity against tumor tissue.

5. The composition of claim 4, wherein the targeting antibody is bound to a Fc receptor on the bone marrow cell.

6. The composition of claim 4, wherein the composition has a therapeutic effect on tumor tissue.

7. The composition of claim 6, wherein the therapeutic effect comprises tumor shrinkage of at least 60% of the tumor.

8. The composition of claim 6, wherein the tumor tissue comprises a brain cancer, bladder cancer, breast cancer, cervical cancer, colorectal cancer, liver cancer, kidney cancer, lymphoma, leukemia, lung cancer, melanoma, metastatic melanoma, mesothelioma, neuroblastoma, ovarian cancer, prostate cancer, gastric cancer, pancreatic cancer, renal cancer, skin cancer, thymoma, sarcoma, non-Hodgkin's lymphoma, Hodgkin's lymphoma, or uterine cancer.

9. A method of enhancing phagocytic activity of a phagocytic cell toward MUC1 expressing tumor tissue in a mammal, the method comprising administering to the mammal an effective amount of the composition of claim 4, wherein the effective amount of the composition provides an SIRPα repressed bone marrow cell bound to a MUC1 targeting antibody, and wherein the effective amount enhances phagocytic activity and has a therapeutic effect in the mammal.

10. The method of claim 9, wherein the SIPRα repressed bone marrow cell differentiates into a mature macrophage.

11. The method of claim 9, wherein the therapeutic effect comprises tumor tissue shrinkage of at least 60% of the tumor tissue.

12. The method of claim 9, wherein the macrophage is bound to the MUC1 targeting antibody through an Fc receptor on the macrophage.

13. The method of claim 9, wherein the composition of claim 4 is administered intravenously to the mammal.

14. The method of claim 9, wherein the mammal is a human.

15. A method of enhancing phagocytic activity of a phagocytic cell toward MUC1 expressing tumor tissue in a mammal, the method comprising administering to the mammal an effective amount of the composition of claim 1, wherein the effective amount of the composition provides an SIRPα repressed macrophage bound to a MUC1 targeting antibody, and wherein the effective amount enhances phagocytic activity and has a therapeutic effect in the mammal.

16. The method of claim 15, wherein the composition of claim 1 is administered intravenously to the mammal.

17. The method of claim 15, wherein the mammal is a human.

18. A method of treating a MUC1 expressing tumor in a mammal, the method comprising administering to the mammal an effective amount of the composition of claim 1, wherein the effective amount of the composition provides an SIRPα repressed macrophage bound to a MUC1 targeting antibody, and wherein the effective amount of the composition has a therapeutic effect in the mammal, thereby treating the MUC1 expressing tumor tissue.

19. The method of claim 18, wherein the therapeutic effect comprises tumor tissue shrinkage of at least 60% of the tumor tissue.

20. The method of claim 18, wherein the macrophage is bound to the MUC1 targeting antibody through an Fc receptor on the macrophage.

21. The method of claim 18, wherein the composition of claim 1 is administered intravenously to the mammal.

22. The method of claim 18, wherein the mammal is a human.

23. A method of treating a MUC1 expressing tumor in a mammal, the method comprising administering to the mammal an effective amount of the composition of claim 4, wherein the effective amount of the composition provides an SIRPα repressed bone marrow cell bound to a MUC1 targeting antibody, and wherein the effective amount of the composition has a therapeutic effect in the mammal, thereby treating the MUC1 expressing tumor tissue.

24. The method of claim 23, wherein the SIPRα repressed bone marrow cell differentiates into a mature macrophage.

25. The method of claim 23, wherein the bone marrow cell is bound to the MUC1 targeting antibody through an Fc receptor on the bone marrow cell.

26. The method of claim 23 wherein the composition of claim 4 is administered intravenously to the mammal.

27. The method of claim 23 wherein the mammal is human.

28. The method of claim 23, wherein the therapeutic effect comprises tumor tissue shrinkage of at least 60% of the tumor tissue.

29. A method of modifying macrophage activity to target a MUC1 expressing tissue in a mammal, the method comprising contacting a macrophage cell with the composition of claim 1 to provide a target antibody loaded modified macrophage having modified macrophage activity, wherein the modified macrophage has enhanced phagocytic activity and a therapeutic effect on the targeted tissue in the mammal.

30. The method of claim 29, wherein the modified macrophage has a stronger phagocytic activity than a native macrophage of the mammal.

31. A method of modifying phagocytic activity to target a MUC1 expressing tissue in a mammal, the method comprising contacting a bone marrow cell with the composition of claim 4 to provide a target antibody loaded modified bone marrow cell having modified phagocytic activity, wherein the modified bone marrow cell has enhanced phagocytic activity and a therapeutic effect on the targeted tissue in the mammal.

32. The method of claim 31, wherein the target antibody loaded modified bone marrow cell differentiates into a mature macrophage.

33. A method of modulating phagocytic activity to target a MUC1 expressing tissue in a mammal, the method comprising administering to the mammal and effective amount of the composition of claim 1 and an opsonin, wherein the effective amount of the composition of claim 1 modulates phagocytic activity and has a therapeutic effect on the targeted tissue in the mammal.

34. A method of modulating phagocytic activity to target a MUC1 expressing tissue in a mammal, the method comprising administering to the mammal and effective amount of the composition of claim 4 and an opsonin, wherein the effective amount of the composition of claim 4 modulates phagocytic activity and has a therapeutic effect on the targeted tissue in the mammal.

35. A method of treating a MUC1 expressing tumor in a mammal, the method comprising administering to the mammal an effective amount of the composition of claim 1 and an opsonin, thereby treating the tumor tissue.

36. A method of treating a MUC1 expressing tumor in a mammal, the method comprising administering to the mammal an effective amount of the composition of claim 4 and an opsonin, thereby treating the tumor tissue.

* * * * *